US011207325B2

(12) United States Patent
Chan et al.

(10) Patent No.: US 11,207,325 B2
(45) **Date of Patent: *Dec. 28, 2021**

(54) TRIAZOLOPYRIMIDINE COMPOUNDS AND USES THEREOF

(71) Applicant: Novartis AG, Basel (CH)

(72) Inventors: Ho Man Chan, Arlington, MA (US); Xiang-Ju Justin Gu, Shanghai (CN); Ying Huang, Shanghai (CN); Ling Li, Shanghai (CN); Yuan Mi, Shanghai (CN); Wei Qi, Shanghai (CN); Martin Sendzik, Belmont, MA (US); Yongfeng Sun, Shanghai (CN); Long Wang, Shanghai (CN); Zhengtian Yu, Shanghai (CN); Hailong Zhang, Englewood, CO (US); Ji Yue (Jeff) Zhang, Shanghai (CN); Man Zhang, Shanghai (CN); Qiong Zhang, Shanghai (CN); Kehao Zhao, Newton, MA (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/863,631

(22) Filed: Apr. 30, 2020

(65) Prior Publication Data

US 2020/0323859 A1 Oct. 15, 2020

Related U.S. Application Data

(63) Continuation of application No. 16/246,380, filed on Jan. 11, 2019, now abandoned, which is a continuation of application No. 15/538,348, filed as application No. PCT/IB2015/059843 on Dec. 21, 2015, now Pat. No. 10,220,036.

(30) Foreign Application Priority Data

Dec. 23, 2014 (WO) ................ PCT/CN2014/094644
Nov. 23, 2015 (WO) ................ PCT/CN2015/095320

(51) Int. Cl.

| | |
|---|---|
| *A61K 31/539* | (2006.01) |
| *A61K 31/343* | (2006.01) |
| *A61K 31/5377* | (2006.01) |
| *A61K 31/541* | (2006.01) |
| *A61K 31/551* | (2006.01) |
| *C07D 487/04* | (2006.01) |
| *A61K 31/519* | (2006.01) |
| *A61K 45/06* | (2006.01) |

(52) U.S. Cl.

CPC ........ *A61K 31/519* (2013.01); *A61K 31/5377* (2013.01); *A61K 31/541* (2013.01); *A61K 31/551* (2013.01); *A61K 45/06* (2013.01); *C07D 487/04* (2013.01)

(58) Field of Classification Search

CPC ................ A61K 31/539; A61K 31/343; A61K 31/5377; A61K 31/541; A61K 31/551; C07D 487/04

See application file for complete search history.

(56) References Cited

U.S. PATENT DOCUMENTS

| | | | |
|---|---|---|---|
| 7,563,589 | B2 | 7/2009 | Zhang et al. |
| 8,586,313 | B2 | 11/2013 | Laird et al. |
| 8,691,507 | B2 | 4/2014 | Copeland et al. |
| 8,895,526 | B2 | 11/2014 | Stillman et al. |
| 2006/0127408 | A1 | 6/2006 | Young et al. |
| 2006/0246505 | A1 | 11/2006 | Walther |
| 2006/0287341 | A1 | 12/2006 | Wu et al. |
| 2009/0170715 | A1 | 7/2009 | Glinsky |
| 2009/0286984 | A1 | 11/2009 | Raeppel et al. |
| 2010/0137411 | A1 | 6/2010 | Green et al. |
| 2012/0184543 | A1 | 7/2012 | Tang et al. |

(Continued)

FOREIGN PATENT DOCUMENTS

| | | |
|---|---|---|
| JP | 2004-238296 A | 8/2004 |
| WO | 2001053834 | 7/2001 |

(Continued)

OTHER PUBLICATIONS

Alajez et al. "Enhancer of Zeste Homolog 2 (EZH2) is Overexpressed in Recurrent Nasopharyngeal Carcinoma and is Regulated by miR-26a miR-101 and miR-98" Cell Death and Disease 1:e85 2010.
Bai et al. "Inhibition Enhancer of Zeste Homologue 2 Promotes Senescence and Apoptosis Induced by Doxorubicin in p53 Mutant Gastric Cancer Cells" Cell Prolif 47(3):211-218 2014.
Béguelin et al. "EZH2 Is Required for Germinal Center Formation and Somatic EZH2 Mutations Promote Lymphoid Transformation" Cancer Cell 23(5):677-692 May 13, 2013.

(Continued)

*Primary Examiner* — Brenda L Coleman
(74) *Attorney, Agent, or Firm* — Daniel E. Raymond

(57) ABSTRACT

A compound of Formula (I), or a pharmaceutically acceptable salt thereof, is provided that has been shown to be useful for treating a PRC2-mediated disease or disorder:

(I)

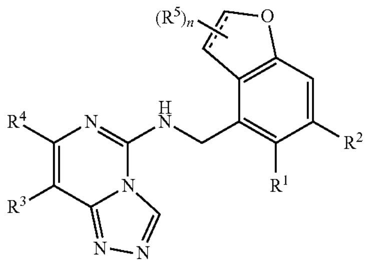

wherein $R^1$, $R^2$, $R^3$, $R^4$, $R^5$, and n are as defined herein.

19 Claims, No Drawings

(56) References Cited

U.S. PATENT DOCUMENTS

| | | | |
|---|---|---|---|
| 2013/0244256 | A1 | 9/2013 | Clarke et al. |
| 2014/0213475 | A1 | 7/2014 | Lawrence et al. |

FOREIGN PATENT DOCUMENTS

| | | | |
|---|---|---|---|
| WO | 03044021 | A2 | 5/2003 |
| WO | 2003034997 | A2 | 5/2003 |
| WO | 2010064019 | | 6/2010 |
| WO | 2011112766 | | 9/2011 |
| WO | 2012151277 | | 11/2012 |
| WO | 2014078813 | | 5/2014 |
| WO | 2014100080 | | 6/2014 |
| WO | 2014124326 | | 8/2014 |
| WO | 2014144747 | A1 | 9/2014 |
| WO | 2014153030 | | 9/2014 |
| WO | 2015123365 | | 8/2015 |
| WO | 2016075289 | | 5/2016 |
| WO | 2016096907 | | 6/2016 |
| WO | 2016102272 | | 6/2016 |
| WO | 2016106138 | | 6/2016 |

OTHER PUBLICATIONS

Bender et al. Reduced H3K27me3 and DNA Hypomethylation are Major Drivers of Gene Expression in K27M Mutant Pediatric High-Grade Gliomas Cancer Cell 24(5):660-672 Nov. 11, 2013.

Bhan et al. "Histone Methyltransferase EZH2 Is Transcriptionally Induced by Estradiol as Well as Estrogenic Endocrine Disruptors Bisphenol-A and Diethylstilbestrol" Journal of Molecular Biology 426(20):3426-3441 Oct. 9, 2014.

Bilter et al. "Synthetic Lethality by Targeting EZH2 Methyltransferase Activity in ARID1A-Mutated Cancers" Nat Med 21(3):231-238 Mar. 2015.

Borbone et al. "Enhancer of Zeste Homolog 2 Overexpression Has a Role in the Development of Anaplastic Thyroid Carcinomas" The Journal of Clinical Endocrinology and Metabolism 96(4):1029-1038 Aug. 2011.

Chang et al. "EZH2 Promotes Expansion of Breast Tumor Initiating Cells through Activation of RAF1-β-Catenin Signaling" Cancer Cell 19(1):86-100 2011.

Chen et al. "Cyclin-Dependent Kinases Regulate Epigenetic Gene Silencing Through Phosphorylation of EZH2" Nat. Cell Boil. 12(11):1108-1114 2010.

Chen et al. "JNK and STAT3 Signaling Pathways Converge on Akt-Mediated Phosphorylation of EZH2 in Bronchial Epithelial Cells Induced by Arsenic" Cell Cycle 12(1):112-121 2013.

U.S. Appl. No. 16/246,380.

U.S. Appl. No. 15/538,348.

TRIAZOLOPYRIMIDINE COMPOUNDS AND USES THEREOF

FIELD OF THE INVENTION

The present disclosure relates to triazolopyrimidine compounds, compositions comprising such compounds, and their use for the treatment of Polycomb Repressive Complex 2 (PRC2)-mediated diseases or disorders.

BACKGROUND

Polycomb group (PcG) proteins are chromatin modifying enzymes that are dysregulated in many human cancers. The Polycomb Repressive Complex 2 (PRC2), which includes SUZ12 (suppressor of zeste 12), EED (embryonic ectoderm development) and the catalytic subunit, EZH2 (enhancer of zeste homolog 2), represses genes by methylating the core histone H3 lysine 27 (H3K27me3) at and around the promoter regions of target genes. PRC2 is the critical component of cellular machinery involved in the epigenetic regulation of gene transcription and plays critical function in development and tissue differentiation and regeneration. Although EZH2 is the catalytic subunit, PRC2 requires at least EED and SUZ12 for its methyltransferase activity. EED, SUZ12 and EZH2 are overexpressed in many cancers, including but not limited to breast cancer, prostate cancer, hepatocellular carcinoma and etc. EZH2 activating mutations have been identified in DLBCL (diffused large B cell lymphoma) patients and FL (follicular lymphoma) patients. Inhibition of PRC2 methyltransferase activity by compounds competing with the cofactor S-adenosyl methionine (SAM) in DLBCL reverses H3K27 methylation, re-activates expression of target genes and inhibits tumor growth/proliferation. Therefore, PRC2 provides a pharmacological target for DLBCL and other cancers. In particular, the need exists for small molecules that inhibit the activity of PRC2. The present invention fulfills this need.

SUMMARY

The present disclosure provides a compound of Formula (I):

(I)

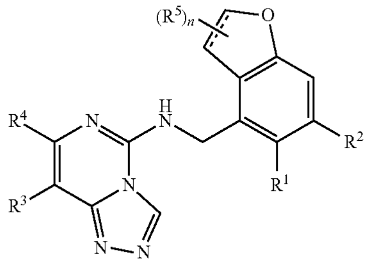

wherein $R^1$, $R^2$, $R^3$, $R^4$, $R^5$, and n are as defined herein, including stereoisomers, tautomers, pharmaceutically acceptable salts, polymorphs, or solvates thereof, which are useful for the treatment of PRC2-mediated diseases or disorders.

The present disclosure also provides processes and intermediates for making the compounds of the present disclosure.

The present disclosure also provides pharmaceutical compositions comprising at least one of the compounds of the present disclosure and at least one pharmaceutically acceptable carrier, diluent or excipient. The pharmaceutical composition may further comprise at least one additional therapeutic agent. Of particular interest are additional therapeutic agents selected from: other anti-cancer agents, immunomodulators, anti-allergic agents, anti-nausea agents (or anti-emetics), pain relievers, cytoprotective agents, and combinations thereof.

The compounds of the present disclosure may be used in the treatment of diseases or disorders mediated by EED and/or PRC2.

The compounds of the present disclosure may be used in therapy.

The compounds of the present disclosure may be used for the manufacture of a medicament for the treatment of diseases or disorders mediated by EED and/or PRC2.

The present disclosure provides a method for the treatment of diseases or disorders mediated by EED and/or PRC2, comprising administering to a patient in need thereof a therapeutically effective amount of a first therapeutic agent optionally with a second therapeutic agent, wherein the first therapeutic agent is a compound of the present disclosure and the second therapeutic agent is one other type of therapeutic agent.

Examples of diseases or disorders mediated by EED and/or PRC2 include, but are not limited to, diffused large B cell lymphoma (DLBCL), follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neuroblastoma, schwannoma, glioma, glioblastoma and astrocytoma, cervical cancer, colon cancer, melanoma, endometrial cancer, esophageal cancer, head and neck cancer, lung cancer, nasopharyngeal carcinoma, ovarian cancer, pancreatic cancer, renal cell carcinoma, rectal cancer, thyroid cancers, parathyroid tumors, uterine tumors, and soft tissue sarcomas such as rhabdomyosarcoma (RMS), Kaposi sarcoma, synovial sarcoma, osteosarcoma and Ewing's sarcoma.

The present disclosure provides a method for the treatment of diseases or disorders mediated by EED and/or PRC2, comprising administering to a patient in need thereof a therapeutically effective amount of a first therapeutic agent optionally with a second therapeutic agent, wherein the first therapeutic agent is an EED inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, and hepatocellular carcinoma.

The compounds of the present disclosure can be used alone, in combination with other compounds of the present disclosure, or in combination with one or more, preferably one to two other agent(s), simultaneously or sequentially.

Other features and advantages of the present disclosure will be apparent from the following detailed description and claims.

DETAILED DESCRIPTION

I. Compounds

In a first aspect, the present disclosure provides, inter alia, a compound of Formula (I):

(I)

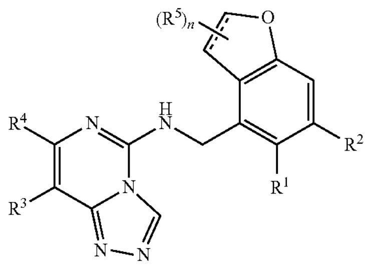

or a pharmaceutically acceptable salt thereof, wherein:

— is a single bond or a double bond;

$R^1$ and $R^2$ are independently H or halogen;

$R^3$ is independently selected from: halogen, phenyl, and a 5- to 6-membered heteroaryl comprising carbon atoms and 1-4 heteroatoms selected from N, $NR^a$, O, and $S(O)_p$; wherein said phenyl and heteroaryl are substituted with 0-3 $R^{3A}$;

each $R^{3A}$ is independently selected from: halogen, CN, —$(O)_m$—($C_1$-$C_6$ alkyl substituted with 0-1 $R^{3B}$), $C_1$-$C_6$ haloalkyl, $C_1$-$C_6$ haloalkoxy, $R^{3C}$, —$OR^{3C}$, —C(═O)$R^{3D}$, $NR^{3E}R^{3F}$, —C(═O)$NR^{3E}R^{3F}$, —NHC(═O)$R^{3D}$, —S(═O)$_2R^{3D}$, —S(═O)$_2NR^{3E}R^{3F}$, —NHS(═O)$_2$($C_2$-$C_4$alkyl), and —$CR^{3C}R^{3E}R^{3G}$;

$R^{3B}$ is independently selected from: OH, $NR^eR^f$, $C_1$-$C_4$ alkoxy, —C(═O)$NR^eR^f$, —S(═O)$_2$($C_1$-$C_4$ alkyl), —NHC(═O)($C_1$-$C_4$ alkyl), and a 5- to 6-membered heterocycloalkyl comprising carbon atoms and 1-2 heteroatoms selected from N, $NR^a$, O, and $S(O)_p$; wherein said heterocycloalkyl is substituted with 0-2 $R^c$;

each $R^{3C}$ is independently selected from: $C_3$-$C_6$ cycloalkyl, phenyl, and a 4- to 7-membered heterocycle comprising carbon atoms and 1-4 heteroatoms selected from N, $NR^a$, O, and $S(O)_p$; wherein each moiety is substituted with 0-2 $R^c$;

each $R^{3D}$ is independently selected from: $C_1$-$C_4$ alkyl and $R^{3C}$;

$R^{3E}$ and $R^{3G}$ are, at each occurrence, independently selected from: H and $C_1$-$C_4$ alkyl;

each $R^{3F}$ is independently selected from: H and $C_1$-$C_4$ alkyl substituted with 0-1 $R^d$.

$R^4$ is independently selected from: H, halogen and $C_1$-$C_4$ alkyl; $R^5$ is independently selected from OH and $C_1$-$C_4$ alkyl;

each $R^a$ is independently selected from: H, →O, $C_1$-$C_4$ alkyl substituted with 0-1 $R^b$, —C(═O)H, —C(═O)($C_1$-$C_4$alkyl), —$CO_2$($C_1$-$C_4$alkyl), $C_3$-$C_6$cycloalkyl, and benzyl;

$R^b$ is independently selected from: halogen, OH and $C_1$-$C_4$ alkoxy;

each $R^c$ is independently selected from: ═O, halogen, OH, $C_1$-$C_4$ alkyl, $C_1$-$C_4$haloalkyl, $C_1$-$C_4$ alkoxy, and $C_1$-$C_4$ haloalkoxy;

$R^d$ is independently selected from: OH and $NR^eR^f$;

$R^e$ and $R^f$ are, at each occurrence, independently selected from: H and $C_1$-$C_4$ alkyl;

each p is independently selected from 0, 1 and 2; and m and n are, at each occurrence, independently selected from 0 and 1.

In another aspect, the present disclosure provides a compound of Formula (IA):

(IA)

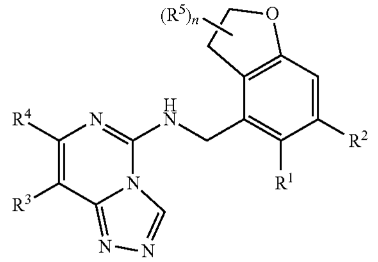

or a pharmaceutically acceptable salt thereof, within the scope of the first aspect;

wherein:

$R^1$ and $R^2$ are independently H or halogen;

$R^3$ is independently selected from: halogen, phenyl, and a 5- to 6-membered heteroaryl comprising carbon atoms and 1-4 heteroatoms selected from N, $NR^a$, O, and $S(O)_p$; wherein said phenyl and heteroaryl are substituted with 0-3 $R^{3A}$;

each $R^{3A}$ is independently selected from: halogen, CN, —$(O)_m$—($C_1$-$C_6$ alkyl substituted with 0-1 $R^{3B}$), $C_1$-$C_6$ haloalkyl, $C_1$-$C_6$ haloalkoxy, $R^{3C}$, —$OR^{3C}$, —C(═O)$R^{3D}$, $NR^{3E}R^{3F}$, —C(═O)$NR^{3E}R^{3F}$, —NHC(═O)$R^{3D}$, —S(═O)$_2R^{3D}$, —S(═O)$_2NR^{3E}R^{3F}$, —NHS(═O)$_2$($C_1$-$C_4$alkyl), and —$CR^{3C}R^{3E}R^{3G}$;

$R^{3B}$ is independently selected from: OH, $NR^eR^f$, $C_1$-$C_4$ alkoxy, —C(═O)$NR^eR^f$, —S(═O)$_2$($C_2$-$C_4$ alkyl), —NHC(═O)($C_1$-$C_4$ alkyl), and a 5- to 6-membered heterocycloalkyl comprising carbon atoms and 1-2 heteroatoms selected from N, $NR^a$, O, and $S(O)_p$; wherein said heterocycloalkyl is substituted with 0-2 $R^c$;

each $R^{3C}$ is independently selected from: $C_3$-$C_6$ cycloalkyl, phenyl, and a 4- to 7-membered heterocycle comprising carbon atoms and 1-4 heteroatoms selected from N, $NR^a$, O, and $S(O)_p$; wherein each moiety is substituted with 0-2 $R^c$;

each $R^{3D}$ is independently selected from: $C_1$-$C_4$ alkyl and $R^{3C}$;

$R^{3E}$ and $R^{3G}$ are, at each occurrence, independently selected from: H and $C_1$-$C_4$ alkyl;

each $R^{3F}$ is independently selected from: H and $C_1$-$C_4$alkyl substituted with 0-1 $R^d$;

$R^4$ is independently selected from: H, halogen and $C_1$-$C_4$ alkyl;

$R^5$ is independently $C_1$-$C_4$ alkyl;

each $R^a$ is independently selected from: H, →O, $C_1$-$C_4$ alkyl substituted with 0-1 $R^b$, —C(═O)H, —C(═O)($C_1$-$C_4$alkyl), —$CO_2$($C_1$-$C_4$alkyl), $C_3$-$C_6$ cycloalkyl, and benzyl;

$R^b$ is independently selected from: halogen, OH and $C_1$-$C_4$ alkoxy;

each $R^c$ is independently selected from: ═O, halogen, OH, $C_1$-$C_4$ alkyl, $C_1$-$C_4$haloalkyl, $C_1$-$C_4$ alkoxy, and $C_1$-$C_4$ haloalkoxy;

$R^d$ is independently selected from: OH and $NR^eR^f$;

$R^e$ and $R^f$ are, at each occurrence, independently selected from: H and $C_1$-$C_4$ alkyl;

each p is independently selected from 0, 1 and 2; and m and n are, at each occurrence, independently selected from 0 and 1.

In a second aspect, the present disclosure includes a compound of Formula (I) or (IA), or a pharmaceutically acceptable salt thereof, within the scope of the first aspect; wherein:

each $R^{3A}$ is independently selected from: halogen, CN, —$(O)_m$—($C_1$-$C_4$ alkyl substituted with 0-1 $R^{3B}$), $C_1$-$C_4$ haloalkyl, $C_1$-$C_4$ haloalkoxy, $R^{3C}$, —C(═O)$R^{3D}$, $NR^{3E}R^{3F}$, —C(═O)$NR^{3E}R^{3F}$, —S(═O)$_2R^{3D}$, —S(═O)$_2NHR^{3F}$, —NHS(═O)$_2$($C_1$-$C_4$ alkyl), —O—$C_3$-$C_6$cycloalkyl, and

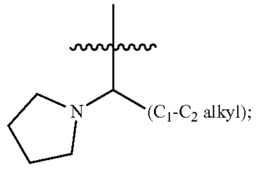

$R^a$ is independently selected from: H, →O, $C_1$-$C_4$ alkyl substituted with 0-1 $R^b$, —C(═O)H, —C(═O)($C_1$-$C_4$ alkyl), —$CO_2$($C_1$-$C_4$ alkyl), and $C_3$-$C_6$ cycloalkyl;

$R^4$ is H;

m is independently selected from 0 and 1; and n is 0.

In a third aspect, the present disclosure includes a compound of Formula (I) or (IA), or a pharmaceutically acceptable salt thereof, within the scope of the first or second aspect; wherein:

$R^1$ is independently H or F;

$R^2$ is H; and $R^3$ is independently selected from: phenyl and a 6-membered heteroaryl comprising carbon atoms and 1-2 heteroatoms selected from N and $NR^a$; wherein said phenyl and heteroaryl are substituted with 0-3 $R^{3A}$.

In a fourth aspect, the present disclosure includes a compound of Formula (I) or (IA), or a pharmaceutically acceptable salt thereof, within the scope of any one of the first, second and third aspects; wherein:

$R^3$ is independently selected from: phenyl, pyridyl, pyrimidyl, pyridazinyl and pyrazinyl; wherein each moiety is substituted with 0-3 $R^{3A}$.

In a fifth aspect, the present disclosure includes a compound of Formula (I) or (IA), or a pharmaceutically acceptable salt thereof, within the scope of any of the first to fourth aspects, wherein:

$R^3$ is independently selected from:

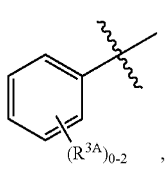

,

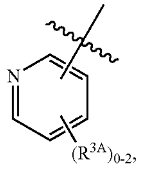

and

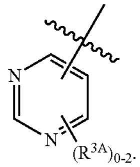

In a sixth aspect, the present disclosure includes a compound of Formula (I) or (IA), or a pharmaceutically acceptable salt thereof, within the scope of any of the first to fifth aspects, wherein:

$R^3$ is independently selected from:

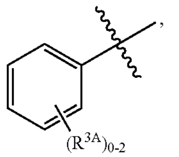

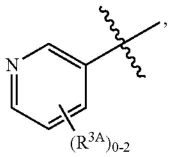

and

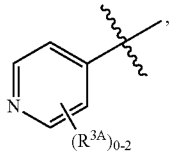

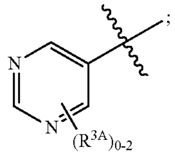

each $R^{3A}$ is independently selected from: halogen, CN, $(O)_m$—($C_1$-$C_4$ alkyl substituted with 0-1 $R^{3B}$), $C_1$-$C_4$ haloalkyl, $C_1$-$C_4$ haloalkoxy, —C(═O)$NH_2$, —C(═O)NH($C_1$-$C_4$ alkyl), —C(═O)N($C_1$-$C_4$ alkyl)$_2$, —C(═O)N($C_2$-$C_4$ alkyl)($CH_2$)$_2$N($C_1$-$C_4$ alkyl)$_2$, —$CH_2$NHC(═O)($C_1$-$C_4$ alkyl), —S(═O)$_2R^{3D}$, —S(═O)$_2$NH($C_1$-$C_4$ alkyl substituted with 0-1 OH), —NHS(═O)$_2$($C_1$-$C_4$ alkyl), $NH_2$, —NH($C_1$-$C_4$ alkyl), —N($C_1$-$C_4$ alkyl)$_2$, $C_3$—C cycloalkyl,

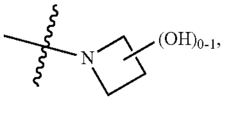

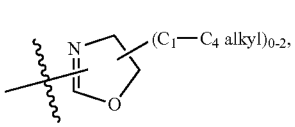

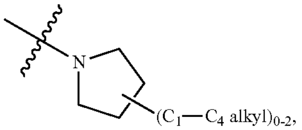

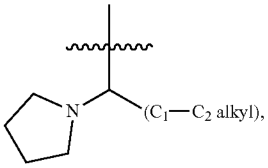

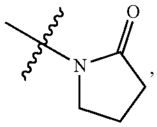

,

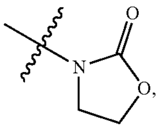

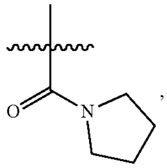

,

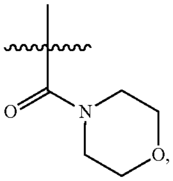

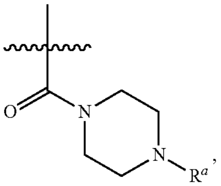

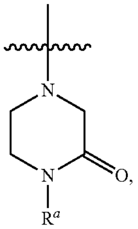

,

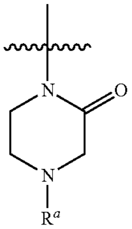

,

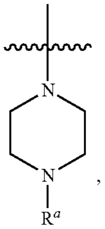

,

-continued

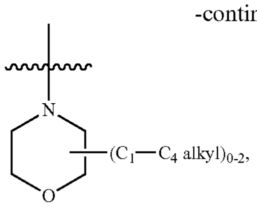, 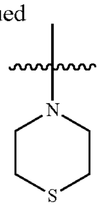, and 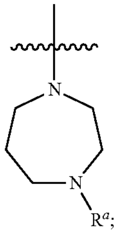;

$R^{3B}$ is independently selected from: OH, $NH_2$, $NH(C_1\text{-}C_4$ alkyl), $N(C_1\text{-}C_4$ alkyl$)_2$, $C_1\text{-}C_4$ alkoxy, —C(═O)$N(C_1\text{-}C_4$ alkyl$)_2$, —S(═O)$_2(C_1\text{-}C_4$ alkyl),

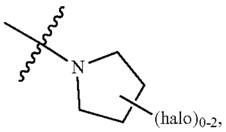, 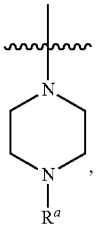, and 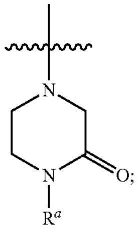;

$R^{3D}$ is independently selected from: $C_1\text{-}C_4$ alkyl and 1H-piperidin-4-yl; and each $R^a$ is independently selected from: H, $C_1\text{-}C_4$alkyl, —C(═O)H, —C(═O)($C_1\text{-}C_4$ alkyl), and —$CO_2(C_1\text{-}C_4$ alkyl).

In a seventh aspect, the present disclosure includes a compound of Formula (I) or (IA), or a pharmaceutically acceptable salt thereof, within the scope of any of the first to sixth aspects, wherein:

$R^3$ is independently selected from:

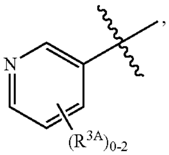, and 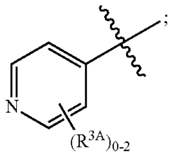;

each $R^{3A}$ is independently selected from: halogen, CN, —$(O)_m$—($C_1\text{-}C_4$ alkyl substituted with 0-1 $R^{3B}$), $C_1\text{-}C_4$ haloalkyl, $C_1\text{-}C_4$ haloalkoxy, —C(═O)$NH_2$, —C(═O)NH($C_1\text{-}C_4$ alkyl), —C(═O)$N(C_1\text{-}C_4$ alkyl$)_2$, —C(═O)$N(C_1\text{-}C_4$ alkyl)$(CH_2)_2N(C_1\text{-}C_4$ alkyl$)_2$, —$CH_2NHC$(═O)($C_1\text{-}C_4$ alkyl), —S(═O)$_2(C_1\text{-}C_4$ alkyl), $NH_2$, $NH(C_1\text{-}C_4$ alkyl), $N(C_1\text{-}C_4$ alkyl$)_2$, $C_3\text{-}C_6$ cycloalkyl,

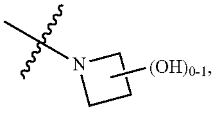, 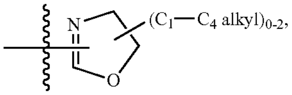, 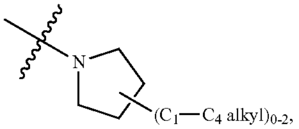, 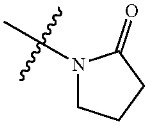, 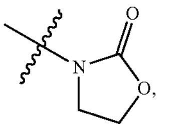, 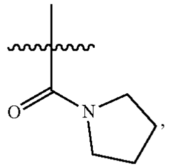, 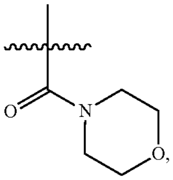, 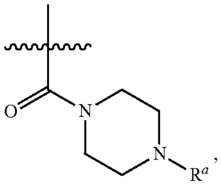, 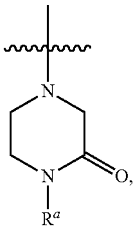, 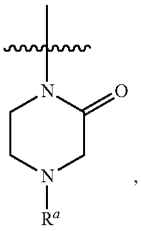, 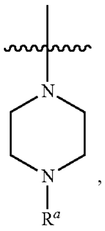, 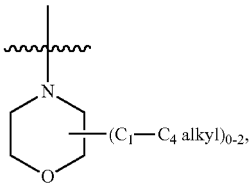, 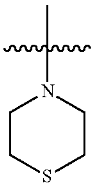, and 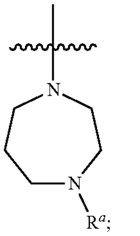;

$R^{3B}$ is independently selected from: OH, $N(C_1\text{-}C_4$ alkyl$)_2$, $C_1\text{-}C_4$ alkoxy, —C(═O)$N(C_1\text{-}C_4$ alkyl$)_2$, —S(═O)$_2(C_1\text{-}C_4$ alkyl),

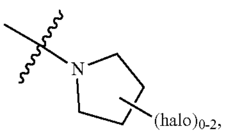, 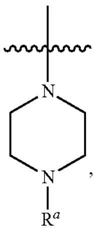, and

-continued

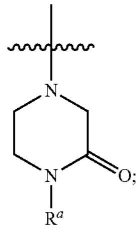

and each $R^a$ is independently selected from: H, $C_1$-$C_4$alkyl, —C(═O)H, —C(═O)($C_1$-$C_4$ alkyl), and —$CO_2$($C_1$-$C_4$ alkyl).

In an eighth aspect, the present disclosure includes a compound of Formula (I) or (IA), or a pharmaceutically acceptable salt thereof, within the scope of any of the first to seventh aspects, wherein:

each $R^{3A}$ is independently selected from: F, Cl, $CH_3$, —$CH_2OH$, $CH_2F$, $CHF_2$, $CF_3$, CN, —$OCH_3$, —$OCH_2CH_3$, —$OCH(CH_3)_2$, —$OCHF_2$, —C(═O)N($CH_3$)$_2$, —$CH_2$NHC(═O)$CH_3$, —S(═O)$_2CH_3$, $NH_2$, cyclopropyl,

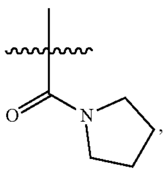,
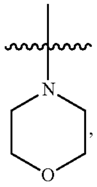, and
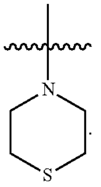.

In a ninth aspect, the present disclosure provides a compound of Formula (IA-1):

(IA-1)

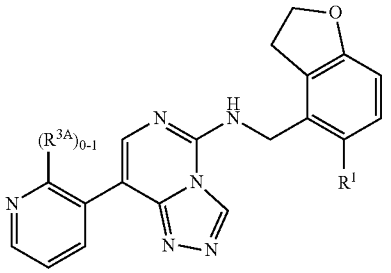

or a pharmaceutically acceptable salt thereof, within the scope of any of the above aspects; wherein:

$R^1$ is independently H or F; and $R^{3A}$ is independently selected from: F, $CH_3$, —$CH_2OH$, $CH_2F$, $CHF_2$, $CF_3$, and —$OCH_3$.

In a tenth aspect, the present disclosure includes a compound of Formula (I) or (IA), or a pharmaceutically acceptable salt thereof, within the scope of the first or second aspect; wherein:

$R^1$ is independently H or F;

$R^2$ is H;

$R^3$ is independently a 5-membered heteroaryl comprising carbon atoms and 1-4 heteroatoms selected from N, $NR^a$, O, and $S(O)_p$; wherein said heteroaryl is substituted with 0-3 $R^{3A}$; and $R^a$ is independently selected from: H, $C_1$-$C_4$ alkyl substituted with 0-1 $R^b$, —C(═O)H, —C(═O)($C_1$-$C_4$alkyl), —$CO_2$($C_1$-$C_4$alkyl), $C_3$-$C_6$ cycloalkyl, and benzyl.

In an eleventh aspect, the present disclosure includes a compound of Formula (I) or (IA), or a pharmaceutically acceptable salt thereof, within the scope of any one of the first, second and tenth aspects; wherein:

$R^3$ is independently selected from:

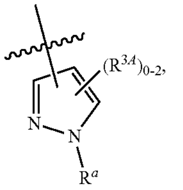
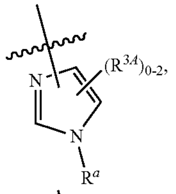
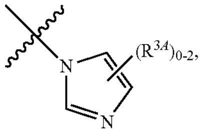
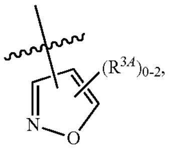 and
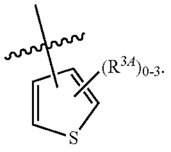

In another aspect, the present disclosure includes a compound of Formula (I) or (IA), or a pharmaceutically acceptable salt thereof, within the scope of any one of the first, second and tenth aspects; wherein:

$R^3$ is independently selected from:

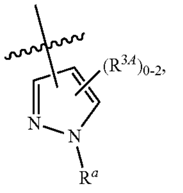
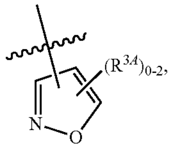 and
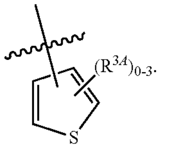

In a twelfth aspect, the present disclosure includes a compound of Formula (I) (IA), or (IA-1), or a pharmaceutically acceptable salt thereof, within the scope of any of the above aspects, wherein:

$R^1$ is F.

In a thirteenth aspect, the present disclosure provides a compound selected from the exemplified examples or a pharmaceutically acceptable salt thereof, including all compounds of Examples 1 to 245.

In a fourteenth aspect, the present disclosure provides a compound selected from:

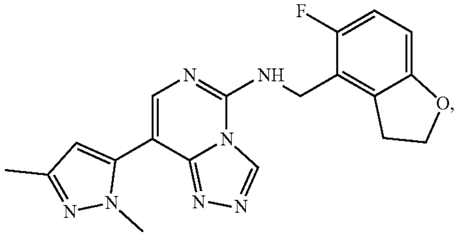

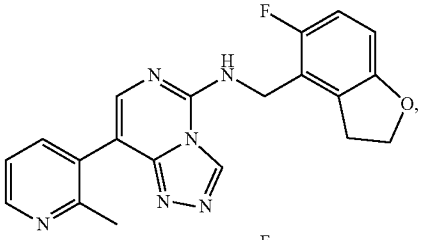

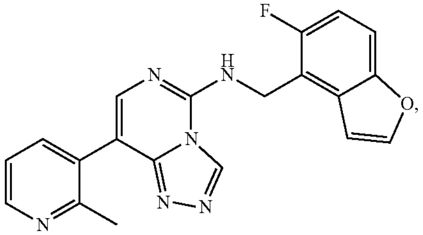

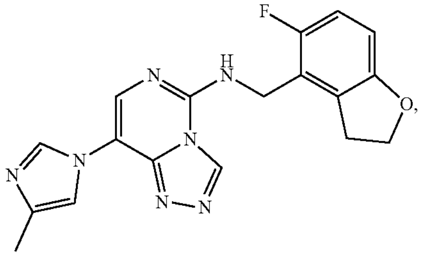

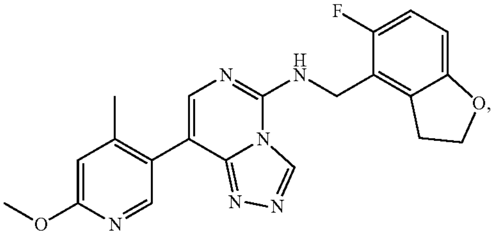

and

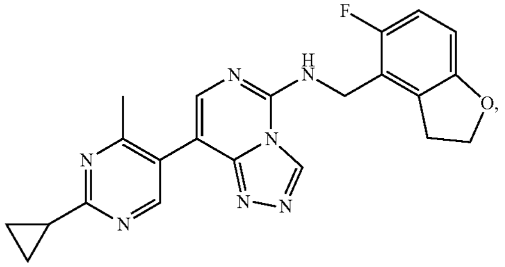

or a pharmaceutically acceptable salt thereof.

In another embodiment, provided is a compound of Example 1 or a pharmaceutically acceptable salt thereof, wherein the compound is 8-(1,3-dimethyl-1H-pyrazol-5-yl)-N-((5-fluoro-2,3-dihydrobenzofuran-4-yl)methyl)-[1,2,4]triazolo[4,3-c]pyrimidin-5-amine.

In another embodiment, provided is a compound of Example 1, wherein the compound is 8-(1,3-dimethyl-1H-pyrazol-5-yl)-N-((5-fluoro-2,3-dihydrobenzofuran-4-yl)methyl)-[1,2,4]triazolo[4,3-c]pyrimidin-5-amine.

In another embodiment, provided is a compound of Example 2 or a pharmaceutically acceptable salt thereof, wherein the compound is N-((5-fluoro-2,3-dihydrobenzofuran-4-yl)methyl)-8-(2-methylpyridin-3-yl)-[1,2,4]triazolo[4,3-c]pyrimidin-5-amine.

In another embodiment, provided is a compound of Example 2, wherein the compound is N-((5-fluoro-2,3-dihydrobenzofuran-4-yl)methyl)-8-(2-methylpyridin-3-yl)-[1,2,4]triazolo[4,3-c]pyrimidin-5-amine.

In another embodiment, provided is a compound of Example 5 or a pharmaceutically acceptable salt thereof, wherein the compound is N-((5-fluoro-2,3-dihydrobenzofuran-4-yl)methyl)-8-(6-methoxy-4-methylpyridin-3-yl)-[1,2,4]triazolo[4,3-c]pyrimidin-5-amine.

In another embodiment, provided is a compound of Example 5, wherein the compound is N-((5-fluoro-2,3-dihydrobenzofuran-4-yl)methyl)-8-(6-methoxy-4-methylpyridin-3-yl)-[1,2,4]triazolo[4,3-c]pyrimidin-5-amine.

In another embodiment, provided is a compound of Example 8 or a pharmaceutically acceptable salt thereof, wherein the compound is 8-(2-cyclopropyl-4-methylpyrimidin-5-yl)-N-((5-fluoro-2,3-dihydrobenzofuran-4-yl)methyl)-[1,2,4]triazolo[4,3-c]pyrimidin-5-amine.

In another embodiment, provided is a compound of Example 8, wherein the compound is 8-(2-cyclopropyl-4-methylpyrimidin-5-yl)-N-((5-fluoro-2,3-dihydrobenzofuran-4-yl)methyl)-[1,2,4]triazolo[4,3-c]pyrimidin-5-amine.

In another embodiment, provided is a compound of Example 207 or a pharmaceutically acceptable salt thereof, wherein the compound is N-((5-fluorobenzofuran-4-yl)methyl)-8-(2-methylpyridin-3-yl)-[1,2,4]triazolo[4,3-c]pyrimidin-5-amine.

In another embodiment, provided is a compound of Example 207, wherein the compound is N-((5-fluorobenzofuran-4-yl)methyl)-8-(2-methylpyridin-3-yl)-[1,2,4]triazolo[4,3-c]pyrimidin-5-amine.

In another embodiment, provided is a compound of Example 233 or a pharmaceutically acceptable salt thereof, wherein the compound is N-((5-fluoro-2,3-dihydrobenzofuran-4-yl)methyl)-8-(4-methyl-1H-imidazol-1-yl)-[1,2,4]triazolo[4,3-c]pyrimidin-5-amine.

In another embodiment, provided is a compound of Example 233, wherein the compound is N-((5-fluoro-2,3-dihydrobenzofuran-4-yl)methyl)-8-(4-methyl-1H-imidazol-1-yl)-[1,2,4]triazolo[4,3-c]pyrimidin-5-amine.

In another aspect, the present disclosure provides a compound or a pharmaceutically acceptable salt thereof, selected from any subset list of compounds within the scope of the thirteenth aspect.

In another embodiment, provided is the compound or a pharmaceutically acceptable salt thereof, within the scope of any one of the first to seventh aspects, wherein:

$R^3$ is independently

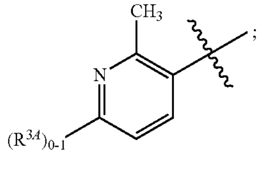

and each $R^{3A}$ is independently selected from: $C_1$-$C_4$ alkyl, $C_1$-$C_4$ alkoxy, $C_1$-$C_4$haloalkoxy, —CON($C_1$-$C_4$ alkyl)$_2$, —S(═O)$_2$($C_2$-$C_4$ alkyl), and $C_3$-$C_6$ cycloalkyl.

In another embodiment, provided is the compound or a pharmaceutically acceptable salt thereof, within the scope of any one of the first to seventh aspects, wherein:

$R^3$ is independently

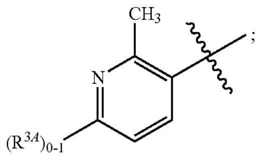

and each $R^{3A}$ is independently selected from: $CH_3$, $OCH_3$, —CON($CH_3$)$_2$, —S(═O)$_2$($CH_3$), and cyclopropyl.

In another embodiment, provided is the compound or a pharmaceutically acceptable salt thereof, within the scope of any one of the first to seventh aspects, wherein:

$R^3$ is independently

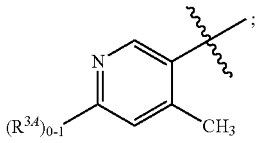

and each $R^{3A}$ is independently selected from: $C_1$-$C_4$ alkoxy, $C_1$-$C_4$ haloalkoxy, and —O—$C_3$-$C_6$ cycloalkyl.

In another embodiment, provided is the compound or a pharmaceutically acceptable salt thereof, within the scope of any one of the first to seventh aspects, wherein:

$R^3$ is independently

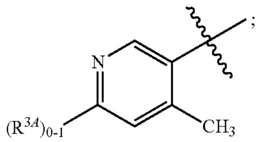

and each $R^{3A}$ is independently selected from: $OCH_3$, $OCH_2CH_3$, —$OCHF_2$, and —O-cyclopropyl.

In another embodiment, provided is the compound or a pharmaceutically acceptable salt thereof, within the scope of any one of the first to seventh aspects, wherein:

$R^3$ is independently

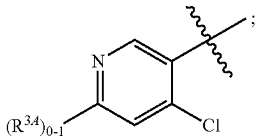

and each $R^{3A}$ is independently selected from: $C_1$-$C_4$ alkoxy, $C_1$-$C_4$ haloalkoxy, and —O—$C_3$-$C_6$ cycloalkyl.

In another embodiment, provided is the compound or a pharmaceutically acceptable salt thereof, within the scope of any one of the first to sixth aspects, wherein:

$R^3$ is independently

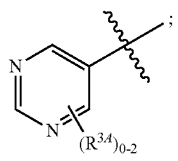

and each $R^{3A}$ is independently selected from: halogen, CN, $C_1$-$C_4$ alkyl, $C_1$-$C_4$ alkoxy, $C_1$-$C_4$ haloalkyl, $C_1$-$C_4$haloalkoxy, N($C_1$-$C_4$ alkyl)$_2$, and $C_3$-$C_6$ cycloalkyl.

In another embodiment, provided is the compound or a pharmaceutically acceptable salt thereof, within the scope of any one of the first to sixth aspects, wherein:

$R^3$ is independently

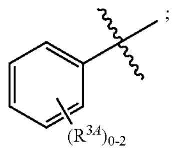

each $R^{3A}$ is independently selected from: halogen, CN, —(O)$_m$—($C_1$-$C_4$ alkyl substituted with 0-1 $R^{3B}$), $C_1$-$C_4$ haloalkyl, $C_1$-$C_4$ haloalkoxy, C(═O)$NH_2$, —S(═O)$_2R^{3c}$, —S(═O)$_2$NH($C_1$-$C_4$ alkyl substituted with 0-1 OH), —NHS(═O)$_2$($C_1$-$C_4$ alkyl),

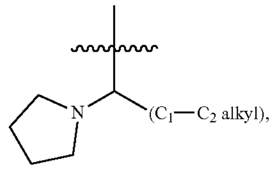

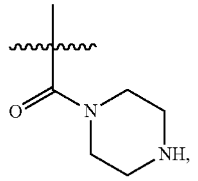

and

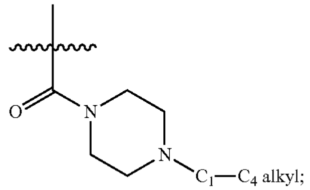

$R^{3B}$ is independently selected from: OH, $NH_2$, N($C_1$-$C_4$ alkyl)$_2$, and —S(═O)$_2$($C_1$-$C_4$ alkyl); and $R^{3c}$ is independently selected from: $C_1$-$C_4$ alkyl and 1H-piperidin-4-yl.

In another aspect, the present disclosure includes a compound of Formula (IA), or a pharmaceutically acceptable salt thereof, within the scope of any one of the first, second, tenth, and eleventh aspects; wherein:

$R^3$ is independently selected from: and

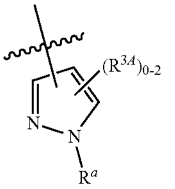

and

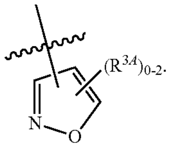

In another aspect, the present disclosure includes a compound of Formula (IA), or a pharmaceutically acceptable salt thereof, within the scope of any one of the first, second, tenth, and eleventh aspects; wherein:

$R^3$ is independently

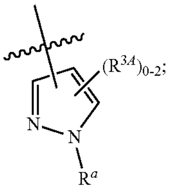

each $R^{3A}$ is independently selected from: $C_1$-$C_4$ alkyl, $C_1$-$C_4$ alkoxy, $C_1$-$C_4$haloalkyl, and $C_1$-$C_4$ haloalkoxy;

$R^a$ is independently selected from: H, $C_1$-$C_4$ alkyl substituted with 0-1 $R^b$, and $C_3$-$C_6$cycloalkyl; and $R^b$ is independently selected from: OH and $C_1$-$C_4$ alkoxy.

In another embodiment, the compounds of the present disclosure have $IC_{50}$ values ≤5 μM, using the EED Alphascreen binding, LC-MS and/or ELISA assays disclosed herein, preferably, $IC_{50}$ values ≤1 μM, more preferably, $IC_{50}$ values ≤0.5 μM, even more preferably, $IC_{50}$ values ≤0.1 μM.

II. Other Embodiments

In another embodiment, the present disclosure provides a composition comprising at least one of the compounds of the present disclosure or a pharmaceutically acceptable salt thereof.

In another embodiment, the present disclosure provides a pharmaceutical composition comprising at least one of the compounds of the present disclosure or a pharmaceutically acceptable salt thereof and at least one pharmaceutically acceptable carrier, diluent or excipient.

In another embodiment, the present disclosure provides a pharmaceutical composition, comprising a therapeutically effective amount of at least one of the compounds of the present disclosure or a pharmaceutically acceptable salt thereof and at least one pharmaceutically acceptable carrier, diluent or excipient.

The pharmaceutical composition is useful in the treatment of diseases or disorders mediated by EED and/or PRC2.

In another embodiment, the present disclosure provides a pharmaceutical composition as defined above further comprising additional therapeutic agent(s).

In another embodiment, the present disclosure provides a process for making a compound of the present disclosure.

In another embodiment, the present disclosure provides an intermediate for making a compound of the present disclosure.

In another embodiment, the present disclosure provides a compound of the present disclosure, for use in therapy, alone, or optionally in combination with another compound of the present disclosure and/or at least one other type of therapeutic agent.

In another embodiment, the present disclosure provides a compound of the present disclosure for use in therapy, for the treatment of diseases or disorders mediated by EED and/or PRC2, alone, or optionally in combination with another compound of the present disclosure and/or at least one other type of therapeutic agent.

In another embodiment, the present disclosure provides a method for the treatment of diseases or disorders mediated by EED and/or PRC2, comprising administering to a patient in need of such treatment a therapeutically effective amount of at least one of the compounds of the present disclosure, alone, or optionally in combination with another compound of the present disclosure and/or at least one other type of therapeutic agent.

In another embodiment, the present disclosure provides a method for the treatment of diseases or disorders mediated by EED and/or PRC2, comprising administering to a patient in need thereof a therapeutically effective amount of a first and second therapeutic agent, wherein the first therapeutic agent is a compound of the present disclosure and the second therapeutic agent is one other type of therapeutic agent.

In another embodiment, the present disclosure also provides the use of a compound of the present disclosure for the manufacture of a medicament for the treatment of diseases or disorders mediated by EED and/or PRC2, alone, or optionally in combination with another compound of the present disclosure and/or at least one other type of therapeutic agent.

In another embodiment, the present disclosure provides a combined preparation of a compound of the present disclosure and additional therapeutic agent(s) for use in therapy.

In another embodiment, the present disclosure provides a combination of a compound of the present disclosure and additional therapeutic agent(s) for simultaneous or separate use in therapy.

In another embodiment, the present disclosure provides a combined preparation of a compound of the present disclosure and additional therapeutic agent(s) for simultaneous, separate or sequential use in the treatment of diseases or disorders mediated by EED and/or PRC2. The compound may be administered as a pharmaceutical composition described herein.

Examples of diseases or disorders mediated by EED and/or PRC2 include, but are not limited to, diffused large B cell lymphoma (DLBCL), follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neurobalstoma, glioma, glioblastoma and astrocytoma, cervical cancer, colon cancer, melanoma, endometrial cancer, esophageal cancer, head and neck cancer, lung cancer, nasopharhyngeal carcinoma, ovarian cancer, pancreatic cancer, renal cell carcinoma, rectal cancer, thyroid cancers, parathyroid tumors, uterine tumors, and soft tissue sarcomas selected from rhabdomyosarcoma (RMS), Kaposi sarcoma, synovial sarcoma, osteosarcoma and Ewing's sarcoma.

In another embodiment, the present disclosure provides a method for the treatment of diseases or disorders mediated by EED and/or PRC2, comprising administering to a patient in need thereof a therapeutically effective amount of a first optionally with a second therapeutic agent, wherein the first therapeutic agent is an EED inhibitor and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, and hepatocellular carcinoma.

In another embodiment, additional therapeutic agent(s) used in combined pharmaceutical compositions or combined methods or combined uses, are selected from one or more, preferably one to three, of the following therapeutic agents: other anti-cancer agents, immunomodulators, anti-allergic agents, anti-nausea agents (or anti-emetics), pain relievers, cytoprotective agents, and combinations thereof.

Various (enumerated) embodiments of the disclosure are described herein. It will be recognized that features specified in each embodiment may be combined with other specified features to provide further embodiments of the present disclosure. It is also understood that each individual element of the embodiments is its own independent embodiment.

Other features of the present disclosure should become apparent in the course of the above descriptions of exemplary embodiments that are given for illustration of the disclosure and are not intended to be limiting thereof.

III. Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "a," "an," "the" and similar terms used in the context of the present disclosure (especially in the context of the claims) are to be construed to cover both the singular and plural unless otherwise indicated herein or clearly contradicted by the context.

As used herein, the term "heteroatoms" refers to nitrogen (N), oxygen (O) or sulfur (S) atoms, in particular nitrogen or oxygen.

Unless otherwise indicated, any heteroatom with unsatisfied valences is assumed to have hydrogen atoms sufficient to satisfy the valences.

As used herein, the terms "alkyl" refers to a hydrocarbon radical of the general formula $C_nH_{2n+1}$. The alkane radical may be straight or branched. For example, the term "$C_1$-$C_{10}$ alkyl" or "$C_1$ to $C_{10}$ alkyl" refers to a monovalent, straight, or branched aliphatic group containing 1 to 10 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like).

The term "alkylene" refers to a divalent alkyl group. For example, the term "$C_1$-$C_6$ alkylene" or "$C_1$ to $C_6$ alkylene" refers to a divalent, straight, or branched aliphatic group containing 1 to 6 carbon atoms (e.g., methylene ($-CH_2-$), ethylene ($-CH_2CH_2-$), n-propylene ($-CH_2CH_2CH_2-$), iso-propylene ($-CH(CH_3)CH_2-$), n-butylene, sec-butylene, iso-butylene, tert-butylene, n-pentylene, isopentylene, neopentylene, n-hexylene and the like).

The term "alkoxy" refers to an alkyl linked to an oxygen, which may also be represented as —O—R or —OR, wherein the R represents the alkyl group. "CC alkoxy" or "$C_1$ to $C_6$ alkoxy" is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halogen" or "halo" may be fluorine, chlorine, bromine or iodine (preferred halogens as substituents are fluorine and chlorine).

"Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" represents a haloalkyl group as defined above with the indicated number of carbon atoms attached through an oxygen bridge. For example, "$C_1$-$C_6$ haloalkoxy" or "$C_1$ to $C_6$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "oxo" or —C(O)— refers to a carbonyl group. For example, a ketone, aldehyde, or part of an acid, ester, amide, lactone, or lactam group.

The term "cycloalkyl" refers to nonaromatic carbocyclic ring that is fully hydrogenated ring, including mono-, bi- or poly-cyclic ring systems. "$C_3$-$C_8$ cycloalkyl" or "$C_3$ to $C_8$ cycloalkyl" is intended to include $C_3$, $C_4$, $C_5$, $C_6$, $C_7$ and $C_8$ cycloalkyl groups. Example cycloalkyl groups include, but are not limited to, cyclopropyl, cyclobutyl, cyclopentyl, cyclohexyl, and norbornyl.

The term "aryl" refers to 6- to 10-membered aromatic carbocyclic moieties having a single (e.g., phenyl) or a fused ring system (e.g., naphthalene.). A typical aryl group is phenyl group.

The term "benzyl", as used herein, refers to a methyl group on which one of the hydrogen atoms is replaced by a phenyl group.

"Heterocycloalkyl" means cycloalkyl, as defined in this application, provided that one or more of the ring carbons indicated, are replaced by a moiety selected from —O—, —N=, —NR—, —C(O)—, —S—, —S(O)— and $-S(O)_2-$, wherein R is hydrogen, $C_1$-$C_4$alkyl or a nitrogen protecting group (for example, carbobenzyloxy, p-methoxybenzyl carbonyl, t-butoxycarbonyl, acetyl, benzoyl, benzyl, p-methoxy-benzyl, p-methoxy-phenyl, 3,4-dimethoxybenzyl, and the like). For example, a 3 to 8 membered heterocycloalkyl includes epoxy, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholino, piperazinyl, piperidinyl, piperidinylone, pyrazolidinyl, hexahydropyrimidinyl, 1,4-dioxa-8-aza-spiro[4.5]dec-8-yl, thiomorpholino, sulfanomorpholino, sulfonomorpholino, octahydropyrrolo [3,2-b]pyrrolyl, and the like.

The term "partially saturated heterocycle" refers to a nonaromatic ring that is partially hydrogenated and may exist as a single ring, bicyclic ring (including fused rings). Unless specified otherwise, said heterocyclic ring is generally a 5- to 10-membered ring containing 1 to 3 heteroatoms selected from —O—, —N═, —NR—, and —S—, (preferably 1 or 2 heteroatoms). Partially saturated heterocyclic rings include groups such as dihydrofuranyl, dihydrooxazolyl, dihydropyridinyl, imidazolinyl, 1H-dihydroimidazolyl, 2H-pyranyl, 4H-pyranyl, 2H-chromenyl, oxazinyl and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b] pyrazinyl, and the like).

The term "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 12-membered ring containing 1 to 3 heteroatoms (preferably 1 or 2 heteroatoms) independently selected from sulfur, oxygen and/or nitrogen. When the term "partially or fully saturated heterocycle" is used, it is intended to include "heterocycloalkyl", and "partially saturated heterocycle". Examples of spiral rings include 2,6-diazaspiro[3.3]heptanyl, 3-azaspiro[5.5] undecanyl, 3,9-diazaspiro[5.5]undecanyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to four heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a heteroaryl fused to an aryl (e.g., phenyl).

When the term "heterocycle" is used, it is intended to include "heterocycloalkyl", "partially or fully saturated heterocycle", "partially saturated heterocycle", "fully saturated heterocycle" and "heteroaryl".

The term "counter ion" is used to represent a negatively charged species such as chloride, bromide, hydroxide, acetate, and sulfate or a positively charged species such as sodium (Na+), potassium (K+), ammonium ($R_nNH_{m+}$, where n=0-4, m=0-4 and m+n=4) and the like.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., ═O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C═C, C═N, or N═N).

In cases wherein there are nitrogen atoms (e.g., amines) on compounds of the present disclosure, these may be converted to N-oxides by treatment with an oxidizing agent (e.g., mCPBA and/or hydrogen peroxides) to afford other compounds of this disclosure. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may be unsubstituted or substituted with up to three R groups, and at each occurrence R is selected independently from the definition of R. For example, with reference to the first aspect, this applies to 0-3 $R^{3A}$ in the $R^3$ definition, such that when $R^3$ is phenyl or 5- to 6-membered heteroaryl, these groups are either unsubstituted (not substituted with $R^{3A}$) or substituted with one, two or three $R^{3A}$ groups which are independently selected at each occurrence from the given definitions for $R^{3A}$. This similarly applies to the definitions for 0-2 $R^c$ in the $R^{3B}$ and $R^{3c}$ definitions, and to 0-1 $R^d$ in the $R^{3F}$ definition.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, for example, a ketone (—CH—C═O) group in a molecule may tautomerize to its enol form (—C═C—OH). Thus, this disclosure is intended to cover all possible tautomers even when a structure depicts only one of them.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compounds of the present invention" or "compounds of the present disclosure" refers to compounds of Formula (I), (IA) or (IA-1), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

It will be recognized by those skilled in the art that the compounds of the present disclosure may contain chiral centers and as such may exist in different isomeric forms. As used herein, the term “isomers” refers to different compounds that have the same molecular formula but differ in arrangement and configuration of the atoms.

“Enantiomers” are a pair of stereoisomers that are non-superimposable mirror images of each other. A 1:1 mixture of a pair of enantiomers is a “racemic” mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g, (1 RS,2RS) as a racemic mixture of (1R,2R) and (1S,2S); (1RS,2SR) as a racemic mixture of (1R,2S) and (1S,2R)). “Diastereoisomers” are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Geometric isomers may occur when a compound contains a double bond or some other feature that gives the molecule a certain amount of structural rigidity. If the compound contains a double bond, the substituent may be E or Z configuration. If the compound contains a disubstituted cycloalkyl, the cycloalkyl substituent may have a cis- or trans-configuration.

Conformational isomers (or conformers) are isomers that can differ by rotations about one or more a bonds. Rotamers are conformers that differ by rotation about only a single a bond.

The term “atropisomer” refers to a structural isomer based on axial or planar chirality resulting from restricted rotation in the molecule.

Unless specified otherwise, the compounds of the present disclosure are meant to include all such possible isomers, including racemic mixtures, optically pure forms and intermediate mixtures. Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation).

The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization.

Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers.

Pharmaceutically acceptable salts are preferred. However, other salts may be useful, e.g., in isolation or purification steps which may be employed during preparation, and thus, are contemplated within the scope of the disclosure.

As used herein, “pharmaceutically acceptable salts” refer to derivatives of the disclosed compounds wherein the parent compound is modified by making acid or base salts thereof. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like, preferably hydrochloric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy,* 22nd Edition, Pharmaceutical Press, London, UK (2012), the disclosure of which is hereby incorporated by reference.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}C$, $^{125}I$ respectively. The present disclosure includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this present disclosure can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present disclosure can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present disclosure do not contain a N-halo, $S(O)_2H$, or S(O)H group.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present disclosure can be provided as amorphous solids or crystalline solids. Lyophilization can be employed to provide the compounds of the present disclosure as a solid.

"EED" refers to the protein product of the gene embryonic ectoderm development.

"PRC2" refers to Polycomb Repressive Complex 2.

The term "PRC2-mediated disease or disorder" refers to any disease or disorder which is directly or indirectly regulated by PRC2. This includes, but is not limited to, any disease or disorder which is directly or indirectly regulated by EED.

The term "diseases or disorders mediated by EED and/or PRC2" refers to diseases or disorders which are directly or indirectly regulated by EED and/or PRC2.

As used herein, the term "patient" encompasses all mammalian species.

As used herein, the term "subject" refers to an animal. Typically the animal is a mammal. A "subject" also refers to any human or non-human organism that could potentially benefit from treatment with an EED inhibitor. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer disease.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat', "treating" or "treatment" of any disease/disorder refers to the treatment of the disease/disorder in a mammal, particularly in a human, and includes: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder, either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present disclosure that will elicit the biological or medical response of a subject, for example, reduction or inhibition of EED and/or PRC2, or ameliorate symptoms, alleviate conditions, slow or delay disease progression, or prevent a disease or disorder mediated by PRC2. When applied to a combination, the term refers to combined amounts of the active ingredients that result in the preventive or therapeutic effect, whether administered in combination, serially, or simultaneously.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "pwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "1H" for proton, "δ" for delta, "s" for singlet, "d" for doublet, "t" for triplet, "q" for quartet, "m" for multiplet, "br" for broad, "Hz" for hertz, "ee" for "enantiomeric excess" and "a", "p", "R", "S", "E", and "Z" are stereochemical designations familiar to one skilled in the art.

The following abbreviations used herein below have the corresponding meanings:

Bn benzyl
Boc tert-butoxy carbonyl
$Boc_2O$ di-tert-butyl dicarbonate
Bu butyl
$Cs_2CO_3$ cesium carbonate anhydrous
$CHCl_3$ chloroform
DAST diethylaminosulfurtrifluoride
DBU 2,3,4,6,7,8,9,10-octahydropyrimido[1,2-a]azepine
DCM dichloromethane
DMAP 4-dimethylaminopyridine
DMF dimethylformamide
DMSO dimethylsulfoxide
DPPA diphenylphosphoryl azide
EA ethyl acetate
Et ethyl
EtOH ethanol
EtOAc ethyl acetate
HATU 2-(7-Aza-1H-benzotriazole-1-yl)-1,1,3,3-tetramethyluronium hexafluorophosphate
HCl hydrochloric acid
i-Bu isobutyl
i-Pr isopropyl
KOAc potassium acetate
$LiAlH_4$ lithium aluminium hydride
LiCl lithium chloride
LiHMDS lithium bis(trimethylsilyl)amide
mCPBA 3-Chloroperoxybenzoic acid
Me methyl
Me4-t-BuXPhos di-tert-butyl(2',4',6'-triisopropyl-3,4,5,6-tetramethyl-[1,1'-biphenyl]-2-yl)phosphane
MeCN acetonitrile
$MnO_2$ manganese dioxide
$N_2$ nitrogen
$NaBH_4$ sodium borohydride
$NaHCO_3$ sodium bicarbonate
$Na_2SO_4$ sodium sulphate
Ph phenyl
$PPh_3$ triphenylphosphine
$Pd(dppf)Cl_2$ [1,1'-bis(diphenylphosphino)ferrocene]dichloropalladium(II)
$Pd(PPh_3)_4$ palladium(O)tetrakis(triphenylphosphine)
$Ph_3P{=}O$ triphenylphosphine oxide
t-Bu or $Bu^t$ tert-butyl
TEA triethylamine
TFA trifluoroacetic acid
THE tetrahydrofuran
$Zn(CN)_2$ zinc cyanide

IV. Synthesis

The compounds of the present disclosure can be prepared in a number of ways known to one skilled in the art of organic synthesis in view of the methods, reaction schemes and examples provided herein. The compounds of the present disclosure can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations,* $2^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present disclosure, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis,* 4th Ed., Wiley (2007). Protecting groups incorporated in making of the compounds of the present disclosure, such as the trityl protecting group, may be shown as one regioisomer but may also exist as a mixture of regioisomers.

Scheme 1 (below) describes potential routes for producing the compounds of the present disclosure which include compounds of Formula (IA). Compounds of Formula (IA) can be made substantially optically pure by either using substantially optically pure starting material or by separation chromatography, recrystallization or other separation techniques well-known in the art. For a more detailed description, see the Example section below.

Scheme 1

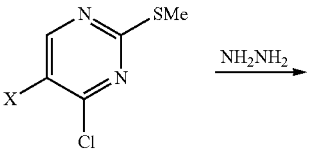

1

-continued

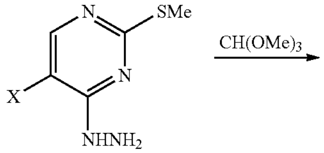

2

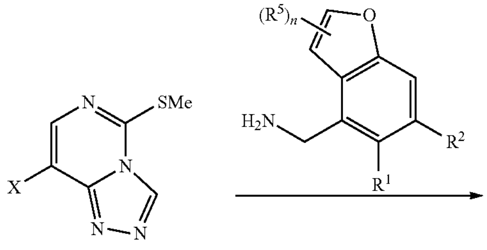

3

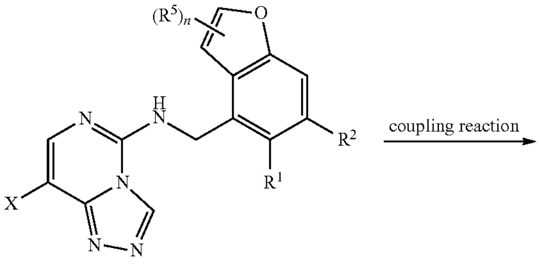

4

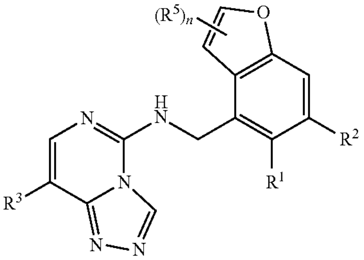

5

X: Br or F

Under Scheme 1, the 5-chloro- or 5-bromo-substituted 4-chloro-2-(methylthio)pyrimidine 1 was treated with hydrazine to form the 5-chloro- or 5-bromo-substituted 4-hydrazinyl-2-(methylthio)pyrimidine 2, which was transformed to the cyclized product 3 upon treatment with trimethyl orthoformate or triethyl orthoformate. Subsequently, 3 was treated with appropriate amine to generate 4, which was followed by cross-coupling reaction with appropriate $R^3$ reagent (e.g., various boronic acid or equivalent with appropriate $R^3$ group) to afford product 5.

Alternatively, in some cases, compounds of the present invention were prepared according to the reaction sequence in Scheme 2. Compound 4 was first protected as 4' and then followed by coupling reaction to add $R^3$ group to afford compound 5'. Final compound 5 was obtained after proper deprotection of compound 5'. For a general description of protecting groups and their use, see Greene, T. W. et al., *Protecting Groups in Organic Synthesis,* 4th Ed., Wiley (2007).

Scheme 2

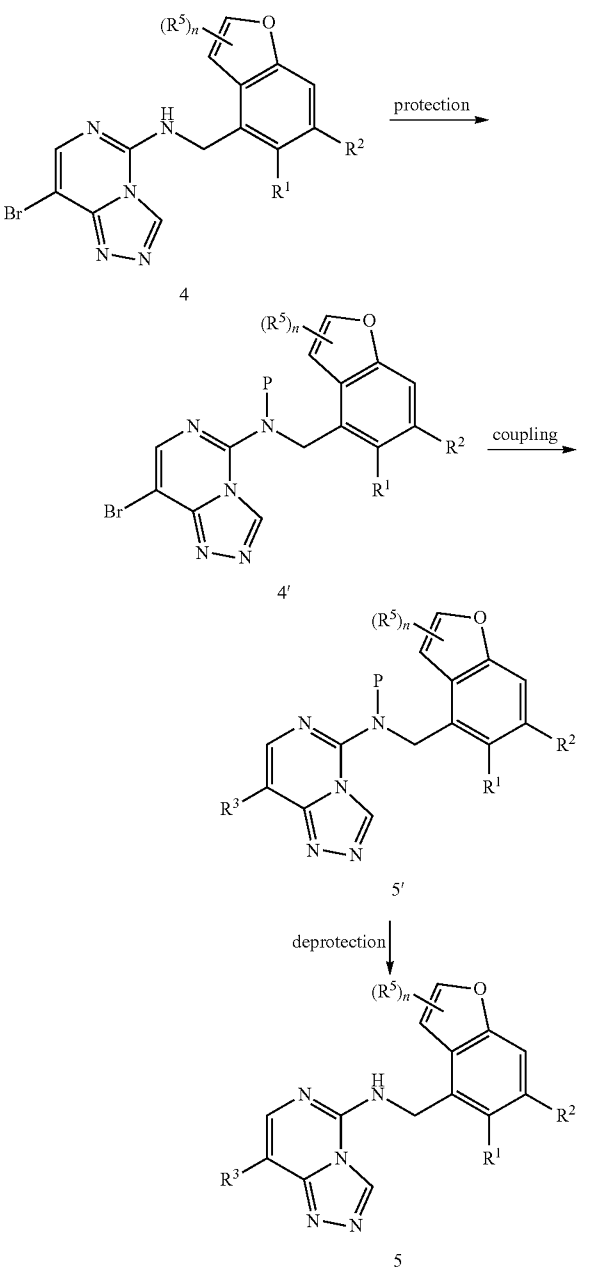

P = protecting group

General Methods

The following methods were used in the exemplified Examples, except where noted otherwise.

Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. For highly polar amines, gradients of DCM and 1 M $NH_3$ in MeOH were used. Reverse phase preparative HPLC was carried out using C18 columns with UV 214 nm and 254 nm or prep LC-MS detection eluting with gradients of Solvent A (water with 0.1% TFA) and Solvent B (acetonitrile with 0.1% TFA) or with gradients of Solvent A (water with 0.05% TFA) and Solvent B (acetonitrile with 0.05% TFA) or with gradients of Solvent A (water with 0.05% ammonia) and Solvent B (acetonitrile with 0.05% ammonia).

LC/MS Methods Employed in Characterization of Examples

Reverse phase analytical HPLC/MS was performed on Agilent LC1200 systems coupled with 6110 (Methods A-D), or 6120 (Method E and F), or 6130 (Method G) Mass Spectrometer.

Method A: Linear gradient of 5% to 95% B over 1.2 min, with 1 min hold at 95% B;
UV visualization at 214 nm and 254 nm
Column: SunFire® C184.6x50 mm 3.5 μm
Flow rate: 2 mL/min
Solvent A: 0.1% trifluoroacetic acid, 99.9% water
Solvent B: 0.1% trifluoroacetic acid, 99.9% acetonitrile.

Method B: Linear gradient of 5% to 95% B over 1.5 min, with 1 min hold at 95% B;
UV visualization at 214 nm and 254 nm
Column: XBridge® C184.6x50 mm 3.5 μm
Flow rate: 2 mL/min
Solvent A: water with 10 mM Ammonium hydrogen carbonate
Solvent B: acetonitrile.

Method C: Linear gradient of 5% to 95% B over 1.2 min, with 1.3 min hold at 95% B,
95% to 5% B over 0.01 min;
UV visualization at 214 nm and 254 nm
Column: SunFire® C184.6x50 mm 3.5 μm
Flow rate: 2 mL/min
Solvent A: 0.1% trifluoroacetic acid, 99.9% water
Solvent B: 0.1% trifluoroacetic acid, 99.9% acetonitrile.

Method D: Linear gradient of 5% to 95% B over 1.4 min, with 1.6 min hold at 95% B,
95% to 5% B over 0.01 min;
UV visualization at 214 nm and 254 nm
Column: XBridge® C184.6x50 mm 3.5 μm
Flow rate: 1.8 mL/min
Solvent A: water with 10 mM Ammonium hydrogen carbonate
Solvent B: acetonitrile.

Method E: Linear gradient of 5% to 95% B over 1.5 min, with 1 min hold at 95% B;
UV visualization at 214 nm and 254 nm
Column: XBridge® C184.6x50 mm 3.5 μm
Flow rate: 2 mL/min
Solvent A: water with 10 mM Ammonium hydrogen carbonate
Solvent B: acetonitrile.

Method F: Linear gradient of 5% to 95% B over 1.5 min, with 1 min hold at 95% B;
UV visualization at 214 nm and 254 nm and 300 nm
Column: XBridge® C184.6x30 mm 2.5 μm
Flow rate: 1.8 mL/min
Solvent A: water with 0.1% ammonia
Solvent B: acetonitrile.

Method G: Linear gradient of 10% to 95% B over 2 min, with 1 min hold at 95% B;
UV visualization at 214 nm, 254 nm and 300 nm
Column: Sunfire® C184.6x30 mm 2.5 μm
Flow rate: 1.8 mL/min
Solvent A: water
Solvent B: MeOH with 0.1% formic acid.

NMR Employed in Characterization of Examples $^1H$ NMR spectra were obtained with Bruker Fourier transform spectrometers operating at frequencies as follows: $^1H$ NMR: 400 MHz (Bruker). $^{13}C$ NMR: 100 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1H$ NMR spectra appear at 2.49 ppm for $CD_2HSOCD_3$, 3.30 ppm for $CD_2HOD$, 1.94 for $CD_3CN$, and 7.24 ppm for $CDCl_3$, and which in $^{13}C$ NMR spectra appear at 39.7 ppm for $CD_3SOCD_3$, 49.0 ppm for $CD_3OD$, and 77.0 ppm for $CDCl_3$. All $^{13}C$ NMR spectra were proton decoupled.

V. Examples

The following Examples have been prepared, isolated and characterized using the methods disclosed herein. The following examples demonstrate a partial scope of the disclosure and are not meant to be limiting of the scope of the disclosure.

Unless specified otherwise, starting materials are generally available from a non-excluding commercial sources such as TCI Fine Chemicals (Japan), Shanghai Chemhere Co., Ltd.(Shanghai, China), Aurora Fine Chemicals LLC (San Diego, Calif.), FCH Group (Ukraine), Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), Chembridge Corporation (USA), Matrix Scientific (USA), Conier Chem & Pharm Co., Ltd (China), Enamine Ltd (Ukraine), Combi-Blocks, Inc. (San Diego, USA), Oakwood Products, Inc. (USA), Apollo Scientific Ltd. (UK), Allichem LLC. (USA) and Ukrorgsyntez Ltd (Latvia). PharmaBlock R&D Co. Ltd (Nanjing, China), Accela ChemBio Co. Ltd (Shanghai, China), Alputon Inc. (Shanghai, China), J&K Scientific Ltd. (Beijing, China).

INTERMEDIATES

Intermediate 3: 8-bromo-5-(methylthio)-[1,2,4]triazolo[4,3-c]pyrimidine

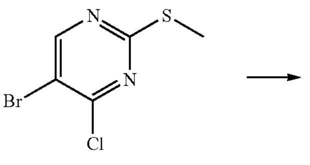

1

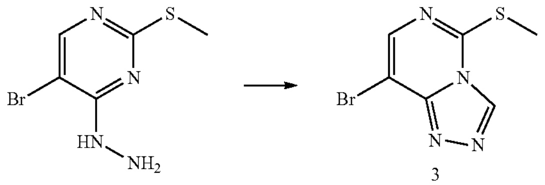

2

3

5-Bromo-4-hydrazinyl-2-(methylthio)pyrimidine (2): To a solution of 5-bromo-4-chloro-2-(methylthio)pyrimidine (1, 49.0 g, 0.205 mol) in ethanol (1000 mL) was added hydrazine (21.5 g, 0.430 mol). The reaction was stirred at rt for 4 h. The resulting suspension was filtered, washed with hexane and dried in vacuum to give the title compound (44.1 g, 92%) as a white solid. $^1H$-NMR (400 MHz, DMSO-$d_6$) δ ppm 2.42 (s, 3H), 8.08 (s, 1H). LC-MS: [M+H]+=234.9; 236.9.

Intermediate 3: 5-bromo-4-hydrazinyl-2-(methylthio)pyrimidine (2) (40.0 g, 0.17 mol) was dissolved in 200 mL triethoxymethane. The mixture was heated at reflux and stirred for 3 h. The reaction mixture was concentrated under reduced pressure, the residue was purified by flash chromatography (EA:PE=1:15~1:1) to give the title compound (38.3 g, 92%) as a white solid. $^1H$-NMR (400 MHz, methanol-$d_4$) δ ppm 2.82 (s, 3H), 8.03 (s, 1H), 8.87 (s, 1H). LC-MS: [M+H]+=245.0; 247.0.

Intermediate A1: 8-bromo-N-((5-fluoro-2,3-dihydrobenzofuran-4-yl)methyl)-[1,2,4]triazolo[4,3-c]pyrimidin-5-amine

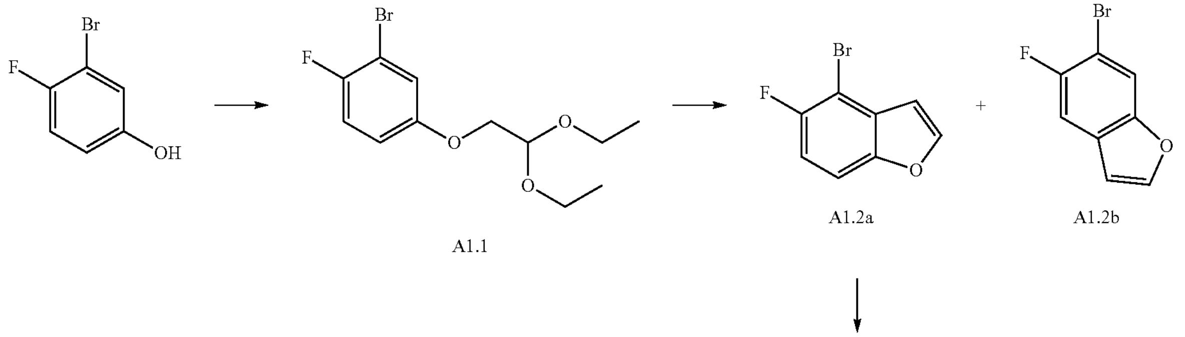

A1.1

A1.2a

A1.2b

-continued

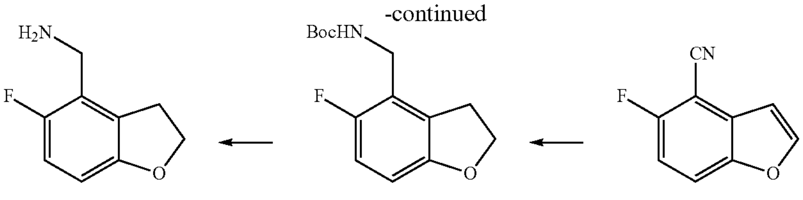

A1.5 A1.4 A1.3

2-Bromo-4-(2,2-diethoxyethoxy)-1-fluorobenzene (A1.1): To a solution of 3-bromo-4-fluorophenol (500 g, 2.62 mol) and 2-bromo-1,1-diethoxyethane (670 g, 3.4 mol) in 2.0 L DMF was added $K_2CO_3$ (1085 g, 7.86 mol) in one portion. The suspension was heated at 110° C. and stirred overnight under $N_2$. After cooling to rt, the reaction was diluted with 10.0 L $H_2O$, and extracted with EtOAc (2.0 L×3). The combined organic phase was washed with brine twice, dried over anhydrous $Na_2SO_4$, filtered and concentrated under reduced pressure. The residue was purified on silica gel (EtOAc/hexane=0:100 to 5:100) to give the title compound (810 g, 80%) as a yellow oil. $^1$H-NMR (400 MHz, methanol-d4) δ ppm 1.27 (t, 6H), 3.65 (q, 2H), 3.78 (q, 2H), 3.97 (d, 2H), 4.82 (t, 1H), 3.97 (d, 2H), 6.84 (dd, 1H), 7.04 (dd, 1H), 7.13 (d, 1H).

4-Bromo-5-fluorobenzofuran (A1.2a along with regioisomer A1.2b): To a solution of PPA (1324 g, 3.93 mol) in toluene (2.0 L) was add A1.1 (810 g, 2.62 mol) over 30 min at 95° C. The reaction mixture was stirred at 95° C. for 2 h. After cooling to rt, 4.0 L ice-water was added slowly. The mixture was extracted with PE (2.0 L×2), the combined organic phase was washed with brine (2.0 L×2), dried over anhydrous $Na_2SO_4$, filtered and concentrated under reduced pressure. The residue was purified on silica gel (EtOAc/PE=0:100 to 5:100) to give a mixture of A1.2a and A1.2b (A1-2a: A1-2b=1:0.7, 310 g, 55% yield) as a yellow oil.

5-Fluorobenzofuran-4-carbonitrile (A1.3): To a mixture of A1.2a and A1.2b (310 g, 1.44 mol) and $Zn(CN)_2$ (253 g, 2.16 mol) in 1.0 L DMF was added $Pd(PPh_3)_4$ (162 g, 0.14 mol) under $N_2$. The reaction mixture was heated at 100° C. and stirred for 18 h. After cooling to rt, the mixture was diluted with 5.0 L of water, and extracted with EtOAc (1.0 L×2). The combined organic phase was washed with brine (1 L), dried over $Na_2SO_4$ (anhydrous), filtered and concentration under reduced pressure. The residue was purified by flush column (mobile phase: EtOAc/PE=1:70 in 30 min, Ret. Time=11 min, flow rate:120 mL/min) to give the title compound (92 g, 40%) as a white solid. $^1$H-NMR (400 MHz, methanol-$d_4$) δ ppm 7.07 (d, 1H), 7.30 (dd, 1H), 7.89 (dd, 1H), 8.10 (dd, 1H).

tert-Butyl ((5-fluoro-2,3-dihydrobenzofuran-4-yl)methyl) carbamate (A1.4): To a solution of A1.3 (44.5 g, 276.4 mmol) and $Boc_2O$ (90.0 g, 414.6 mmol) in 1.0 L MeOH was added Pd/C (5 g, 10% wt). The reaction mixture was degassed with $H_2$ and stirred under $H_2$ overnight. The mixture was filtered through celite, washed with MeOH (300 mL×2), the filtrate was concentrated under reduced pressure. The residue was recrystallized from PE to give the title compound (61.0 g, 93%) as a white solid. $^1$H-NMR (400 MHz, DMSO-$d_6$) δ ppm 1.38 (s, 9H), 3.21 (t, 2H), 4.12 (d, 2H), 4.53 (t, 2H), 6.63 (dd, 1H), 6.86 (dd, 1H), 7.25 (br s, 1H). LC-MS: $[M-^tBu+H]^+$=212.1.

(5-Fluoro-2,3-dihydrobenzofuran-4-yl)methanamine (A1.5): A solution of A1.4 (18.3 g, 68.5 mmol) in 50 mL HCl/Dioxane (4 mol/L) was stirred at rt for 4 h. The mixture was concentrated under reduced pressure. The residue was diluted with a mixture solvent (MeOH:MeCN=1:10, 500 mL), then $K_2CO_3$ (18.0 g, 342.5 mmol) was added. The mixture was heated at 60° C. and stirred for 3 h, cooled to rt, filtered, and concentrated under reduced pressure. The crude product was purified on silica gel (MeOH:EtOAc=0: 100 to 1:4) to give the title compound (9.2 g, 80%) as a yellow oil. $^1$H-NMR (400 MHz, methanol-$d_4$) δ ppm 3.27 (t, 2H), 3.77 (s, 2H), 4.56 (t, 2H), 6.59 (dd, 1H), 6.81 (dd, 1H). LC-MS: $[M+H]^+$=168.1.

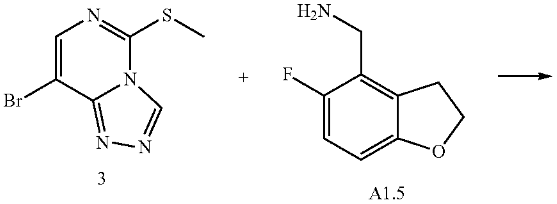

3 A1.5

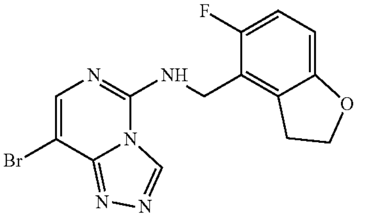

A1

Intermediate A1: A mixture of A1.5 (1.41 g, 8.2 mmol) and 8-bromo-5-(methylthio)-[1,2,4]triazolo[4,3-c]pyrimidine (3) (1.0 g, 4.1 mmol) was heated at 40° C. and stirred for 16 h. After cooling to the rt, the mixture was diluted with EtOAc (35 mL). The precipitate was filtered and washed with EtOAc (3 mL×3), dried in vacuum to give the title compound (1.0 g, 67%) as a white solid. $^1$H NMR (500 MHz, DMSO) δ ppm 3.27 (t, 2H), 4.53 (t, 2H), 4.66 (d, 2H), 6.71 (dd, 1H), 6.95 (t, 1H), 7.85 (s, 1H), 8.75 (t, 1H), 9.48 (s, 1H). LC-MS: $[M+H]^+$=363.7; 365.7.

Intermediate A2: 8-bromo-N-((2,3-dihydrobenzofuran-4-yl)methyl)-[1,2,4]triazolo[4,3-c]pyrimidin-5-amine (2,3-dihydrobenzofuran-4-yl)methanamine A2.3

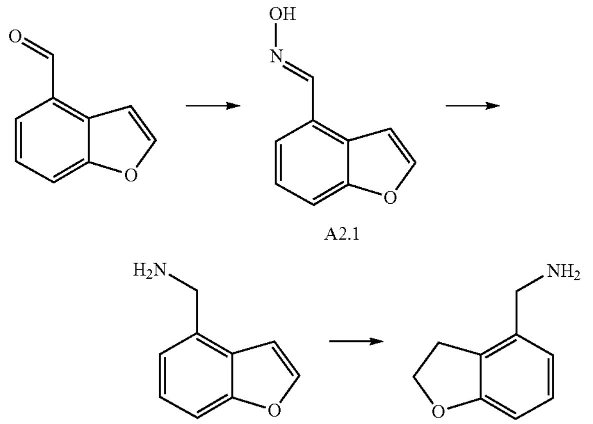

A2.1

A2.2 A2.3

(E)-Benzofuran-4-carbaldehyde oxime (A2.1): A mixture of benzofuran-4-carbaldehyde (5 g, 34.2 mmol), $NH_2OH.HCl$ (4.72 g, 68.4 mmol) and NaOH (5.47 g, 136.8 mmol) in $CH_3OH$ (75 mL), and water (75 mL) was heated to 25° C. and stirred for 3 h. The mixture was concentrated, the residue was diluted with EA (150 ml), the organic layer was washed successively with 1N HCl (100 mL×2), sat. $NaHCO_3$ (100 mL×2) and brine (100 mL), dried over $Na_2SO_4$, filtered and concentrated to give the title compound (5 g, 90%) as a white solid. LC-MS: $[M+H]^+$=162.0.

Benzofuran-4-ylmethanamine (A2.2): A mixture of A2.1 (5 g, 31 mmol), $NH_4.OH$ (43 mL) and Raney Ni (2.66 g, 31 mmol) in $CH_3OH$ (585 mL) was stirred at 20° C. for 16 h under $H_2$ atmosphere. The mixture was filtered, and the filtrate was concentrated to give the title compound (4.2 g, 92%) as oil. LC-MS: $[M+H]^+$=148.1.

(2,3-Dihydrobenzofuran-4-yl)methanamine (A2.3): A mixture of A2.2 (2.2 g, 15 mmol), Pd/C (2 g, wt %:10%) and $CH_3OH$ (40 mL) was heated to 48° C. and stirred for 16 h under $N_2$ atmosphere. The mixture was cooled to rt, filtered, and the filtrate was concentrated to give the title compound (2 g, 90%). $^1$H NMR (400 MHz, $CDCl_3$) δ ppm 3.20 (t, 2H), 3.84 (s, 2H), 4.60 (t, 2H), 6.72 (d, 1H), 6.85 (d, 1H), 7.13 (t, 1H).

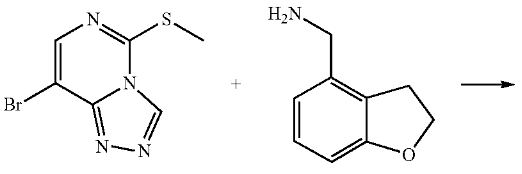

3 A2.3

-continued

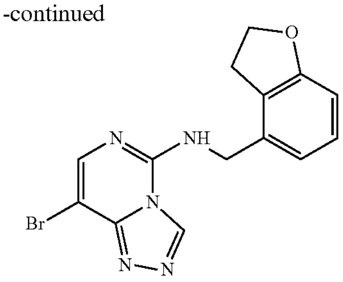

A2

Intermediate A2: The title compound was prepared by a method similar to that of A1 by replacing (5-fluoro-2,3-dihydrobenzofuran-4-yl)methanamine (A1.5) with A2.3. $^1$H NMR (400 MHz, DMSO) δ ppm 3.19 (t, 2H), 4.50 (t, 2H), 4.64 (s, 2H), 6.68 (d, 1H), 6.84 (d, 1H), 7.05 (t, 1H), 7.81 (s, 1H), 9.48 (s, 1H). LC-MS: $[M+H]^+$=346.0.

Intermediate A3: 8-Bromo-N-((2-methyl-2,3-dihydrobenzofuran-4-yl)methyl)-[1,2,4]triazolo[4,3-c]pyrimidin-5-amine

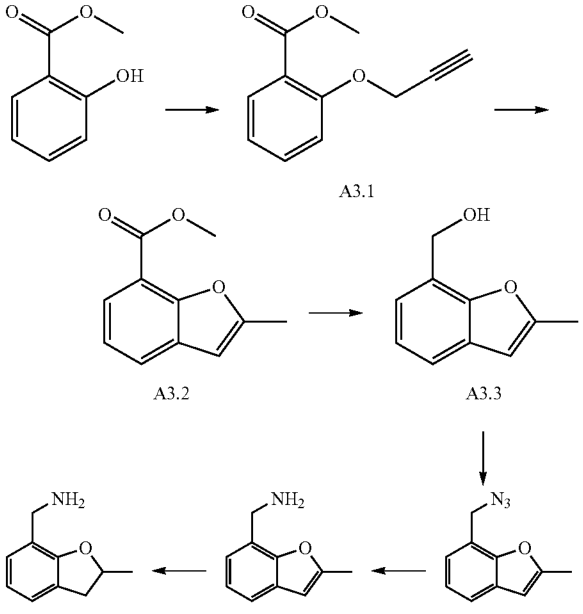

A3.1

A3.2 A3.3

A3.6 A3.5 A3.4

Methyl 2-(prop-2-yn-1-yloxy)benzoate (A3.1): To a solution of methyl 2-hydroxybenzoate (3.0 g, 19.72 mmol) in DMF (20 mL) was added 3-bromoprop-1-yne (6 mL, 19.72 mmol) and $K_2CO_3$ (8.18 g, 59.2 mmol). The mixture was sitted at 20° C. overnight, diluted with DCM and washed with water (80 mL×3). The organic layer was dried with $Na_2SO_4$ and concentrated. The residue was purified with flash chromatography, triturated by EA/Hexane=10% to give the title compound (3.0 g, 90%). $^1$H NMR (400 MHz, $CDCl_3$) δ ppm 2.53 (s, 1H), 3.90 (s, 3H), 4.10 (s, 2H), 7.06 (t, 1H), 7.15 (d, 1H), 7.48 (t, 1H), 7.82 (d, 1H). LC-MS: $[M+H]^+$=190.9.

Methyl 2-methylbenzofuran-7-carboxylate (A3.2): A mixture of A3.1 (1.0 g, 5.26 mmol) and cesium fluoride (1.038 g, 6.84 mmol) in N,N-diethylaniline (5 mL, 5.26 mmol) was irritated by microwave at 200° C. for 30 min. After diluted with either insoluble materials were removed by decantation. The crude products were separated on column chromatography by using a mixed solvent of hexane and ethyl acetate(10:1, v/v) to give the title compound (500 mg, 50%). $^1H$ NMR (400 MHz, $CDCl_3$) δ ppm 2.55 (s, 3H), 4.01 (s, 3H), 6.44 (s, 1H), 7.22-7.27 (m, 1H), 7.66 (d, 1H), 7.86 (d, 1H). LC-MS: $[M+H]^+$=191.0.

(2-Methylbenzofuran-7-yl)methanol (A3.3): A solution of A3.2 (1.0 g, 5.26 mmol) in THE (3 mL) was added $LiAlH_4$ (10.52 mL, 10.52 mmol). The mixture was stirred for 1 h at 0° C. and warmed to rt for 2 h, quenched with 1 M HCl solution and filtered, concentrated to give the title compound as the crude product, which will be used in next step without further purification.

4-(Azidomethyl)-2-methylbenzofuran (A3.4): To a stirred solution of A3.3 (350 mg, 2.158 mmol) in toluene (10 mL) was added DPPA (683 mg, 2.482 mmol). The reaction mixture was cooled to 0° C., and DBU (0.390 mL, 2.59 mmol) was added dropwise. The reaction mixture was allowed to warm to rt, and stirred under $N_2$ overnight. The mixture was adjusted to pH=5~6 by 1N HCl, then extracted with EtOAc. The water phase was neutralized by sat. $NaHCO_3$, then extracted with EtOAc. The combined organic phase was washed successively with $NaHCO_3$ and brine, dried, and concentrated, the residue was purified by column chromatography (5% EtOAc in hexane as eluent) to afford the title compound (200 mg, 50%) as a colorless liquid. $^1H$ NMR (400 MHz, $CDCl_3$) δ ppm 2.49 (s, 3H), 4.64 (s, 2H), 7.15-7.17 (m, 2H), 7.45-7.48 (m, 1H).

(2-methylbenzofuran-4-yl)methanamine (A3.5): To a solution of A3.4 (50 mg, 0.267 mmol) in THE (5 mL) and Water (0.2 mL) was added $PPh_3$ (140 mg, 0.534 mmol). The mixture was stirred at 25° C. for 2 h, concentrated under reduced pressure, the residue was purified with flash chromatography to give the title compound (30 mg, 70%) as a colorless oil. (The $Ph_3P{=}O$ and $PPh_3$ came out in 50% PE/EA and the amine came out in 20% DCM/MeOH). LC-MS: $[M+H]^+$=162.1.

(2-Methyl-2,3-dihydrobenzofuran-4-yl)methanamine (A3.6): To a solution of A3.5 (100 mg, 0.372 mmol) in Methanol (10 mL) was added Hydrochloric acid (0.1 mL, 3.29 mmol) and Pd/C (10%) (39.6 mg). The reaction was stirred at 50° C. for 12 h under hydrogen atmosphere, filtered and the concentrated. The residue was purified with flash chromatography (DCM:MeOH=10:1) to afford the title compound (60 mg, 50%). $^1H$ NMR (400 MHz, MeOD) δ ppm 1.41-1.47 (m, 3H), 2.76-2.91 (m, 1H), 4.05 (s, 2H), 4.93-5.00 (m, 2H), 6.74-6.79 (m, 1H), 6.88 (d, 2H), 7.16-7.18 (m, 1H). LC-MS: $[M+H]^+$=164.1.

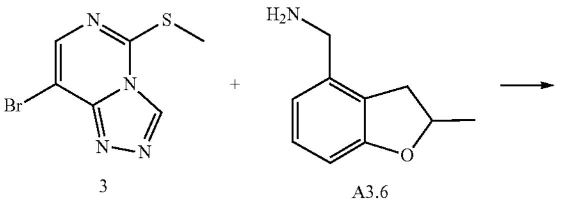

3 + A3.6

-continued

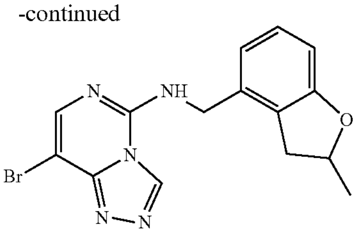

A3

Intermediate A3: The title compound was prepared by a method similar to that of Intermediate A1 by replacing (5-fluoro-2,3-dihydrobenzofuran-4-yl)methanamine (A1.5) with A3.6. $^1H$ NMR (Methanol-d4) δ:1.40-1.47 (m, 3H), 2.75-2.90 (m, 1H), 3.35-3.44 (m, 1H), 4.71 (d, 2H), 4.93-4.98 (m, 1H), 6.63-6.79 (m, 1H), 6.87-6.90 (m, 1H), 7.04-7.16 (m, 1H), 7.86 (d, 1H), 9.30 (d, 1H). LC-MS: $[M+H]^+$=359.7.

Intermediate B (Boronic Acid or Ester that are not Commercially Unavailable for Synthesis of Compounds in Table 2)

2,4-Dimethyl-5-(4,4,5,5-tetramethyl-1,3,2-dioxaborolan-2-yl)pyrimidine (B1)

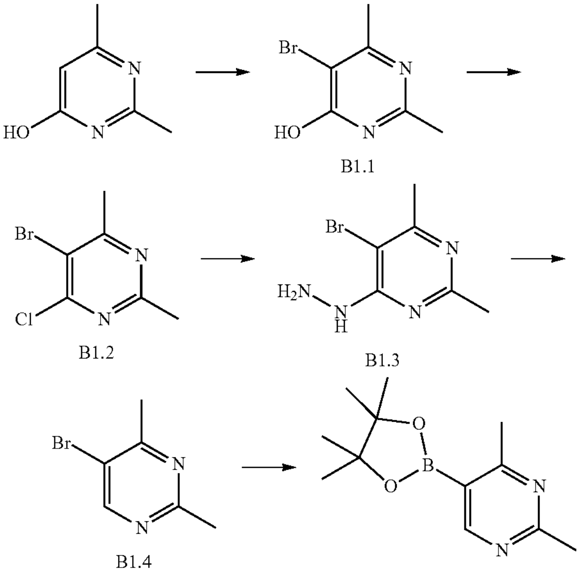

B1.1 B1.2 B1.3 B1.4 B1

5-Bromo-2,6-dimethylpyrimidin-4-ol (B1.1): Bromine (153.4 g, 0.96 mol, 1.2 eq) was added dropwise to a solution of 2,6-dimethylpyrimidin-4-ol (100 g, 0.8 mol, 1.0 eq) in 1.0 L of chloroform. Then the mixture was stirred at 50° C. overnight. After cooling to rt, excess solvent was evaporated and 500 mL of ethyl acetate was added, which was removed under reduced pressure again. This process was repeated three times. The yellow solid was stirred in 100 mL of ethyl acetate for 30 min at rt. After filtration, the residue was washed with ethyl acetate (100 mL×2) to give the title compound (135 g, 82%) as a white solid. LC-MS: $[M+H]^+$=205.2.

5-Bromo-4-chloro-2,6-dimethylpyrimidine (B1.2): A mixture of B1.1 (134 g, 0.66 mol) in 500 mL of $POCl_3$ was stirred at 110° C. for 18 h. Excess $POCl_3$ was removed under vacuum, the residue was poured into 1000 g crushed ice. Then solid $NaHCO_3$ was added carefully to adjust pH to 8-9. The aqueous was extracted with ethyl acetate (1.5 L×3), and the combined organic layers were washed with brine (1.0 L×2), dried over $Na_2SO_4$, concentrated to give the title compound (71 g, 48%) as a white solid. LC-MS: $[M+H]^+$=223.0.

5-Bromo-4-hydrazinyl-2,6-dimethylpyrimidine (1.3): To a mixture of Hydrazine hydrate (NH2NH2.H2O, 32 g, 0.64 mol, 98%) in 350 mL ethanol was added a solution of B1.2 (70 g, 0.32 mol) in 350 mL methanol dropwise at 0° C. The reaction mixture was stirred at rt for 16 h. The solvent was removed by reduced pressure, the residue was diluted with 500 mL of water, extracted with $CHCl_3$ (500 mL×3). The combined organic layers were washed with 500 mL brine, dried over $Na_2SO_4$, and concentrated to give the title compound (63 g, 91%) as a yellow solid. LC-MS: $[M+H]^+$=219.0.

5-Bromo-2,4-dimethylpyrimidine (B1.4): To a suspension of $MnO_2$ (96 g, 1.1 mol) in 1.0 L $CHCl_3$ was added a solution of B1.3 (47 g, 0.22 mol) in 1.0 L $CHCl_3$ dropwise at 0° C. The mixture was stirred for 2 h at rt. After filtration and concentration, the residue was purified on 100-200 mesh silica gel column (PE:EA=100:0 to 50:50) to give the title compound (30 g, 73%) as a yellow solid. LC-MS: $[M+H]^+$=189.1.

Intermediate B1: A mixture of B1.4 (12 g, 64 mmol), bis(pinacolato)diboron (22.8 g, 89.6 mmol, 1.4 eq), KOAc (18.8 g, 192 mmol, 3.0 eq), and Pd(dppf)$Cl_2$ (2.34 g, 3.2 mmol) in 200 mL of anhydrous dioxane was heated at 90° C. and stirred for 4 h under $N_2$. The solvent was removed under reduced pressure, the residue was diluted with 300 mL mixed solvent (PE:EA=4:1), filtered and concentrated. The crude product was purified by flash column chromatography (PE:EA=2:1 to 1:1) to give the title compound (10 g, 66%) as a yellow oil. LC-MS: $[M+H]^+$=235.1.

Intermediate B2: (1-Isopropyl-3-methyl-1H-pyrazol-4-yl)boronic Acid

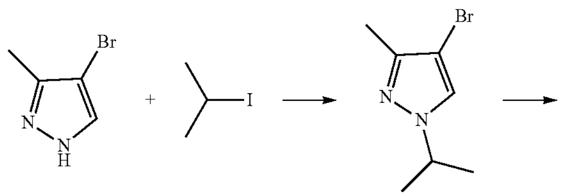

B2.1

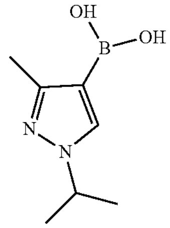

B2

4-Bromo-1-isopropyl-3-methyl-1H-pyrazole (B2.1): A mixture of 4-bromo-3-methyl-1H-pyrazole (2 g, 12.5 mmol), 2-iodopropane (6.37 g, 37.5 mmol), $Cs_2CO_3$ (6.25 g, 50 mmol) and acetonitrile (30 mL) was stirred at 90° C. for 12 h. The reaction mixture was filtered with MeOH (15 ml) and the filtrate was concentrated. The residue was purified by flash chromatography on silica gel (UV214, PE:DMC=100:1 to 50:50) to afford the title compound (700 mg, 56%) as a clear oil. LC-MS: $[M+H]^+$=203.1.

Intermediate B2: To a solution of B2.1 (202 mg, 1.0 mmol) in THE (5 mL) was added n-BuLi (0.5 mL, 1.2 mmol, 2.4 M in THF) under $N_2$ at −78° C. The reaction was stirred at −78° C. for 30 min, and then triisopropyl borate (564 mg, 3.0 mmol) in THE (2 mL) was added dropwise with stirring on at −78° C. The mixture was stirred at −78° C. for 2 h. The mixture was quenched with water (3 mL), the aqueous layer was purified by flash chromatography (silica gel, UV214, $NH_4HCO_3$\water\MeOH=0.5\100\1) to give the title compound (100 mg, 60%) as a white solid. LC-MS: $[M+H]^+$=169.1.

Intermediate B3: 2-methoxy-4-methyl-5-(4,4,5,5-tetramethyl-1,3,2-dioxaborolan-2-yl)pyridine

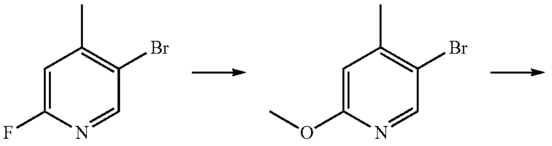

B3.1

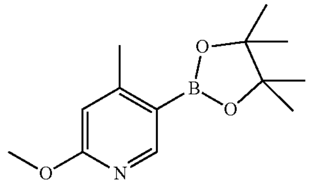

B3

5-Bromo-2-methoxy-4-methylpyridine (B3.1): Sodium (4.8 g, 0.2 mol) was added to a stirred solution of 80 mL $CH_3OH$ portion by portion. After addition, 5-bromo-2-fluoro-4-methylpyridine (7.6 g, 40 mmol) was added subsequently by neat. Then the clear solution was stirred at rt overnight. The reaction was quenched by water (400 mL), extracted with dichloromethane (300 mL×3). The combined organic phase was washed with brine, dried over sodium sulphate, filtered and concentrated to give the title compound (6.95 g, 86%) as a pale yellow solid. $^1H$ NMR (500 MHz, $CDCl_3$) δ 2.31 (s, 3H), 3.87 (s, 3H), 6.61 (s, 1H), 8.15 (s, 1H).

Intermediate B3: The title compound was prepared by a method similar to that of Intermediate B1 by replacing B1.4 with B3.1. LC-MS: $[M+H]^+$=250.1.

Intermediate B4: 6-cyclopropyl-2-methyl-3-(4,4,5,5-tetramethyl-1,3,2-dioxaborolan-2-yl)pyridine

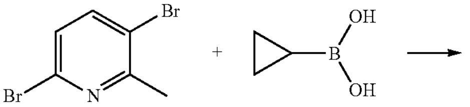

-continued

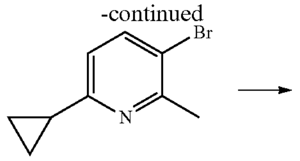

B4.1

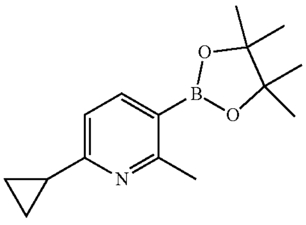

B4

3-Bromo-6-cyclopropyl-2-methylpyridine (B4.1): A mixture of 3,6-dibromo-2-methylpyridine (250 mg, 1 mmol), cyclopropylboronic acid (86 mg, 1 mmol), $Cs_2CO_3$ (975 mg, 3 mmol), $Pd(PPh_3)_4$ (160 mg, 0.2 mmol) and dioxane (5 mL) was stirred at 120° C. under $N_2$ with microwave for 30 min. The mixture was filtered with MeOH (15 mL), the filtrate was purified by Prep-TLC (silica gel, UV254, PE) to afford the title compound (100 mg, 47%) as a clear oil. $^1H$ NMR (400 MHz, $CDCl_3$) b ppm 0.95-0.98 (m, 4H), 1.36-1.99 (m, 1H), 2.56 (s, 3H), 6.76 (d, 1H), 7.59 (d, 1H).

Intermediate B4: The title compound was prepared by a method similar to that of Intermediate B1 by replacing B1.4 with B4.1. LC-MS: $[M+H]^+$=260.3.

Intermediate B5: 2-(((tert-butyldimethylsilyl)oxy)methyl)-3-(4,4,5,5-tetramethyl-1,3,2-dioxaborolan-2-yl)pyridine

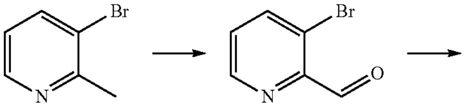

B5.1

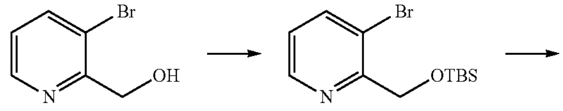

B5.2 B5.3

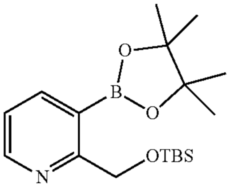

B5

3-Bromopicolinaldehyde (B5.1): A mixture of 3-bromo-2-methylpyridine (5 g, 29 mmol), $SeO_2$ (17.5 mg, 116 mmol) in dioxane (70 mL) was heated to 120° C. and stirred for 18 h. The mixture was concentrated and purified by silica gel (PE:EA=4:1) to give the title compound (3 g, 55%) as a white solid. LC-MS: $[M+H]^+$=188.1.

(3-Bromopyridin-2-yl)methanol(B5.2): To a mixture of B5.1 (1 g, 5.4 mmol) in MeOH (20 mL) and THF (10 mL)

was cooled to 0° C., $NaBH_4$ (0.82 g, 21.6 mmol) was added in portions. The mixture was stirred for 4 h at rt. The mixture was concentrated, diluted with water (40 mL), extracted with DCM (40 mL×3), the organic layer was washed with brine, dried over $Na_2SO_4$, filtered and concentrated to give the title compound (1 g, 99%) as a white solid. LC-MS: $[M+H]^+$=190.0.

3-Bromo-2-(((tert-butyldimethylsilyl)oxy)methyl)pyridine (15.3): A mixture of B5.2 (1 g, 5.4 mmol), DMAP (0.33 g, 1.08 mmol), TBSCl (0.97 g, 6.48 mmol) and imidazole (0.48 g, 7 mmol) in DCM (30 mL) was stirred for 18 h at rt. The mixture was diluted with DCM (50 mL), washed with water (30 mL) and brine (30 mL), dried over $Na_2SO_4$, filtered and concentrated, the residue was purified on silica gel (PE:EA=100:0 to 50:50) to give the title compound (1.1 g, 68%) as a colorless oil. LC-MS: $[M+H]^+$=304.0.

Intermediate B5: The title compound was prepared by a method similar to that of Intermediate B1 by replacing B1.4 with B5.3. LC-MS: $[M+H]^+$=350.1.

Intermediate B6:1,3,5-Trimethyl-4-(4,4,5,5-tetramethyl-1,3,2-dioxaborolan-2-yl)-1H-pyrazole

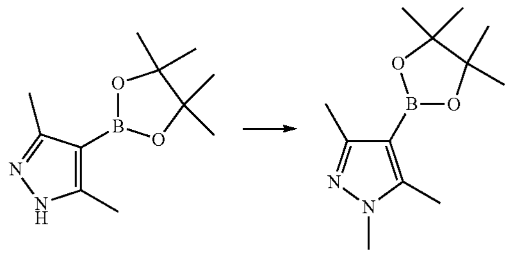

B6

A mixture of 3,5-dimethyl-4-(4,4,5,5-tetramethyl-1,3,2-dioxaborolan-2-yl)-1H-pyrazole (10 g, 45 mmol), iodomethane (9.6 g, 67.5 mmol), $K_2CO_3$ (15.5 g, 112.5 mmol) in acetone (50 mL) was stirred at 60° C. for 12 h. The reaction mixture was filtered, washed with MeOH (35 ml), the filtrate was concentrated to afford the title compound (8 g, 75%) as a white solid. LC-MS: $[M+H]^+$=237.2.

Intermediate B7: 2-(difluoromethyl)-3-(4,4,5,5-tetramethyl-1,3,2-dioxaborolan-2-yl)pyridine

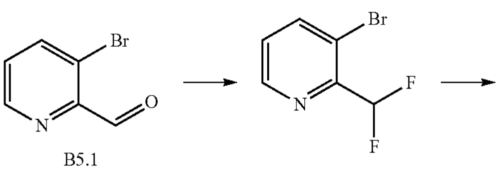

B5.1 B7.1

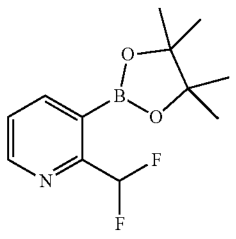

B7

3-Bromo-2-(difluoromethyl)pyridine (17.1): To a solution of 3-bromopicolinaldehyde (B5.1) (3.0 g, 16.1 mmol) in DCM (20 mL) was added DAST (5.2 g, 32.2 mmol) at 0° C. The reaction mixture was stirred at 0° C. for 2 h under $N_2$, then $NaHCO_3$ solution was added under ice bath. The mixture was extracted with DCM (60 mL), the organic layer was dried and concentrated. The residue was purified by flash chromatography to give the title compound (2.5 g, 75%) as a gray solid, which was used in the next step without further purification.

Intermediate B7: The title compound was prepared by a method similar to that of Intermediate B1 by replacing B1.4 with B7.1. The crude product was used in the next step without further purification.

Intermediate B8: 2-cyclopropyl-4-methyl-5-(4,4,5,5-tetramethyl-1,3,2-dioxaborolan-2-yl)pyrimidine

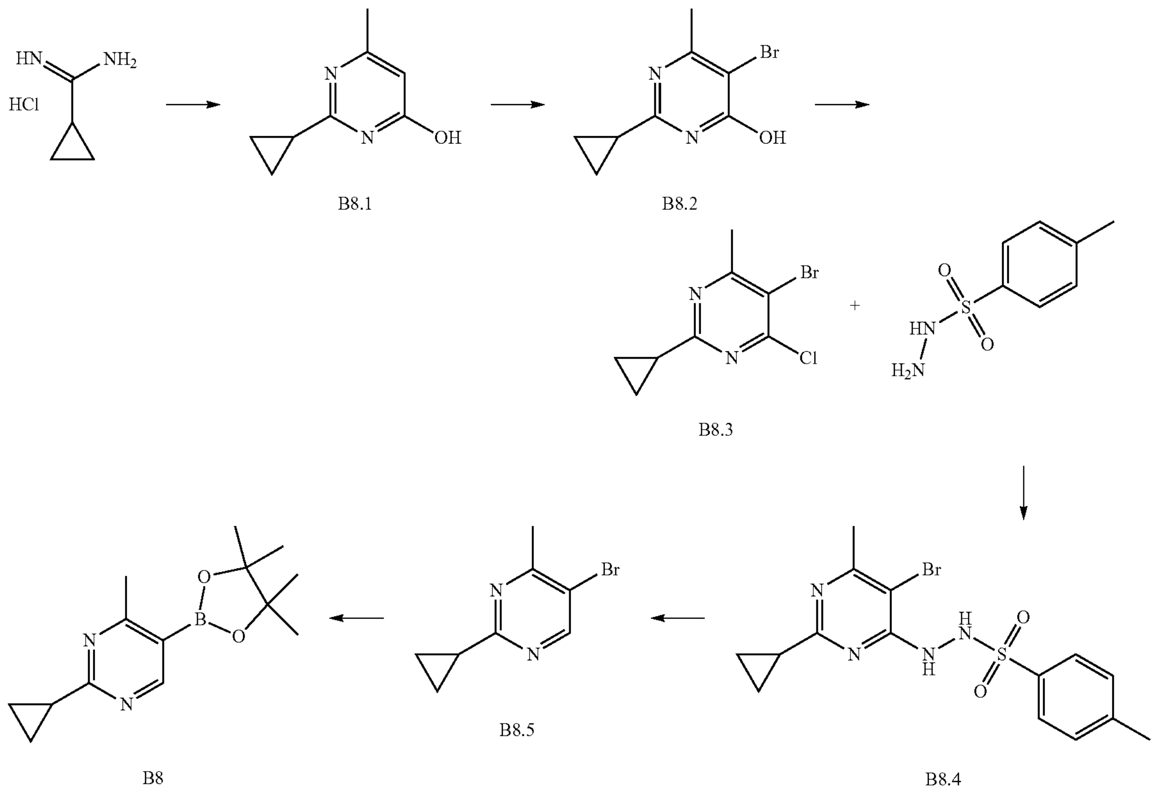

2-Cyclopropyl-6-methylpyrimidin-4-ol (B8.1): A mixture of cyclopropane-carboximidamide hydrochloride (2.0 g, 16.7 mmol), methyl 3-oxobutanoate (1.9 g, 16.7 mmol) and $CH_3ONa$ (1.8 g, 33.4 mmol) in MeOH (200 mL) was stirred at rt for 18 h. Then the mixture was diluted with Sat. $Na_2SO_3$ (50 mL), then concentrated under reduced pressure. The residue was dissolved in 50 mL water, adjusted pH to 4. After cooling to 5° C., the solid was collected and dried in vacuum to give the title compound (2.0 g, 98%) as a yellow solid. The crude product was used in the next step without further purification. LC-MS: $[M+H]^+$=151.2.

5-Bromo-2-cyclopropyl-6-methylpyrimidin-4-ol(B8.2): A mixture of B8.1 (2.0 g, 13.3 mmol) and KOH (744 mg, 13.3 mmol) in $H_2O$ (15 mL) was added $Br_2$ (0.7 mL) at 0° C. The reaction mixture was stirred at rt for 2 h. The solid was filtered to give the title compound (1.5 g, 57%) as a white solid. The crude product was used in the next step without further purification. LC-MS: $[M+H]^+$=231.0.

5-Bromo-4-chloro-2-cyclopropyl-6-methylpyrimidine (B8.3): A mixture of B8.2 (1.5 g, 6.55 mmol) and DMF (1.26 mL, 16.38 mmol) in Toluene (20 mL) was added dropwise a solution of $POCl_3$ (0.72 mL) in Toluene (5 mL) at 0° C. The reaction mixture was stirred at rt for 3 h, then poured into $Na_2CO_3$ (1M, 30 mL), extracted with EA (20 mL×3). The combined organic phase was concentrated to give the title compound (1.0 g, 62%) as a yellow oil. The crude product was used in the next step without further purification. LC-MS: $[M+H]^+$=248.9.

N'-(5-Bromo-2-cyclopropyl-6-methylpyrimidin-4-yl)-4-methylbenzenesulfonohydrazide (18.4): A mixture of B8.3 (1.0 g, 4.06 mmol), 4-methylbenzenesulfonohydrazide (2.6 g, 13.8 mmol) in $CHCl_3$ (50 mL) was stirred at 90° C. for 16 h. The solid was filtered and washed with DCM (5 mL) to give the title compound (0.60 g, 37.5%) as a white solid. The crude product was used in the next step without further purification. LC-MS: $[M+H]^+$=397.0.

5-Bromo-2-cyclopropyl-4-methylpyrimidine (B8.5): A mixture of B8.4 (600 mg, 1.51 mmol) in $Na_2CO_3$ (8 mL, 4.53 mmol) was stirred at 90° C. for 1 h. The mixture was diluted with EA (20 mL). The organic phase was separated and concentrated to give the title compound (200 mg, 62%) as a brown oil. The crude product was used in the next step without further purification. LC-MS: $[M+H]^+$=213.0.

Intermediate B8: The title compound was prepared by a method similar to that of Intermediate B1 by replacing B1.4 with B8.5. The crude product was used in the next step without further purification. LC-MS: $[M+H]^+$=261.2.

Intermediate B9: (3-(difluoromethyl)-1-methyl-1H-pyrazol-4-yl)boronic Acid

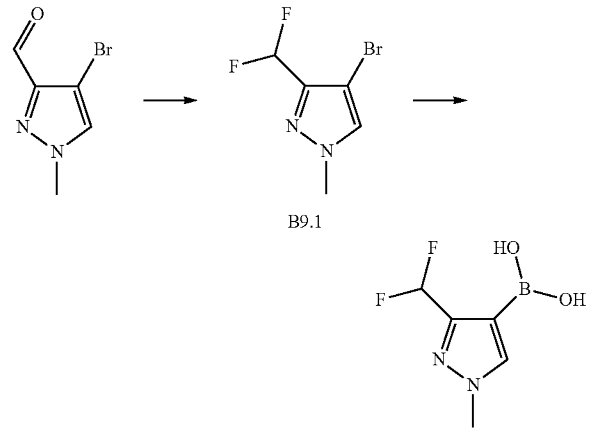

B9.1

B9

4-Bromo-3-(difluoromethyl)-1-methyl-1H-pyrazole (19.1): The title compound was prepared by a method similar to that of B7.1 by replacing 3-bromopicolinaldehyde (B5.1) with 4-bromo-1-methyl-1H-pyrazole-3-carbaldehyde. $^1$H NMR (400 MHz, $CDCl_3$) δ ppm 3.91 (s, 3H), 6.66 (t, 1H), 7.43 (s, 1H). LC-MS: $[M+H]^+$=213.1.

Intermediate B9: The title compound was prepared by a method similar to that of Intermediate B2 by replacing 4-bromo-1-isopropyl-3-methyl-1H-pyrazole (B2.1) with B9.1. LC-MS: $[M+H]^+$=177.2.

Intermediate B10: 2-isopropoxy-4-methyl-5-(4,4,5,5-tetramethyl-1,3,2-dioxaborolan-2-yl)pyrimidine

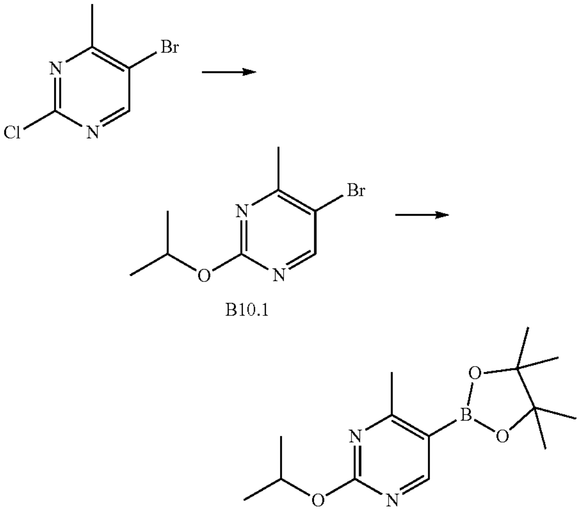

B10.1

B10

5-Bromo-2-isopropoxy-4-methylpyrimidine (B10.1): To a solution of 5-bromo-2-chloro-4-methylpyrimidine (3.0 g, 14.5 mmol) in THE (30 mL) was added NaH (1.74 g, 44 mmol), it was stirred at rt for 0.5 h. Then propan-2-ol (2.6 g, 44 mmol) was added, the mixture was stirred at rt for 3 h. The mixture was concentrated, the residue was diluted with water (20 mL), extracted with EA (20×3 mL). The organic layer was dried and concentrated, the crude product was purified by flash chromatography (silica gel; EA:PE=1:4) to give the title compound (2.8 g, 83%)) as a gray solid. LC-MS: $[M+H]^+$=231.0; 232.9.

Intermediate B10: The title compound was prepared by a method similar to that of Intermediate B1 by replacing B1.4 with B10.1. LC-MS: $[M+H]^+$=279.3.

Intermediate B11: 2-(Difluoromethoxy)-4-methyl-5-(4,4,5,5-tetramethyl-1,3,2-dioxaborolan-2-yl)pyridine

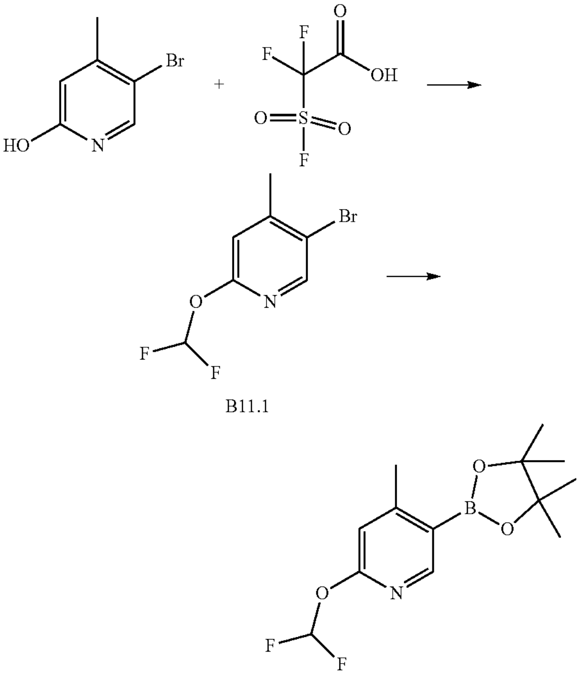

B11.1

B11

5-Bromo-2-(difluoromethoxy)-4-methylpyridine (B11.1): To a solution of 5-bromo-4-methylpyridin-2-ol (8 g, 42.55 mmol) and 2,2-difluoro-2-(fluorosulfonyl)acetic acid (9.1 g, 51.06 mmol) in 40 mL $CH_3CN$ was added $Na_2SO_4$ (606 mg, 4.255 mmol) in one portion. The suspension was stirred at rt overnight, then concentrated under vacuum, the residue was purified on silica gel (PE/EtOAc=0-9%) to give the title compound (500 mg, 37%) as a yellow oil. $^1$H NMR (500 MHz, DMSO-$d_6$) δ 2.39 (s, 3H), 7.19 (s, 1H), 7.51-7.80 (m, 1H), 8.39 (s, 1H). LC-MS: $[M+H]^+$=239.9.

Intermediate B11: The title compound was prepared by a method similar to that of Intermediate B1 by replacing B1.4 with B11.1. LC-MS: $[M+H]^+$=286.2.

Intermediate B12: 1-(5-(4,4,5,5-tetramethyl-1,3,2-dioxaborolan-2-yl)pyridin-3-yl)pyrrolidin-2-one

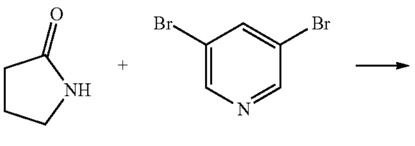

-continued

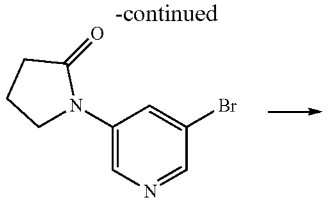

B12.1

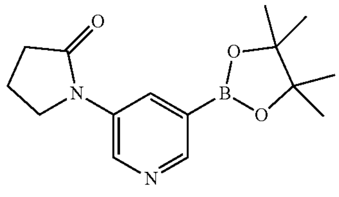

B12

1-(5-Bromopyridin-3-yl)pyrrolidin-2-one (B12.1): A mixture of 3,5-dibromopyridine (500 mg, 2.1 mmol), pyrrolidin-2-one (170 mg, 2.0 mmol), $K_2CO_3$ (1.04 g, 7.56 mmol), CuI (4 mg, 0.021 mmol), N1,N1,N2,N2-tetramethylethane-1,2-diamine (3 mg, 0.021 mmol) and dioxane (10 mL) was stirred at 110° C. for 12 h. 30 mL of $H_2O$ was added to the mixture and extracted with ethyl acetate (20 mL×3). The combined organic layers was washed with water (25 mL×3) and brine (20 mL×3), dried over $Na_2SO_4$, concentrated and purified by flash chromatography (silica gel, 40 g, UV254, PE\EA=100\1 to 2\1) to give the title compound (240 mg, 47%) as a gray solid. LC-MS: $[M+H]^+$=243.1.

Intermediate 812: The title compound was prepared by a method similar to that of Intermediate B1 by replacing B1.4 with B12.1. LC-MS: [M+H]+=206.2.

Intermediate B13: 3-(3-(methylsulfonyl)propoxy)-5-(4,4,5,5-tetramethyl-1,3,2-dioxaborolan-2-yl)pyridine

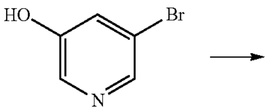

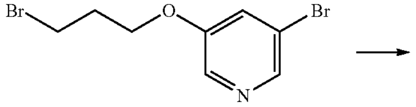

B13.1

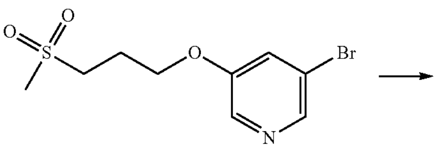

B13.2

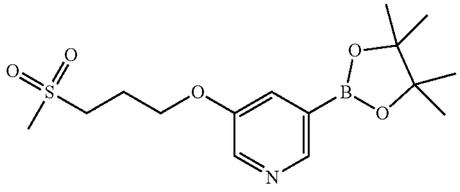

B13

3-Bromo-5-(3-bromopropoxy)pyridine (B13.1): A mixture of 5-bromopyridin-3-ol (500 mg, 2.87 mmol), 1,3-dibromopropane (870 mg, 4.31 mmol), NaH (230 mg, 5.74 mmol) and DMF (10 mL) was stirred at 0° C. for 12 h. The mixture was added water (10 mL), extracted with EA (10 mL×3), the extracts were washed with water (25 mL×3) and brine (20 mL×3), dried over $Na_2SO_4$, concentrated and purified by flash chromatography (silica gel, 40 g, PE/EA=100/1 to 2/1) to give the title compound (300 mg, 36%) as a gray solid. LC-MS: $[M+H]^+$=296.0.

3-Bromo-5-(3-(methylsulfonyl)propoxy)pyridine (813.2): A mixture of B13.1 (300 mg, 1.02 mmol), $NaOSOCH_3$ (156 mg, 1.53 mmol), and DMSO (2 mL) was stirred at rt overnight. 10 mL water was added to the mixture, extracted with ethyl acetate (10 mL×3), the organis layers were washed with water (25 mL×3) and brine (20 mL×3), dried over $Na_2SO_4$, concentrated and purified by flash chromatography (silica gel, 40 g, UV254, PE\EA=100\1 to 2\1) to give the title compound (120 mg, 40%) as a gray solid. LC-MS: $[M+H]^+$=294.0.

Intermediate B13: The title compound was prepared by a method similar to that of Intermediate B1 by replacing B1.4 with B13.2. The crude product was used in the next step without further purification. LC-MS: $[M+H]^+$=260.1.

Intermediate B14: 3-(5-(4,4,5,5-tetramethyl-1,3,2-dioxaborolan-2-yl)pyridin-2-yl)oxazolidin-2-one

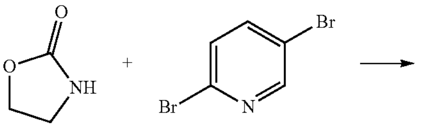

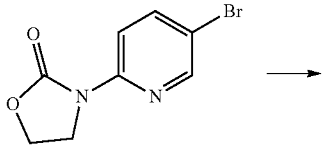

B14.1

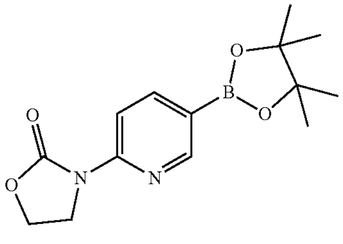

B14

3-(5-Bromopyridin-2-yl)oxazolidin-2-one (B14.1): A mixture of 2,5-dibromopyridine (1.0 g, 4.21 mmol), pyrrolidin-2-one (1.1 g, 12.7 mmol), $K_2CO_3$ (1.16 g, 8.42 mmol), CuI (40 mg, 0.21 mmol), N1,N1,N2,N2-tetramethylethane-1,2-diamine (50 mg, 0.42 mmol) and dioxane (10 ml) was stirred at 110° C. for 12 h. The mixture was added water (30 mL), extracted with EA (20 mL×3), the extracts were washed with water (25 mL×3) and brine (20 mL×3), dried over $Na_2SO_4$, concentrated and purified by flash chromatography (silica gel, 40 g, UV254, PE\EA=100\1 to 2\1) to give the title compound (380 mg, 37%) as a gray solid. LC-MS: $[M+H]^+$=244.9.

Intermediate B14: The title compound was prepared by a method similar to that of Intermediate B1 by replacing B1.4 with B14.1. LC-MS: $[M+H]^+$=291.0.

Intermediate B15: 3-(2-(methylsulfonyl)ethoxy)-5-(4,4,5,5-tetramethyl-1,3,2-dioxaborolan-2-yl)pyridine

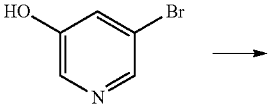

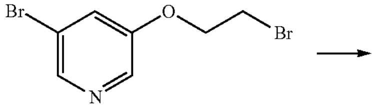

B15.1

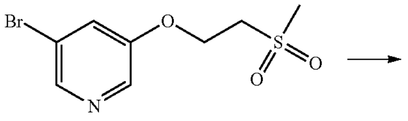

B15.2

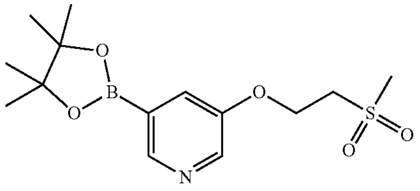

B15

3-Bromo-5-(2-bromoethoxy)pyridine (B15.1): A mixture of 5-bromopyridin-3-ol (500 mg, 2.87 mmol), 1,2-dibromoethane (810 mg, 4.31 mmol), $K_2CO_3$ (792 mg, 5.74 mmol) and DMF (10 mL) was stirred at rt for 12 h. The mixture was diluted with 10 mL water, extracted with EA (10 mL×3), the organic layers were washed with water (25 mL×3) and brine (20 mL×3), dried over $Na_2SO_4$, concentrated and purified by flash chromatography (silica gel, 40 g, PE/EA=100/1 to 2/1) to give the title compound (200 mg, 20%) as a gray solid. LC-MS: $[M+H]^+$=279.9.

3-Bromo-5-(2-(methylsulfonyl)ethoxy)pyridine (B15.2): A mixture of B15.1 (200 mg, 0.71 mmol), $NaOSOCH_3$ (126 mg, 1.07 mmol), and DMSO (2 mL) was stirred at rt overnight. The mixture was added water (10 mL), extracted with EA (10 mL×3), the extracts were washed with water (25 mL×3) and brine (20 mL×3), dried over $Na_2SO_4$, concentrated and purified by flash chromatography (silica gel, 40 g, PE/EA=100/1 to 2/1) to give the title compound (150 mg, 61%) as a gray solid. LC-MS: $[M+H]^+$=280.0.

Intermediate B15: The title compound was prepared by a method similar to that of Intermediate B1 by replacing B1.4 with B15.2. LC-MS: $[M+H]^+$=328.2.

Intermediate B16: 6-(2-oxopiperazin-1-yl)pyridin-3-ylboronic Acid

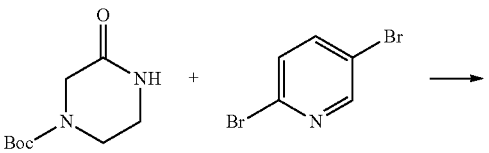

-continued

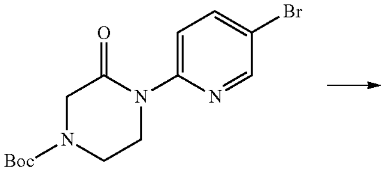

B16.1

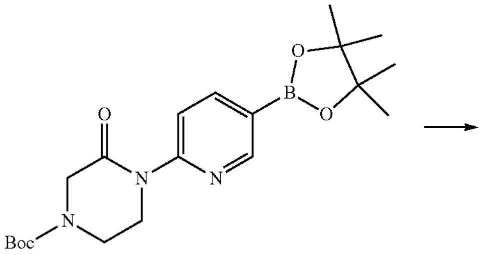

B16.2

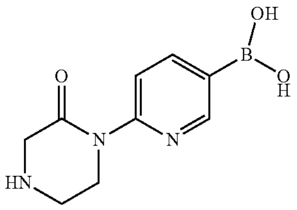

B16 tert-Butyl 4-(5-bromopyridin-2-yl)-3-oxopiperazine-1-carboxylate (B16.1): A mixture of 2,5-dibromopyridine (1.0 g, 4.21 mmol), pyrrolidin-2-one (2.54 g, 12.7 mmol), $K_2CO_3$ (1.16 g, 8.42 mmol), CuI (40 mg, 0.21 mmol), N1,N1,N2,N2-tetramethylethane-1,2-diamine (92 mg, 0.63 mmol) and dioxane (10 mL) was stirred at 110° C. for 12 h. The mixture was added water (30 mL), extracted with EA (20 mL×3), the organic layers were washed with water (25 mL×3) and brine (20 mL×3), dried over $Na_2SO_4$, concentrated and purified by flash chromatography (silica gel, 40 g, PE/EA=100/1 to 2/1) to give the title compound (750 mg, 50%) as a gray solid. LC-MS: $[M+H]^+$=356.1.

tert-Butyl 3-oxo-4-(5-(4,4,5,5-tetramethyl-1,3,2-dioxaborolan-2-yl)pyridin-2-yl)piperazine-1-carboxylate (B16.2): The title compound was prepared by a method similar to that of Intermediate B1 by replacing B1.4 with B16.1. The crude product was used in the next step without further purification. LC-MS: $[M+H]^+$=404.0.

Intermediate B16: A mixture of B16.2 (100 mg, 0.31 mmol) in HCl/dioxane (0.6 mL) was stirred at rt for 2 h. The mixture was added water (30 mL), extracted with EA (20 mL×3), the extracts were washed with water (25 mL×3) and brine (20 mL×3), dried over $Na_2SO_4$, concentrated and purified by Prep-HPLC to give the title compound (50 mg, 40%) as a gray solid. LC-MS: $[M+H]^+$=222.2.

Intermediate B17: N-(2-hydroxyethyl)-4-(4,4,5,5-tetramethyl-1,3,2-dioxaborolan-2-yl)benzenesulfonamide

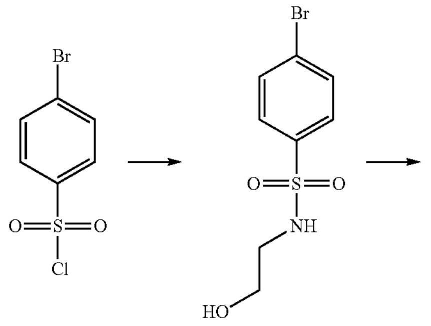

B17.1

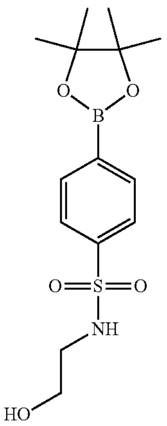

B17

4-Bromo-N-(2-hydroxyethyl)benzenesulfonamide (B17.1): To a solution of 4-bromobenzene-1-sulfonyl chloride (2.0 g, 7.9 mmol) in DCM (30 mL) was added 2-aminoethanol (4.8 g, 79 mmol) and DIPEA (2.0 g, 15.8 mmol) at 0° C., then the reaction mixture was stirred at rt overnight. The precipitate was collected by filtration, washed with EtOH (10 mL×2), dried in vacuum to give the title compound (1.8 g, yield 90%) as a white solid. LC-MS: $[M+H]^+$=281.9.

Intermediate B17: The title compound was prepared by a method similar to that of Intermediate B1 by replacing B1.4 with B17.1. LC-MS: $[M+H]^+$=328.0.

Intermediate B18: 6-(2-methylpyrrolidin-1-yl)pyridin-3-ylboronic Acid

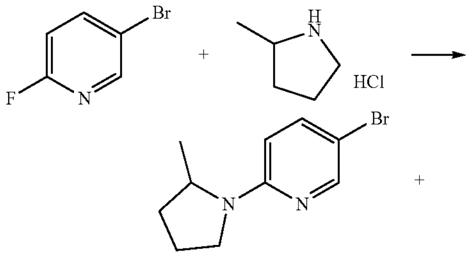

B18.1

-continued

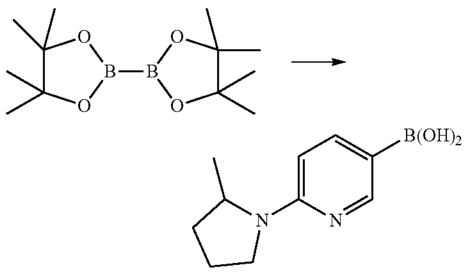

B18

5-Bromo-2-(2-methylpyrrolidin-1-yl)pyridine (B18.1): To a solution of 5-bromo-2-fluoropyridine (5.71 mmol, 1 g) in $H_2O$ (3 mL) was added 2-methylpyrrolidine hydrochloride (8.57 mmol, 0.73 g) and $K_2CO_3$ (11.43 mmol, 1.58 g) and the mixture was stirred at 115° C. for 3 h. The mixture was concentrated and purified by flash chromatography (reverse phase, C-18, 10 mmol $NH_4HCO_3$:$CH_3OH$=0-80%, UV254&UV214) to give the title compound (900 mg, 65%) of as a yellow oil. LC-MS: $[M+H]^+$=241.1.

Intermediate B18: To a solution of B18.1 (0.622 mmol, 150 mg), bis(pinacolato)diboron (158 mg, 0.622 mmol) and KOAc (1.24 mmol, 121 mg) in dioxane (6 mL) was added $Pd(dppf)Cl_2$ (0.062 mmol, 45.5 mg). The reaction mixture was heated at 90° C. for 2 h under $N_2$. After cooling to the rt, the mixture was filtered, and the filtrate was used in the next step without further purification. LC-MS: $[M+H]^+$=207.2.

Intermediate B19: (4-methyl-5-(4,4,5,5-tetramethyl-1,3,2-dioxaborolan-2-yl)pyridin-2-yl)(pyrrolidin-1-yl)methanone

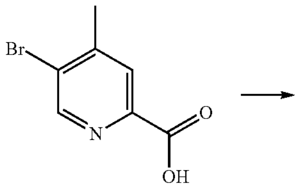

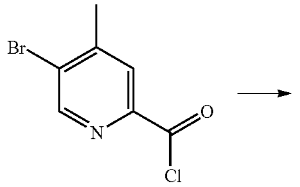

B19.1

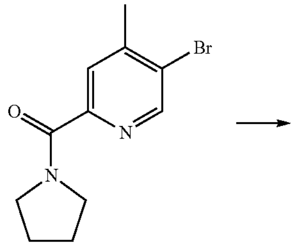

B19.2

-continued

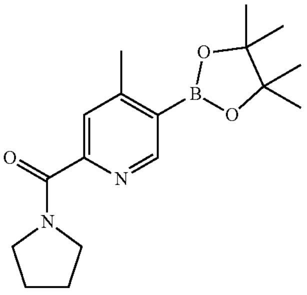

B19

5-Bromo-4-methylpicolinoyl chloride (B19.1): A mixture of 5-bromo-4-methylpicolinic acid (5.6 mmol, 1.2 g) and 10 mL thionyl chloride was stirred at 90° C. for 2 h. After cooling to the rt, the mixture was concentrated to give the title compound (1 g, 77%) as a yellow solid. LC-MS: $[M+H]^+$=236.1.

(5-Bromo-4-methylpyridin-2-yl)(pyrrolidin-1-yl)methanone (B19.2): To a solution of pyrrolidine (3.21 mmol, 228 mg) in 10 mL DCM at 0° C. was added DIPEA (6.42 mmol, 829 mg). After stirring at 0° C. for 10 min, to the mixture was added B19.1 (2.14 mmol, 500 mg) portionwise, stirred at 0° C. for 20 min, then allowed to warming to rt, and stirred for another 2 h, concentrated and purification by flash chromatography (silica gel, PE:EA=0-40%, UV254&UV280 nm) to give the title compound (560 mg, 97%) as a yellow solid. LC-MS: $[M+H]^+$=269.1.

Intermediate B19: The title compound was prepared by a method similar to that of Intermediate B1 by replacing B1.4 with B19.2. LC-MS: $[M+H]^+$=317.3.

Intermediate B20:,4-trimethyl-5-(4,4,5,5-tetramethyl-1,3,2-dioxaborolan-2-yl)picolinamide

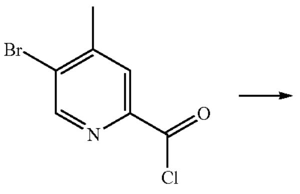

B19.1

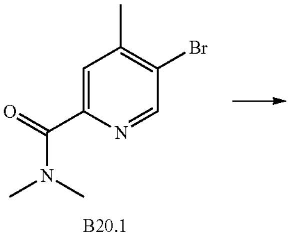

B20.1

-continued

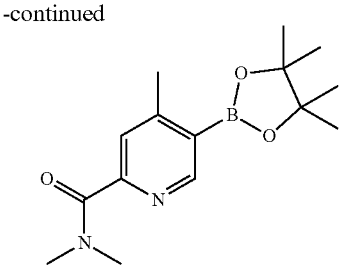

B20

5-Bromo-N,N,4-trimethylpicolinamide (B20.1): To a solution of dimethylamine hydrochloride (3.21 mmol, 262 mg) in 10 mL DCM at 0° C. was added DIPEA (6.424 mmol, 829 mg). The mixture was stirred at 0° C. for 10 min, B19.1 (2.141 mmol, 500 mg) was added portionwise. The mixture was stirred at 0° C. for 20 min, then warming to rt for 2 h, concentrated and purification by flash chromatography (silica gel, PE:EA=0-50%, UV254&UV280 nm) to give the title compound (560 mg, 97%) as a yellow solid. LC-MS: $[M+H]^+$=243.1.

Intermediate B20: The title compound was prepared by a method similar to that of Intermediate B1 by replacing B1.4 with B20.1. LC-MS: $[M+H]^+$=291.2.

Intermediate B21: 2-(3,5-dimethyl-4-(4,4,5,5-tetramethyl-1,3,2-dioxaborolan-2-yl)-1H-pyrazol-1-yl) ethanol

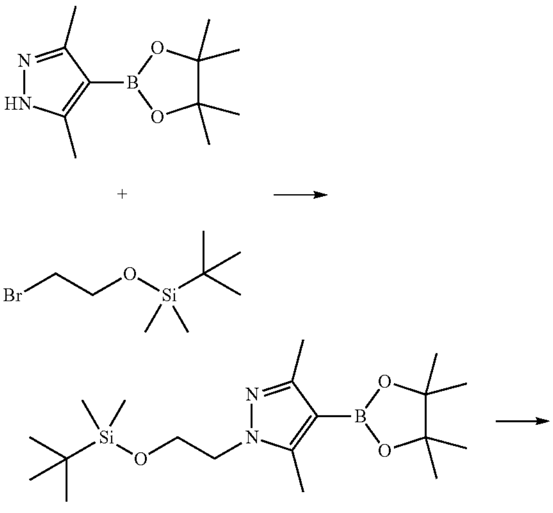

B21.1

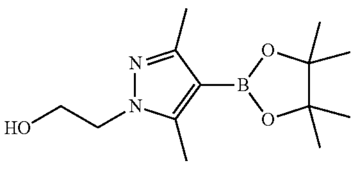

B21

1-(2-((tert-Butyldimethylsilyl)oxy)ethyl)-3,5-dimethyl-4-(4,4,5,5-tetramethyl-1,3,2-dioxaborolan-2-yl)-1H-pyrazole (B21.1): To a solution of 3,5-dimethyl-4-(4,4,5,5-tetramethyl-1,3,2-dioxaborolan-2-yl)-1H-pyrazole (300 mg, 1.35 mmol) in $CH_3CN$ (5 mL) was added $Cs_2CO_3$ (800 mg, 2.702 mmol) and (2-bromoethoxy)(tert-butyl)dimethylsilane (50 mg, 1.892 mmol). The mixture was stirred at 90° C. over night concentrated and purified by flash Chromatography (silica gel, PE:EA=0-15%, UV254 &UV280) to give the title compound (300 mg, 77%) as a yellow oil. LC-MS: $[M+H]^+$=381.7.

Intermediate B21: To a solution of B21.1 (300 mg, 0.79 mmol) in THE (6 mL) was added TBAF (412 mg, 1.58 mmol). The mixture was stirred at 30° C. for 3 h, concentrated under reduced pressure to give the title compound (100 mg, 48%) as a yellow oil. LC-MS: $[M+H]^+$=267.

Intermediate B22: 1-(2-methoxyethyl)-3,5-dimethyl-4-(4,4,5,5-tetramethyl-1,3,2-dioxaborolan-2-yl)-1H-pyrazole

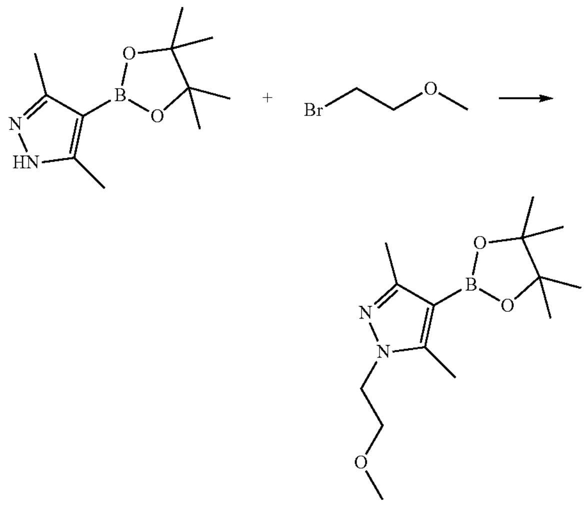

B22

To a solution of 3,5-dimethyl-4-(4,4,5,5-tetramethyl-1,3,2-dioxaborolan-2-yl)-1H-pyrazole (0.68 mmol, 150 mg) in $CH_3CN$ (5 mL) was added 1-bromo-2-methoxyethane (0.95 mmol, 130.5 mg). The mixture was stirred at 90° C. for 6 h, concentrated under reduced pressure, purified by flash chromatography (silica gel, PE:EA=0-20%, UV254 & UV280 nm) to give the title compound (100 mg, 52%) as a yellow solid. LC-MS: $[M+H]^+$=281.5.

Intermediate B23: 3-methyl-2-(methylsulfonyl)-5-(4,4,5,5-tetramethyl-1,3,2-dioxaborolan-2-yl)pyridine

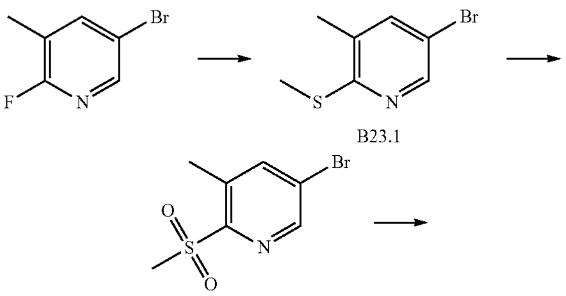

B23.1

B23.2

-continued

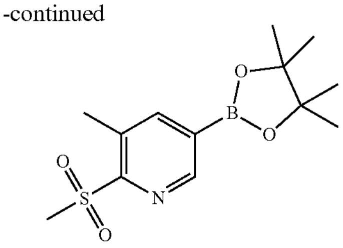

B23

5-Bromo-3-methyl-2-(methylthio)pyridine (B23.1): A mixture of 5-bromo-2-fluoro-3-methylpyridine (1 g, 5.26 mmol), $CH_3SNa$ (479 mg, 6.84 mmol) in DMF (10 mL) was stirred for 3.5 h at 0° C. under $N_2$. The mixture was diluted with 50 mL water, extracted with ethyl acetate (50 mL×3). The combined organic layers were successively washed with 50 mL water and 50 mL brine, dried over $Na_2SO_4$, concentrated to give the title compound (1.1 g, 95%) as a white solid. LC-MS: $[M+H]^+$=218.

5-Bromo-3-methyl-2-(methylsulfonyl)pyridine (B23.2): To a mixture of B23.1 (1.1 g, 5 mmol) in DCM (11 mL) was added m-CPBA (2.58 g, 15 mmol) at 0° C. The mixture was stirred overnight at rt, then quenched by 2 mol/L aq. NaOH solution (50 mL), extracted with ethyl acetate (50 mL×2). The combined organic layers were washed successively with 50 mL $H_2O$ and 50 mL brine, dried over $Na_2SO_4$, concentrated to give the title compound (1.2 g, 96%) as a white solid. LC-MS: $[M+H]^+$=249.9.

Intermediate B23: The title compound was prepared by a method similar to that of Intermediate B1 by replacing B1.4 with B23.2. LC-MS: $[M+H]^+$=216.1 (the $ms^+$ of the corresponding boronic acid).

Intermediate B24: (5-methyl-6-morpholinopyridin-3-yl)boronic Acid

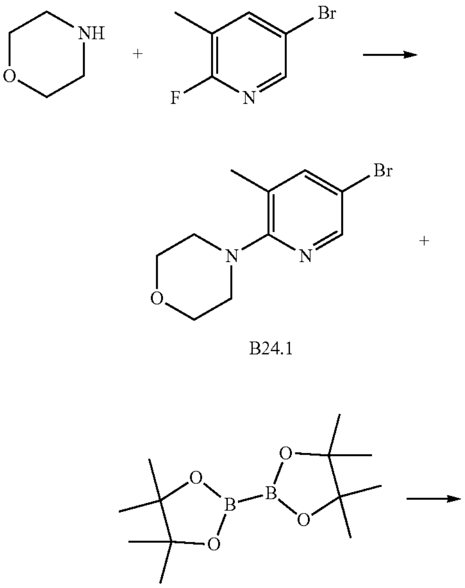

B24.1

B24.2

-continued

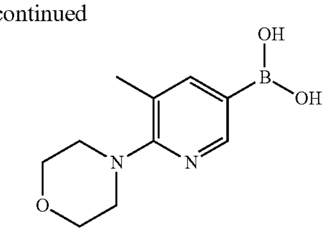

B24

4-(5-bromo-3-methylpyridin-2-yl)morpholine (B24.1): A mixture of 5-bromo-2-fluoro-3-methylpyridine (2.5 g, 13.2 mmol), morpholine (3.4 g, 39.6 mmol), $K_2CO_3$ (5.5 g, 39.6 mmol) in 40 mL DMSO was heated to 120° C. and stirred for 16 h. The mixture was cooled to rt. 200 mL water was added, extracted with ethyl acetate (150 mL×3). The combined organic layers was washed with 150 mL water and 150 mL brine, dried over $Na_2SO_4$, concentracted to give the title compound (1.8 g, 53%) as a white solid. LC-MS: $[M+H]^+$=257.0.

Intermediate B24: The title compound was prepared by a method similar to that of Intermediate B18 by replacing B18.1 with B24.1. LC-MS: $[M+H]^+$=223.3.

Intermediate B25: 2-(5-(4,4,5,5-tetramethyl-1,3,2-dioxaborolan-2-yl)pyridin-2-yl)propan-2-ol

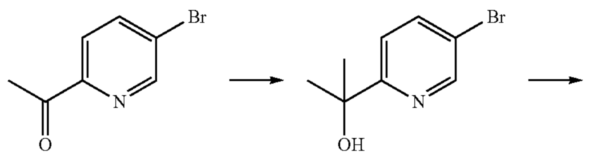

B25.1

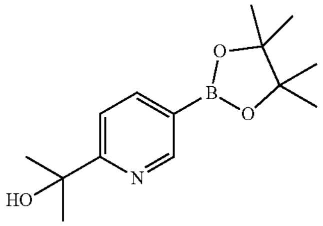

B25

2-(5-Bromopyridin-2-yl)propan-2-ol(B25.1): To a mixture of 1-(5-bromopyridin-2-yl)ethanone (400 mg, 2 mmol) in 8 mL THE was added 6 mL $CH_3MgBr$ (1 mol/L) at −15° C. under $N_2$ atmosphere. The mixture was stirred for 5 h at 25° C., quenched with sat. $NH_4Cl$ (30 mL) and stirred for 1 h, extracted with ethyl actetate (50 mL×2). The combined organic layers were washed with 50 mL water and 50 mL brine, dried over $Na_2SO_4$, concentrated. The residue was purified on silica gel (PE/EA=10:1) to give title compound (180 mg, 42%) as a colorless oil. $^1$H-NMR (400 MHz, $CDCl_3$) δ ppm 1.54 (s, 6H), 7.31 (dd, 1H), 7.82 (dd, 1H), 8.58 (d, 1H).

Intermediate B25: The title compound was prepared by a method similar to that of Intermediate B1 by replacing B1.4 with B25.1. LC-MS: $[M+H]^+$=264.2.

Intermediate B26: 4-methyl-2-(methylsulfonyl)-5-(4,4,5,5-tetramethyl-1,3,2-dioxaborolan-2-yl)pyridine

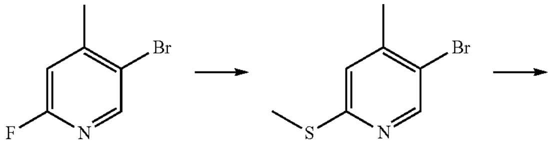

B26.1

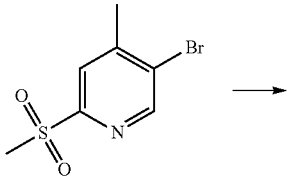

B26.2

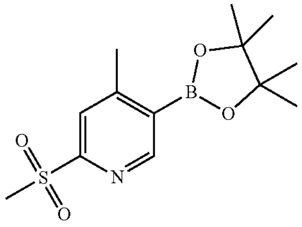

B26

The title compound was prepared by a method similar to that of Intermediate B23 by replacing 5-bromo-2-fluoro-3-methylpyridine with 5-bromo-2-fluoro-4-methylpyridine. LC-MS: $[M+H]^+$=298.1.

Intermediate B27: 2-methyl-6-(methylsulfonyl)-3-(4,4,5,5-tetramethyl-1,3,2-dioxaborolan-2-yl)pyridine

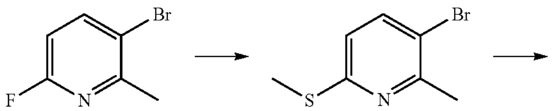

B27.1

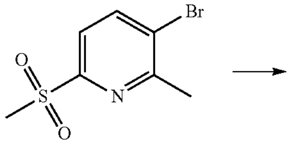

B27.2

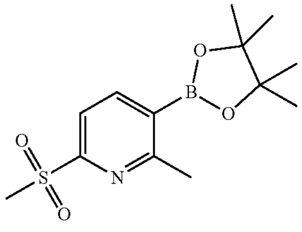

Intermediate B27

The title compound was prepared by a method similar to that of Intermediate B23 by replacing 5-bromo-2-fluoro-3-methylpyridine with 3-bromo-6-fluoro-2-methylpyridine. LC-MS: $[M+H]^+$=298.1.

Intermediate B28: 4-(5-(4,4,5,5-tetramethyl-1,3,2-dioxaborolan-2-yl)pyridin-2-yl)piperazin-2-one

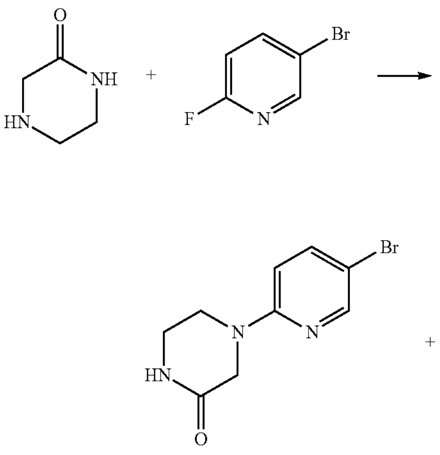

B28.1

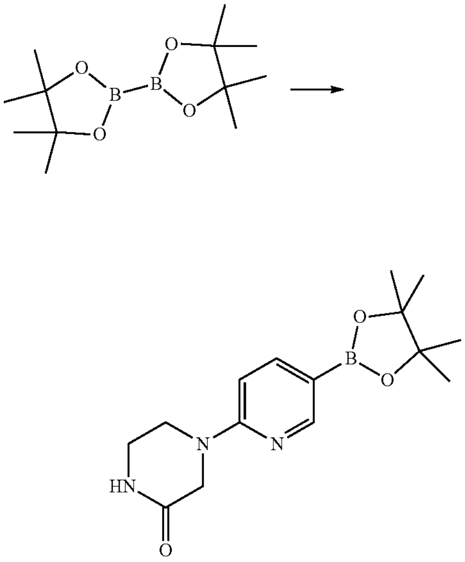

B28

4-(5-Bromopyridin-2-yl)piperazin-2-one (B28.1): A mixture of 5-bromo-2-fluoropyridine (1 g, 5.68 mmol), piperazin-2-one (1.7 g, 17 mmol), $K_2CO_3$ (2.35 g, 17 mmol) in 20 mL DMSO was heated at 120° C. and stirred for 16 h. The mixture was cooled to rt, 80 mL water was added, extracted with ethyl acetate (60 mL×3), the combined organic layer was washed with 100 mL water, and 100 mL brine, dried over $Na_2SO_4$, concentrated, the residue was purified on silica gel (DCM/MeOH=10:1) to give the title compound (250 mg, 17%) as a white solid. LC-MS: $[M+H]^+$=255.9.

Intermediate B28: The title compound was prepared by a method similar to that of Intermediate B1 by replacing B1.4 with B28.1. LC-MS: $[M+H]^+$=304.3.

Intermediate B29: 4,4,5,5-Tetramethyl-2-(2-methyl-4-(methylsulfonyl)phenyl)-1,3,2-dioxaborolane

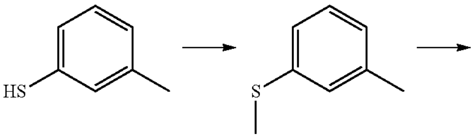

B29.1

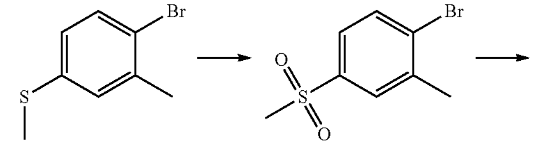

B29.2 B29.3

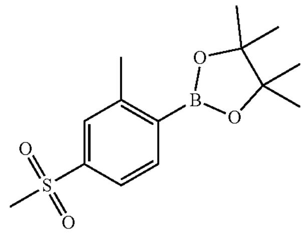

Intermediate B29

Methyl(m-tolyl)sulfane (B29.1): To a mixture of 3-methylbenzenethiol (2 g, 16 mmol) in 20 mL of DMF was added NaH (0.96 g, 24 mmol) at 0° C. The mixture was stirred for 30 min at 25° C. After cooling to 0° C., $CH_3I$ (22.7 g, 160 mmol) was added dropwise. The mixture was stirred for 2 h at rt, diluted with 100 mL water, extracted with ethyl acetate (60 mL×3). The combined organic layers were washed with brine (50 mL×1), dried over $Na_2SO_4$, concentrated. The residue was purified by silica gel (eluted with PE/EA=100:0) to give the title compound (1.3 g, 59%) as a colorless oil. The crude product was used in the next step without further purification.

(4-Bromo-3-methylphenyl)(methyl)sulfane (B29.2): A mixture of B29.1 (1.3 g, 9.4 mmol) in 30 mL of AcOH was cooled to 0° C., $Br_2$ (1.5 g, 9.42 mmol) was added dropwise, and the mixture was stirred for 3 h at 25° C. The mixture was concentrated and purified on silica gel (eluted with PE) to give the title compound (1.7 g, 85%) as a colorless oil. The crude product was used in the next step without further purification.

1-Bromo-2-methyl-4-(methylsulfonyl)benzene (B29.3): To a mixture of B29.2 (1.7 g, 7.83 mmol) in 20 mL DCM was added m-CPBA (4.04 g, 23.5 mmol) at 0° C. The mixture was stirred for 16 h at 25° C., quenched by 40 mL water, then extracted with DCM (50 mL×2), the combined organic layers were washed with brine (50 mL), dried over $Na_2SO_4$, concentrated. The residue was purified on silica gel (eluted with PE/EA=7:3) to give the title compound (1.3 g, 66%) as a white solid. $^1H$ NMR (400 MHz, $CDCl_3$) δ ppm 2.50 (s, 3H), 3.05 (s, 3H), 7.62 (dd, 2.3 Hz, 1H), 7.74 (d, 1H), 7.80 (d, 1H). LC-MS: $[M+H]^+$=249.1.

Intermediate B29: The title compound was prepared by a method similar to that of Intermediate B1 by replacing B1.4 with B29.3. The crude product was used in the next step without further purification. LC-MS: $[M+H]^+=314.0$.

Intermediate B30: (6-(3-(dimethylamino)-3-oxopropyl)pyridin-3-yl)boronic Acid

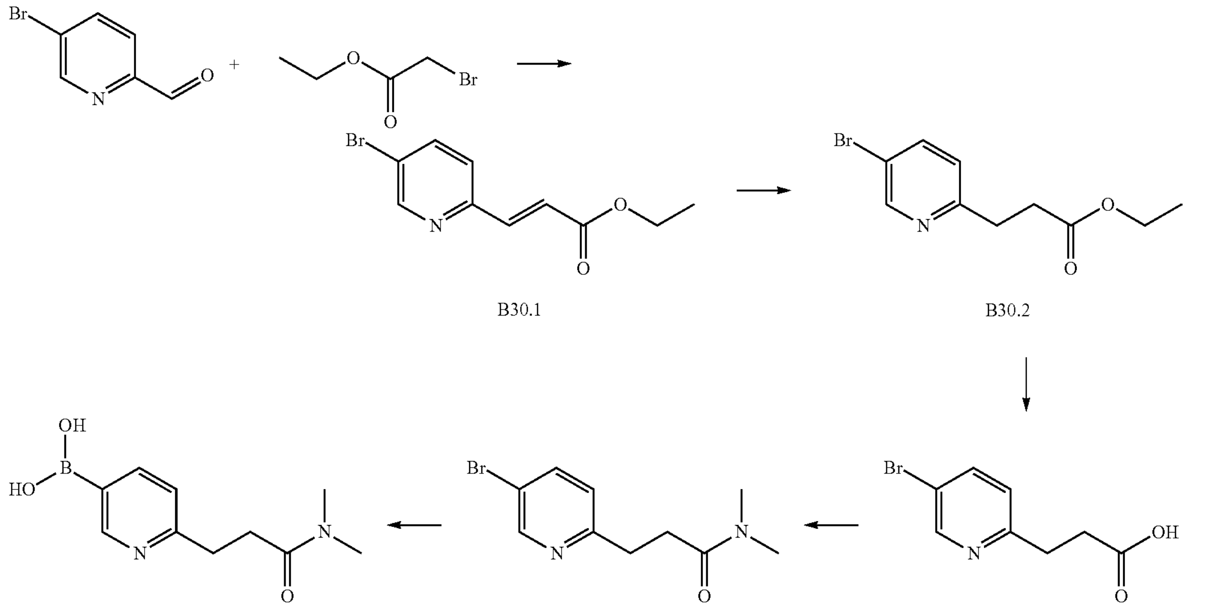

B30.1 B30.2

B30 B30.4 B30.3

(E)-Ethyl 3-(5-bromopyridin-2-yl)acrylate (B30.1): A mixture of 5-bromopicolinaldehyde (0.93 g, 5 mmol), ethyl 2-bromoacetate (1.25 g, 7.5 mmol), $NaHCO_3$ (1.26 g, 15 mmol), $PPh_3$ (1.83 g, 7 mmol), water (10 mL) in 5 mL ethyl acetate was stirred for 16 h at 25° C. under $N_2$ atmosphere. The mixture was diluted with water (30 mL), extracted with ethyl acetate (40 mL×2), the combined organic layers was washed with water (40 mL) and brine (40 mL), dried over $Na_2SO_4$, concentrated. The residue was purified on silica gel (PE/EA=6:1) to give the title compound (1.1 g, 85%) as a white solid. LC-MS: $[M+H]^+=256.0$.

Ethyl 3-(5-bromopyridin-2-yl)propanoate (B30.2): A mixture of B30.1 (1 g, 3.9 mmol), CuCl (406 mg, 4.1 mmol) in 20 mL MeOH was cooled to 0° C., $NaBH_4$ (1.18 g, 31.2 mmol) was added in portions, the mixture was stirred for 5 h at 0° C. under $N_2$ atmosphere. The mixture was filtered, concentrated to dryness. The residue was purified on silica gel (PE/EA=0 to 20%) to give the title compound (600 mg, 60%) as a colorless oil. LC-MS: $[M+H]^+=260.0$.

3-(5-Bromopyridin-2-yl)propanoic acid (B30.3): A mixture of ethyl B30.2 (600 mg, 2.32 mmol), NaOH (928 mg, 23.2 mmol) in the mixed solution of THE (14 mL), water (7 mL) and MeOH (7 mL) was stirred for 2 h at 40° C. The mixture was adjusted to pH=2-3 by 1N HCl, then concentrated. The residue was diluted with water (30 mL), extracted with DCM/MeOH (10/1) (40 mL×4), dried over $Na_2SO_4$, concentrated to give the title compound (375 mg, 70%) as a white solid. LC-MS: $[M+H]^+=232.0$.

3-(5-Bromopyridin-2-yl)-N,N-dimethylpropanamide (B30.4): A mixture of B30.3 (400 mg, 1.74 mmol), dimethylamine hydrochloride (570 mg, 6.96 mmol), HATU (992 mg, 2.61 mmol), DIEA (1.79 g, 13.92 mmol) and DCM (20 mL) was stirred for 5 h at 25° C. under $N_2$ atmosphere. The mixture was diluted with water (30 mL), extracted with EA (30 mL×3), the combined organics was washed with water (40 mL) and brine(40 mL), dried over $Na_2SO_4$, concentrated. The residue was purified by Prep-HPLC to give the title compound (260 mg, 58%) as a white solid. LC-MS: $[M+H]^+=259.0$.

Intermediate B30: The title compound was prepared by a method similar to that of Intermediate B18 by replacing B18.1 with B30.4. The crude product was used in the next step without further purification. LC-MS: $[M+H]^+=305.3$ for boronic acid pinacol ester; 223.1 for boronic acid.

Intermediate B31: 2,6-dimethyl-4-(5-(4,4,5,5-tetramethyl-1,3,2-dioxaborolan-2-yl)pyridin-2-yl)morpholine

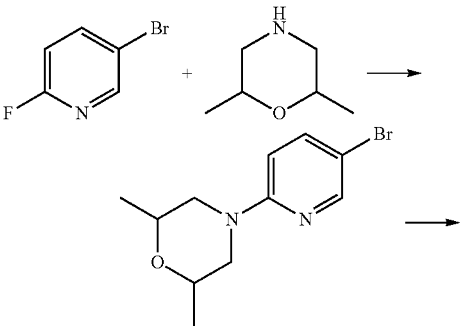

B31.1

-continued

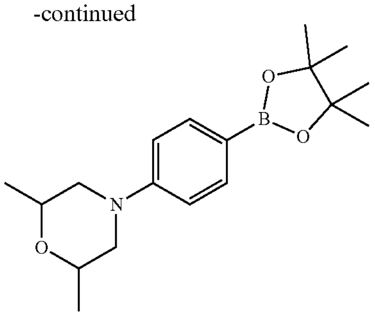

B31

4-(5-Bromopyridin-2-yl)-2,6-dimethylmorpholine (B31.1): 5-bromo-2-fluoropyridine (3.0 g, 20 mmol) was added to a solution of 2,6-dimethylmorpholine (6.9 g, 60 mmol) and $K_2CO_3$ (8.3 g, 60 mmol) in 10 mL DMSO. The reaction mixture was heated at 130° C. for 16 h. The reaction mixture was cooled to rt and 100 mL $H_2O$ was added, followed by extraction with EtOAc (2×100 mL). The organic layers were washed sequentially with brine (100 mL), dried over $Na_2SO_4$ and concentrated under reduced pressure to give the title compound (4.38 g, 81%) as a yellow solid. LC-MS: $[M+H]^+$=273.0.

Intermediate B31: The title compound was prepared by a method similar to that of Intermediate B1 by replacing B1.4 with B31.1. LC-MS: $[M+H]^+$=319.0.

Intermediate B32: 4,4,5,5-tetramethyl-2-(4-(2-(methylsulfonyl)ethoxy)phenyl)-1,3,2-dioxaborolane

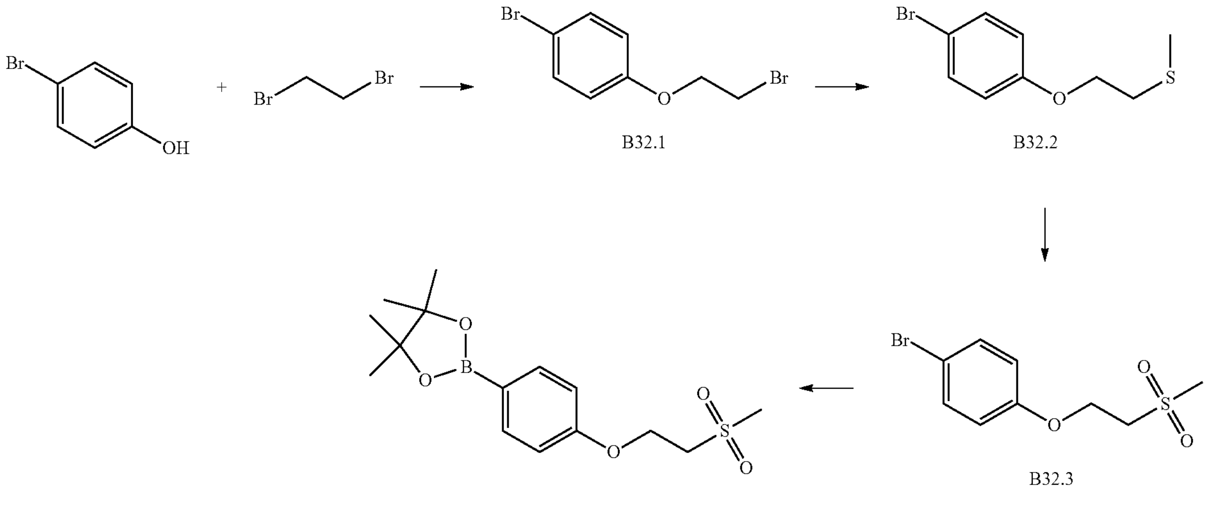

B32.1 B32.2 B32.3 B32

1-Bromo-4-(2-bromoethoxy)benzene (B32.1): A mixture of 4-bromophenol (4.3 g, 25 mmol), 4-bromophenol (12.7 g, 67.5 mmol), NaOH (1.6 g, 40 mmol) in $H_2O$ (20 mL) was heated to reflux for 11 h. DCM (50 mL) was added. The organic phase was separated and concentrated to give the title compound (4.2 g, 60%). The crude product was used in the next step without further purification.

(2-(4-Bromophenoxy)ethyl)(methyl)sulfane (B32.2): A mixture of B32.1 (4.3 g, 25 mmol), $CH_3SNa$ (6.12 g, 45 mmol) in DMF (50 mL) was heated at 90° C. for 18 h. DCM (50 mL) and water (100 mL) was added. The organic phase was separated and concentrated to give the title compound (2.9 g, 80%). The crude product was used in the next step without further purification.

1-Bromo-4-(2-(methylsulfonyl)ethoxy)benzene (B32.3): A mixture of B32.2 (2.9 g, 12 mmol), m-CPBA (7.28 g, 36 mmol) in DCM (50 mL) was stirred at rt for 18 h. DCM (50 mL) and water (100 mL) was added. The organic phase was separated and concentrated. The residue was purified with silica gel chromatography eluted with PE/EtOAc=1/1 to give the title compound (2.7 g, 80%) as a pale yellow solid. The crude product was used in the next step without further purification.

Intermediate B32: The title compound was prepared by a method similar to that of Intermediate B1 by replacing B1.4 with B32.3. LC-MS: $[M+H]^+$=327.2.

Intermediate B33: 2-(2-(3,3-difluoropyrrolidin-1-yl)ethyl)-5-(4,4,5,5-tetramethyl-1,3,2-dioxaborolan-2-yl)pyridine

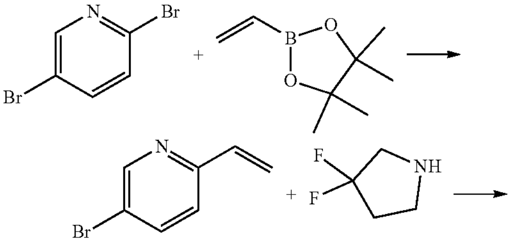

B33.1

-continued

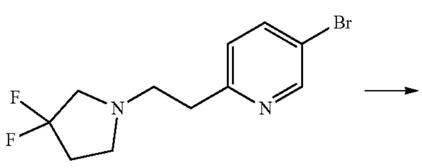

B33.2

-continued

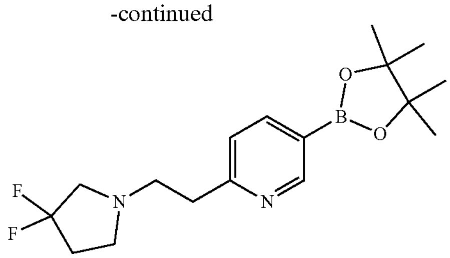

B33

5-Bromo-2-vinylpyridine (B33.1): $Pd(PPh_3)_4$ (500 mg, 0.4 mmol) was added to a stirred suspension of 2,5-dibromopyridine (5 g, 21 mmol) and 4,4,5,5-tetramethyl-2-vinyl-1,3,2-dioxaborolane (3.6 g, 23 mmol) in a mixture of 1,4-dioxane (40 mL) and a saturated solution of sodium carbonate (12 mL). The mixture was stirred at 100° C. for 16 h in a sealed tube under nitrogen. The mixture was diluted with dichloromethane (200 mL) and washed with water (100 mL). The organic layer was separated, dried over $Na_2SO_4$, filtered and concentrated under reduced pressure. The crude product was purified by flash column chromatography (silica gel column, dichloromethane in heptane 20/80 to 80/20) to give the title compound (2.9 g, 77%). The crude product was used in the next step without further purification. LC-MS: $[M+H]^+$=186.0.

5-Bromo-2-(2-(3,3-difluoropyrrolidin-1-yl)ethyl)pyridine (B33.2): B33.1 (500 mg, 2.72 mmol) was added to a solution of 3,3-difluoropyrrolidine (930 mg, 8.16 mmol) in acetic acid (3 mL), and the mixture was stirred at 100° C. for 18 h. A saturated aqueous sodium bicarbonate solution was added, and the mixture was extracted with ethyl acetate (50 mL). The organic layer was dried over anhydrous sodium sulfate, concentrated, and the residue was then purified by column chromatography on silica gel (hexane:ethyl acetate=10:1, chloroform:methanol=10:1) to give the title compound (500 mg, 68%). The crude product was used in the next step without further purification. LC-MS: $[M+H]^+$=293.0.

Intermediate B33: The title compound was prepared by a method similar to that of Intermediate B1 by replacing B1.4 with B33.2. LC-MS: $[MH]^+$=257.2 (boronic acid's $MH^+$).

Intermediate B34: (6-(2-(dimethylamino)ethyl)pyridin-3-yl)boronic Acid

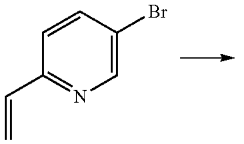

B33.1

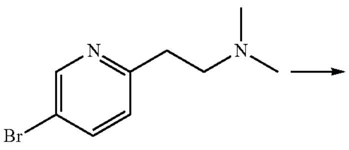

B34.1

-continued

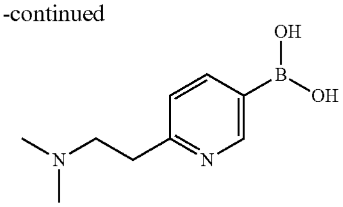

B34

2-(5-Bromopyridin-2-yl)-N,N-dimethylethanamine (B34.1): A solution of 2.0 M dimethylamine (27 mL, 54 mmol) in THE was added to a solution of 5-bromo-2-vinylpyridine (1.0 g, 5.4 mmol) in acetic acid (7 mL). The mixture was stirred at 80° C. overnight and at 90 CC for two days, then quenched by saturated aqueous sodium bicarbonate solution, extracted with ethyl acetate, dried over anhydrous sodium sulfate. concentrated, and the residue was then purified by column chromatography on silica gel (hexane: ethyl acetate=10:1, chloroform:methanol=10:1) to give the title compound (900 mg, 60%). The crude product was used in the next step without further purification. LC-MS: $[M+H]^+$=231.1.

Intermediate B34: The title compound was prepared by a method similar to that of Intermediate B18 by replacing B18.1 with B34.1. LC-MS: $[M+H]^+$=195.2.

Intermediate B35: 2-(methoxymethyl)-3-methyl-5-(4,4,5,5-tetramethyl-1,3,2-dioxaborolan-2-yl)pyridine

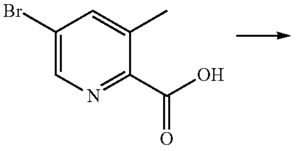

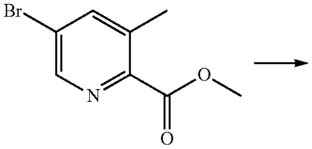

B35.1

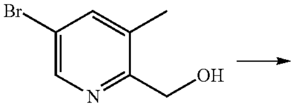

B35.2

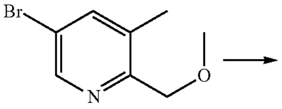

B35.3

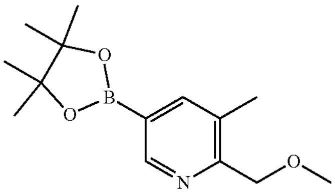

B35

Methyl 5-bromo-3-methylpicolinate (B35.1): To a solution of 5-bromo-3-methylpicolinic acid (500 mg, 2.31 mmol) in MeOH (10 mL) was added $SOCl_2$ (275 mg, 23.1 mmol) at rt. Then the reaction mixture was stirred at 90° C. for 4 h. The solvent was removed to give the title compound (500 mg, 94%) as a off white solid. The crude product was used in the next step without further purification. LC-MS: $[M+H]^+$=232.0.

(5-Bromo-3-methylpyridin-2-yl)methanol(B35.2): To a solution of B35.1 (500 mg, 2.17 mmol) in MeOH (15 mL) was added $NaBH_4$ (826 mg, 21.7 mmol) at rt. Then the reaction mixture was stirred at 90° C. for 2 h. The solvent was removed. The residue was dissolved in EtOAc (20 mL) and washed with water (15 mL). The organic phase was concentrated to give the title compound (300 mg, 68%) as a pale yellow oil. The crude product was used in the next step without further purification. LC-MS: $[M+H]^+$=204.2.

5-Bromo-2-(methoxymethyl)-3-methylpyridine (B35.3): Methyl iodide (254 mg, 1.79 mmol) was added to a stirred suspension of B35.2 (300 mg, 1.49 mmol) and NaH (89 mg, 2.23 mmol) in THE (8 mL). The reaction mixture was stirred at rt for 1 h. DCM (20 mL) and water (15 mL) were added. The organic phase was separated and concentrated. The residue was purified with Prep-TLC (PE/EtOAc=2/1) to give the title compound (310 mg, 96%) as a solid. The crude product was used in the next step without further purification. LC-MS: $[M+H]^+$=218.1.

Intermediate B35: The title compound was prepared by a method similar to that of Intermediate B1 by replacing B1.4 with B35.3. LC-MS: $[M+H]^+$=264.0.

Intermediate B36: 4-(2-(5-(4,4,5,5-tetramethyl-1,3,2-dioxaborolan-2-yl)pyridin-2-yl)ethyl)piperazin-2-one

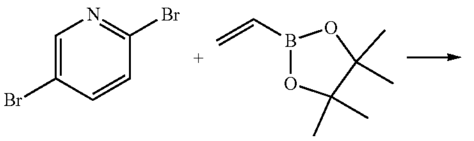

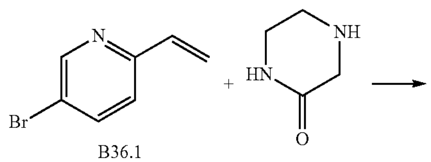

B36.1

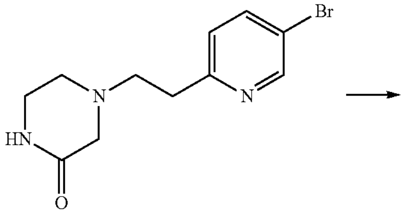

B36.2

-continued

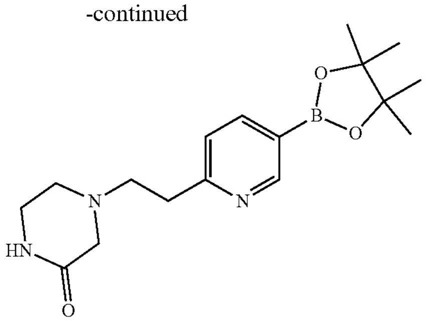

B36

The title compound was prepared by a method similar to that of Intermediate B33 by replacing 3,3-difluoropyrrolidine with piperazin-2-one. LC-MS: $[M+H]^+$=332.0.

Intermediate B37: 4-(5-(4,4,5,5-tetramethyl-1,3,2-dioxaborolan-2-yl)pyridin-2-yl)-1,4-diazepane-1-carbaldehyde

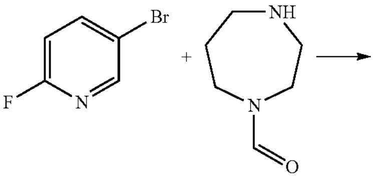

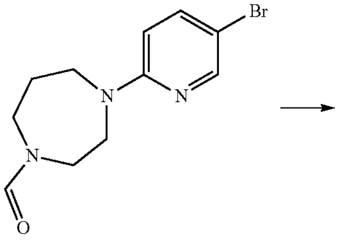

B37.1

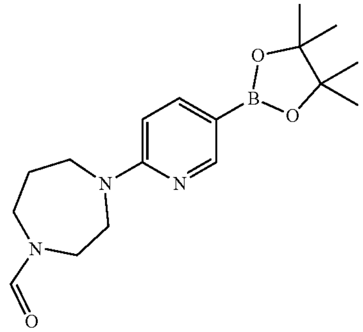

B37

The title compound was prepared by a method similar to that of Intermediate B31 by replacing 2,6-dimethylmorpholine with 1-formyl-1,4-diazepan-6-ylium. LC-MS: $[M+H]^+$=332.3.

Intermediate B38: 4-(2-(5-(4,4,5,5-tetramethyl-1,3,2-dioxaborolan-2-yl)pyridin-2-yl)ethyl)piperazine-1-carbaldehyde

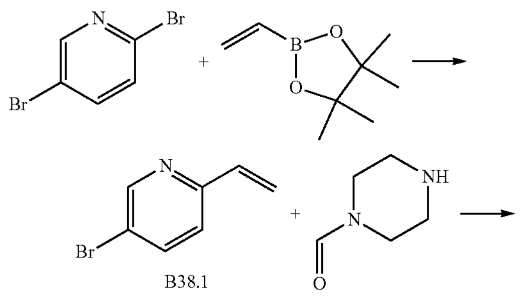

B38.1

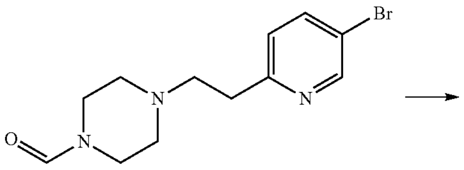

B38.2

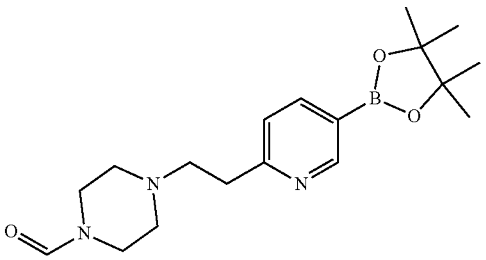

B38

The title compound was prepared by a method similar to that of Intermediate B33 by replacing 3,3-difluoropyrrolidine with piperazine-1-carbaldehyde. LC-MS: [M+H]+=346.3.

Intermediate B39: 2-(4-(5-(4,4,5,5-tetramethyl-1,3,2-dioxaborolan-2-yl)pyridin-2-yl)piperazin-1-yl)ethanol

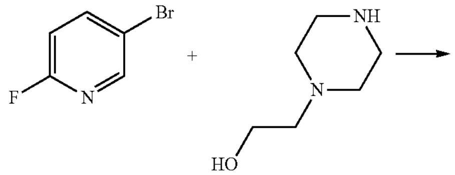

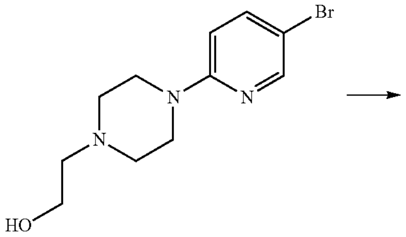

B39.1

-continued

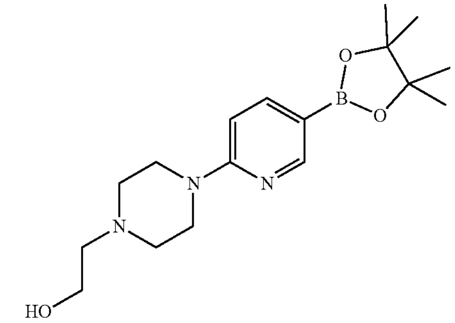

B39

The title compound was prepared by a method similar to that of Intermediate B31 by replacing 2,6-dimethylmorpholine with 2-(piperazin-1-yl)ethanol. LC-MS: [M+H]+=334.2.

Intermediate B40: (6-(Dimethylcarbamoyl)pyridin-3-yl)boronic Acid

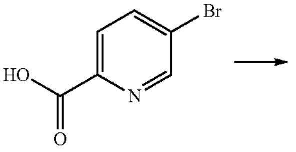

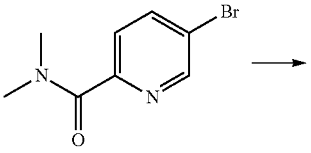

B40.1

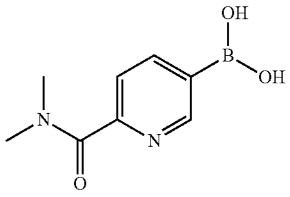

B40

5-Bromo-N,N-dimethylpicolinamide (B40.1): To a solution of 5-bromopicolinic acid (1.5 g, 7.42 mmol) in DCM (15 mL) was added Oxalyl chloride (5 mL) at 0° C. The mixture reaction was stirred at 40° C. for 1 hr, concentrated under reduced pressure. The residue was diluted with DCM (20 ml), and DIPEA (1.5 g) and dimethylamine (600 mg) was added successively. The mixture was stirred for 1 h, concentrated, the residue was purified by flash chromatography by using PE/EA 5:1 to afford the title compound (700 mg, 49%). The crude product was used in the next step without further purification. LC-MS: $[M+H]^+$=231.1.

Intermediate B40: The title compound was prepared by a method similar to that of Intermediate B18 by replacing B18.1 with B40.1. The crude product was used in the next step without further purification. LC-MS: $[M+H]^+$=195.4.

Intermediate B41: Pyrrolidin-1-yl(5-(4,4,5,5-tetramethyl-1,3,2-dioxaborolan-2-yl)pyridin-2-yl)methanone

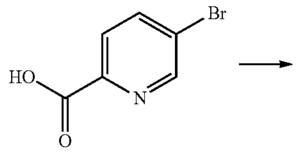

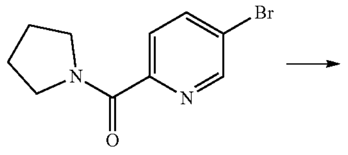

B41.1

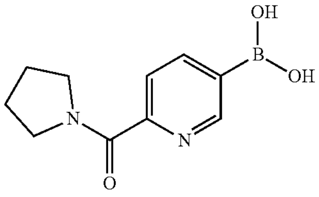

B41

(5-Bromopyridin-2-yl)(pyrrolidin-1-yl)methanone (1B41.1): The title compound was prepared by a method similar to that of Intermediate B40.1 by replacing dimethylamine with pyrrolidine.

Intermediate B41: To a solution of B41.1 (70 mg), bis (pinacolato)diboron (77 mg, 0.305 mmol) and KOAc (59 mg, 0.604 mmol) in dioxane (2 mL) was added Pd(dppf)$Cl_2$ (20 mg). The reaction mixture was heated at 110° C. for 2 hr under $N_2$. After cooling to rt, the mixture was filtered, the filtrate was used in the next step without further purification. LC-MS: $[M+H]^+$=303.2 (for boronic acid, LC-MS: $[M+H]^+$=221.2.)

Intermediate B42: N-methyl-5-(4,4,5,5-tetramethyl-1,3,2-dioxaborolan-2-yl)picolinamide

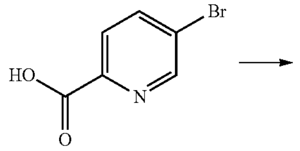

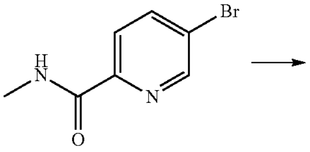

B42.1

-continued

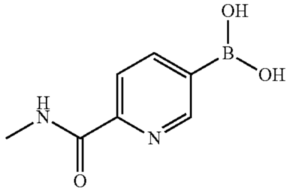

B42

The title compound was prepared by a method similar to that of Intermediate B41 by replacing dimethylamine with methanamine. The crude product was used in the next step without further purification. LC-MS: $[M+H]^+$=181.1.

Intermediate B43: N-Ethyl-5-(4,4,5,5-tetramethyl-1,3,2-dioxaborolan-2-yl)picolinamide

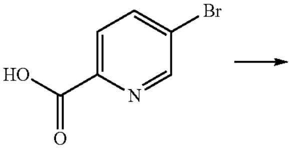

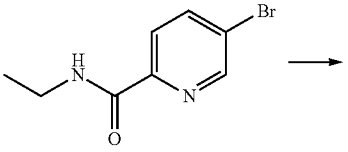

B43.1

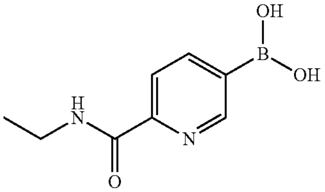

B43

The title compound was prepared by a method similar to that of Intermediate B41 by replacing dimethylamine with ethanamine. The crude product was used in the next step without further purification.

Intermediate B44: N-(2-(Dimethylamino)ethyl)-N-methyl-5-(4,4,5,5-tetramethyl-1,3,2-dioxaborolan-2-yl)picolinamide

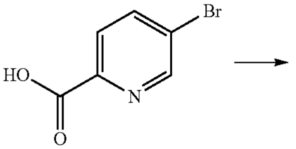

-continued

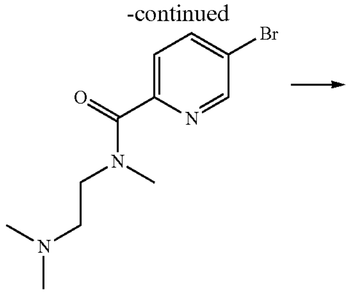

B44.1

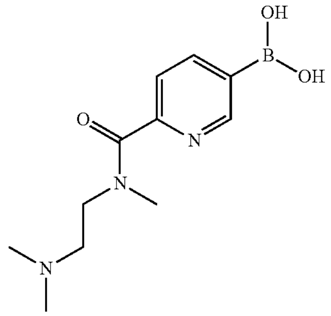

B44

The title compound was prepared by a method similar to that of Intermediate B41 by replacing dimethylamine with N1,N1,N2-trimethylethane-1,2-diamine. The crude product was used in the next step without further purification. LC-MS: $[M+H]^+$=252.2.

Intermediate B45: (5-(4,4-Dimethyl-4,5-dihydrooxazol-2-yl)pyridin-3-yl)boronic Acid

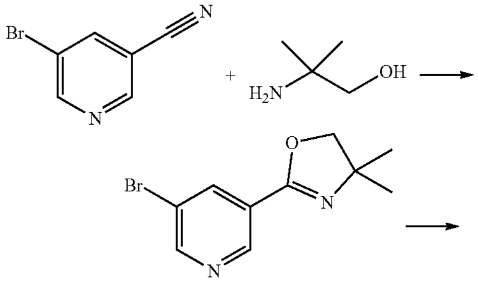

B45.1

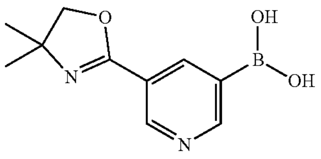

B45

2-(5-Bromopyridin-3-yl)-4,4-dimethyl-4,5-dihydrooxazole (B45.1): Zinc chloride (73.7 mg, 0.55 mmol) was placed in a 100 mL round bottom flask, melted three times under high pressure and allowed to cool to ambient temperature under $N_2$ before a solution of 5-bromonicotinonitrile (1 g, 5.5 mmol) and 2-amino-2-methylpropan-1-ol (513 mg, 5.8 mmol) in dry chlorobenzene (15 mL) was added. The resulting mixture was refluxed for 48 h under $N_2$. The volatiles were removed in vacuo and water (20 mL) was added. The aqueous layer was extracted with DCM (3×10 mL) and the combined organic extract was washed with water, brine, dried over $Na_2SO_4$ and concentrated in vacuo. The crude product was purified by flash chromatography on silica gel (PE\EA: 100\1 to 3\1) afforded the title compound (1 g, 71%) as a white solid. LC-MS: $[M+H]^+$=257.1.

Intermediate B45: The title compound was prepared by a method similar to that of Intermediate B18 by replacing B18.1 with B45.1. LC-MS: $[M+H]^+$=221.2.

Intermediate B46: (6-(4,4-dimethyl-4,5-dihydrooxazol-2-yl)pyridin-3-yl)boronic Acid

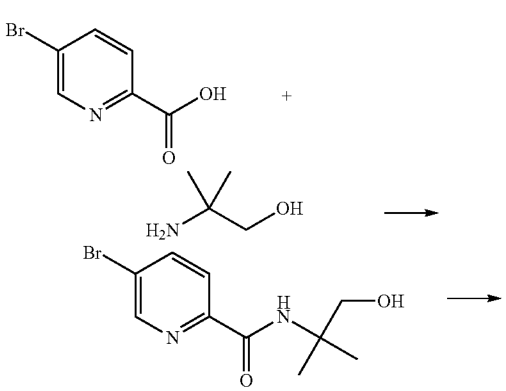

B46.1

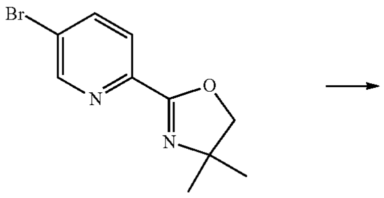

B46.2

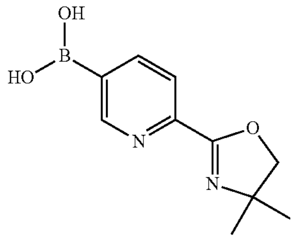

B46

5-Bromo-N-(1-hydroxy-2-methylpropan-2-yl)picolinamide (B46.1): Thionyl chloride (10 mL, 150 mmol) was added to solid 5-bromopicolinic acid (1.2 g, 6 mmol) at ambient temperature under $N_2$. The resulting mixture was refluxed for 2 h and the volatiles were removed in vacuo. The crude acid chloride was dissolved in dry DCM (20 mL) and the solution was slowly added at 0° C. to a solution of 2-amino-2-methylpropan-1-ol (1.6 g, 18 mmol) in DCM (5 mL). After stirring 48 h at ambient temperature, solvents were removed in vacuo and the crude product was purified by flash chromatography on silica gel (PE/EA=100/1 to 5/1) to the title compound (1.5 g, 93%) as a white solid. LC-MS: $[M+H]^+$=273.1.

2-(5-Bromopyridin-2-yl)-4,4-dimethyl-4,5-dihydrooxazole (B46.2): A solution of B46.1 (1 g, 3.7 mmol) in thionyl chloride (967 mmol, 5 mL) was stirred 12 h at ambient temperature. The solvent was removed in vacuo and dry DCM (20 mL) was added. The separated organic layer was washed with aqueous 2N NaOH (2×25 mL), dried over $MgSO_4$, and concentrated in vacuo. The crude product was purified by flash chromatography on silica gel (PE/EA=100/1 to 1/1) to afford the title compound (850 mg, 91%) as a white solid. LC-MS: $[M+H]^+$=257.0.

Intermediate B46: The title compound was prepared by a method similar to that of Intermediate B18 by replacing B18.1 with B46.2). LC-MS: $[M+H]^+$=221.1.

Intermediate B47: (5-(Methoxymethyl)-6-methylpyridin-3-yl)boronic Acid

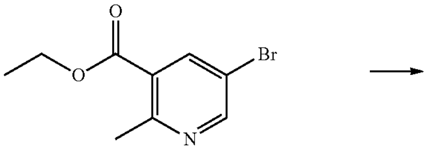

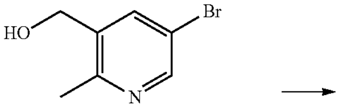

B47.1

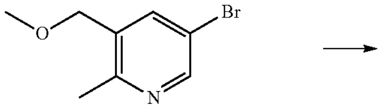

B47.2

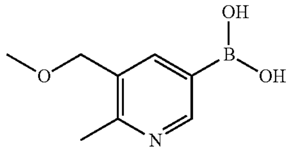

B47

(5-Bromo-2-methylpyridin-3-yl)methanol(B47.1): To a solution of ethyl 5-bromo-2-methylnicotinate (1.0 g, 4.1 mmoL) in MeOH (15 mL) was added sodium borohydride (500 mg, 12.5 mmol) portion wise at 0° C. After 1 h, the reaction was quenched by the addition of water (10 mL). The reaction was then extracted with DCM (3×10 mL). The extracts were combined, dried over $Na_2SO_4$, concentrated and purified by column chromatography on silica gel (PE/EA=100/1 to 5/1) to afford the title compound (650 mg, 79%) as a white solid. LC-MS: $[M+H]^+$=201.9.

5-Bromo-3-(methoxymethyl)-2-methylpyridine (B47.2): To a mixture of B47.1 (200 mg, 1.0 mmol) in THE (10 ml) was added NaH (60% wt, 48 mg, 1.2 mmol) slowly at 0° C. The mixture was stirred at 0° C. for 30 min, then $CH_3I$ (213 mg, 1.5 mmol) was added dropwise. The reaction mixture was stirred at 0° C. for another 2 h, quenched by water (5 ml), extracted with EA (10 ml×3), the combined extracts were washed with brine (10 ml×3), dried over $Na_2SO_4$, concentrated and purified by Prep-TLC (silica gel, UV254, PE/EA=5/1) to give the title compound (100 mg, 70%) as a clear oil. LC-MS: $[M+H]^+$=217.9.

Intermediate B47: The title compound was prepared by a method similar to that of Intermediate B18 by replacing B18.1 with B47.2. LC-MS: $[M+H]^+$=182.2.

Intermediate C1: 8-bromo-N-((5-fluorobenzofuran-4-yl)methyl)-[1,2,4]triazolo[4,3-c]pyrimidin-5-amine

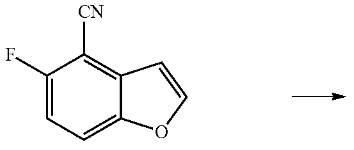

A1.3

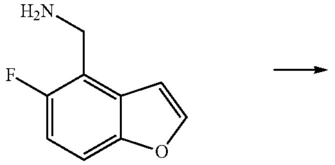

C1.1

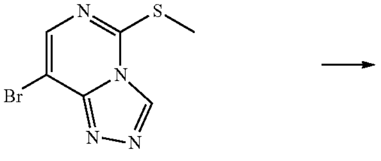

3

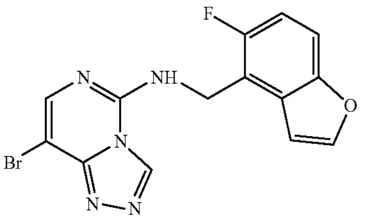

C1

(5-Fluorobenzofuran-4-yl)methanamine (C1.1): To a solution of 5-fluorobenzofuran-4-carbonitrile (A1.3)(1 g, 6.2 mmol) in MeOH (15 mL) and $NH_4OH$ (2 mL) was added Raney Ni (500 mg) under $N_2$. The resulting suspension was degassed under vacuum and backfilled with $H_2$ via a balloon. The reaction was then stirred at RT under a balloon of $H_2$ overnight, filtered through with a pad Celite. The filtrate was concentrated was purified by flash chromatography (DCM-DCM\MeOH=10\1) to give the title compound (900 mg, 88%) as a yellow oil. LC-MS: $[M+H]^+$=166.

8-Bromo-N-((5-fluorobenzofuran-4-yl)methyl)-[1,2,4]triazolo[4,3-c]pyrimidin-5-amine (C1): A mixture of (5-fluorobenzofuran-4-yl)methanamine (C1.1) (203 mg, 1.23 mmol) and 8-bromo-5-(methylthio)-[1,2,4]triazolo[4,3-c]pyrimidine (3) (200 mg, 0.82 mmol) was stirred at 40° C. for 12 h. After the completion of the reaction, EA (15 mL) was added. The solid was filtered and washed with EA (3 mL×3). The solid was collected to afford the title compound as a white solid (50 mg, 17%). LC-MS: $[M+H]^+$=362.

Intermediate C2: (4-((8-bromo-[1,2,4]triazolo[4,3-f] pyrimidin-5-ylamino)methyl)-5-fluoro-2,3-dihydrobenzofuran-3-ol

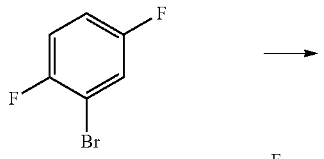

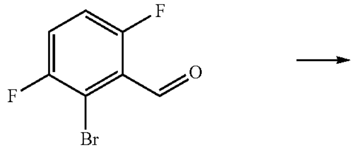

C2.1

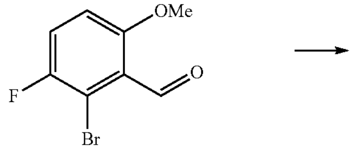

C2.2

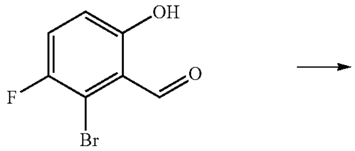

C2.3

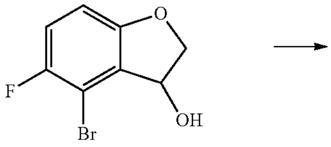

C2.4

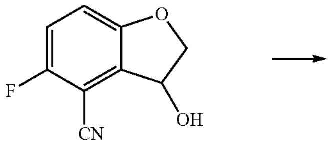

C2.5

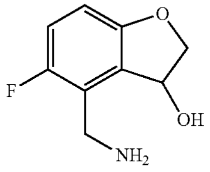

C2.6

2-Bromo-3,6-difluorobenzaldehyde (C2.1): To a solution of 2-bromo-1,4-difluorobenzene (16 g, 83 mol) in 200 mL THF under $N_2$ atmosphere at −78° C. was added LDA (54 mL, 108 mmol) dropwise. After stirring at −78° C. for 45 min, DMF (18.2 g, 249 mmol) was added. The mixture was stirred for another 2 h at −78° C. The reaction mixture was warmed up to 0° C., added 200 mL and sat. $NH_4Cl$ was added. The resulting mixture was extracted with EtOAc (200 mL×2). The combined organic layer was washed with brine (400 mL×1), dried over anhydrous $Na_2SO_4$, filtered and concentrated under vacuum to give crude product. The crude product was purified by column chromatography (silica, EtOAc/PE=1/30) to give the title compound (11 g, 60%) as a yellow solid. 1H NMR (500 MHz, $CDCl_3$) δ ppm 7.57-7.34 (m, 2H), 10.20 (dd, 1H).

2-Bromo-3-fluoro-6-methoxybenzaldehyde (C2.2): To a solution of 2-bromo-3,6-difluorobenzaldehyde (C2.1)(8.4 g, 38.0 mmol) in dry THF (40 mL) and MeOH (80 mL) was added a solution of MeONa (2.26 g, 41.8 mmol) in MeOH (40 mL) at 60° C. in a period of 30 min, and the resulting mixture was stirred at 60° C. for 16 h. Solvent was removed and water (100 mL) was added, and the resulting mixture was stirred at RT for 30 min. The solid was collected by filtration, and then triturated with PE/EA 10:1 to obtain the title compound as a yellow solid (7.04 g, 80%). $^1H$ NMR (500 MHz, $CDCl_3$) δ ppm 3.92 (s, 3H), 6.94 (dd, 1H), 7.31-7.24 (m, 1H), 10.38 (s, 1H). LC-MS: $[M+H]^+$=233.1.

2-Bromo-3-fluoro-6-hydroxybenzaldehyde (C2.3): To a solution of 2-bromo-3-fluoro-6-methoxybenzaldehyde (C2.2) (5 g, 21.4 mol) in 100 mL DCM under $N_2$ at −78° C. was added $BBr_3$ (26 mL, 26 mmol, 1.0 mol/L in DCM) dropwise. The solution was stirred at −78° C. for 30 min and at rt overnight. 100 mL sat. $NH_4Cl$ was added at 0° C. and stirred for 20 min. The resulting mixture was extracted with DCM (150 mL×2). The combined organic layer was washed with 400 mL brine, dried ($Na_2SO_4$), filtered and concentrated in vacuo. The resulting crude product was purified by column chromatography (gradient elution with 0-50% EA in PE) to give the title compound (4 g, 85%) as a yellow solid: $^1H$ NMR (500 MHz, $CDCl_3$) δ ppm 6.94 (dd, 1H), 7.29 (dt, 1H), 10.33 (s, 1H), 11.78 (s, 1H).

5-fluoro-3-hydroxy-2,3-dihydrobenzofuran-4-carbonitrile (C2.5): A solution of 2-bromo-3-fluoro-6-hydroxybenzaldehyde (C2.4) (2.7 g, 11.6 mol), $Zn(CN)_2$ (2 g, 17.4 mmol) and $Pd(PPh_3)_4$ (1.4 g, 1.2 mmol) in 50 mL DMF was stirred under $N_2$ at 120° C. for 16 h. The reaction mixture was cooled to rt and 150 mL of water was added. The mixture was extracted with EtOAc (200 mL×2). The combined organic layer was washed with 200 mL brine, dried ($Na_2SO_4$), filtered and concentrated in vacuo. The resulting crude product was purified by column chromatography (gradient elution: 0-50% EA in PE) to give the title compound (1 g, 60%) as a white solid. $^1H$ NMR (500 MHz, $CDCl_3$) δ ppm 2.91 (d, 1H), 4.55 (dd, 1H), 4.69 (dd, 1H), 5.63 (s, 1H), 7.17-7.01 (m, 2H).

4-(Aminomethyl)-5-fluoro-2,3-dihydrobenzofuran-3-ol (C2.6): To a solution of 5-fluoro-3-hydroxy-2,3-dihydrobenzofuran-4-carbonitrile (C2.5) (1 g, 5.6 mol) in 20 mL THF was added $BH_3$-THF (22.4 mL, 22.4 mmol) dropwise. The solution was stirred at 60° C. for 16 h. The reaction mixture was cooled to rt, and MeOH was added carefully. The resulting mixture was stirred for 30 min. The process was repeated for three times. The crude product was purified by prep-H PLC to give the title compound (600 mg, 60%) as a white solid. $^1H$ NMR (500 MHz, DMSO-$d_6$) δ ppm 3.71 (d, 1H), 3.89 (d, 1H), 4.28 (dd, 1H), 4.52 (dd, 1H), 5.47 (dd, 1H),), 6.70 (dd, 1H), 7.00 (dd, 1H).

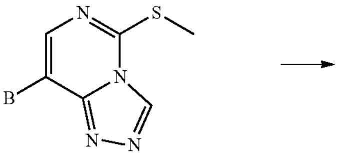

3

-continued

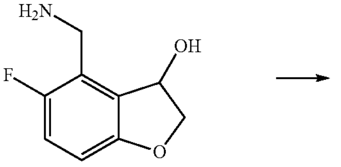

C2.6

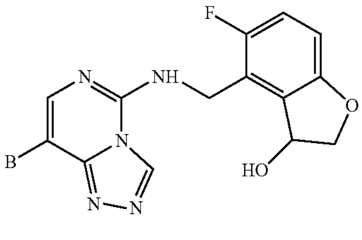

C2

4-(((8-Bromo-[1,2,4]triazolo[4,3-c]pyrimidin-5-yl) amino)methyl)-5-fluoro-2,3-dihydrobenzofuran-3-ol (C2): To a solution of 4-(aminomethyl)-5-fluoro-2,3-dihydrobenzofuran-3-ol (3) (400 mg, 1.6 mmol) in 2 mL dichloromethane was added 4-(aminomethyl)-5-fluoro-2,3-dihydrobenzofuran-3-ol (C2.6) (586 mg, 3.2 mmol) and the resulting suspension was stirred at 100° C. for 3 h. The mixture was purified by column chromatography (eluted with 10% MeOH in DCM) to give the title compound (105 mg, 17%) as a white solid. LC-MS: $[M+H]^+=382.0$.

Intermediate C3: 8-bromo-N-((5-fluoro-2-methoxy-2,3-dihydrobenzofuran-4-yl)methyl)-[1,2,4]triazolo [4,3-c]pyrimidin-5-amine

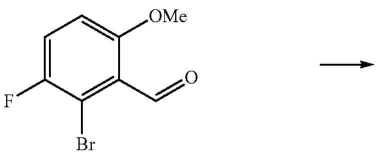

C2.2

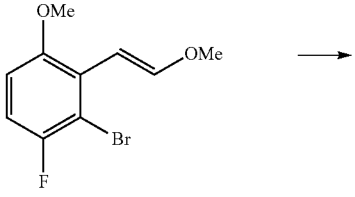

C3.1

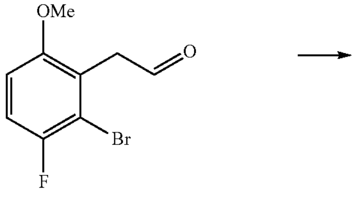

C3.2

-continued

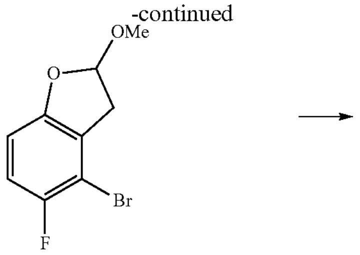

C3.3

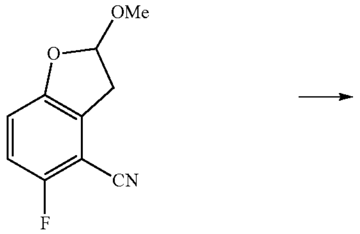

C3.4

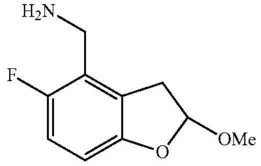

C3.5

2-Bromo-1-fluoro-4-methoxy-3-(2-methoxyvinyl)benzene (C3.1): To a suspension of (methoxymethyl)triphenylphosphonium (57.41 g, 0.167 mol) in dry THF (250 mL) was added LHMDS (1 M in THF, 178.5 mL, 178.5 mmol) at 0° C. over a period of 30 min. The resulting mixture was stirred at 0° C. for 45 min, followed by addition of a solution of 2-bromo-3-fluoro-6-methoxybenzaldehyde (C2.2) (26.0 g, 0.11 mol) in dry THF (100 mL) over in 30 min. The resulting mixture was stirred at 25° C. for 2.5 h, and quenched with $NH_4Cl$ (200 mL), and extracted with $Et_2O$ (150 mL×2). The combined organic layer was washed with brine (150 mL×1), dried ($Na_2SO_4$), filtered and concentrated in vacuo. The residue was purified by column chromatography (silica, eluent: EtOAc in PE: 3%) to afford the title compound as a yellow solid (25.68 g, 88.2%). $^1H$ NMR (400 MHz, $CDCl_3$) δ ppm 7.53 (d, 1H), 6.92-6.82 (m, 1H), 6.77 (dd, 1H), 5.99 (d, 1H), 3.84 (s, 3H), 3.75 (s, 3H).

2-(2-Bromo-3-fluoro-6-methoxyphenyl)acetaldehyde (C3.2): To a solution of 2-bromo-1-fluoro-4-methoxy-3-(2-methoxyvinyl)benzene (C3.1) (25.68 g, 98.4 mmol) in THF (200 mL) was added 3 N HCl (100 mL, 300 mmol). The resulting mixture was heated at 60° C. for 10 h, cooled to rt and extracted with DCM (130 mL×3). The combined organic layer was washed with $NaHCO_3$ solution (150 mL×1), brine (150 mL×1), dried ($Na_2SO_4$), filtered and concentrated in vacuo. The residue was purified with column chromatography (silica, eluted with EtOAc in PE: 2%~4%). The crude product was triturate with PE/EtOAc (10:1, 30 mL) for 1 h. The solid was collected by filtration, washed with PE, and dried in vacuo to afford the title compound as a white solid (13.5 g, 55.5%). $^1H$ NMR (500 MHz, $CDCl_3$) δ ppm 3.80 (s, 3H), 3.96 (d, 2H), 6.82 (dd, 1H), 7.07 (dd, 1H), 9.67 (t, 1H).

4-Bromo-5-fluoro-2-methoxy-2,3-dihydrobenzofuran (C3.3): To a solution of 2-(2-bromo-3-fluoro-6-methoxyphenyl)acetaldehyde (C3.2) (11.5 g, 46.56 mmol) in DCM (100 mL) at −78° C. was added $BBr_3$ (1M in DCM, 140 mL, 140 mmol) dropwise in 30 min. The resulting mixture was warmed to rt and stirred for 4 h. The mixture was cooled to 0° C., quenched with MeOH (30 mL) carefully and stirred at 0° C. for 2 h. The resulting mixture was extracted with DCM (100 mL×3), and the combined organic layer was washed with satd. $NaHCO_3$ (150 mL×1), brine (150 mL×1), dried ($Na_2SO_4$), filtered and concentrated in vacuo. The residue was purified by column chromatography (silica, eluted with EtOAc in PE 1.0%-4.0%) to afford the title compound as a white solid (8.6 g, 75%). $^1$H NMR (500 MHz, $CDCl_3$) δ ppm 3.06 (dd, 1H), 3.33 (dd, 1H), 3.52 (s, 3H), 5.67 (dd, 1H), 6.70 (dd, 1H), 6.90 (t, 1H).

5-Fluoro-2-methoxy-2,3-dihydrobenzofuran-4-carbonitrile (C3.4): A mixture of 4-bromo-5-fluoro-2-methoxy-2,3-dihydrobenzofuran (C3.3) (4.0 g, 16.19 mmol), $Zn(CN)_2$ (3.8 g, 32.39 mmol), $Pd(PPh_3)_4$ (936 mg, 0.81 mmol) in DMF (35 mL) was heated at 120° C. for 16 h. The reaction mixture was extracted with EtOAc (50 mL×4). The combined organic layers were washed with LiCl (5% aq. 30 mL×2), brine (15 mL×1), dried ($Na_2SO_4$), filtered and concentrated in vacuo. The residue was purified by column chromatography (silica, eluted with EtOAc in PE 2%-4%) to afford the title compound as a white solid (2.0 g, 64%). $^1$H NMR (500 MHz, $CDCl_3$) δ ppm 3.21 (dd, 1H), 3.48 (dd, 1H), 3.53 (s, 3H), 5.73 (dd, 1H), 7.04-6.92 (m, 2H).

(5-Fluoro-2-methoxy-2,3-dihydrobenzofuran-4-yl)methanamine (C3.5): A mixture of 5-fluoro-2-methoxy-2,3-dihydrobenzofuran-4-carbonitrile (C3.4) (2.0 g, 8.1 mmol), Raney Ni (0.2 g), in 7 N $NH_3$ in MeOH (60 mL) and MeOH (30 mL) was purged with $H_2$ and stirred at rt under $H_2$ for 30 min. The reaction mixture was filtered with Celite and washed with MeOH (100 mL). The filtrate was concentrated in vacuo, and the residue was purified with column chromatography (silica, eluted with EtOAc in PE 10%-40%; then 1 N $NH_3$ in MeOH/DCM 10%-15%) to afford the title compound as a yellow oil (1.85 g, 90%). $^1$H NMR (500 MHz, $CDCl_3$) δ ppm 3.07 (d, 1H), 3.36 (dd, 1H), 3.55-3.48 (m, 3H), 3.81 (d, 2H), 5.65 (dd, 1H), 6.67 (dd, 1H), 6.84 (t, 1H). LC-MS: $[M+H]^+$=198.2.

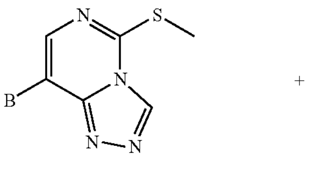

3

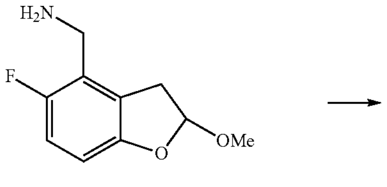

C3.5

-continued

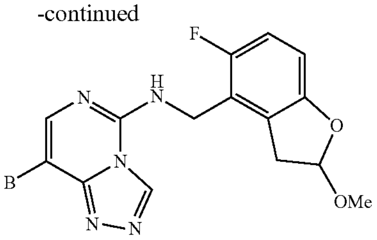

C3

8-Bromo-N-((5-fluoro-2-methoxy-2,3-dihydrobenzofuran-4-yl)methyl)-[1,2,4]triazolo[4,3-c]pyrimidin-5-amine (C3): A mixture of (5-fluoro-2-methoxy-2,3-dihydrobenzofuran-4-yl)methanamine (C3.5) (500 mg, 2.54 mmol), 8-bromo-5-(methylthio)-[1,2,4]triazolo[4,3-c]pyrimidine (3) (320 mg, 1.30 mmol) in DCM (2 mL) was heating at 50° C. in a open vessel overnight. The reaction mixture was purified by column chromatography (silica, eluted with EtOAc in PE 10%~50%; then MeOH in DCM 1%-3.5%) to afford the title compound as a yellow solid (230 mg, 46%). $^1$H NMR (500 MHz, $CDCl_3$) δ ppm 3.20 (d, 1H), 3.44 (dd, 1H), 3.48 (s, 3H), 4.79-4.69 (m, 2H), 5.63 (dd, 1H), 6.65 (dd, 1H), 6.79 (t, 1H), 6.97 (t, 1H), 7.79 (s, 1H), 9.10 (s, 1H). LC-MS: $[M+H]^+$=394.0.

Example 1

8-(1,3-Dimethyl-1H-pyrazol-5-yl)-N-((5-fluoro-2,3-dihydrobenzofuran-4-yl)methyl)-[1,2,4]triazolo[4,3-c]pyrimidin-5-amine

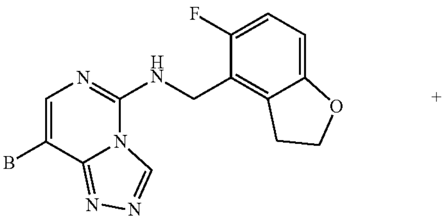

A1

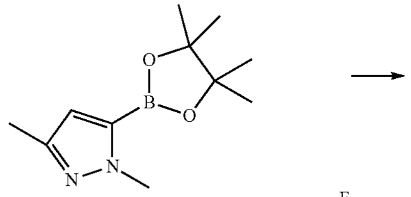

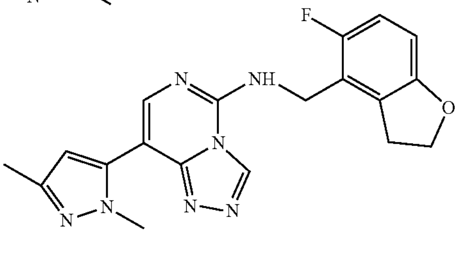

Example 1

To a solution of A1 (70 mg, 0.19 mmol) in dioxane (3 mL) and $H_2O$ (1 mL) was added 1,3-dimethyl-1H-pyrazol-5- ylboronic acid (43.2 mg, 0.31 mmol), $NaHCO_3$ (49 mg, 0.58 mmol) and Pd(dppf)$Cl_2$ (14.1 mg, 0.019 mmol). The mixture was heated at 95° C. and stirred for 40 min, then concentrated under reduced pressure. The crude product was purified by prep-HPLC to give the title compound (11 mg, 15%) as a white solid. $^1$H-NMR (400 MHz, DMSO-$d_6$) δ ppm 2.19 (s, 3H), 3.18 (t, 2H), 3.73 (s, 3H), 4.55 (t, 2H), 4.72 (s, 2H), 6.29 (s, 1H), 6.72 (dd, 1H), 6.95 (dd, 1H), 7.74 (s, 1H), 8.84 (br s, 1H), 9.47 (s, 1H). LC-MS: $[M+H]^+$=380.2.

Example 2

N-((5-Fluoro-2,3-dihydrobenzofuran-4-yl)methyl)-8-(2-methylpyridin-3-yl)-[1,2,4]triazolo[4,3-c]pyrimidin-5-amine

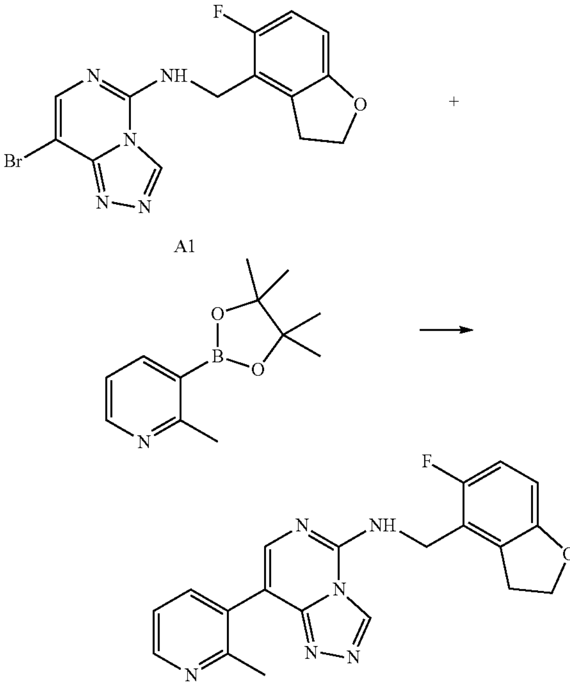

Example 2

To a mixture of A1 (40 mg, 0.110 mmol) in 1,4-dioxane (3 mL), MeCN (0.30 mL) and water (0.30 mL) was added (2-methylpyridin-3-yl)boronic acid (30.1 mg, 0.220 mmol), potassium carbonate (45.5 mg, 0.330 mmol) and Pd($Ph_3P$)$_4$ (12.69 mg, 10.98 µmol). The resulting mixture was stirred under $N_2$ at 110° C. for 3 h, cooled to rt, and evaporated under vacuum. The residue was purified on flash chromatography (DCM:MeOH=10:1) to afford Example 2 as a white solid (20 mg, 46.0%).

Alternatively, Example 2 was prepared as follows. To a suspension of A1 (25.5 g, 70 mmol), 2-methyl-3-(4,4,5,5-tetramethyl-1,3,2-dioxaborolan-2-yl)pyridine (30.6 g, 140 mmol) and $NaHCO_3$ (35.3 g, 420 mmol) in a mixture solution of 1,4-dioxane (300 mL) and $H_2O$ (100 mL) was added $PdCl_2$(dppf) (5.94 g, 612 mmol). The mixture was degassed with $N_2$, heated at 110° C. for 1 h. The resulting mixture was cooled to rt and concentrated under reduced pressure. The residue was purified over column chromatography (EtOAc:MeOH=20:1) to give 14 g of the desired product. 200 mL of acetone was added to the product, and the resulting suspension was heated at 50° C. for 2 h. The white solid was collected by filtration and dried under vacuum to give Example 2 (13.6 g, 52%)$^1$H-NMR (500 MHz, DMSO-d;) δ ppm 2.40 (s, 3H), 3.33 (t, 2H), 4.56 (t, 2H), 4.72 (s, 2H), 6.72 (dd, 1H), 6.96 (dd, 1H), 7.31 (dd, 1H), 7.66 (s, 1H), 7.74 (d, 1H), 8.51 (d, 1H), 8.72 (t, 1H), 9.49 (s, 1H). LC-MS: $[M+H]^+$=376.9.

To a suspension of Example 2 (6.0 g, 15.94 mmol) in 100 mL of IPA, a solution of 0.5 N HCl in IPA (33.0 mL, 16.50 mmol) was added dropwise at rt. The suspension was stirred at 50° C. for 12 h, then cooled to rt and stirred for 5 h. The resulting solid was collected by filtration, and dried at 40° C. under vacuum for 2 days to afford the hydrochloride salt of Example 2 as a white solid (6.5 g, 98%) $^1$H NMR (DMSO-$d_6$) δ ppm 2.65 (s, 3H), 3.35 (t, 2H), 4.57 (t, 2H), 4.74 (d, 2H), 6.73 (dd, 1H), 6.97 (dd, 1H), 7.83 (s, 1H), 7.85-7.94 (m, 1H), 8.46 (d, 1H), 8.80 (dd, 1H), 9.07 (t, 1H), 9.58 (s, 1H). LC-MS: $[M+H]^+$=376.9.

Example 3

8-(2,4-Dimethylpyrimidin-5-yl)-N-((5-fluoro-2,3-dihydrobenzofuran-4-yl)methyl)-[1,2,4]triazolo[4,3-c]pyrimidin-5-amine

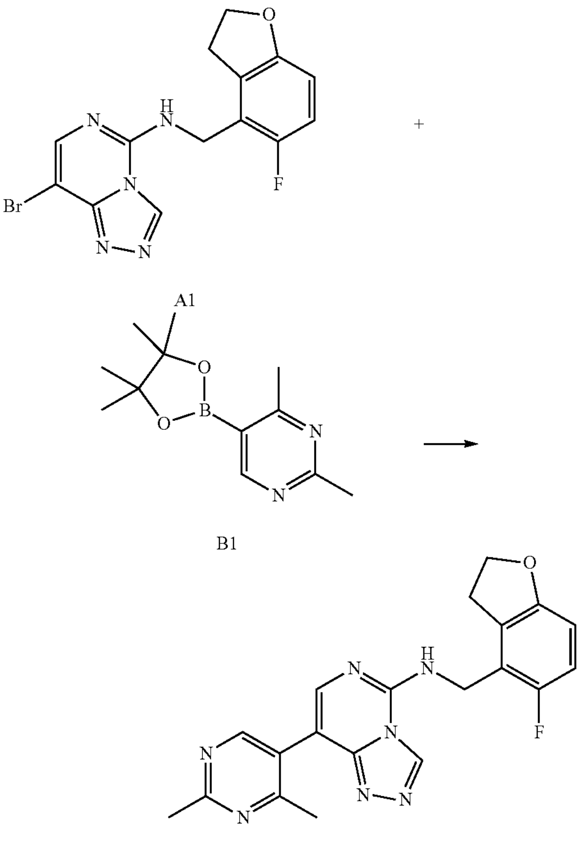

Example 3

The title compound was prepared by using a procedure similar to that of Example 1 by replacing 1,3-dimethyl-1H-pyrazol-5-ylboronic acid with B1. $^1$H NMR (500 MHz, DMSO-$d_6$) b 2.39 (s, 3H), 2.65 (s, 3H), 3.33 (t, 2H), 4.56 (t, 2H), 4.73 (d, 2H), 6.73 (dd, 1H), 6.97 (dd, 1H), 7.72 (s, 1H), 8.60 (s, 1H), 8.83 (br s, 1H), 9.50 (s, 1H). LC-MS: $[M+H]^+$=392.1.

Example 4

N-((5-Fluoro-2,3-dihydrobenzofuran-4-yl)methyl)-8-(1-isopropyl-3-methyl-1H-pyrazol-4-yl)-[1,2,4]triazolo[4,3-c]pyrimidin-5-amine

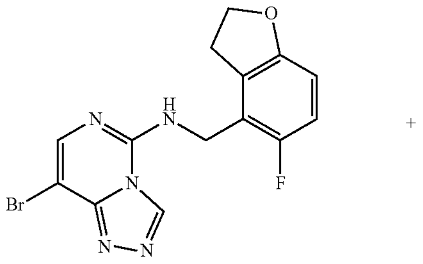

A1

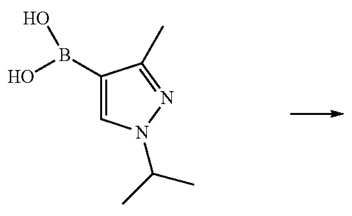

B2

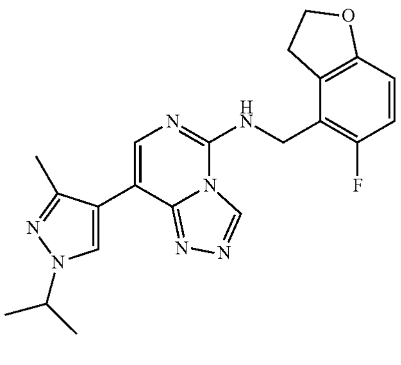

Example 4

The title compound was prepared by using a procedure similar to that of Example 1 by replacing 1,3-dimethyl-1H-pyrazol-5-ylboronic acid with B2. $^1$H-NMR (400 MHz, DMSO-$d_6$) δ ppm 1.43 (d, 6H), 2.35 (s, 3H), 3.30 (t, 2H), 4.48-4.56 (m, 3H), 4.69 (d, 2H), 6.70 (dd, 1H), 6.95 (dd, 1H), 7.73 (s, 1H), 8.30 (s, 1H), 8.50 (br s, 1H), 9.45 (s, 1H). LC-MS: $[M+H]^+$=408.2.

Example 5

N-((5-Fluoro-2,3-dihydrobenzofuran-4-yl)methyl)-8-(6-methoxy-4-methylpyridin-3-yl)-[1,2,4]triazolo[4,3-c]pyrimidin-5-amine

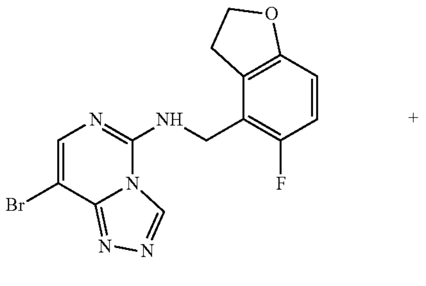

A1

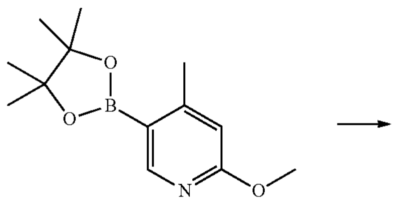

B3

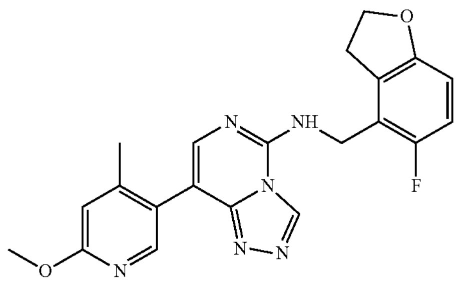

Example 5

The title compound was prepared by using a procedure similar to that of Example 1 by replacing 1,3-dimethyl-1H-pyrazol-5-ylboronic acid with B3. $^1$H NMR (500 MHz, DMSO-$d_6$) δ 2.18 (s, 3H), 3.35 (t, 2H), 3.88 (s, 3H), 4.56 (t, 2H), 4.71 (d, 2H), 6.73 (dd, 1H), 6.81 (s, 1H), 6.96 (dd, 1H), 7.59 (s, 1H), 8.07 (s, 1H), 8.68 (br s, 1H), 9.46 (s, 1H). LC-MS: $[M+H]^+$=407.1.

Example 6

8-(6-Cyclopropyl-2-methylpyridin-3-yl)-N-((5-fluoro-2,3-dihydrobenzofuran-4-yl)methyl)-[1,2,4]triazolo[4,3-c]pyrimidin-5-amine

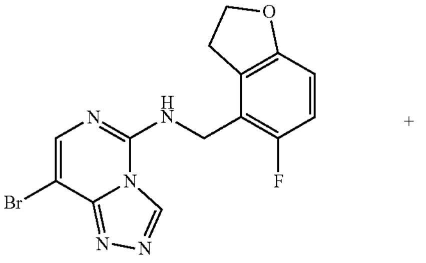

A1

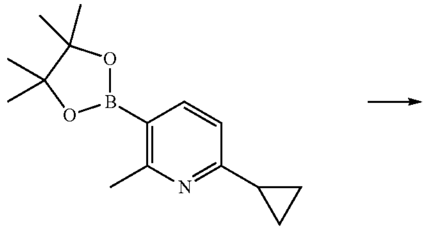

B4

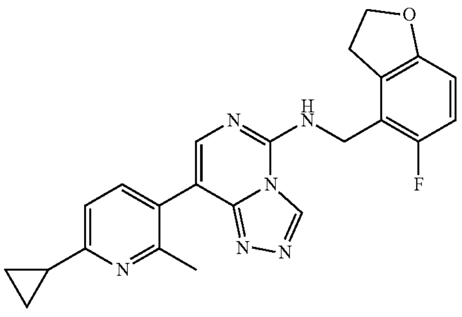

Example 6

The title compound was prepared by using a procedure similar to that of Example 1 by replacing 1,3-dimethyl-1H-pyrazol-5-ylboronic acid with B4. $^1$H NMR (400 MHz, DMSO-de) δ ppm 0.90-0.97 (m, 4H), 2.09-2.13 (m, 1H), 2.31 (s, 3H), 3.30 (t, 2H), 4.55 (t, 2H), 4.71 (s, 2H), 6.71 (dd, 1H), 6.96 (dd, 1H), 7.18 (d, 1H), 7.56-7.60 (m, 2H), 8.68 (br s, 1H), 9.46 (s, 1H). LC-MS: $[M+H]^+$=417.2.

Example 7

(3-(5-(((5-fluoro-2,3-dihydrobenzofuran-4-yl)methyl)amino)-[1,2,4]triazolo[4,3-c]pyrimidin-8-yl)pyridin-2-yl)methanol

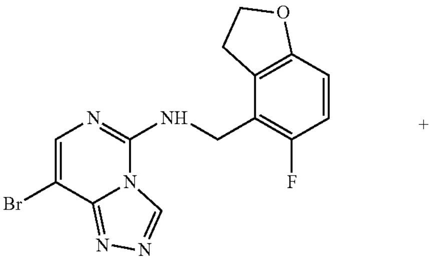

A1

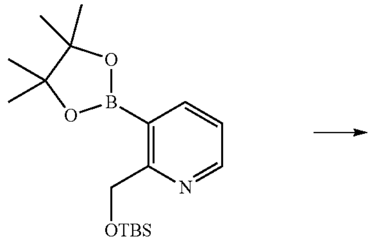

B5

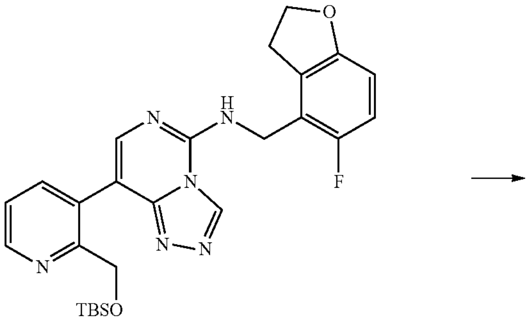

7.1

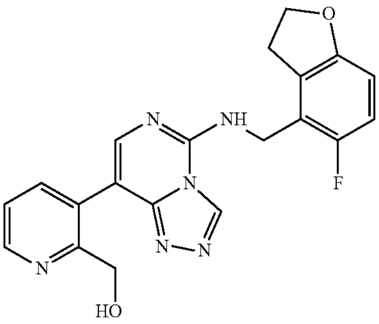

Example 7

8-(2-(((tert-Butyldimethylsilyl)oxy)methyl)pyridin-3-yl)-N-((5-fluoro-2,3-dihydrobenzofuran-4-yl)methyl)-[1,2,4]triazolo[4,3-c]pyrimidin-5-amine (7.1): The title compound was prepared by using a procedure similar to that of Example 1 by replacing 1,3-dimethyl-1H-pyrazol-5-ylboronic acid with B5. LC-MS: $[M+H]^+$=507.1.

Example 7: To a mixture 7.1 (30 mg, 0.08 mmol) in THF (3 mL) was added TBAF (0.6 mL, 0.6 mmol) and stirred for 4 h. The mixture was concentrated and purified by Prep-HPLC to afford the title compound (20 mg, 87%) as a white solid. $^{1}$H-NMR (500 MHz, DMSO-$d_6$) δ ppm 3.34 (t, 2H), 4.51 (d, 2H), 4.57 (t, 2H), 4.73 (d, 2H), 5.11 (t, 1H), 6.72 (dd, 1H), 6.74 (dd, 1H), 7.44 (dd, 1H), 7.76 (s, 1H), 7.89 (dd, 1H), 8.61 (dd, 1H), 8.74 (br s, 1H), 9.48 (s, 1H). LC-MS: $[M+H]^+$=393. 1.

Example 8

8-(2-Cyclopropyl-4-methylpyrimidin-5-yl)-N-((5-fluoro-2,3-dihydrobenzofuran-4-yl)methyl)-[1,2,4]triazolo[4,3-c]pyrimidin-5-amine

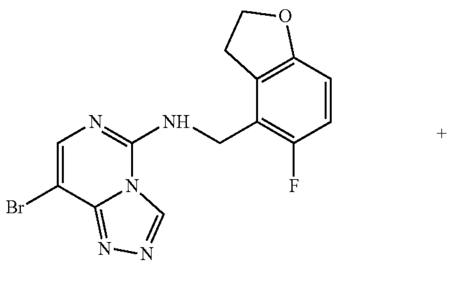

A1

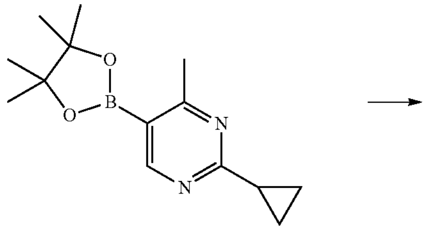

B8

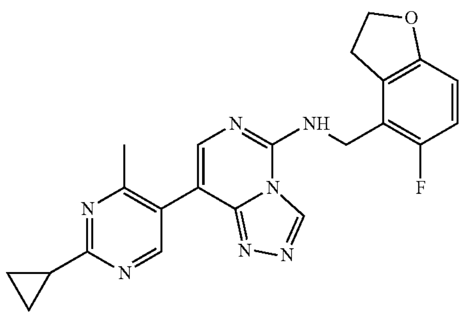

Example 8

The title compound was prepared by using a procedure similar to that of Example 1 by replacing 1,3-dimethyl-1H-pyrazol-5-ylboronic acid with B8. $^{1}$H-NMR (400 MHz, DMSO-$d_6$) δ ppm 1.04-1.08 (m, 4H), 2.21-2.24 (m, 1H), 2.36 (s, 3H), 3.33 (t, 2H), 4.56 (t, 2H), 4.72 (d, 2H), 6.72 (dd, 1H), 6.96 (dd, 1H), 7.71 (s, 1H), 8.53 (s, 1H), 8.80 (br s, 1H), 9.48 (s, 1H). LC-MS: $[M+H]^+$=418.1.

Example 9

N-((5-fluoro-2,3-dihydrobenzofuran-4-yl)methyl)-8-(2-isopropoxy-4-methylpyrimidin-5-yl)-[1,2,4]triazolo[4,3-c]pyrimidin-5-amine

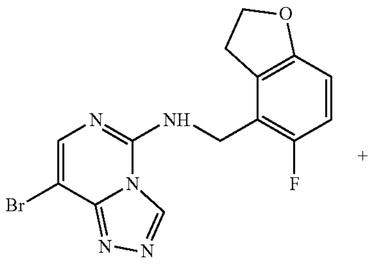

A1

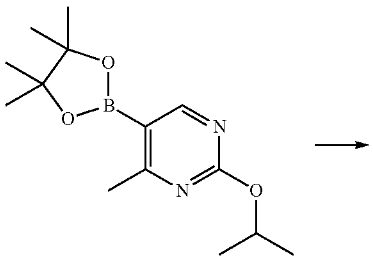

B10

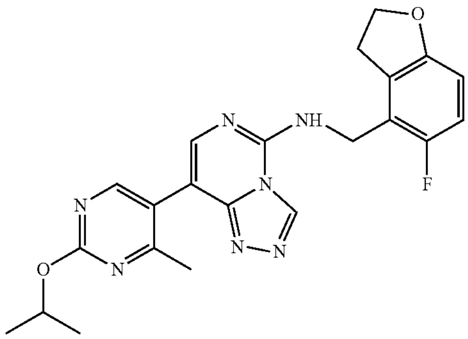

Example 9

The title compound was prepared by using a procedure similar to that of Example 1 by replacing 1,3-dimethyl-1H-pyrazol-5-ylboronic acid with B10. $^{1}$H-NMR (400 MHz, DMSO-$d_6$) δ ppm 1.35 (d, 6H), 2.34 (s, 3H), 3.36 (t, 2H), 4.57 (t, 2H), 4.72 (s, 2H), 5.28 (t, 1H), 6.72 (dd, 1H), 6.97 (dd, 1H), 7.68 (s, 1H), 8.47 (s, 1H), 8.76 (br s, 1H), 9.48 (s, 1H). LC-MS: $[M+H]^+$=436.1.

Example 10

3-(5-(((5-fluoro-2,3-dihydrobenzofuran-4-yl)methyl)amino)-[1,2,4]triazolo[4,3-c]pyrimidin-8-yl)pyridine 1-oxide

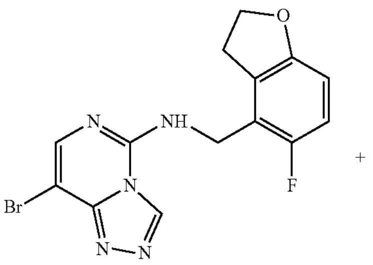

A1

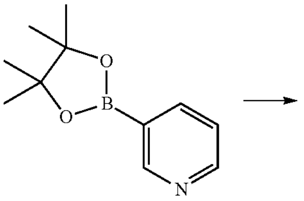

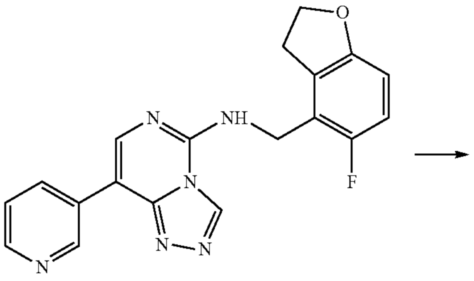

10.1

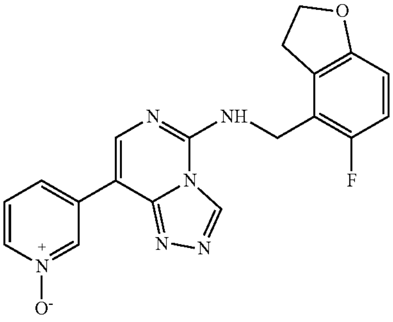

Example 10

N-((5-fluoro-2,3-dihydrobenzofuran-4-yl)methyl)-8-(pyridin-3-yl)-[1,2,4]triazolo[4,3-c]pyrimidin-5-amine (10.1): The title compound was prepared by using a procedure similar to that of Example 1 by replacing 1,3-dimethyl-1H-pyrazol-5-ylboronic acid with 3-(4,4,5,5-tetramethyl-1,3,2-dioxaborolan-2-yl)pyridine. Example 10: To a mixture of 10.1 (110 mg, 0.3 mmol) in $CHCl_3$ (5 mL) was added mCPBA (163 mg, 0.6 mmol). The reaction mixture was stirred for 16 h at rt. The mixture was concentrated and purified by Prep-HPLC to give the title compound (7 mg, 6%) as a white solid. $^1$H NMR (500 MHz, DMSO-$d_6$) δ ppm 3.30 (s, 2H), 4.55 (t, 2H), 4.74 (s, 2H), 6.72 (dd, 1H), 6.95 (dd, 1H), 7.51 (dd, 1H), 8.12 (d, 1H), 8.19 (d, 1H), 8.32 (d, 1H), 8.98 (s, 1H), 9.17 (s, 1H), 9.52 (s, 1H). LC-MS: $[M+H]^+$=379.2.

Example 207

N-((5-Fluorobenzofuran-4-yl)methyl)-8-(2-methylpyridin-3-yl)-[1,2,4]triazolo[4,3-c]pyrimidin-5-amine

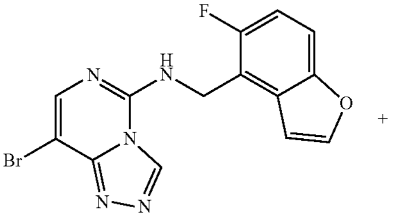

C1

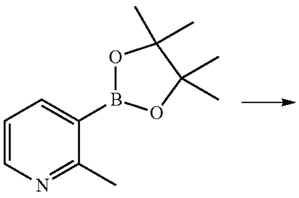

-continued

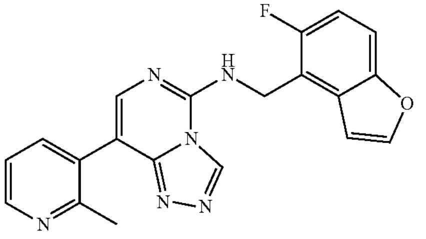

11

To a solution of 8-bromo-N-((5-fluorobenzofuran-4-yl)methyl)-[1,2,4]triazolo[4,3-c]pyrimidin-5-amine (C1) (50 mg, 0.14 mmol) in dioxane (2 ml) was added 2-methyl-3-(4,4,5,5-tetramethyl-1,3,2-dioxaborolan-2-yl)pyridine (45 mg, 0.21 mmol), $Pd(dppf)Cl_2$ (23 mg, 0.028 mmol), $NaHCO_3$ (35 mg, 0.42 mmol) and water (1 mL). The reaction mixture was purged with $N_2$ for 3 times, then stirred at 90° C. for 1 h. The mixture was filtered, the solid was washed with DMSO (2 mL). The filtrate was concentrated and purified by prep-HPLC ($NH_4HCO_3$) to give the title compound (13 mg, 48%) as a white solid. $^1$H-NMR (400 MHz, DMSO-$d_6$) δ ppm 2.40 (s, 3H), 5.01 (s, 2H), 7.21-7.25 (m, 2H), 7.31 (dd, 1H), 7.62 (dd, 1H), 7.66 (s, 1H), 7.75 (d, 1H), 8.08 (d, 1H), 8.50 (t, 1H), 8.86 (s, 1H), 9.46 (s, 1H). LC-MS: $[M+H]^+$=375.1.

Example 233

N-((5-fluoro-2,3-dihydrobenzofuran-4-yl)methyl)-8-(4-methyl-1H-imidazol-1-yl)-[1,2,4]triazolo[4,3-c]pyrimidin-5-amine

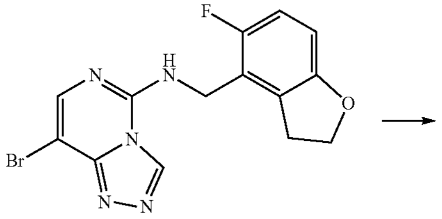

A1

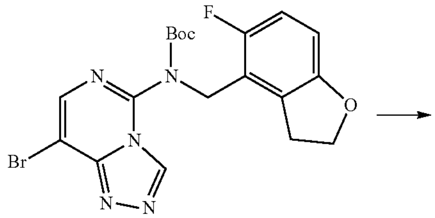

C4.1

-continued

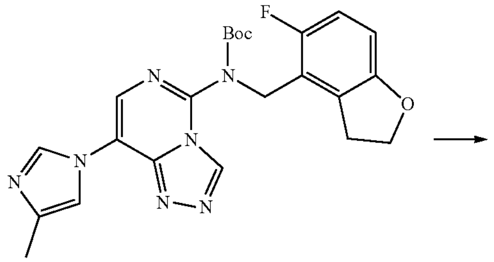

C4.2

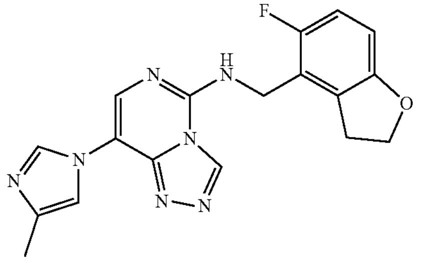

Example 233 tert-Butyl (5-fluoro-2,3-dihydrobenzofuran-4-yl)methyl (8-(4-methyl-1H-imidazol-1-yl)-[1,2,4]triazolo[4,3-c]pyrimidin-5-yl)carbamate (C4.2): A suspension of $Pd_2(dba)_3$ (18 mg, 0.02 mmol) and $Me_4$-t-BuXPhos (19.2 mg, 0.04 mmol) in 1.0 mL anhydrous dioxane was heated at 100° C. for 10 min under $N_2$. The resulting mixture was transferred into a stirring suspension of C4.1 (90 mg, 0.2 mmol), 4-methyl-1H-imidazole (72 mg, 0.88 mmol) and $K_3PO_4$ (110 mg, 0.52 mmol) in 2.0 mL anhydrous dioxane. The reaction mixture was stirred at 120° C. overnight, then cooled to rt and filtered, solid residue was washed with EtOAc several times. The filtrate and EtOAc washings were combined and concentrated under reduced pressure to give the crude product C4.2, which was used in the next step without purification. LC-MS: $[M+H]^+$=466.2.

N-((5-Fluoro-2,3-dihydrobenzofuran-4-yl)methyl)-8-(4-methyl-1H-imidazol-1-yl)-[1,2,4]triazolo[4,3-c]pyrimidin-5-amine (233): A solution of C4.2 (93 mg, 0.2 mmol) in 6 mL 1,1,1,3,3,3-hexafluoropropan-2-ol was heated in a Biotage Microwave Reactor at 100° C. for 1 h. Solvent was removed under vacuum to provide yellow oil and was purified by prep-HPLC to give titled compound as a white solid (19% yield 8 mg). $^1$H NMR (500 MHz, DMSO) δ ppm 2.19 (s, 3H), 0.31 (t, 2H), 4.55 (t, 2H), 4.70 (s, 2H), 6.71 (dd, 1H), 6.93-6.98 (m, 1H), 7.53 (s, 1H), 7.99 (s, 1H), 8.25 (d, 1H), 8.78 (s, 1H), 9.52 (s, 1H). LC-MS: $[M+H]^+$=366.1.

The following compounds, as identified in Table 2, were prepared using the general procedures as well as the procedures from the examples described above with the appropriate starting materials and reagents.

TABLE 2
| Ex # | Structure | $^1$H NMR (400 MHz, DMSO-$d_6$) or otherwise indicated/LC-MS Data |
|---|---|---|
| 11 | 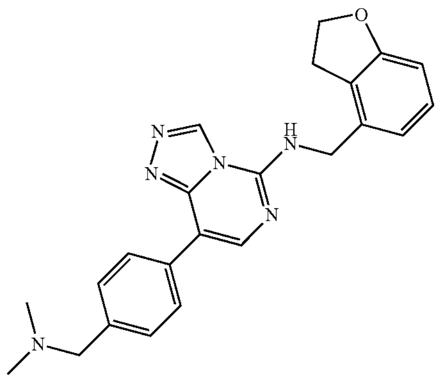 [SMILES: CN(C)Cc1ccc(-c2cnc(NCc3cccc4c3CCO4)n3cnnc23)cc1] | δ ppm 2.18 (s, 6H), 3.25 (t, 2H), 3.43 (s, 2H), 4.56 (t, 2H), 4.72 (s, 2H), 6.70 (d, 1H), 6.89 (d, 1H), 7.08 (t, 1H), 7.38 (d, 2H), 8.01 (s, 1H), 8.05 (d, 2H), 8.80 (s, 1H), 9.51 (s, 1H). LC-MS: $[M + H]^+$ = 401.2 |
| 12 | 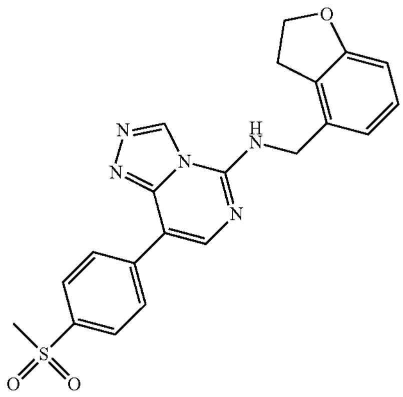 [SMILES: CS(=O)(=O)c1ccc(-c2cnc(NCc3cccc4c3CCO4)n3cnnc23)cc1] | $^1$H-NMR (400 MHz, $CD_3OD$) δ ppm 3.12-3.13 (m, 1H), 3.17 (s, 3H), 3.47-3.48 (m, 1H), 4.58 (m, 2H), 4.82 (s, 2H), 6.68 (d, 1H), 6.92 (d, 1H), 7.09 (t, 1H), 8.05 (d, 2H), 8.12 (s, 1H), 8.27 (d, 2H), 9.32 (s, 1H). LC-MS: $[M + H]^+$ = 421.8 |
| 13 | 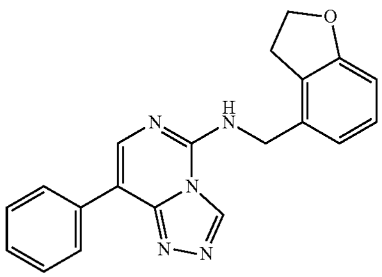 [SMILES: c1ccc(-c2cnc(NCc3cccc4c3CCO4)n3cnnc23)cc1] | $^1$H-NMR (400 MHz, $CD_3OD$) δ ppm 3.13-3.14 (m, 1H), 3.47-3.48 (m, 1H), 4.58 (t, 2H), 4.79 (s, 2H), 6.68 (d, 1H), 6.92 (d, 1H), 7.09 (t, 1H), 7.39 (d, 1H), 7.47 (d, 1H), 7.50-7.51 (m, 2H), 7.89-7.91 (m, 3H), 9.32 (s, 1H). LC-MS: $[M + H]^+$ = 343.9 |
| 14 | 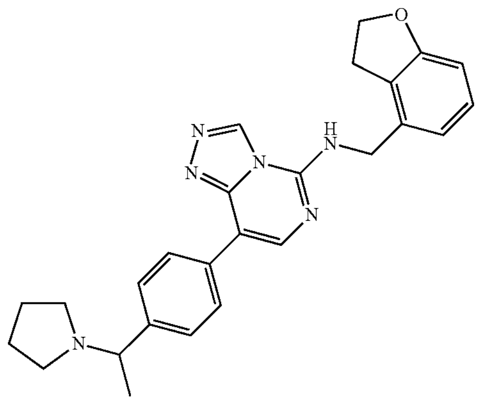 [SMILES: CC(c1ccc(-c2cnc(NCc3cccc4c3CCO4)n3cnnc23)cc1)N1CCCC1] | $^1$H-NMR (400 MHz, $CD_3OD$) δ ppm 1.57-1.58 (m, 3H), 1.90-1.92 (m, 4H), 2.73-2.74 (m, 2H), 2.94-2.95 (m, 2H), 3.26-3.27 (m, 2H), 3.74-3.75 (m, 1H), 4.56 (t, 2H), 4.78 (s, 2H), 6.66 (d, 1H), 6.90 (d, 1H), 7.06 (t, 1H), 7.51 (d, 2H), 7.93-7.95 (m, 3H), 9.32 (s, 1H). LC-MS: $[M + H]^+$ = 440.9 |

TABLE 2-continued
| Ex # | Structure | $^1H$ NMR (400 MHz, DMSO-$d_6$) or otherwise indicated/LC-MS Data |
|---|---|---|
| 15 | 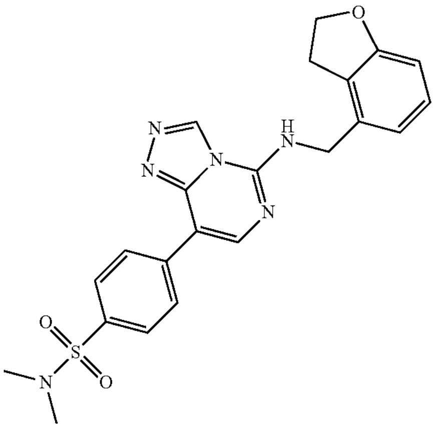 [SMILES: CN(C)S(=O)(=O)c1ccc(-c2cnc(NCc3cccc4c3CCO4)n3cnnc23)cc1] | $^1H$ NMR (400 MHz, $CD_3OD$) δ ppm 2.74 (s, 6H), 2.32 (t, 2H), 4.82 (s, 2H), 5.49 (s, 2H), 6.68 (d, 1H), 6.92 (d, 1H), 7.09 (t, 1H), 7.89 (d, 2H), 8.10 (s, 1H), 8.24 (d, 2H), 9.34 (s, 1H). LC-MS: $[M + H]^+$ = 450.8 |
| 16 | 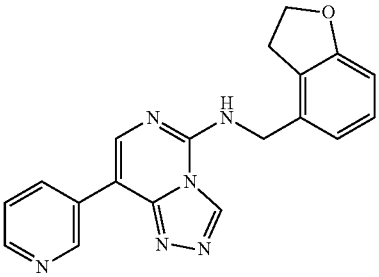 [SMILES: c1cncc(-c2cnc(NCc3cccc4c3CCO4)n3cnnc23)c1] | δ ppm 3.25 (t, 2H), 4.55 (t, 2H), 4.73 (s, 2H), 6.70 (d, 1H), 6.89 (d, 1H), 7.08 (t, 1H), 7.50 (dd, 1H), 8.14 (s, 1H), 8.51 (t, 1H), 8.55 (t, 1H), 8.94 (s, 1H), 9.28 (d, 1H), 9.53 (s, 1H). LC-MS: $[M + H]^+$ = 345.1 |
| 17 | 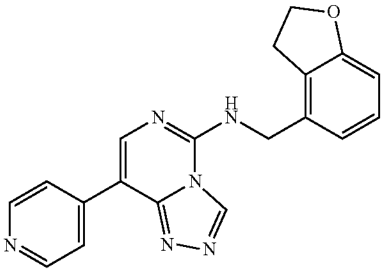 [SMILES: c1cc(CNc2ncc(-c3ccncc3)c3nncn23)c2c(c1)OCC2] | $^1H$-NMR (400 MHz, $CD_3OD$) δ ppm 3.48-3.50 (m, 2H), 4.58 (t, 2H), 4.83 (s, 2H), 6.68 (d, 1H), 6.92 (d, 1H), 7.09 (t, 1H), 8.14-8.15 (m, 2H), 8.25 (s, 1H), 8.59-8.61 (m, 2H), 9.34 (s, 1H). LC-MS: $[M + H]^+$ = 344.9 |
| 18 | 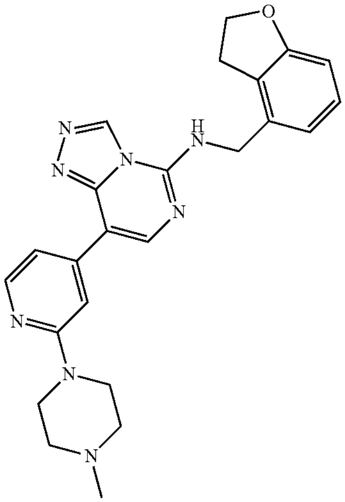 [SMILES: CN1CCN(c2cc(-c3cnc(NCc4cccc5c4CCO5)n4cnnc34)ccn2)CC1] | $^1H$-NMR (400 MHz, $CD_3OD$) δ ppm 2.38 (s, 3H), 2.63-2.64 (m, 4H), 3.48-3.49 (m, 2H), 3.64-3.65 (m, 4H), 4.57 (t, 2H), 4.81 (s, 2H), 6.68 (d, 1H), 6.91 (d, 1H), 7.09 (t, 1H), 7.24 (d, 1H), 7.63 (s, 1H), 8.15-8.17 (m, 2H), 9.33 (s, 1H). LC-MS: $[M + H]^+$ = 442.9 |

TABLE 2-continued
| Ex # | Structure | $^1$H NMR (400 MHz, DMSO-$d_6$) or otherwise indicated/LC-MS Data |
| --- | --- | --- |
| 19 | 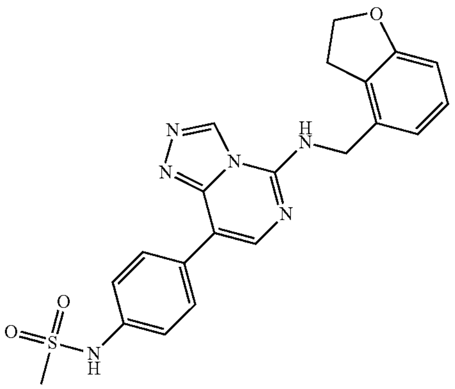 [SMILES: CS(=O)(=O)Nc1ccc(-c2cnc(NCc3cccc4c3CCO4)n3cnnc23)cc1] | $^1$H-NMR (400 MHz, $CD_3OD$) δ ppm 3.01 (s, 3H), 3.47-3.48 (m, 2H), 4.57 (t, 2H), 4.79 (s, 2H), 6.68 (d, 1H), 6.91 (d, 1H), 7.09 (t, 1H), 7.37 (d, 2H), 7.91-7.92 (m, 3H), 9.31 (s, 1H). LC-MS: $[M + H]^+$ = 436.8 |
| 20 | 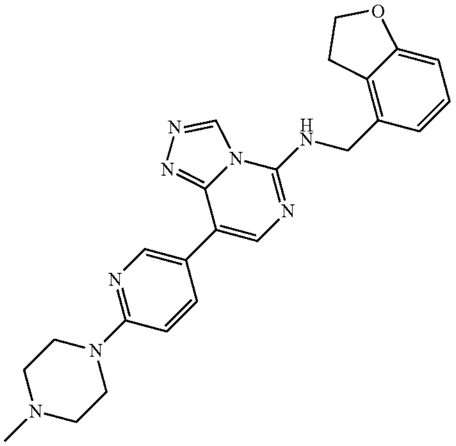 [SMILES: CN1CCN(c2ccc(-c3cnc(NCc4cccc5c4CCO5)n4cnnc34)cn2)CC1] | δ ppm 2.22 (s, 3H), 2.41 (s, 4H), 3.23 (t, 2H), 3.54 (s, 4H), 4.54 (t, 2H), 4.69 (s, 2H), 6.68 (d, 1H), 6.87 (d, 1H), 6.93 (d, 1H), 7.05 (d, 1H), 7.94 (s, 1H), 8.24 (d, 1H), 8.74 (s, 1H), 8.82 (s, 1H), 9.47 (s, 1H). LC-MS: $[M + H]^+$ = 442.9 |
| 21 | 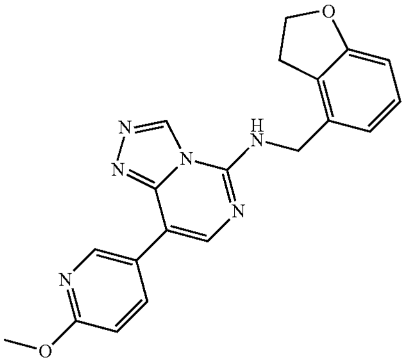 [SMILES: COc1ccc(-c2cnc(NCc3cccc4c3CCO4)n3cnnc23)cn1] | $^1$H-NMR (400 MHz, $CD_3OD$) δ ppm 3.97 (s, 3H), 4.55-4.60 (m, 2H), 4.79 (s, 2H), 5.49 (s, 2H), 6.67 (d, 1H), 6.90-6.94 (m, 2H), 7.09 (t, 1H), 7.90 (s, 1H), 8.21-8.23 (m, 1H), 8.69 (d, 1H), 9.32 (s, 1H). LC-MS: $[M + H]^+$ = 374.9 |
| 22 | 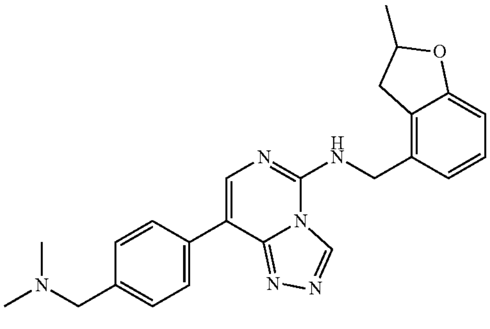 [SMILES: CC1Cc2c(CNc3ncc(-c4ccc(CN(C)C)cc4)c4nncn34)cccc2O1] | $^1$H-NMR (400 MHz, $CD_3OD$) δ ppm 1.21-1.28 (m, 3H), 2.30 (s, 6H), 2.85-2.91 (m, 1H), 3.41-3.42 (m, 1H), 3.47-3.54 (m, 1H), 4.08 (s, 2H), 4.79 (s, 2H), 6.63 (d, 1H), 6.89 (d, 1H), 7.09 (t, 1H), 7.44 (d, 2H), 7.89-7.91 (m, 3H), 9.31 (s, 1H). LC-MS: $[M + H]^+$ = 414.9 |

TABLE 2-continued
| Ex # | Structure | $^1$H NMR (400 MHz, DMSO-$d_6$) or otherwise indicated/LC-MS Data |
| --- | --- | --- |
| 23 | 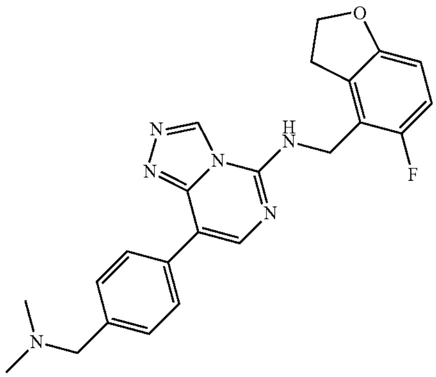 [SMILES: CN(C)Cc1ccc(-c2cnc(NCc3c(F)ccc4c3CCO4)n3cnnc23)cc1] | $^1$H-NMR (400 MHz, $CD_3OD$) δ ppm 2.43 (s, 6H), 3.39-3.41 (m, 2H), 3.72-3.73 (m, 2H), 4.60 (t, 2H), 4.85 (s, 2H), 6.67 (dd, 1H), 6.88 (t, 1H), 7.49 (d, 2H), 7.95-7.99 (m, 3H), 9.36 (s, 1H). LC-MS: $[M + H]^+$ = 419.1 |
| 24 | 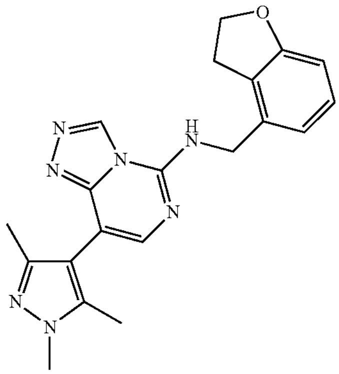 [SMILES: Cc1nn(C)c(C)c1-c1cnc(NCc2cccc3c2CCO3)n2cnnc12] | δ ppm 2.06 (s, 3H), 2.15 (s, 3H), 3.25 (t, 2H), 3.72 (s, 3H), 4.55 (t, 2H), 4.68 (d, 2H), 6.69 (d, 1H), 6.89 (d, 1H), 7.08 (t, 1H), 7.44 (s, 1H), 8.67 (s, 1H), 9.45 (s, 1H). LC-MS: $[M + H]^+$ = 376.2 |
| 25 | 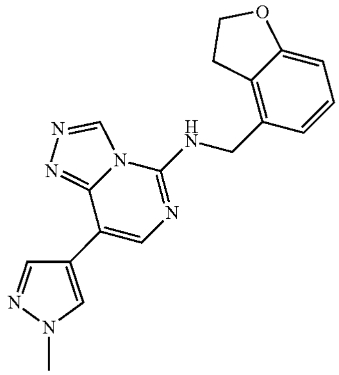 [SMILES: Cn1cc(-c2cnc(NCc3cccc4c3CCO4)n3cnnc23)cn1] | δ ppm 3.23 (t, 2H), 3.91 (s, 3H), 4.54 (t, 2H), 4.67 (d, 2H), 6.68 (d, 1H), 6.86 (d, 1H), 7.06 (t, 1H), 8.00 (s, 1H), 8.11 (s, 1H), 8.43 (s, 1H), 8.66 (t, 1H), 9.47 (s, 1H). LC-MS: $[M + H]^+$ = 348.1 |
| 26 | 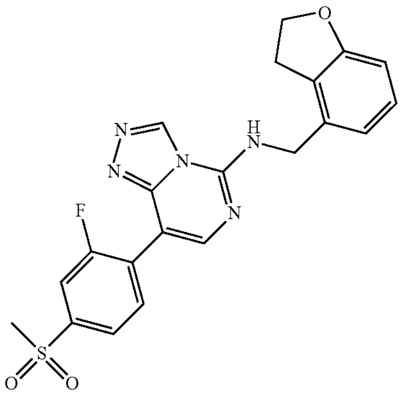 [SMILES: CS(=O)(=O)c1ccc(-c2cnc(NCc3cccc4c3CCO4)n3cnnc23)c(F)c1] | $^1$H-NMR (400 MHz, $CD_3OD$) δ ppm 3.22 (s, 3H), 3.28-3.29 (m, 2H), 4.59 (t, 2H), 4.83 (s, 2H), 6.70 (d, 1H), 6.94 (d, 1H), 7.10 (t, 1H), 7.86-7.92 (m, 2H), 7.99 (s, 1H), 8.13-8.16 (m, 1H), 9.35 (s, 1H). LC-MS: $[M + H]^+$ = 440.1 |

TABLE 2-continued
| Ex # | Structure | $^1$H NMR (400 MHz, DMSO-$d_6$) or otherwise indicated/LC-MS Data |
|---|---|---|
| 27 | 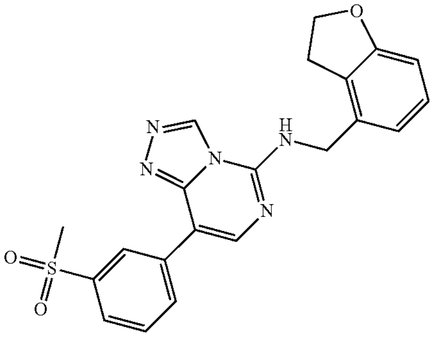 [SMILES: CS(=O)(=O)c1cccc(-c2cnc(NCc3cccc4c3CCO4)n3cnnc23)c1] | $^1$H-NMR (400 MHz, $CD_3OD$) δ ppm 3.24 (s, 3H), 3.35-3.36 (m, 2H), 4.59 (t, 2H), 4.83 (s, 2H), 6.69 (d, 1H), 6.94 (d, 1H), 7.11 (t, 1H), 7.77 (t, 1H), 7.98 (d, 1H), 8.08 (s, 1H), 8.30 (d, 1H), 8.59 (s, 1H), 9.37 (s, 1H). LC-MS: $[M + H]^+$ = 422.1 |
| 28 | 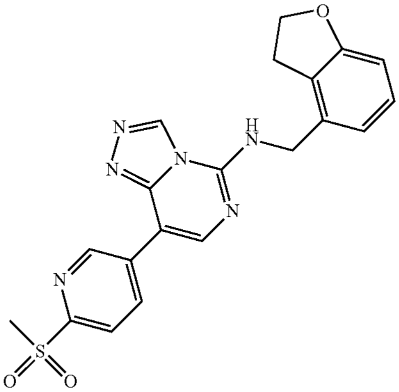 [SMILES: CS(=O)(=O)c1ccc(-c2cnc(NCc3cccc4c3CCO4)n3cnnc23)cn1] | $^1$H-NMR (400 MHz, $CD_3OD$) δ ppm 3.27-3.29 (m, 5H), 4.59 (t, 2H), 4.84 (s, 2H), 6.69 (d, 1H), 6.94 (d, 1H), 7.11 (t, 1H), 8.19 (d, 1H), 8.23 (s, 1H), 8.76 (d, 1H), 9.37 (s, 1H), 9.42 (s, 1H). LC-MS: $[M + H]^+$ = 423.1 |
| 29 | 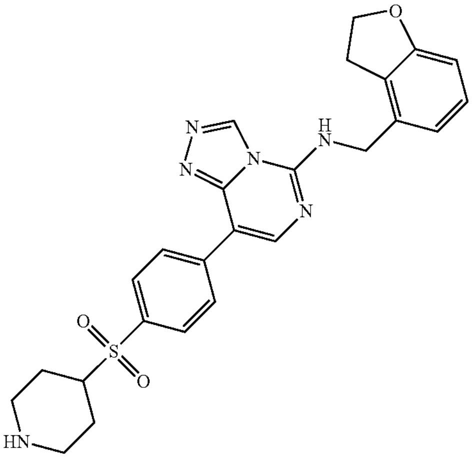 [SMILES: O=S(=O)(c1ccc(-c2cnc(NCc3cccc4c3CCO4)n3cnnc23)cc1)C1CCNCC1] | δ ppm 1.37 (m, 2H), 1.75 (d, 2H), 2.41 (t, 2H), 2.96 (d, 2H), 3.25 (t, 2H), 3.33 (t, 2H), 4.55 (t, 2H), 4.74 (s, 2H), 6.70 (d, 1H), 6.89 (d, 1H), 7.08 (t, 1H), 7.89 (d, 2H), 8.25 (s, 1H), 8.45 (d, 2H), 9.05 (s, 1H), 9.55 (s, 1H). LC-MS: $[M + H]^+$ = 491.0 |
| 30 | 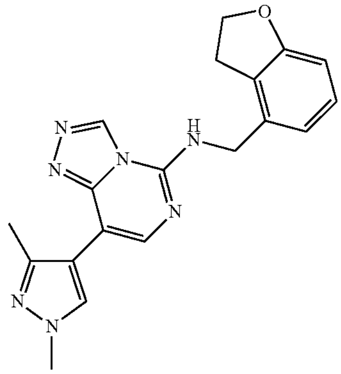 [SMILES: Cc1nn(C)cc1-c1cnc(NCc2cccc3c2CCO3)n2cnnc12] | δ ppm 2.33 (s, 3H), 3.23 (t, 2H), 3.83 (s, 3H), 4.54 (t, 2H), 4.68 (s, 2H), 6.69 (d, 1H), 6.87 (d, 1H), 7.07 (t, 1H), 7.70 (s, 1H), 8.28 (s, 1H), 8.63 (s, 1H), 9.47 (s, 1H). LC-MS: $[M + H]^+$ = 362.2 |

TABLE 2-continued
| Ex # | Structure | $^1$H NMR (400 MHz, DMSO-$d_6$) or otherwise indicated/LC-MS Data |
|---|---|---|
| 31 | 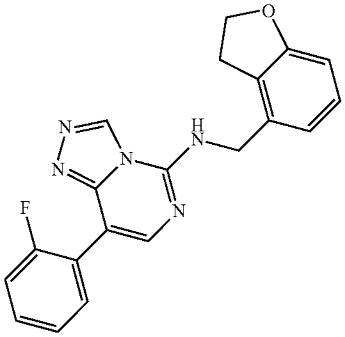 [SMILES: Fc1ccccc1-c1cnc(NCc2cccc3c2CCO3)n2cnnc12] | $^1$H-NMR (400 MHz, $CD_3OD$) δ ppm 3.28-3.29 (m, 2H), 4.59 (t, 2H), 4.81 (s, 2H), 6.70 (d, 1H), 6.94 (d, 1H), 7.11 (t, 1H), 7.25 (t, 1H), 7.29 (d, 1H), 7.43-7.49 (m, 1H), 7.76-7.78 (m, 1H), 7.83 (s, 1H), 9.36 (s, 1H). LC-MS: $[M + H]^+$ = 362.1 |
| 32 | 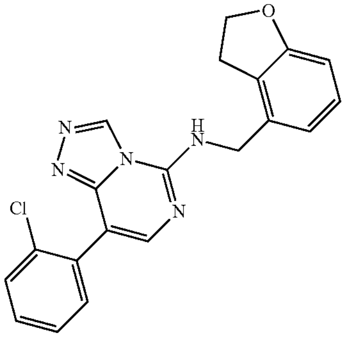 [SMILES: Clc1ccccc1-c1cnc(NCc2cccc3c2CCO3)n2cnnc12] | $^1$H-NMR (400 MHz, $CD_3OD$) δ ppm 3.30 (s, 2H), 4.59 (t, 2H), 4.81 (s, 2H), 6.69 (d, 1H), 6.94 (d, 1H), 7.11 (t, 1H), 7.43-7.46 (m, 2H), 7.54-7.59 (m, 2H), 7.70 (s, 1H), 9.32 (s, 1H). LC-MS: $[M + H]^+$ = 378.2 |
| 33 | 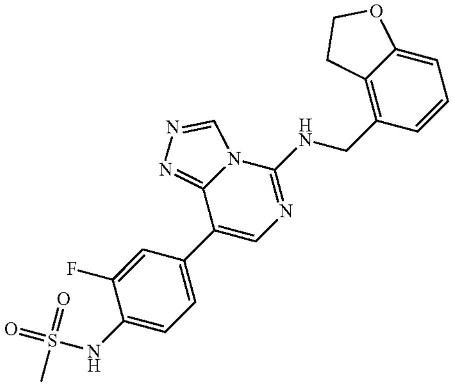 [SMILES: CS(=O)(=O)Nc1ccc(-c2cnc(NCc3cccc4c3CCO4)n3cnnc23)cc1F] | δ ppm 3.05 (s, 3H), 3.24 (t, 2H), 4.55 (t, 2H), 4.72 (s, 2H), 6.69 (d, 1H), 6.88 (d, 1H), 7.07 (t, 1H), 7.46 (t, 1H), 7.97 (dd, 1H), 8.15 (m, 2H), 8.92 (s, 1H), 9.39 (s, 1H), 9.52 (s, 1H). LC-MS: $[M + H]^+$ = 454.9 |
| 34 | 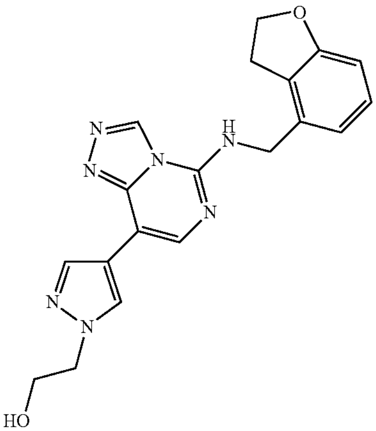 [SMILES: OCCn1cc(-c2cnc(NCc3cccc4c3CCO4)n3cnnc23)cn1] | δ ppm 3.21 (t, 2H), 3.75 (s, 2H), 4.19 (t, 2H), 4.52 (t, 2H), 4.66 (s, 2H), 4.93 (s, 1H), 6.68 (d, 1H), 6.86 (d, 1H), 7.05 (t, 1H), 8.00 (s, 1H), 8.12 (s, 1H), 8.45 (s, 1H), 8.66 (s, 1H), 9.45 (s, 1H). LC-MS: $[M + H]^+$ = 378.2 |

TABLE 2-continued
| Ex # | Structure | $^1$H NMR (400 MHz, DMSO-$d_6$) or otherwise indicated/LC-MS Data |
|---|---|---|
| 35 | 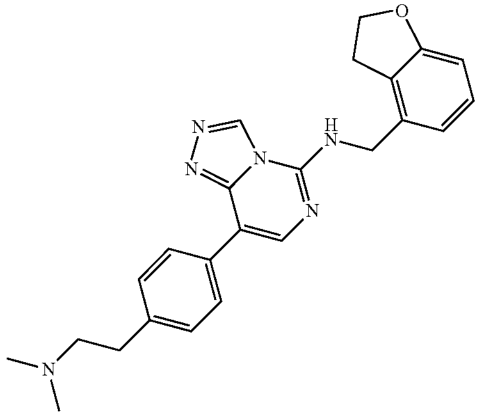 [SMILES: CN(C)CCc1ccc(-c2cnc(NCc3cccc4c3CCO4)n3cnnc23)cc1] | δ ppm 2.19 (s, 6H), 2.47 (t, 2H), 2.74 (t, 2H), 3.24 (t, 2H), 4.55 (t, 2H), 4.71 (d, 2H), 6.69 (d, 1H), 6.88 (d, 1H), 7.07 (t, 1H), 7.31 (d, 2H), 7.98 (d, 2H), 8.03 (s, 1H), 8.80 (s, 1H), 9.51 (s, 1H). LC-MS: $[M + H]^+$ = 415.0 |
| 36 | 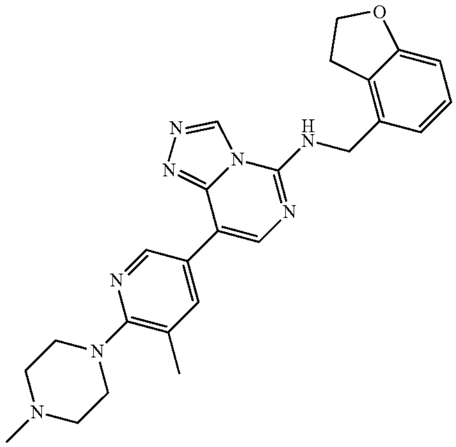 [SMILES: Cc1cc(-c2cnc(NCc3cccc4c3CCO4)n3cnnc23)cnc1N1CCN(C)CC1] | δ ppm 2.24 (s, 3H), 2.31 (s, 3H), 2.50 (t, 4H), 3.12 (t, 4H), 3.24 (t, 2H), 4.55 (t, 2H), 4.71 (s, 2H), 6.69 (d, 1H), 6.87 (d, 1H), 7.07 (t, 1H), 7.99 (s, 1H), 8.20 (d, 1H), 8.77 (d, 1H), 8.82 (s, 1H), 9.50 (s, 1H). LC-MS: $[M + H]^+$ = 457.0 |
| 37 | 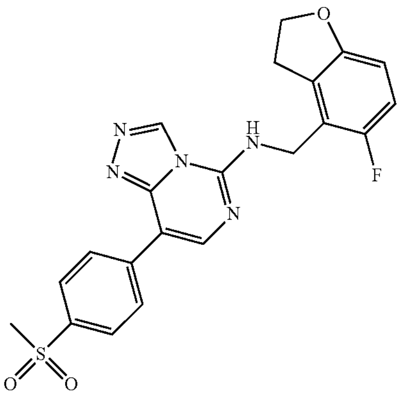 [SMILES: CS(=O)(=O)c1ccc(-c2cnc(NCc3c(F)ccc4c3CCO4)n3cnnc23)cc1] | δ ppm 3.27 (s, 3H), 3.33 (d, 2H), 4.56 (t, 2H), 4.76 (s, 2H), 6.72 (dd, 1H), 6.97 (t, 1H), 8.00 (d, 2H), 8.27 (s, 1H), 8.46 (d, 2H), 9.55 (s, 1H). LC-MS: $[M + H]^+$ = 440.1 |

TABLE 2-continued
| Ex # | Structure | $^{1}H$ NMR (400 MHz, DMSO-$d_6$) or otherwise indicated/LC-MS Data |
|---|---|---|
| 38 | 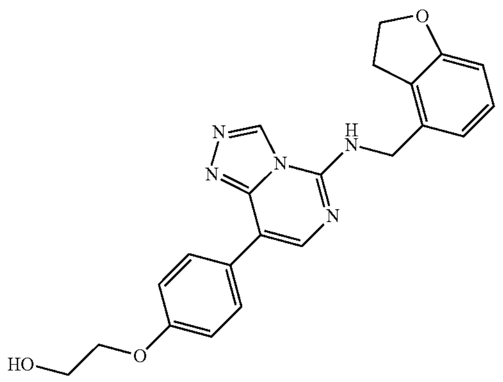 [SMILES: OCCOc1ccc(-c2cnc(NCc3cccc4c3CCO4)n3cnnc23)cc1] | $^{1}H$-NMR (500 MHz, DMSO-$d_6$) δ ppm 3.25 (m, 2H), 3.74 (m, 2H), 4.04 (m, 2H), 4.55 (m, 2H), 4.71 (s, 2H), 4.89 (m, 1H), 6.69 (m, 1H), 6.88 (m, 1H), 7.06 (m, 3H), 7.94 (s, 1H), 8.04 (m, 1H), 8.71 (m, 1H), 9.50 (s, 1H). LC-MS: $[M + H]^+$ = 404.4 |
| 39 | 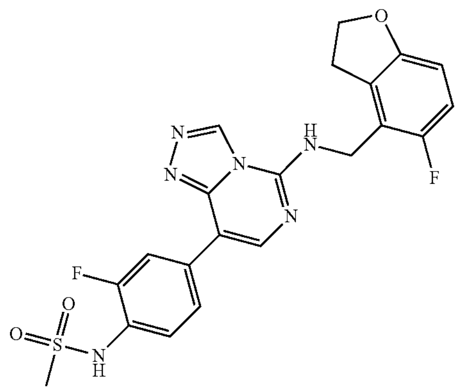 [SMILES: CS(=O)(=O)Nc1ccc(-c2cnc(NCc3c(F)ccc4c3CCO4)n3cnnc23)cc1F] | δ ppm 3.26 (s, 3H), 3.33 (s, 2H), 4.55 (t, 2H), 4.75 (s, 2H), 6.71 (m, 1H), 6.96 (t, 1H), 8.00 (d, 2H), 8.27 (s, 1H), 8.46 (d, 2H), 9.52 (s, 1H). LC-MS: $[M + H]^+$ = 473.2 |
| 40 | 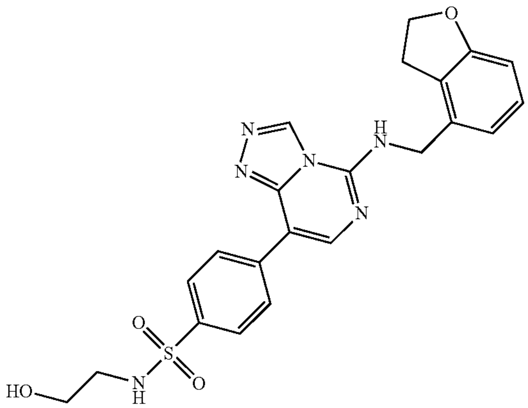 [SMILES: O=S(=O)(NCCO)c1ccc(-c2cnc(NCc3cccc4c3CCO4)n3cnnc23)cc1] | δ ppm 2.79-2.82 (m, 2H), 3.20-3.24 (m, 2H), 3.36-3.40 (m, 2H), 4.51-4.55 (m, 2H), 4.67 (s, 2H), 6.64 (d, 1H), 6.90 (d, 1H), 7.02 (t, 1H), 7.78 (d, 2H), 8.15 (s, 1H), 8.34 (d, 2H), 9.23 (s, 1H). LC-MS: $[M + H]^+$ = 467.1 |
| 41 | 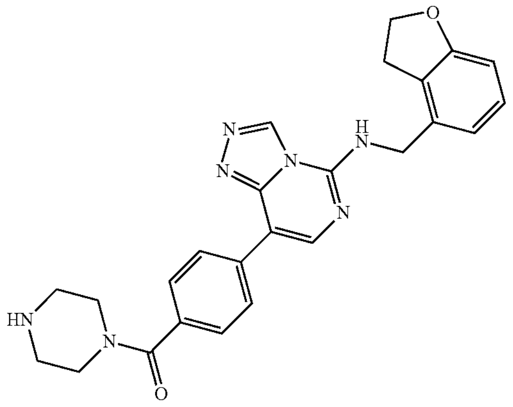 [SMILES: O=C(c1ccc(-c2cnc(NCc3cccc4c3CCO4)n3cnnc23)cc1)N1CCNCC1] | $^{1}H$-NMR (400 MHz, $CD_3OD$) δ ppm 2.82-2.93 (m, 4H), 3.49-3.51 (m, 2H), 3.76-3.77 (m, 2H), 4.59 (t, 2H), 4.81 (s, 2H), 6.69 (d, 1H), 6.93 (d, 1H), 7.09 (t, 1H), 7.55 (d, 2H), 8.02 (s, 1H), 8.08 (d, 2H), 9.35 (s, 1H). LC-MS: $[M + H]^+$ = 456.2 |

TABLE 2-continued
| Ex # | Structure | $^{1}$H NMR (400 MHz, DMSO-$d_6$) or otherwise indicated/LC-MS Data |
|---|---|---|
| 42 | 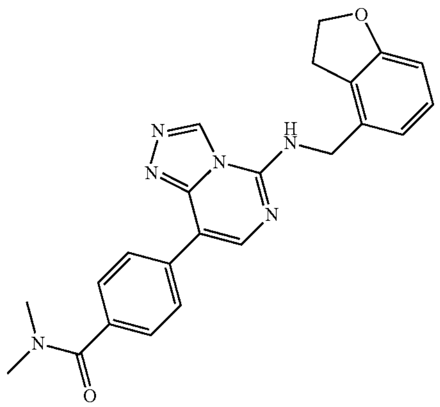 | $^{1}$H-NMR (400 MHz, $CD_3OD$) δ ppm 3.09 (s, 3H), 3.15 (s, 3H), 4.59 (t, 2H), 4.82 (s, 2H), 6.69 (d, 1H), 6.93 (d, 1H), 7.10 (t, 1H), 7.57 (d, 2H), 8.03 (s, 1H), 8.07 (d, 2H), 9.35 (s, 1H). LC-MS: $[M + H]^+$ = 415.2 |
| 43 | 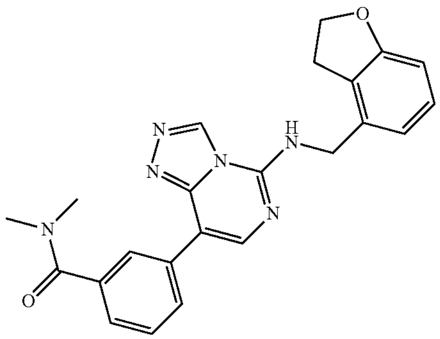 [SMILES: CN(C)C(=O)c1cccc(-c2cnc(NCc3cccc4c3CCO4)n3cnnc23)c1] | $^{1}$H-NMR (400 MHz, $CD_3OD$) δ ppm 3.09 (s, 3H), 3.15 (s, 3H), 4.59 (t, 2H), 4.82 (s, 2H), 6.69 (d, 1H), 6.93 (d, 1H), 7.10 (t, 1H), 7.57 (d, 2H), 8.03 (s, 1H), 8.07 (d, 2H), 9.35 (s, 1H). LC-MS: $[M + H]^+$ = 415.2 |
| 44 | 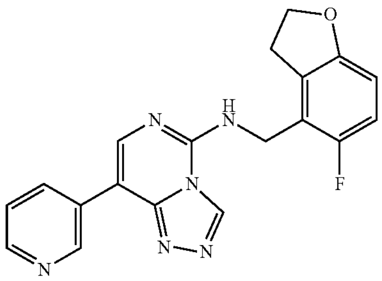 [SMILES: Fc1ccc2c(c1CNc1ncc(-c3cccnc3)c3nncn13)CCO2] | $^{1}$H-NMR (400 MHz, $CD_3OD$) δ ppm 3.41 (t, 2H), 4.60 (t, 2H), 4.85 (s, 2H), 6.65-6.68 (m, 1H), 6.88 (t, 1H), 7.56-7.59 (m, 1H), 8.09 (s, 1H), 8.44-8.47 (m, 1H), 8.55 (d, 1H), 9.16 (s, 1H), 9.37 (s, 1H). LC-MS: $[M + H]^+$ = 363.1 |
| 45 | 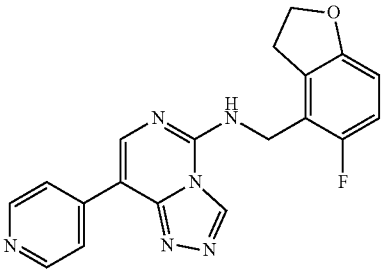 [SMILES: Fc1ccc2c(c1CNc1ncc(-c3ccncc3)c3nncn13)CCO2] | $^{1}$H-NMR (400 MHz, $CD_3OD$) δ ppm 3.41 (t, 2H), 4.60 (t, 2H), 4.87 (s, 2H), 6.66-6.69 (m, 1H), 6.88 (t, 1H), 8.15-8.17 (m, 2H), 8.30 (s, 1H), 8.60-8.62 (m, 2H), 9.38 (s, 1H). LC-MS: LC-MS: $[M + H]^+$ = 363.1 |

TABLE 2-continued
| Ex # | Structure | $^1$H NMR (400 MHz, DMSO-$d_6$) or otherwise indicated/LC-MS Data |
|---|---|---|
| 46 | 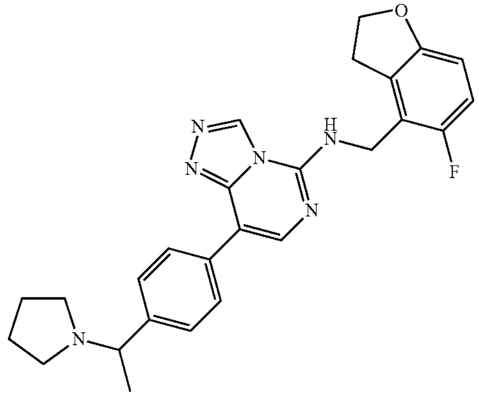 [SMILES: CC(c1ccc(-c2cnc(NCc3c(F)ccc4c3CCO4)n3cnnc23)cc1)N1CCCC1] | $^1$H-NMR (400 MHz, MeOH-$d_4$) δ ppm 1.48 (d, 3H), 1.82-1.85 (m, 4H), 2.46-2.50 (m, 2H), 2.68-2.70 (m, 2H), 3.37-3.42 (m, 3H), 4.60 (t, 2H), 4.83 (s, 2 H), 6.65-6.68 (m, 1H), 6.88 (t, 1H), 7.49 (d, 2H), 7.90 (d, 2H), 7.96 (s, 1H), 9.35 (s, 1 H). LC-MS: $[M + H]^+$ = 459.2 |
| 47 | 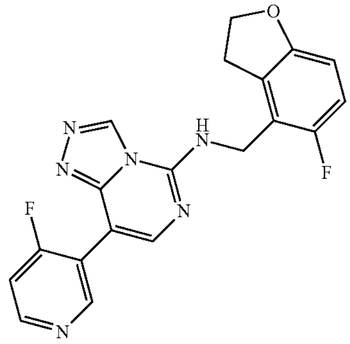 [SMILES: Fc1ccncc1-c1cnc(NCc2c(F)ccc3c2CCO3)n2cnnc12] | $^1$H-NMR (400 MHz, $CD_3OD$) δ ppm 3.36-3.43 (m, 2H), 4.60 (t, 2H), 4.86 (s, 2H), 6.66-6.69 (m, 1H), 6.89 (t, 1H), 7.40-7.44 (m, 1H), 7.96 (s, 1H), 8.60-8.63 (m, 1H), 8.99 (d, 1H), 9.36 (s, 1H). LC-LC-MS: $[M + H]^+$ = 381.1 |
| 48 | 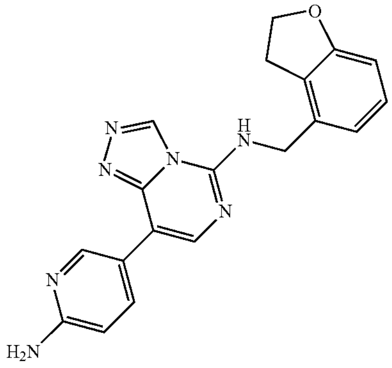 [SMILES: Nc1ccc(-c2cnc(NCc3cccc4c3CCO4)n3cnnc23)cn1] | $^1$H-NMR (400 MHz, $CD_3OD$) δ ppm, 3.15-3.28 (m, 2H), 4.54 (t, 2H), 4.69 (d, 2H), 6.08 (d, 2H), 6.54 (d, 1H), 6.69 (d, 1H), 6.87 (d, 1H), 7.07 (t, 1H), 7.86 (s, 1H), 8.05 (q, 1H), 8.66 (d, 2H), 9.48 (s, 1H). LC-MS: $[M + H]^+$ = 360.2 |
| 49 | 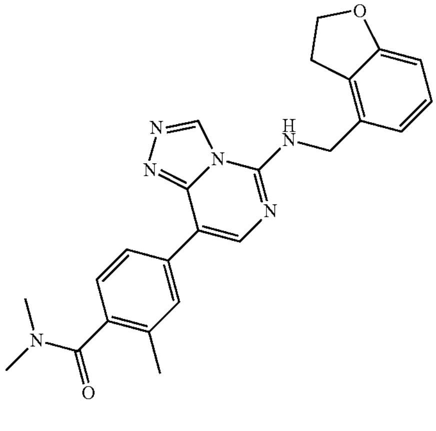 [SMILES: Cc1cc(-c2cnc(NCc3cccc4c3CCO4)n3cnnc23)ccc1C(=O)N(C)C] | $^1$H-NMR (400 MHz, $CD_3OD$) δ ppm 2.26 (s, 3H), 2.81 (s, 3H), 3.03 (s, 3H), 3.25 (t, 2H), 4.53 (t, 2H), 4.72 (s, 2H), 6.69 (d, 1H), 6.88 (d, 1H), 7.06 (t, 1H), 7.23 (d, 1H), 7.97 (m, 3H), 8.86 (s, 1H), 9.51 (s, 1H). LC-MS: $[M + H]^+$ = 429.5 |

TABLE 2-continued
| Ex # | Structure | $^1$H NMR (400 MHz, DMSO-$d_6$) or otherwise indicated/LC-MS Data |
|---|---|---|
| 50 | 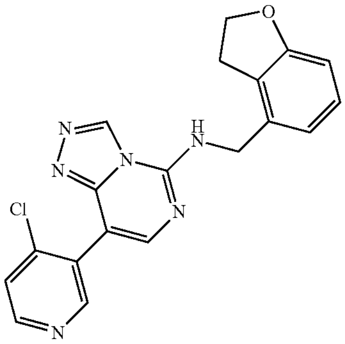 [SMILES: Clc1ccncc1-c1cnc(NCc2cccc3c2CCO3)n2cnnc12] | $^1$H-NMR (400 MHz, $CD_3OD$) δ ppm 3.24-3.30 (m, 2H), 4.56 (t, 2H), 4.72 (d, 1H), 6.71 (d, 1H), 6.91 (d, 1H), 7.08 (d, 1H), 7.72 (s, 1H), 7.76 (s, 1H), 8.59 (d, 1H), 8.72 (s, 1H), 9.50 (s, 1H). LC-MS: $[M + H]^+$ = 378.9 |
| 51 | 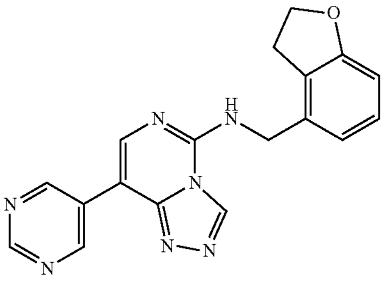 [SMILES: c1cc(CNc2ncc(-c3cncnc3)c3nncn23)c2c(c1)OCC2] | δ ppm 3.25 (t, 2H), 4.56 (t, 2H), 4.74 (s, 2H), 6.71 (d, 1H), 6.90 (d, 1H), 7.06 (t, 1H), 8.28 (s, 1H), 9.15 (s, 1H), 9.54 (s, 3H). LC-MS: $[M + H]^+$ = 346.5 |
| 52 | 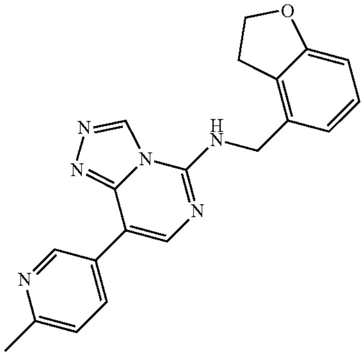 [SMILES: Cc1ccc(-c2cnc(NCc3cccc4c3CCO4)n3cnnc23)cn1] | δ ppm 2.49 (s, 4H), 3.24 (t, 2H), 4.54 (t, 2H), 4.71 (s, 2H), 6.69 (d, 1H), 6.86 (d, 1H), 7.06 (t, 1H), 7.34 (d, 1H), 8.07 (s, 1H), 8.38 (d, 1H), 9.13 (s, 1H), 9.50 (s, 1H). LC-MS: $[M + H]^+$ = 359.2 |
| 53 | 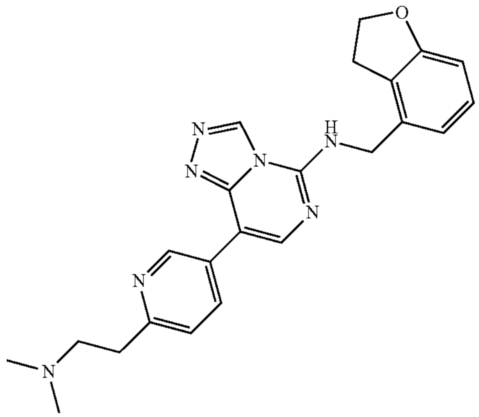 [SMILES: CN(C)CCc1ccc(-c2cnc(NCc3cccc4c3CCO4)n3cnnc23)cn1] | δ ppm 2.28 (s, 6H), 2.75 (m, 2H), 2.96 (m, 2H), 3.26 (m, 2H), 4.57 (m, 2H), 4.72 (m, 2H), 6.70 (d, 1H), 6.89 (d, 1H), 7.09 (m, 1H), 7.41 (d, 1H), 8.09 (s, 1H), 8.95 (m, 1H), 9.30 (m, 1H), 9.52 (s, 1H). LC-MS: $[M + H]^+$ = 416.2 |

TABLE 2-continued
| Ex # | Structure | $^1$H NMR (400 MHz, DMSO-$d_6$) or otherwise indicated/LC-MS Data |
|---|---|---|
| 54 | 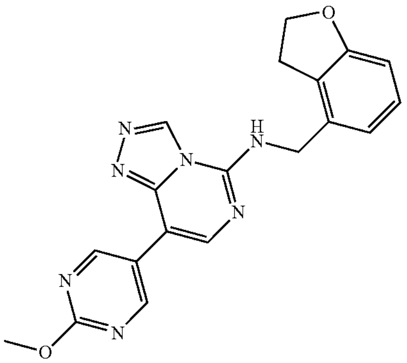 [SMILES: COc1ncc(-c2cnc(NCc3cccc4c3CCO4)n3cnnc23)cn1] | δ ppm 3.19-3.25 (t, 2H), 3.97 (s, 3H), 4.52-4.56 (t, 2H), 4.71 (s, 2H), 6.68-6.70 (d, 1H), 6.86-6.88 (d, 1H), 7.05-7.08 (t, 1H), 8.12 (s, 1H), 9.29 (s, 2H), 9.51 (s, 1H). LC-MS: $[M + H]^+$ = 376.3 |
| 55 | 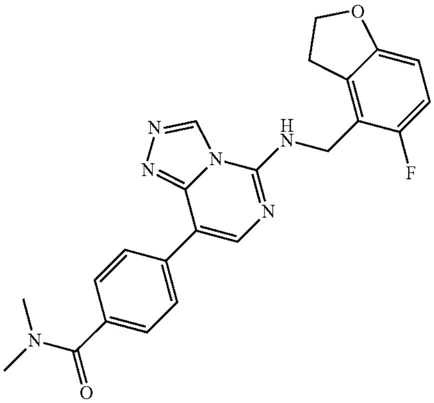 [SMILES: CN(C)C(=O)c1ccc(-c2cnc(NCc3c(F)ccc4c3CCO4)n3cnnc23)cc1] | $^1$H-NMR (400 MHz, $CD_3OD$) δ ppm 3.09 (s, 3H), 3.15 (s, 3H), 3.40 (t, 2H), 4.60 (t, 2H), 4.83 (s, 2H), 6.65-6.69 (m, 1H), 6.87 (t, 1H), 7.57 (d, 2H), 8.06-8.08 (m, 3H), 9.36 (s, 1H). LC-MS: $[M + H]^+$ = 433.2 |
| 56 | 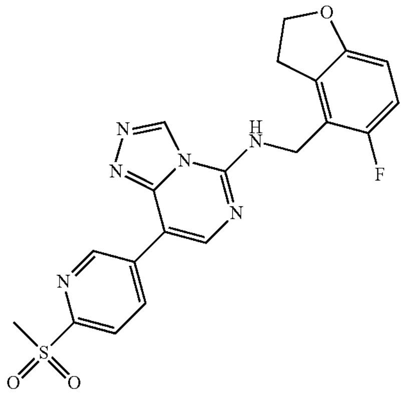 [SMILES: CS(=O)(=O)c1ccc(-c2cnc(NCc3c(F)ccc4c3CCO4)n3cnnc23)cn1] | $^1$H-NMR (400 MHz, $CD_3OD$) δ ppm 3.31 (s, 3H), 3.44 (t, 2H), 4.61 (t, 2H), 4.87 (s, 2H), 6.66-6.69 (m, 1H), 6.88 (t, 1H), 8.19 (d, 1H), 8.26 (s, 1H), 8.77 (d, 1H), 9.39 (s, 1H), 9.42 (s, 1H). LC-MS: $[M + H]^+$ = 441.1 |
| 57 | 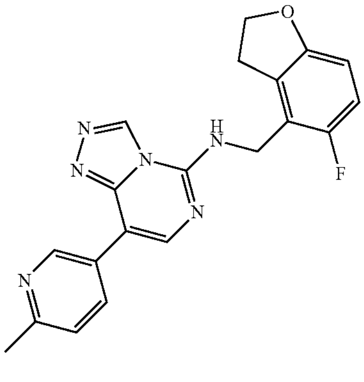 [SMILES: Cc1ccc(-c2cnc(NCc3c(F)ccc4c3CCO4)n3cnnc23)cn1] | $^1$H-NMR (400 MHz, $CD_3OD$) δ ppm 2.61 (s, 3H), 3.41 (t, 2H), 4.60 (t, 2H), 4.84 (s, 2H), 6.65-6.68 (m, 1H), 6.88 (t, 1H), 7.44 (d, 1H), 8.04 (s, 1H), 8.31 (d, 1H), 9.00 (s, 1H), 9.36 (s, 1H). LC-MS: $[M + H]^+$ = 377.2. |

TABLE 2-continued
| Ex # | Structure | $^{1}H$ NMR (400 MHz, DMSO-$d_6$) or otherwise indicated/LC-MS Data |
|---|---|---|
| 58 | 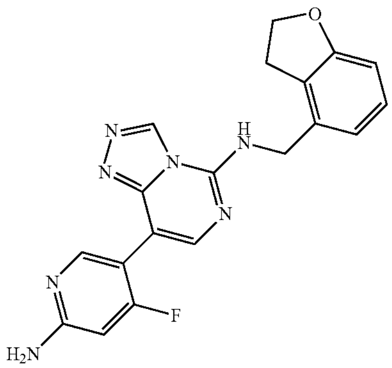 [SMILES: Nc1cc(F)c(-c2cnc(NCc3cccc4c3CCO4)n3cnnc23)cn1] | δ ppm 3.25 (t, 2H), 4.55 (t, 2H), 4.72 (d, 2H), 6.71 (q, 2H), 6.87 (d, 1H), 7.08 (t, 1H), 7.65 (s, 2H), 8.34 (d, 1H), 8.79 (s, 1H), 9.47 (s, 1H). LC-MS $[M + H]^+$= 378.5 |
| 59 | 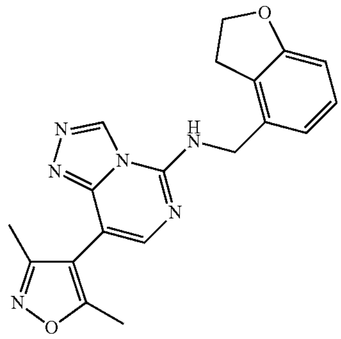 [SMILES: Cc1noc(C)c1-c1cnc(NCc2cccc3c2CCO3)n2cnnc12] | δ ppm 2.20 (s, 3H), 2.38 (s, 3H), 3.25 (t, 2H), 4.56 (t, 2H), 4.70 (s, 2H), 6.71 (d, 1H), 6.90 (d, 1H), 7.09 (d, 1H), 7.65 (s, 1H), 8.87 (s, 1H), 9.48 (s, 1H). LC-MS $[M + H]^+$ = 363.2 |
| 60 | 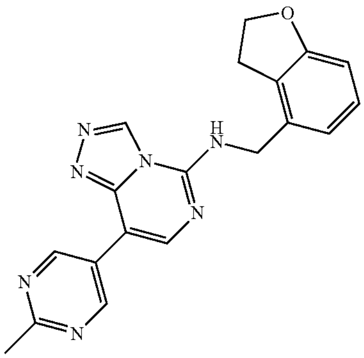 [SMILES: Cc1ncc(-c2cnc(NCc3cccc4c3CCO4)n3cnnc23)cn1] | δ ppm 2.66 (s, 3H), 3.23 (t, 2H), 4.54 (t, 2H), 4.72 (s, 2H), 6.69 (d, 1H), 6.87 (d, 1H), 7.06 (t, 1H), 8.20 (s, 1H), 9.01 (s, 1H), 9.39 (s, 2H), 9.51 (s, 1H). LC-MS: $[M + H]^+$ = 360.0 |
| 61 | 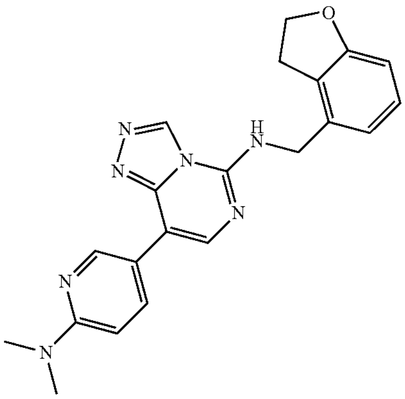 [SMILES: CN(C)c1ccc(-c2cnc(NCc3cccc4c3CCO4)n3cnnc23)cn1] | δ ppm 3.08 (s, 6H), 3.25 (t, 2H), 4.56 (t, 2H), 4.70 (s, 2H), 6.70 (d, 1H), 6.75 (d, 1H), 6.88 (d, 1H), 7.08 (t, 1H), 7.91 (s, 1H), 8.23 (d, 1H), 8.80 (d, 2H), 9.49 (s, 1H). LC-MS: $[M + H]^+$ = 388.2 |

TABLE 2-continued
| Ex # | Structure | $^1$H NMR (400 MHz, DMSO-$d_6$) or otherwise indicated/LC-MS Data |
|---|---|---|
| 62 | 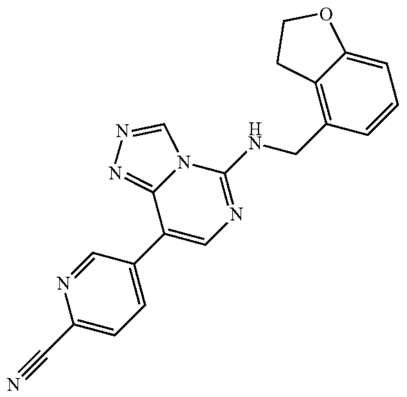 [SMILES: N#Cc1ccc(-c2cnc(NCc3cccc4c3CCO4)n3cnnc23)cn1] | δ ppm 3.24 (t, 2H), 4.55 (t, 2H), 4.75 (s, 2H), 6.70 (d, 1H), 6.88 (d, 1H), 7.07 (t, 1H), 8.13 (d, 1H), 8.39 (s, 1H), 8.86 (q, 1H), 9.08 (d, 1H), 9.54 (s, 1H), 9.55 (d, 1H). LC-MS: $[M + H]^+$= 370.1 |
| 63 | 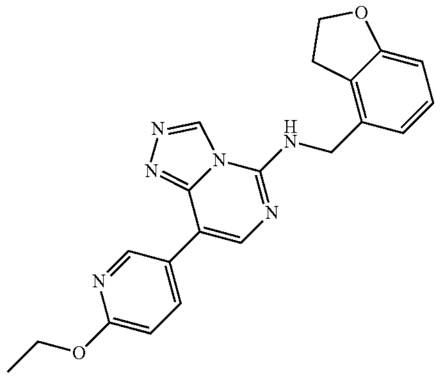 [SMILES: CCOc1ccc(-c2cnc(NCc3cccc4c3CCO4)n3cnnc23)cn1] | δ ppm 1.35 (t, 3H), 3.23 (t, 2H), 4.35 (q, 2H), 4.55 (t, 2H), 4.71 (s, 2H), 6.69 (d, 1H), 6.89 (q, 2H), 7.07 (t, 1H), 8.01 (s, 1H), 8.39 (q, 1H), 8.56 (d, 2H), 9.50 (s, 1H). LC-MS: $[M + H]^+$ = 389.0 |
| 64 | 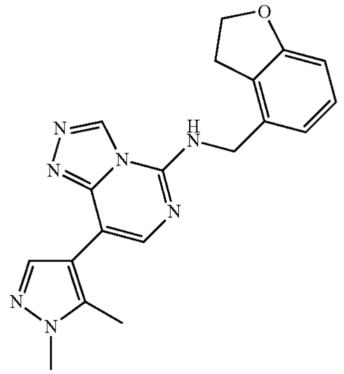 [SMILES: Cc1c(-c2cnc(NCc3cccc4c3CCO4)n3cnnc23)cnn1C] | δ ppm 2.36 (s, 3H), 3.27 (t, 2H), 3.81 (s, 3H), 4.56 (t, 2H), 4.69 (d, 2H), 6.69 (d, 1H), 6.88 (d, 1H), 7.08 (t, 1H), 7.58 (s, 1H), 7.76 (s, 1H), 8.65 (t, 1H), 9.46 (s, 1H). LC-MS: $[M + H]^+$ = 362.0 |
| 65 | 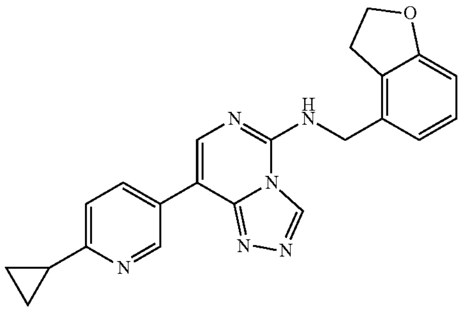 [SMILES: c1cc(CNc2ncc(-c3ccc(C4CC4)nc3)c3nncn23)c2c(c1)OCC2] | δ ppm 0.96-1.00 (m, 4H), 2.15 (t, 1H), 3.24 (t, 2H), 4.56 (t, 2H), 4.72 (s, 2H), 6.70 (d, 1H), 6.88 (d, 1H), 7.08 (t, 1H), 7.39 (d, 1H), 8.06 (s, 1H), 8.36 (q, 1H), 8.87 (s, 1H), 9.07 (s, 1H), 9.51 (s, 1H). LC-MS: $[M + H]^+$ = 385.0 |

TABLE 2-continued
| Ex # | Structure | $^{1}H$ NMR (400 MHz, DMSO-$d_6$) or otherwise indicated/LC-MS Data |
|---|---|---|
| 66 | 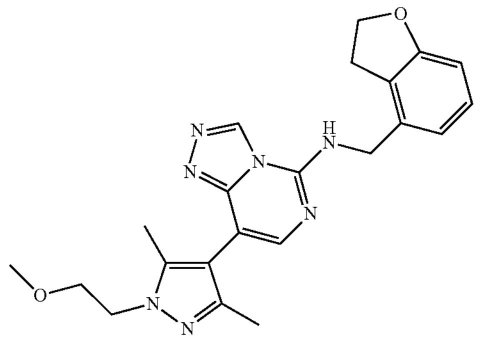 [SMILES: COCCn1nc(C)c(-c2cnc(NCc3cccc4c3CCO4)n3cnnc23)c1C] | δ ppm 2.09 (s, 3H), 2.16 (s, 3H), 3.27 (t, 5H), 3.69 (t, 2H), 4.18 (t, 2H), 4.58 (t, 2H), 4.69 (d, 2H), 6.71 (d, 1H), 6.91 (d, 1H), 7.09 (t, 1H), 7.45 (s, 1H), 8.66 (t, 1H), 9.45 (s, 1H). LC-MS: $[M + H]^+$ = 420.7 |
| 67 | 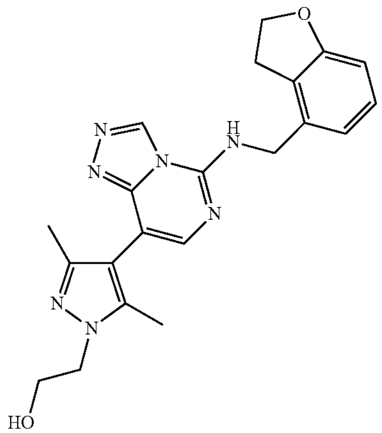 [SMILES: Cc1nn(CCO)c(C)c1-c1cnc(NCc2cccc3c2CCO3)n2cnnc12] | δ ppm 2.08 (s, 3H), 2.18 (s, 3H), 3.27 (q, 2H), 3.74 (q, 2H), 4.07 (t, 2H), 4.57 (t, 2H), 4.69 (s, 2H), 4.91 (t, 1H), 6.71 (d, 1H), 6.91 (d, 1H), 7.09 (t, 1H), 7.44 (s, 1H), 9.15 (s, 1H), 9.45 (s, 1H). LC-MS: $[M + H]^+$ = 406.6 |
| 68 | 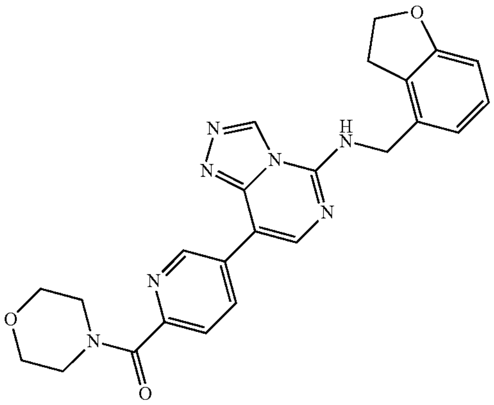 [SMILES: O=C(c1ccc(-c2cnc(NCc3cccc4c3CCO4)n3cnnc23)cn1)N1CCOCC1] | δ ppm 3.25 (t, 2H), 3.57 (d, 4H), 3.68 (s, 4H), 4.55 (t, 2H), 4.74 (s, 2H), 6.71 (d, 1H), 6.87 (d, 1H), 7.08 (t, 1H), 7.74 (d, 1H), 8.24 (s, 1H), 8.70 (q, 1H), 9.33 (d, 1H), 9.53 (s, 1H). LC-MS $[M + H]^+$ = 458.1 |
| 69 | 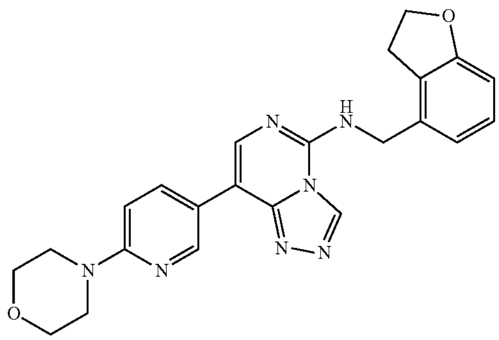 [SMILES: c1cc(CNc2ncc(-c3ccc(N4CCOCC4)nc3)c3nncn23)c2c(c1)OCC2] | $^{1}H$ NMR (500 MHz, DMSO-$d_6$) δ ppm 3.24 (t, 2H), 3.50 (s, 4H), 3.73 (s, 4H), 4.55 (t, 2 H), 4.70 (s, 2H), 6.70 (d, 1H), 6.88 (d, 1H), 6.95 (d, 1H), 7.07 (dd, 1H), 7.96 (s, 1H), 8.28 (t, 1H), 8.76 (s, 1H), 8.86 (s, 1H), 9.50 (s, 1H). LC-MS: [M + H]+ = 430.4 |

TABLE 2-continued
| Ex # | Structure | $^1$H NMR (400 MHz, DMSO-$d_6$) or otherwise indicated/LC-MS Data |
|---|---|---|
| 70 | 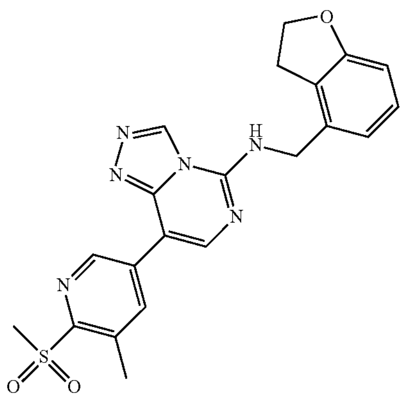 [SMILES: Cc1cc(-c2cnc(NCc3cccc4c3CCO4)n3cnnc23)cnc1S(C)(=O)=O] | δ ppm 2.68 (s, 3H), 3.25 (t, 2H), 3.42 (s, 3H), 4.55 (t, 2H), 4.74 (s, 2H), 6.69 (d, 1H), 6.88 (d, 1H), 7.06 (d, 1H), 8.33 (s, 1H), 8.71 (d, 1H), 9.02 (s, 1H), 9.27 (d, 1H), 9.55 (s, 1H). LC-MS: $[M + H]^+$ = 437.6 |
| 71 | 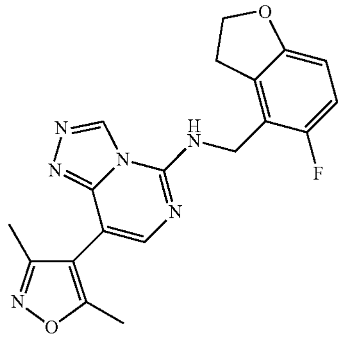 [SMILES: Cc1noc(C)c1-c1cnc(NCc2c(F)ccc3c2CCO3)n2cnnc12] | $^1$H NMR (500 MHz, DMSO-$d_6$) δ ppm 2.20 (s, 3H), 2.37 (s, 3H), 3.33 (d, 2H), 4.56 (t, 2H), 4.72 (s, 2H), 6.72 (dd, 1H), 6.97 (t, 1H), 7.67 (s, 1H), 8.73 (s, 1H), 9.46 (s, 1H). LC-MS: $[M + H]^+$ = 381.1 |
| 72 | 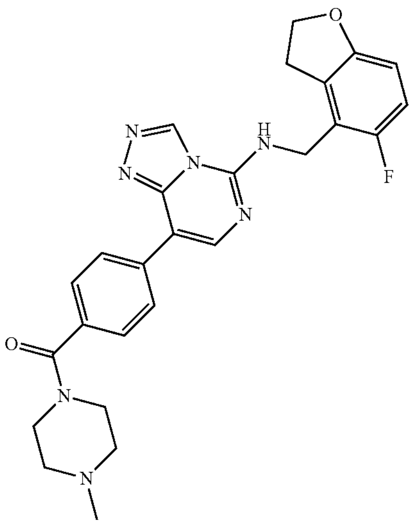 [SMILES: CN1CCN(C(=O)c2ccc(-c3cnc(NCc4c(F)ccc5c4CCO5)n4cnnc34)cc2)CC1] | $^1$H-NMR (400 MHz, $CD_3OD$) δ ppm 2.36 (s, 3H), 2.47-2.56 (m, 4H), 3.39 (t, 2H), 3.56-3.58 (m, 2H), 3.81-3.83 (m, 2H), 4.60 (t, 2H), 4.85 (s, 2H), 6.65-6.68 (m, 1H), 6.88 (t, 1H), 7.56 (d, 2H), 8.06-8.09 (m, 3H), 7.96 (s, 1H), 9.36 (s, 1H). LC-MS: $[M + H]^+$ = 488.2 |

TABLE 2-continued
| Ex # | Structure | $^1H$ NMR (400 MHz, DMSO-$d_6$) or otherwise indicated/LC-MS Data |
|---|---|---|
| 73 | 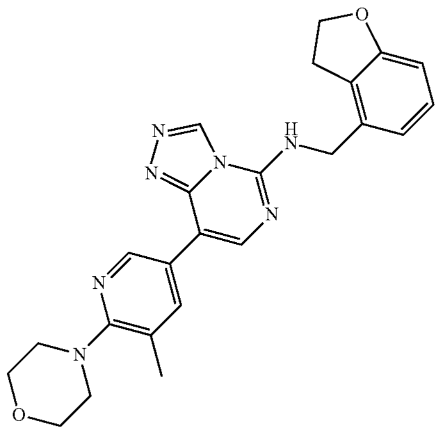 [SMILES: Cc1cc(-c2cnc(NCc3cccc4c3CCO4)n3cnnc23)cnc1N1CCOCC1] | δ ppm 2.33 (s, 3H), 3.11 (t, 4H), 3.24 (t, 2H), 3.75 (s, 4H), 4.55 (t, 2H), 4.71 (s, 2H), 6.69 (d, 1H), 6.87 (d, 1H), 7.07 (t, 1H), 8.00 (s, 1H), 8.23 (s, 1H), 8.80 (d, 2H), 9.50 (s, 1H). LC-MS: $[M + H]^+$ = 444.5 |
| 74 | 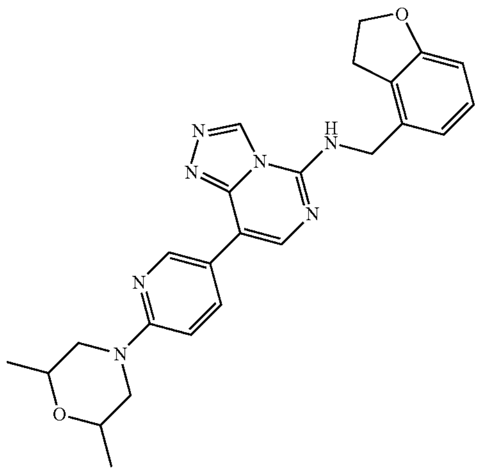 [SMILES: CC1CN(c2ccc(-c3cnc(NCc4cccc5c4CCO5)n4cnnc34)cn2)CC(C)O1] | δ ppm 1.17 (d, 6H), 2.44 (t, 2H), 3.24 (t, 2H), 3.64 (t, 2H), 4.21 (d, 2H), 4.55 (t, 2H), 4.70 (d, 2H), 6.70 (d, 1H), 6.88 (d, 1H), 6.96 (d, 1H), 7.08 (t, 1H), 7.95 (s, 1H), 8.28 (d, 1H), 8.75 (t, 1H), 8.83 (d, 1H), 9.49 (s, 1H). LC-MS: $[M + H]^+$ = 458.6 |
| 75 | 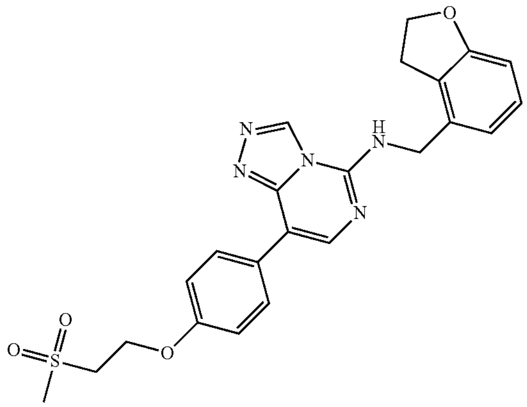 [SMILES: CS(=O)(=O)CCOc1ccc(-c2cnc(NCc3cccc4c3CCO4)n3cnnc23)cc1] | δ ppm 3.11 (s, 3H), 3.25 (t, 2H), 3.66 (t, 2H), 4.43 (t, 2H), 4.56 (t, 2H), 4.70 (s, 2H), 6.70 (d, 1H), 6.88 (d, 1H), 7.06-7.12 (m, 3H), 7.96 (s, 1H), 8.08 (d, 2H), 8.76 (s, 1H), 9.50 (s, 1H). LC-MS: $[M + H]^+$ = 466.1 |

TABLE 2-continued
| Ex # | Structure | $^1H$ NMR (400 MHz, DMSO-$d_6$) or otherwise indicated/LC-MS Data |
|---|---|---|
| 76 | 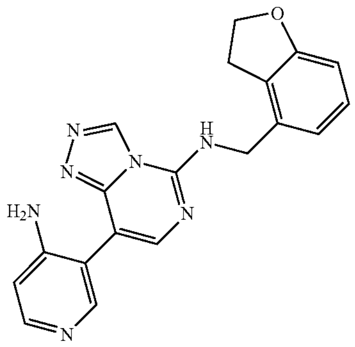 [SMILES: Nc1ccncc1-c1cnc(NCc2cccc3c2CCO3)n2cnnc12] | δ ppm 3.25 (t, 2H), 4.55 (t, 2H), 4.70 (s, 2H), 5.82 (s, 2H), 6.62 (d, 1H), 6.70 (d, 1H), 6.89 (d, 1H), 7.08 (t, 1H), 7.54 (s, 1H), 8.03 (d, 2H), 9.45 (s, 1H). LC-MS: $[M + H]^+$ = 360.0 |
| 77 | 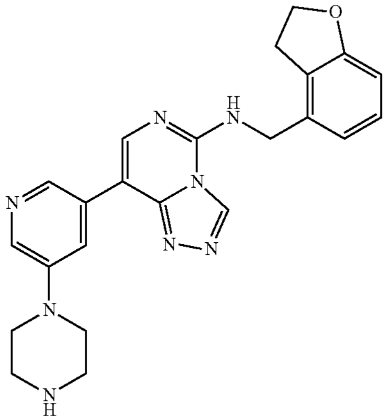 [SMILES: c1cc(CNc2ncc(-c3cncc(N4CCNCC4)c3)c3nncn23)c2c(c1)OCC2] | δ ppm 2.85 (t, 4H), 3.15 (t, 4H), 3.23 (t, 2H), 4.54 (t, 2H), 4.71 (s, 2H), 6.79 (d, 1H), 6.88 (d, 1H), 7.06 (t, 1H), 8.01 (s, 1H), 8.12 (s, 1H), 8.24 (s, 1H), 8.66 (s, 1H), 9.50 (s, 1H). LC-MS: $[M + H]^+$ = 429.0 |
| 78 | 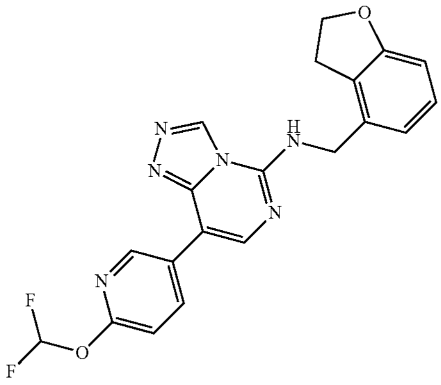 [SMILES: FC(F)Oc1ccc(-c2cnc(NCc3cccc4c3CCO4)n3cnnc23)cn1] | δ ppm 3.25 (t, 2H), 4.55 (t, 2H), 4.73 (s, 2H), 6.72 (d, 1H), 6.88 (d, 1H), 7.08 (t, 1H), 7.23 (d, 1H), 7.59-7.96 (m, 1H), 8.13 (s, 1H), 8.66 (dd, 1H), 8.93 (s, 1H), 8.99 (d, 1H), 9.52 (s, 1H). LC-MS: $[M + H]^+$ = 411.2 |
| 79 | 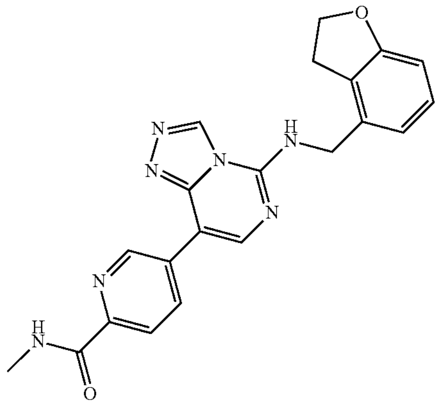 [SMILES: CNC(=O)c1ccc(-c2cnc(NCc3cccc4c3CCO4)n3cnnc23)cn1] | $^1H$ -NMR (500 MHz, DMSO-$d_6$) δ ppm 2.84 (d, 3 H), 3.25 (t, 2H), 4.55 (t, 2 H), 4.74 (s, 2 H), 6.71 (d, 1H), 6.90 (d, 1H), 7.08 (t, 1H), 8.11 (d, 1H), 8.29 (s, 1H), 8.73 (dd, 1H), 8.81 (dd, 1H), 9.00 (s, 1H), 9.39 (d, 1H), 9.54 (s, 1H). ). LC-MS: $[M + H]^+$ = 402.3 |

TABLE 2-continued
| Ex # | Structure | $^1$H NMR (400 MHz, DMSO-$d_6$) or otherwise indicated/LC-MS Data |
|---|---|---|
| 80 | 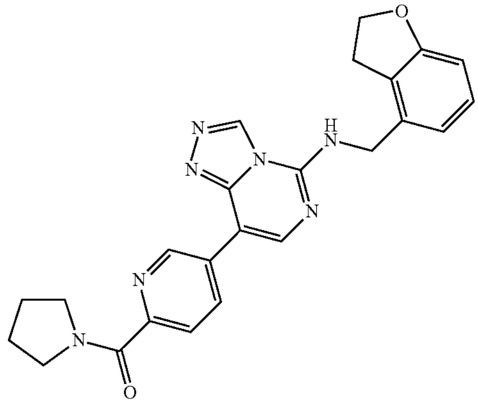 [SMILES: O=C(c1ccc(-c2cnc(NCc3cccc4c3CCO4)n3cnnc23)cn1)N1CCCC1] | δ ppm 1.88 (d, 4H), 3.25 (t, 2H), 3.53 (t, 2H), 3.70 (t, 2H), 4.55 (t, 2H), 4.74 (s, 2H), 6.71 (d, 1H), 6.87 (d, 1H), 7.08 (t, 1H), 7.85 (d, 1H), 8.26 (s, 1H), 8.69 (q, 1H), 9.33 (d, 1H), 9.53 (s, 1H). LC-MS: $[M + H]^+$ = 442.4 |
| 81 | 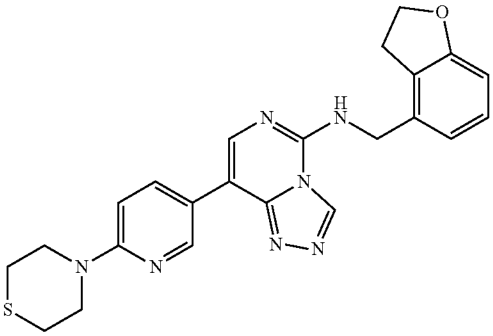 [SMILES: c1cc(CNc2ncc(-c3ccc(N4CCSCC4)nc3)c3nncn23)c2c(c1)OCC2] | $^1$H-NMR (400 MHz, $CD_3OD$) δ ppm 2.67-2.70 (m, 4H), 3.29-3.31 (m, 2H), 4.01-4.04 (m, 4H), 4.59 (t, 2H), 4.79 (s, 2H), 6.69 (d, 1H), 6.93 (t, 1H), 7.09 (t, 1H), 7.86 (s, 1H), 8.11 (d, 1H), 8.68 (s, 1H), 9.32 (s, 1H). LC-MS: $[M + H]^+$ = 446.2 |
| 82 | 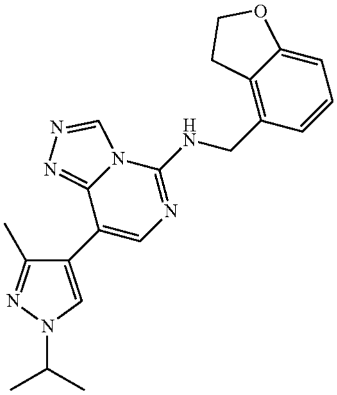 [SMILES: Cc1nn(C(C)C)cc1-c1cnc(NCc2cccc3c2CCO3)n2cnnc12] | $^1$H-NMR (400 MHz, MeOH-$d_4$) δ ppm 1.54-1.56 (m, 6H), 2.40 (s, 3H), 3.27-3.28 (m, 4H), 4.49-4.53 (m, 4 H), 4.78 (s, 2 H), 6.69 (d, 1H), 6.92 (d, 1H), 7.09 (t, 1H), 7.76 (s, 1H), 8.13 (s, 1H), 9.31 (s, 1 H). LC-MS: $[M + H]^+$ = 390.2 |
| 83 | 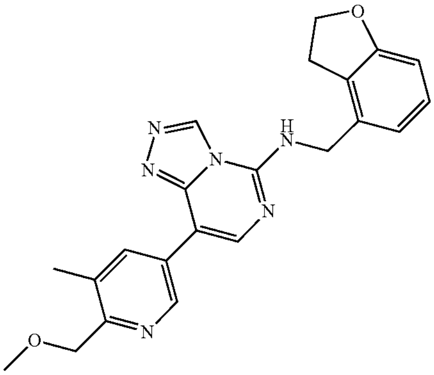 [SMILES: COCc1ncc(-c2cnc(NCc3cccc4c3CCO4)n3cnnc23)cc1C] | δ ppm 2.42 (s, 3H), 3.25 (t, 2H), 4.53-4.58 (m, 4H), 4.73 (d, 2H), 6.70 (d, 1H), 6.89 (d, 1H), 7.08 (t, 1H), 8.13 (s, 1H), 8.33 (d, 1H), 8.93 (t, 1H), 9.05 (d, 1H), 9.52 (s, 1H). LC-MS: $[M + H]^+$ = 403.3 |

TABLE 2-continued
| Ex # | Structure | $^1H$ NMR (400 MHz, DMSO-$d_6$) or otherwise indicated/LC-MS Data |
| --- | --- | --- |
| 84 | 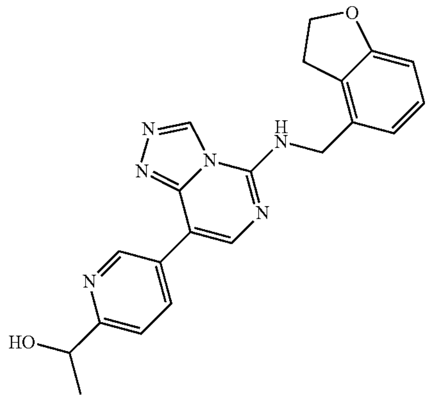 [SMILES: CC(O)c1ccc(-c2cnc(NCc3cccc4c3CCO4)n3cnnc23)cn1] | $^1H$ NMR (500 MHz, DMSO-$d_6$) δ ppm 1.41 (d, 3H), 3.25 (t, 2H), 4.55 (t, 2H), 4.73 (s, 2H), 4.75-4.84 (m, 1H), 5.43 (d, 1H), 6.70 (d, 1H), 6.89 (d, 1H), 7.08 (t, 1H), 7.60 (d, 1H), 8.10 (s, 1H), 8.48 (dd, 1H), 8.93 (s, 1H), 9.15 (d, 1H), 9.52 (s, 1H). LC-MS: $[M + H]^+$ = 389.2 |
| 85 | 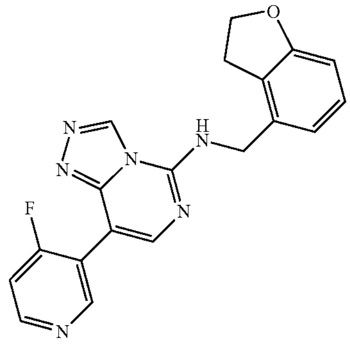 [SMILES: Fc1ccncc1-c1cnc(NCc2cccc3c2CCO3)n2cnnc12] | δ ppm 3.25 (t, 2H), 4.55 (t, 2H), 4.73 (s, 2H), 6.71 (d, 1H), 6.90 (d, 1H), 7.08 (t, 1H), 7.50 (dd, 1H), 7.88 (d, 1H), 8.63 (dd, 1H), 9.02 (d, 2H), 9.51 (s, 1H). LC-MS: $[M + H]^+$ = 363.2 |
| 86 | 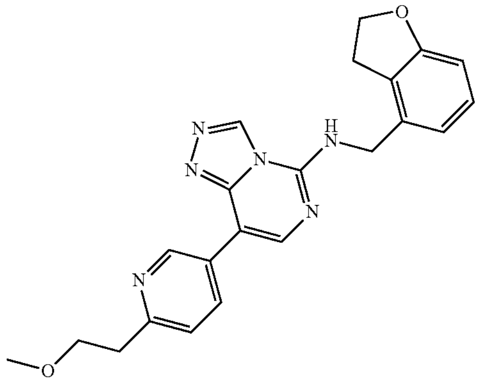 [SMILES: COCCc1ccc(-c2cnc(NCc3cccc4c3CCO4)n3cnnc23)cn1] | $^1H$ NMR (400 MHz, DMSO-$d_6$) δ ppm 3.00 (t, 2H), 3.22-3.27 (m, 5H), 3.72 (t, 2H), 4.55 (t, 2H), 4.73 (s, 2H), 6.70 (d, 1H), 6.89 (d, 1H), 7.07 (t, 1H), 7.39 (d, 1H), 8.09 (s, 1H), 8.39 (dd, 1H), 8.89 (s, 1H), 9.16 (d, 1H), 9.52 (s, 1H). LC-MS: $[M + H]^+$ = 403.3 |
| 87 | 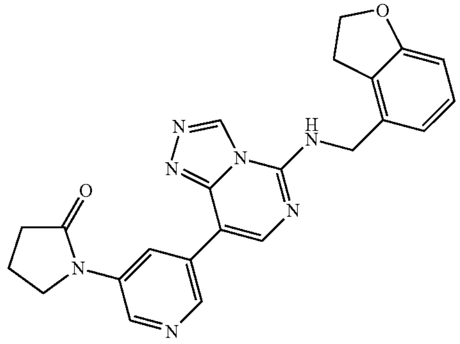 [SMILES: O=C1CCCN1c1cncc(-c2cnc(NCc3cccc4c3CCO4)n3cnnc23)c1] | δ ppm 2.14 (t, 3H), 2.55 (t, 2H), 3.25 (t, 2H), 3.95 (t, 2H), 4.56 (t, 2H), 4.74 (s, 2H), 6.70 (s, 1H), 6.90 (s, 1H), 7.08 (t, 1H), 8.15 (s, 1H), 8.73 (s, 1H), 8.92 (s, 1H), 9.02 (s, 1H), 9.53 (s, 1H). LC-MS: $[M + H]^+$ = 428.2. |

TABLE 2-continued
| Ex # | Structure | $^{1}$H NMR (400 MHz, DMSO-$d_6$) or otherwise indicated/LC-MS Data |
| --- | --- | --- |
| 88 | 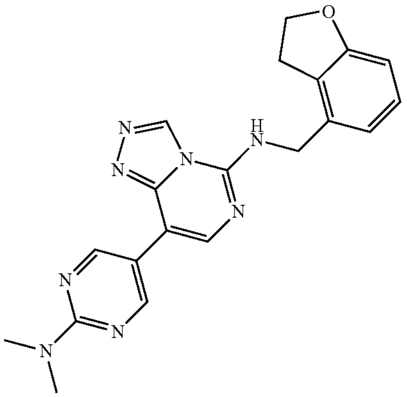 [SMILES: CN(C)c1ncc(-c2cnc(NCc3cccc4c3CCO4)n3cnnc23)cn1] | δ ppm 3.15 (s, 6H), 3.31 (s, 2H), 4.55 (t, 2H), 4.70 (s, 2H), 6.06 (s, 1H), 6.70 (d, 1H), 6.88 (d, 1H), 7.07 (t, 1H), 7.97 (s, 1H), 9.03 (s, 1H), 9.50 (s, 1H). LC-MS: $[M + H]^+$ = 389.2 |
| 89 | 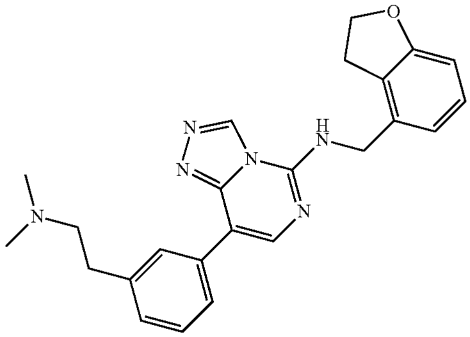 [SMILES: CN(C)CCc1cccc(-c2cnc(NCc3cccc4c3CCO4)n3cnnc23)c1] | δ ppm 2.19 (s, 6H), 2.52-2.54 (m, 2H), 2.78 (t, 2 H), 3.25 (t, 2 H), 4.55 (t, 2 H), 4.72 (s, 2 H), 6.70 (d, 1 H), 6.90 (d, 1 H), 7.08 (t, 1 H), 7.21 (d, 1 H), 7.37 (t, 3 H), 7.90-8.00 (m, 3 H), 8.83 (s, 1 H), 9.51 (s, 1 H). LC-MS: $[M + H]^+$ = 415.2 |
| 90 | 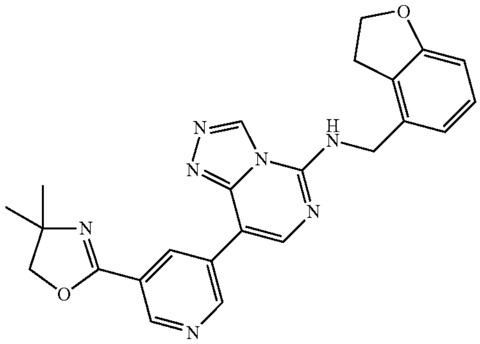 [SMILES: CC1(C)COC(c2cncc(-c3cnc(NCc4cccc5c4CCO5)n4cnnc34)c2)=N1] | δ ppm 1.34 (s, 6H), 3.26 (t, 2H), 4.19 (s, 2H), 4.56 (t, 2H), 4.74 (s, 2H), 6.71 (d, 1H), 6.89 (d, 1H), 7.08 (t, 1H), 8.28 (s, 1H), 8.82-9.49 (m, 4H), 9.54 (s, 1H). LC-MS $[M + H]^+$ = 442.2 |
| 91 | 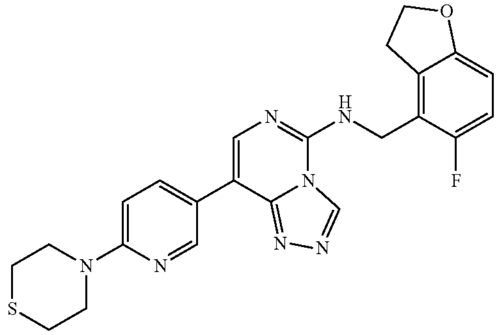 [SMILES: Fc1ccc2c(c1CNc1ncc(-c3ccc(N4CCSCC4)nc3)c3nncn13)CCO2] | $^{1}$H-NMR (400 MHz, MeOH-$d_4$) δ ppm 2.67-2.70 (m, 4H), 3.37-3.39 (m, 2H), 4.01-4.04 (m, 4H), 4.59-4.60 (m, 2H), 4.80-4.82 (m, 2H), 6.65-6.68 (m, 1H), 6.88 (t, 1H), 6.94 (d, 1H), 7.90 (s, 1H), 8.10-8.13 (m, 1H), 8.68 (d, 1H), 9.34 (s, 1H). LC-MS: $[M + H]^+$ = 464.2 |

TABLE 2-continued
| Ex # | Structure | $^1$H NMR (400 MHz, DMSO-$d_6$) or otherwise indicated/LC-MS Data |
|---|---|---|
| 92 | 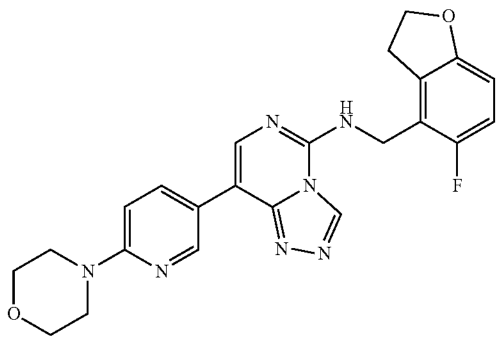 [SMILES: Fc1ccc2c(c1CNc1ncc(-c3ccc(N4CCOCC4)nc3)c3nncn13)CCO2] | $^1$H-NMR (400 MHz, MeOH-$d_4$) δ ppm 3.40-3.42 (m, 2H), 3.55-3.58 (m, 4H), 3.82-3.85 (m, 4H), 4.58-4.62 (m, 2H), 4.80-4.82 (m, 2H), 6.65-6.68 (m, 1H), 6.88 (t, 1H), 6.96 (d, 1H), 7.91 (s, 1H), 8.14-8.16 (m, 1H), 8.71 (d, 1H), 9.35 (s, 1 H). LC-MS: $[M + H]^+$ = 448.2 |
| 93 | 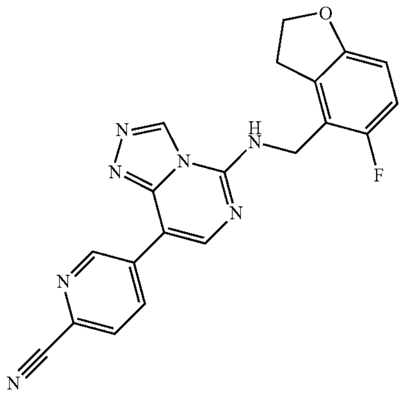 [SMILES: N#Cc1ccc(-c2cnc(NCc3c(F)ccc4c3CCO4)n3cnnc23)cn1] | δ ppm 3.30 (t, 2H), 4.56 (t, 2H), 4.76 (s, 2H), 6.73 (dd, 1H), 6.96 (t, 1H), 8.14 (d, 1H), 8.43 (s, 1H), 8.85 (dd, 1H), 9.06 (d, 1H), 9.54 (s, 1H), 9.56 (d, 1H). LC-MS: $[M + H]^+$ = 388.1 |
| 94 | 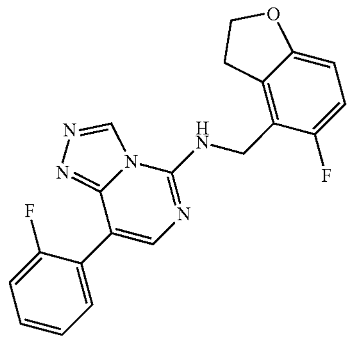 [SMILES: Fc1ccccc1-c1cnc(NCc2c(F)ccc3c2CCO3)n2cnnc12] | δ ppm 3.33 (t, 2H), 4.56 (t, 2H), 4.74 (d, 2H), 6.73 (dd, 1H), 6.97 (t, 1H), 7.33 (dd, 2H), 7.45 (d, 1H), 7.85 (t, 2H), 8.84 (d, 1H), 9.49 (s, 1H). LC-MS: $[M + H]^+$ = 380.0 |
| 95 | 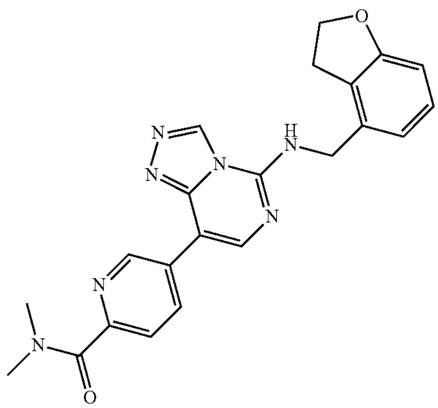 [SMILES: CN(C)C(=O)c1ccc(-c2cnc(NCc3cccc4c3CCO4)n3cnnc23)cn1] | δ ppm 3.03 (d, 6H), 3.25 (t, 2H), 4.55 (t, 2H), 4.74 (d, 2H), 6.70 (d, 1H), 6.90 (d, 1H), 7.08 (t, 1H), 7.69 (d, 1H), 8.24 (s, 1H), 8.67 (dd, 1H), 9.02 (t, 1H), 9.32 (d, 1H), 9.54 (s, 1H). LC-MS: $[M + H]^+$ = 416.2 |

TABLE 2-continued
| Ex # | Structure | $^1$H NMR (400 MHz, DMSO-$d_6$) or otherwise indicated/LC-MS Data |
|---|---|---|
| 96 | 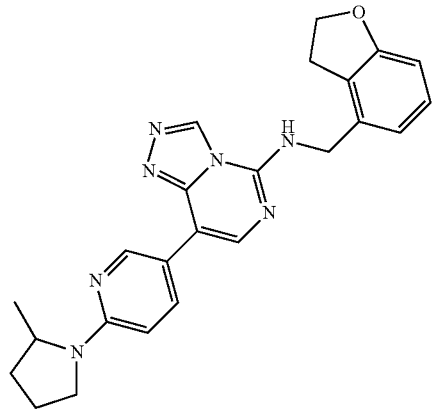 [SMILES: CC1CCCN1c1ccc(-c2cnc(NCc3cccc4c3CCO4)n3cnnc23)cn1] | δ ppm 1.36 (d, 3H), 1.95-1.99 (m, 1H), 2.22-2.37 (m, 3H), 3.31 (t, 2H), 3.62 (dd, 1H), 3.80 (t, 1H), 4.38 (t, 1H), 4.60 (t, 2H), 4.82 (s, 2H), 6.69 (d, 1H), 6.93 (d, 1H), 7.12 (t, 1H), 7.30 (d, 1H), 8.13 (s, 1H), 8.57 (d, 1H), 8.88 (s, 1H), 9.37 (s, 1H). LC-MS: $[M + H]^+ = 428.2$ |
| 97 | 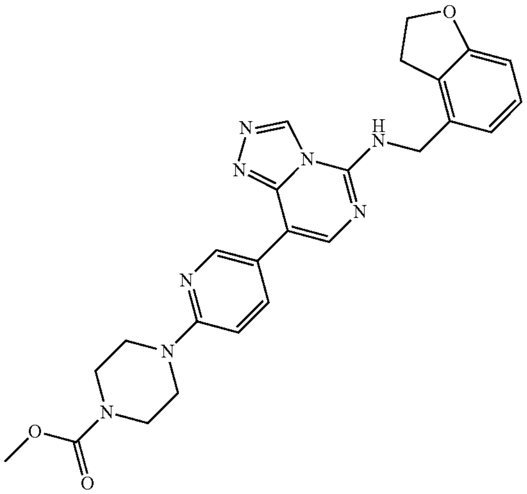 [SMILES: COC(=O)N1CCN(c2ccc(-c3cnc(NCc4cccc5c4CCO5)n4cnnc34)cn2)CC1] | δ ppm 3.23 (t, 2H), 3.57-3.64 (m, 11H), 4.55 (t, 2H), 4.70 (s, 2H), 6.69 (d, 1H), 6.87 (d, 1H), 6.97 (t, 1H), 7.07 (t, 1H), 7.96 (s, 1H), 8.28 (dd, 1H), 8.76 (s, 1H), 8.85 (d, 1H), 9.50 (d, 1H). LC-MS: $[M + H]^+ = 487.2$ |
| 98 | 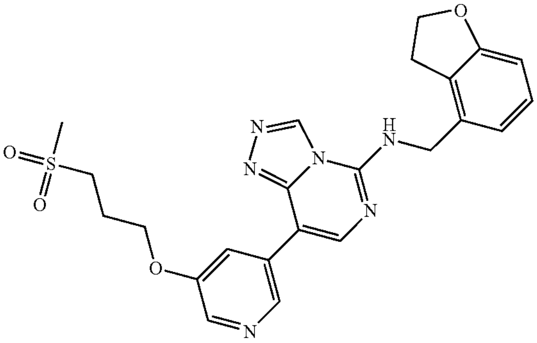 [SMILES: CS(=O)(=O)CCCOc1cncc(-c2cnc(NCc3cccc4c3CCO4)n3cnnc23)c1] | δ ppm 2.16-2.23 (m, 2H), 3.03 (s, 3H), 3.23 (t, 2H), 3.30 (s, 2H), 4.24 (t, 2H), 4.54 (t, 2H), 4.72 (s, 2H), 6.68 (d, 1H), 6.88 (s, 1H), 7.06 (t, 1H), 8.16 (t, 1H), 8.19 (s, 1H), 8.26 (s, 1H), 8.92 (s, 2H), 9.52 (s, 1H). LC-MS: $[M + H]^+ = 481.2$ |

TABLE 2-continued
| Ex # | Structure | $^1$H NMR (400 MHz, DMSO-$d_6$) or otherwise indicated/LC-MS Data |
|---|---|---|
| 99 | 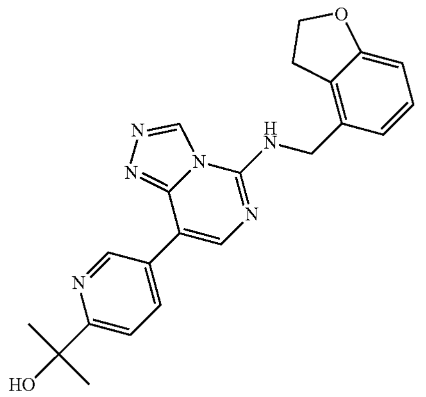 [SMILES: CC(C)(O)c1ccc(-c2cnc(NCc3cccc4c3CCO4)n3cnnc23)cn1] | δ ppm 1.48 (s, 6H), 3.25 (t, 2H), 4.55 (t, 2H), 4.72 (s, 2H), 5.27 (s, 1H), 6.69 (d, 1H), 6.88 (d, 1H), 7.08 (t, 1H), 7.73 (d, 1H), 8.09 (s, 1H), 8.45 (m, 1H), 8.88 (s, 1H), 9.13 (s, 1H), 9.53 (s, 1H). LC-MS: $[M + H]^+$ = 403.1 |
| 100 | 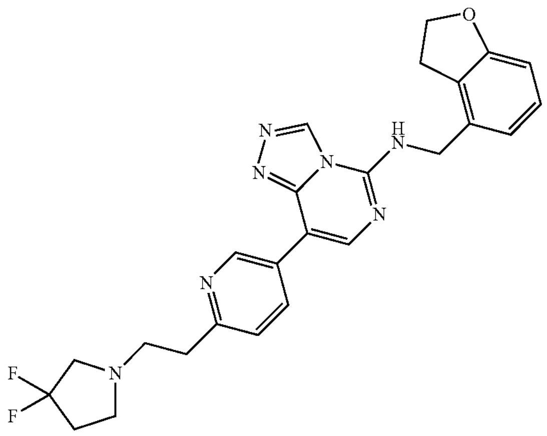 [SMILES: FC1(F)CCN(CCc2ccc(-c3cnc(NCc4cccc5c4CCO5)n4cnnc34)cn2)C1] | δ ppm 2.18-2.27 (m, 2H), 2.73 (d, 2H), 2.84 (d, 2H), 2.88-3.00 (m, 4H), 3.24 (t, 2H), 4.55 (t, 2H), 4.72 (s, 2H), 6.70 (d, 1H), 6.88 (d, 1H), 7.07 (t, 1H), 7.41 (d, 1H), 8.09 (s, 1H), 8.39 (dd, 1H), 8.95 (s, 1H), 9.16 (d, 1H), 9.54 (s, 1H). LC-MS: [M + H]+ = 478.2 |
| 101 | 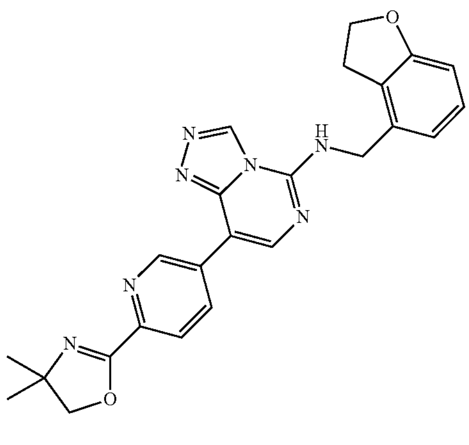 [SMILES: CC1(C)COC(c2ccc(-c3cnc(NCc4cccc5c4CCO5)n4cnnc34)cn2)=N1] | δ ppm 1.32 (s, 6H), 3.24 (t, 2H), 4.16 (s, 2H), 4.55 (t, 2H), 4.74 (s, 2H), 6.69 (d, 1H), 6.89 (d, 1H), 7.07 (t, 1H), 8.05 (d, 1H), 8.29 (s, 1H), 8.70 (dd, 1H), 9.41 (d, 1H), 9.53 (s, 1H), 10.23 (s, 1H). LC-MS: $[M + H]^+$ = 442.0. |

TABLE 2-continued
| Ex # | Structure | $^1$H NMR (400 MHz, DMSO-$d_6$) or otherwise indicated/LC-MS Data |
|---|---|---|
| 102 | 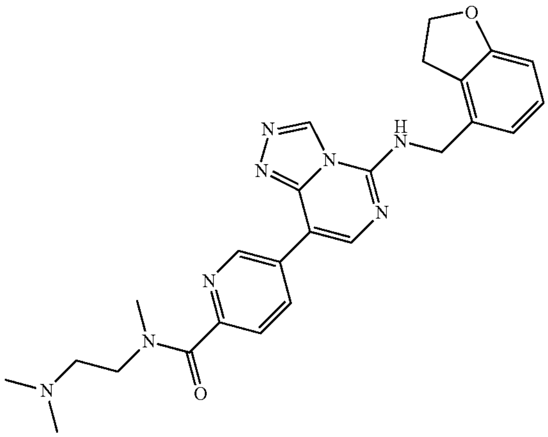 [SMILES: CN(C)CCN(C)C(=O)c1ccc(-c2cnc(NCc3cccc4c3CCO4)n3cnnc23)cn1] | δ ppm 2.04 (s, 3H), 2.31 (s, 3H), 2.52 (t, 2H), 3.03 (s, 3H), 3.25 (t, 2H), 3.50 (m, 2H), 4.55 (t, 2H), 4.73 (d, 2H), 6.70 (d, 1H), 6.89 (d, 1H), 7.08 (t, 1H), 7.66 (dd, 1H), 8.24 (d, 1H), 8.66 (dd, 1H), 9.04 (t, 1H), 9.32-9.34 (m, 1H), 9.56 (s, 1H). LC-MS: $[M + H]^+$ = 473.0 |
| 103 | 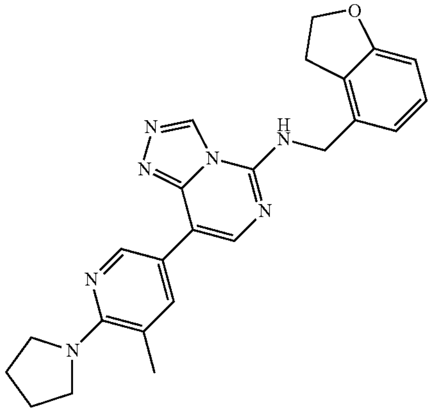 [SMILES: Cc1cc(-c2cnc(NCc3cccc4c3CCO4)n3cnnc23)cnc1N1CCCC1] | δ ppm 1.87 (dd, 4H), 2.38 (s, 3H), 3.24 (t, 2H), 3.53 (t, 4H), 4.55 (t, 2H), 4.69 (s, 2H), 6.69 (d, 1H), 6.88 (d, 1H), 7.07 (t, 1H), 7.90 (s, 1H), 8.03 (d, 1H), 8.65 (d, 1H), 8.72 (s, 1H), 9.48 (s, 1H). LC-MS: $[M + H]^+$ = 428.3 |
| 104 | 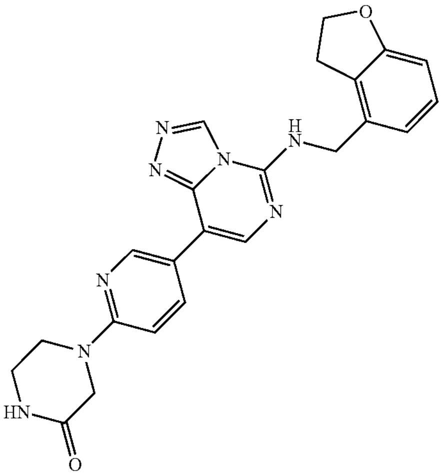 [SMILES: O=C1CN(c2ccc(-c3cnc(NCc4cccc5c4CCO5)n4cnnc34)cn2)CCN1] | δ ppm 2.46 (s, 2H), 3.24 (t, 2H), 3.80 (t, 2 H), 4.09 (s, 2H), 4.55 (t, 2H), 4.70 (d, 2H), 6.69 (d, 1H), 6.87 (d, 1H), 7.06-7.09 (m, 2H), 8.03 (s, 1H), 8.19 (s, 1H), 8.38 (d, 1H), 8.82 (d, 1H), 8.90 (d, 1H), 9.50 (s, 1H). LC-MS: $[M + H]^+$ = 443.1 |

TABLE 2-continued
| Ex # | Structure | $^1$H NMR (400 MHz, DMSO-$d_6$) or otherwise indicated/LC-MS Data |
|---|---|---|
| 105 | 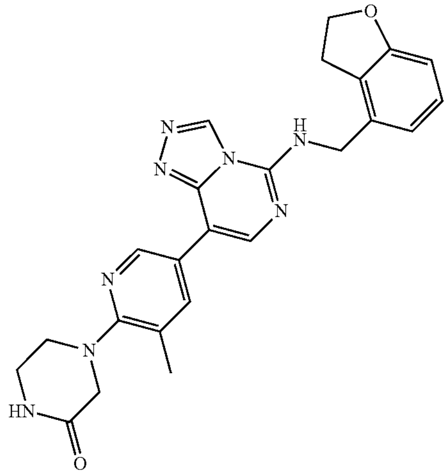 [SMILES: Cc1cc(-c2cnc(NCc3cccc4c3CCO4)n3cnnc23)cnc1N1CCNC(=O)C1] | δ ppm 2.34 (s, 3H), 3.24 (t, 4H), 3.35 (t, 2H), 3.74 (s, 2H), 4.55 (t, 2H), 4.70 (s, 2H), 6.71 (d, 1H), 6.88 (d, 1H), 7.09 (t, 1H), 7.90 (s, 1H), 8.02 (s, 1H), 8.27 (d, 1H), 8.80 (d, 1H), 8.84 (s, 1H), 9.51 (s, 1H). LC-MS: [M + H]$^+$ = 457.2 |
| 106 | 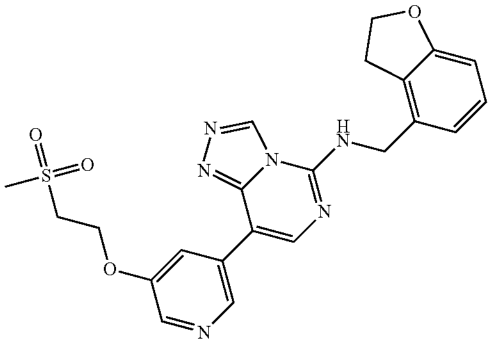 [SMILES: CS(=O)(=O)CCOc1cncc(-c2cnc(NCc3cccc4c3CCO4)n3cnnc23)c1] | δ ppm 3.10 (s, 3H), 3.24 (s, 2H), 3.69 (s, 2H), 4.51-4.56 (m, 4H), 4.72 (s, 2H), 6.69 (d, 1H), 6.88 (d, 1H), 7.06 (dd, 1H), 8.16-8.23 (m, 2H), 8.30 (s, 1H), 8.99 (s, 1H), 9.52 (s, 1H). LC-MS: [M + H]$^+$ = 466.9 |
| 107 | 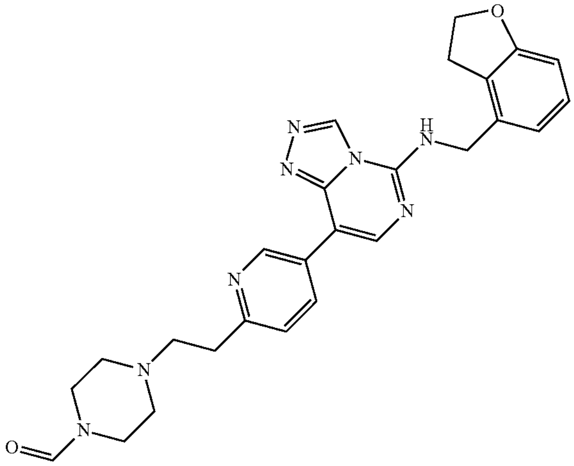 [SMILES: O=CN1CCN(CCc2ccc(-c3cnc(NCc4cccc5c4CCO5)n4cnnc34)cn2)CC1] | δ ppm 2.40-2.48 (m, 4H), 2.74 (t, 2H), 2.96 (t, 2H), 3.25 (t, 2H), 3.33-3.37 (m, 4H), 4.55 (t, 2H), 4.72 (s, 2H), 6.70 (d, 1H), 6.89 (d, 1H), 7.08 (t, 1H), 7.41 (d, 1H), 8.00 (s, 1H), 8.09 (s, 1H), 8.40 (dd, 1H), 8.91 (Brs, 1H), 9.16 (d, 1H), 9.51 (s, 1H). LC-MS: [M + H]$^+$ = 485.2 |

TABLE 2-continued
| Ex # | Structure | $^1$H NMR (400 MHz, DMSO-$d_6$) or otherwise indicated/LC-MS Data |
|---|---|---|
| 108 | 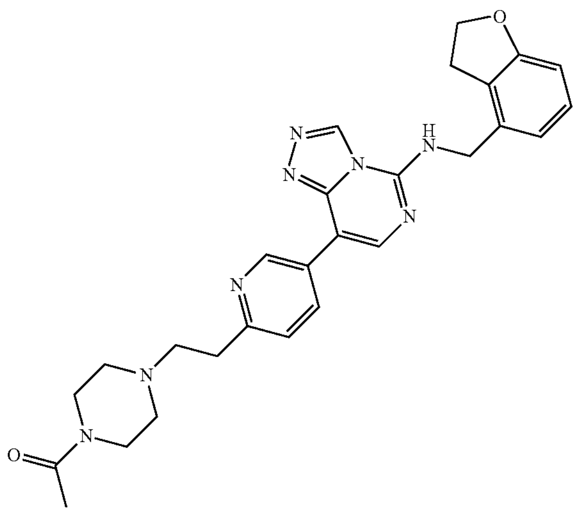 [SMILES: CC(=O)N1CCN(CCc2ccc(-c3cnc(NCc4cccc5c4CCO5)n4cnnc34)cn2)CC1] | δ ppm 1.98 (s, 3H), 2.39-2.47 (m, 4H), 2.72 (t, 2H), 2.95 (t, 2H), 3.25 (t, 2H), 3.37-3.44 (m, 4H), 4.55 (t, 2H), 4.72 (s, 2H), 6.70 (d, 1H), 6.89 (d, 1H), 7.08 (t, 1H), 7.41 (d, 1H), 8.09 (s, 1H), 8.40 (dd, 1H), 8.91 (Brs, 1H), 9.16 (d, 1H), 9.51 (s, 1H). LC-MS: $[M + H]^+$ = 499.2 |
| 109 | 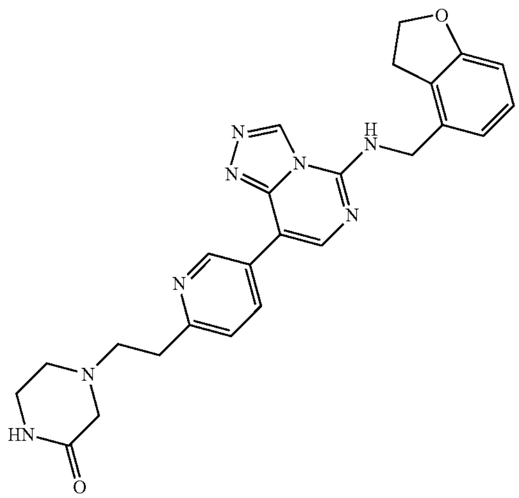 [SMILES: O=C1CN(CCc2ccc(-c3cnc(NCc4cccc5c4CCO5)n4cnnc34)cn2)CCN1] | δ ppm 2.63 (t, 2H), 2.77 (t, 2H), 2.94-3.00 (m, 4H), 3.14 (t, 2H), 3.25 (t, 2H), 4.55 (t, 2H), 4.73 (s, 2H), 6.70 (d, 1H), 6.89 (d, 1H), 7.08 (t, 1H), 7.41 (d, 1H), 7.74 (s, 1H), 8.10 (s, 1H), 8.41 (dd, 1H), 8.91 (Brs, 1H), 9.17 (d, 1H), 9.51 (s, 1H). LC-MS: $[M + H]^+$ = 471.3 |
| 110 | 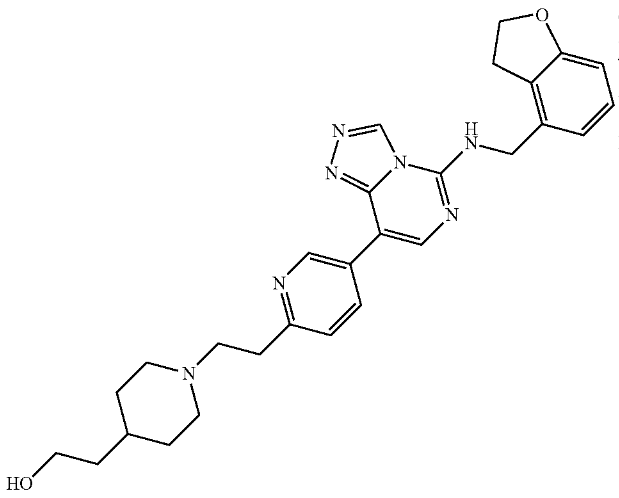 [SMILES: OCCC1CCN(CCc2ccc(-c3cnc(NCc4cccc5c4CCO5)n4cnnc34)cn2)CC1] | δ ppm 2.44 (t, 2H), 2.50 (t, 2H), 3.42 (t, 2H), 3.35 (t, 2H), 3.54-3.57 (m, 6H), 4.47 (t, 1H), 4.55 (t, 2H), 4.70 (d, 2H), 6.70 (d, 1H), 6.87 (d, 1H), 6.94 (d, 1H), 7.07 (t, 1H), 7.94 (s, 1H), 8.25 (dd, 1H), 8.74 (Brs, 1H), 8.82 (d, 1H), 9.49 (s, 1H). LC-MS: $[M + H]^+$ = 473.2 |

TABLE 2-continued
| Ex # | Structure | $^1$H NMR (400 MHz, DMSO-$d_6$) or otherwise indicated/LC-MS Data |
|---|---|---|
| 111 | 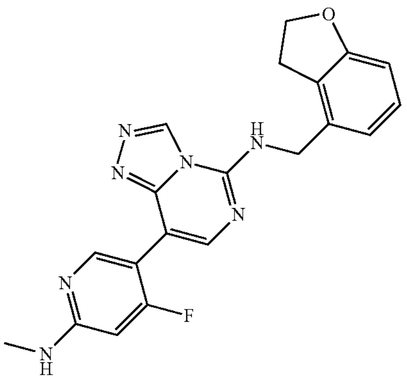 [SMILES: CNc1cc(F)c(-c2cnc(NCc3cccc4c3CCO4)n3cnnc23)cn1] | δ ppm 2.82 (d, 3H), 3.24 (t, 2H), 4.55 (t, 2H), 4.69 (s, 2H), 6.35 (d, 1H), 6.70 (d, 1H), 6.87-6.95 (m, 2H), 7.07 (t, 1H), 7.66 (s, 1H), 8.39 (d, 1H), 8.78 (s, 1H), 9.47 (s, 1H). LC-MS: [M + H]$^+$ = 392.0 |
| 112 | 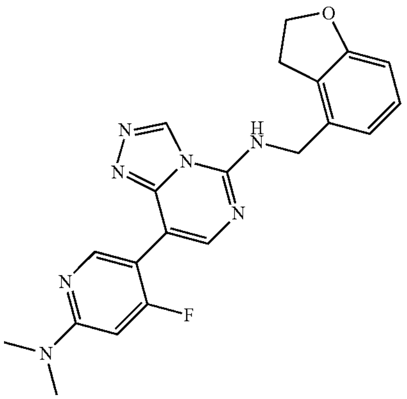 [SMILES: CN(C)c1cc(F)c(-c2cnc(NCc3cccc4c3CCO4)n3cnnc23)cn1] | δ ppm 3.08 (s, 6H), 3.24 (t, 2H), 4.55 (t, 2H), 4.70 (d, 2H), 6.61 (d, 1H), 6.70 (d, 1H), 6.88 (d, 1H), 7.07 (t, 1H), 7.68 (s, 1H), 8.51 (d, 1H), 8.81 (s, 1H), 9.47 (s, 1H). LC-MS: [M + H]$^+$ = 406.2 |
| 113 | 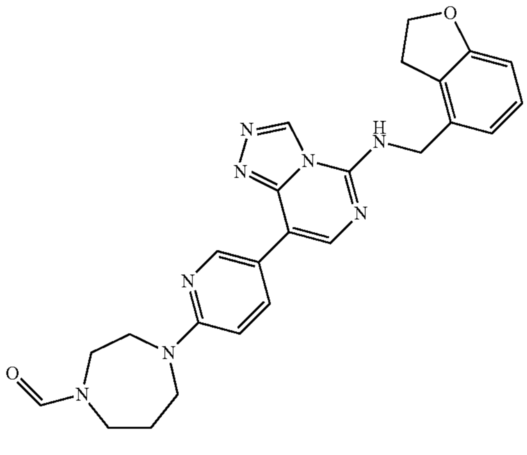 [SMILES: O=CN1CCCN(c2ccc(-c3cnc(NCc4cccc5c4CCO5)n4cnnc34)cn2)CC1] | δ ppm 1.79-1.80 (m, 2H), 3.24 (t, 2H), 3.46 (t, 2H), 3.58 (t, 2H), 3.68-3.76 (m, 2H), 3.81-3.89 (m, 2H), 4.55 (t, 2H), 4.70 (s, 2H), 6.70 (d, 1H), 6.82 (d, 1H), 6.88 (d, 1H), 7.07 (t, 1H), 7.82 (s, 1H), 7.92 (d, 1H), 8.04 (s, 1H), 8.21-8.24 (m, 1H), 8.71 (s, 1H), 8.80 (dd, 1H), 9.49 (s, 1H). LC-MS: [M + H]$^+$ = 471.2 |

TABLE 2-continued
| Ex # | Structure | $^1$H NMR (400 MHz, DMSO-$d_6$) or otherwise indicated/LC-MS Data |
|---|---|---|
| 114 | 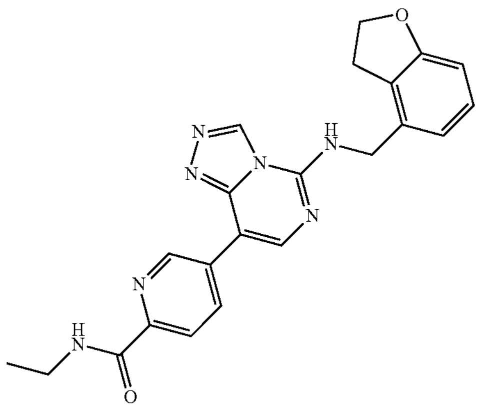 [SMILES: CCNC(=O)c1ccc(-c2cnc(NCc3cccc4c3CCO4)n3cnnc23)cn1] | δ ppm 1.15 (t, 3H), 3.25 (t, 2H), 3.37 (t, 2H), 4.55 (t, 2H), 4.74 (s, 2H), 6.70 (d, 1H), 6.89 (d, 1H), 7.07 (t, 1H), 8.12 (t, 1H), 8.28 (s, 1H), 8.75 (dd, 1H), 8.83 (t, 2H), 9.38 (d, 1H), 9.55 (s, 1H). LC-MS: [M + H]$^+$ = 416.0 |
| 115 | 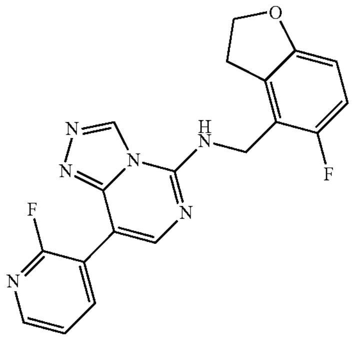 [SMILES: Fc1ccc2c(c1CNc1ncc(-c3cccnc3F)c3nncn13)CCO2] | δ ppm 3.13 (t, 2H), 4.54 (t, 2H), 4.75 (s, 2H), 6.71 (dd, 1H), 6.96 (t, 1H), 7.49 (d, 1H), 7.95 (s, 1H), 8.25 (t, 1H), 8.51 (td, 1H), 8.89 (s, 1H), 9.49 (s, 1H). LC-MS: [M + H]$^+$ = 381.0 |
| 116 | 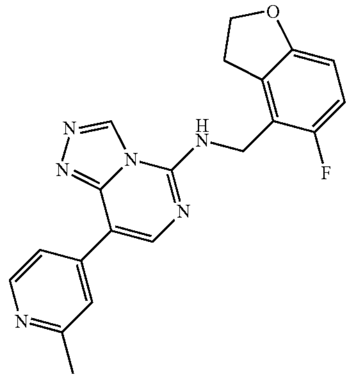 [SMILES: Cc1cc(-c2cnc(NCc3c(F)ccc4c3CCO4)n3cnnc23)ccn1] | δ ppm 2.51 (t, 3H), 3.29 (t, 2H), 4.54 (t, 2H), 4.74 (s, 2H), 6.70 (dd, 1H), 6.95 (t, 1H), 7.99 (d, 1H), 8.10 (s, 1H), 8.33 (s, 1H), 8.47 (d, 1H), 8.94 (s, 1H), 9.51 (s, 1H). LC-MS: [M + H]$^+$ = 376.9 |
| 117 | 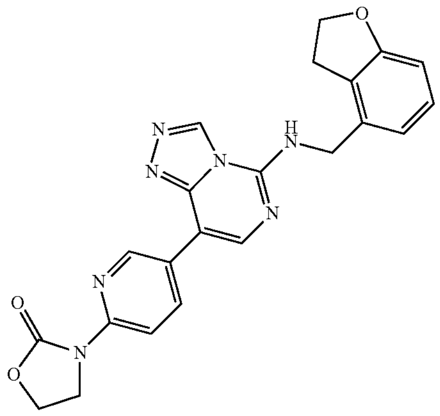 [SMILES: O=C1OCCN1c1ccc(-c2cnc(NCc3cccc4c3CCO4)n3cnnc23)cn1] | δ ppm 3.23 (t, 2H), 4.22 (t, 2H), 4.48 (t, 2H), 4.54 (t, 4H), 4.71 (s, 2H), 6.69 (d, 1H), 6.87 (d, 1H), 7.06 (t, 1H), 8.09 (s, 1H), 8.15 (d, 1H), 8.54 (dd, 1H), 8.90 (s, 1H), 9.10 (s, 1H), 9.51 (s, 1H); LC-MS: [M + H]$^+$ = 430.2 |

TABLE 2-continued
| Ex # | Structure | $^1H$ NMR (400 MHz, DMSO-$d_6$) or otherwise indicated/LC-MS Data |
|---|---|---|
| 118 | 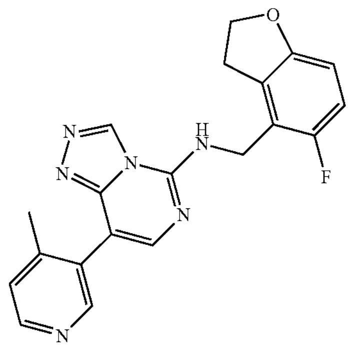 | δ ppm 2.24 (s, 3H), 3.34 (t, 2H), 4.56 (t, 2H), 4.73 (s, 2H), 6.73 (dd, 1H), 6.96 (t, 1H), 7.38 (d, 1H), 7.67 (s, 1H), 8.48 (t, 2H), 9.48 (s, 1H). LC-MS: $[M + H]^+$ = 377.2 |
| 119 | 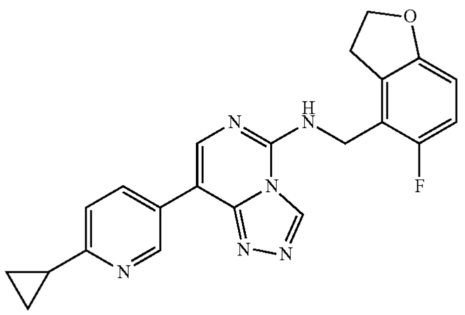 [SMILES: Fc1ccc2c(c1CNc1ncc(-c3ccc(C4CC4)nc3)c3nncn13)CCO2] | $^1H$ NMR (400 MHz, MeOH-$d_4$) δ ppm 1.04 (dt, 2H), 1.09 (dt, 3H), 2.22 (s, 4H), 3.41 (t, 2H), 4.60 (t, 2H), 4.84 (d, 3H), 6.67 (dd, 1H), 6.88 (dd, 1H), 7.35 (d, J = 8.3 Hz, 1H), 8.01 (s, 1H), 8.25 (dd, 1H), 8.94 (d, 1H), 9.36 (s, 1H). LC-MS: $[M + H]^+$ = 403.2 |
| 120 | 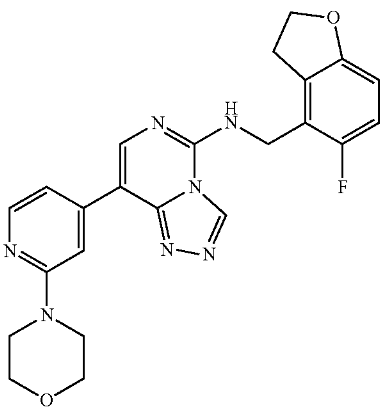 [SMILES: Fc1ccc2c(c1CNc1ncc(-c3ccnc(N4CCOCC4)c3)c3nncn13)CCO2] | $^1H$ NMR (400 MHz, MeOH-$d_4$) δ ppm 3.41 (t, 2H), 3.55-3.59 (m, 4H), 3.83-3.87 (m, 4H), 4.61 (t, 2H), 4.86 (s, 2H), 6.67 (dd, 1H), 6.84-6.91 (m, 1H), 7.30 (dd, 1H), 7.62 (d, 1H), 8.17-8.21 (m, 2H), 9.36 (s, 1H). LC-MS: $[M + H]^+$ = 448.0 |
| 121 | 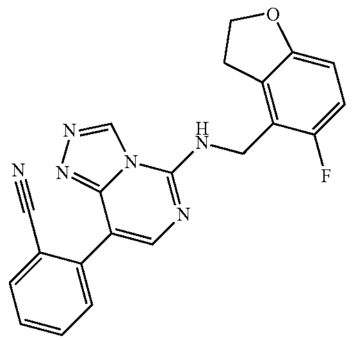 [SMILES: N#Cc1ccccc1-c1cnc(NCc2c(F)ccc3c2CCO3)n2cnnc12] | δ ppm 3.32 (d, 2H), 4.56 (t, 2H), 4.71 (d, 2H), 6.73 (dd, 1H), 6.92-7.01 (m, 1H), 7.24 (d, 1H), 7.45 (td, 1H), 7.49-7.57 (m, 2H), 7.59 (s, 1H), 7.65 (dd, 1H), 7.76 (s, 1H), 8.65 (s, 1H), 8.45 (s, 1H). LC-MS: $[M + H]^+$ = 387.0 |

TABLE 2-continued
| Ex # | Structure | $^1$H NMR (400 MHz, DMSO-$d_6$) or otherwise indicated/LC-MS Data |
| --- | --- | --- |
| 122 | 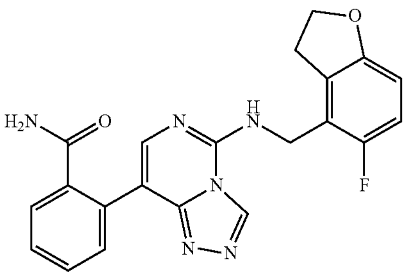 [SMILES: NC(=O)c1ccccc1-c1cnc(NCc2c(F)ccc3c2CCO3)n2cnnc12] | $^1$H NMR (400 MHz, MeOH-$d_4$) δ ppm 3.41 (d, 3H), 4.61 (t, 2H), 4.87 (d, 2H), 5.52 (s, 1H), 6.68 (dd, 1H), 6.86-6.95 (m, 1H), 7.56-7.65 (m, 2H), 7.78-7.88 (m, 2H), 7.90-7.97 (m, 2H), 9.37 (s, 1H). LC-MS: $[M + H]^+$ = 405.0 |
| 123 | 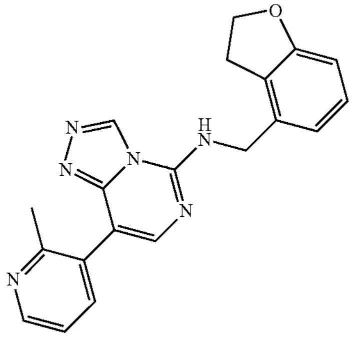 [SMILES: Cc1ncccc1-c1cnc(NCc2cccc3c2CCO3)n2cnnc12] | $^1$H NMR (400 MHz, MeOH-$d_4$) δ ppm 2.49 (s, 3H), 3.34-3.36 (m, 2H), 4.60 (t, 2H), 4.82 (s, 2H), 6.70 (d, 1H), 6.95 (d, 1H), 7.12 (t, 1H), 7.41 (s, 1H), 7.70 (s, 1H), 7.85 (dd, 1H), 8.51 (dd, 1H), 9.34 (s, 1H) LC-MS: $[M + H]^+$ = 359.0 |
| 124 | 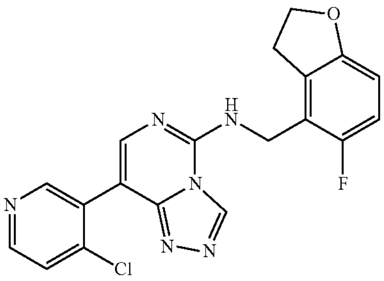 [SMILES: Fc1ccc2c(c1CNc1ncc(-c3cnccc3Cl)c3nncn13)CCO2] | δ ppm 3.32 (t, 2H), 4.56 (t, 2H), 4.74 (s, 2H), 6.73 (dd, 1H), 6.96 (t, 1H), 7.73 (d, 1H), 7.79 (s, 1H), 8.59 (d, 1H), 8.72 (d, 2H), 9.49 (s, 1H). LC-MS: $[M + H]^+$ = 397.1 |
| 125 | 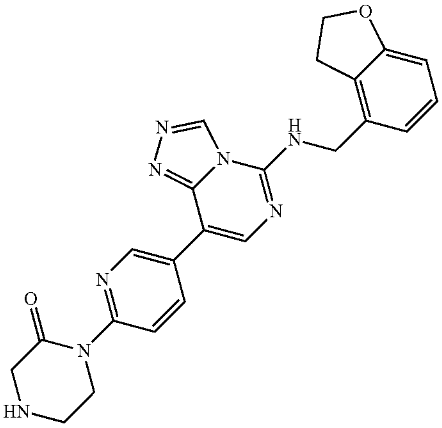 [SMILES: O=C1CNCCN1c1ccc(-c2cnc(NCc3cccc4c3CCO4)n3cnnc23)cn1] | δ ppm 3.05 (t, 2H), 3.25 (t, 2H), 3.47 (s, 2H), 3.89 (t, 2H), 4.55 (t, 2H), 4.72 (s, 2H), 6.69 (d, 1H), 6.89 (d, 1H), 7.07 (t, 1H), 7.95 (d, 1H), 8.13 (s, 1H), 8.50 (dd, 1H), 9.08 (s, 1H), 9.17 (s, 1H), 9.53 (s, 1H). LC-MS: $[M + H]^+$ = 443.2 |

TABLE 2-continued
| Ex # | Structure | $^1$H NMR (400 MHz, DMSO-$d_6$) or otherwise indicated/LC-MS Data |
| --- | --- | --- |
| 126 | 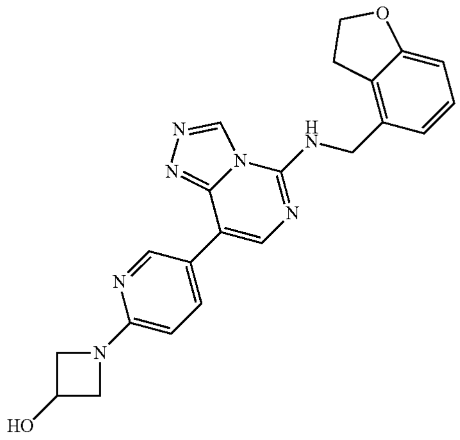 [SMILES: OC1CN(c2ccc(-c3cnc(NCc4cccc5c4CCO5)n4cnnc34)cn2)C1] | δ ppm 3.24 (t, 2H), 3.71 (q, 2H), 4.20 (t, 2H), 4.53-4.61 (m, 3H), 4.70 (d, 2H), 5.69 (d, 1H), 6.50 (d, 1H), 6.69 (d, 1H), 6.86 (d, 1H), 7.07 (t, 1H), 7.91 (s, 1H), 8.21 (dd, 1H), 8.74-8.76 (m, 2H), 9.49 (s, 1H). LC-MS: $[M + H]^+$ = 416.2 |
| 127 | 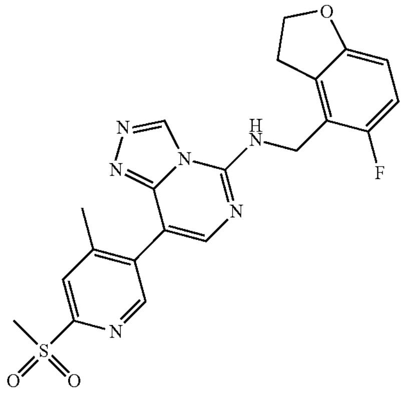 [SMILES: Cc1cc(S(C)(=O)=O)ncc1-c1cnc(NCc2c(F)ccc3c2CCO3)n2cnnc12] | δ ppm 2.41 (s, 3H), 3.35 (t, 5H), 4.56 (t, 2H), 4.74 (s, 2H), 6.73 (dd, 1H), 6.96 (t, 1H), 7.79 (s, 1H), 8.08 (s, 1H), 8.72 (d, 2H), 9.51 (s, 1H). LC-MS: $[M + H]^+$ = 455.1 |
| 128 | 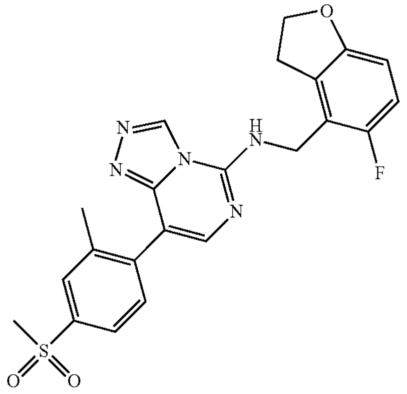 [SMILES: Cc1cc(S(C)(=O)=O)ccc1-c1cnc(NCc2c(F)ccc3c2CCO3)n2cnnc12] | δ ppm 2.33 (s, 3H), 3.28 (s, 3H), 3.35 (t, 2H), 4.57 (t, 2H), 4.73 (t, 2H), 6.73 (dd, 1H), 6.98 (t, 1H), 7.63 (d, 1H), 7.68 (s, 1H), 7.82 (dd, 1H), 7.91 (s, 1H), 8.79 (s, 1H), 9.49 (s, 1H). LC-MS: $[M + H]^+$ = 454.1 |

TABLE 2-continued
| Ex # | Structure | $^1$H NMR (400 MHz, DMSO-$d_6$) or otherwise indicated/LC-MS Data |
|---|---|---|
| 129 | 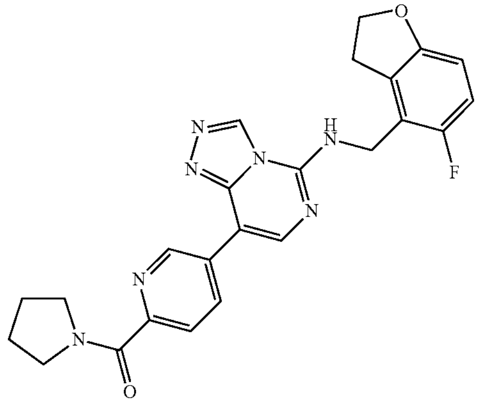 [SMILES: O=C(c1ccc(-c2cnc(NCc3c(F)ccc4c3CCO4)n3cnnc23)cn1)N1CCCC1] | δ ppm 1.87 (t, 4H), 3.34 (t, 2H), 3.53 (t, 2H), 3.68 (dd, 2H), 4.56 (t, 2H), 4.74 (s, 2H), 6.73 (dd, 1H), 6.96 (t, 1H), 7.84 (d, 1H), 8.29 (s, 1H), 8.69 (dd, 1H), 8.90 (s, 1H), 9.36 (d, 1H), 9.53 (s, 1H). LC-MS: [M + H]$^+$ = 460.2 |
| 130 | 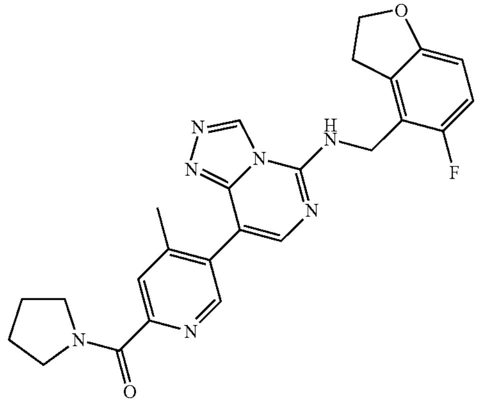 [SMILES: Cc1cc(C(=O)N2CCCC2)ncc1-c1cnc(NCc2c(F)ccc3c2CCO3)n2cnnc12] | δ ppm 1.83-1.88 (m, 4H), 2.31 (s, 3H), 3.23 (t, 2H), 3.54 (t, 2H), 3.67 (t, 2H), 4.57 (t, 2H), 4.74 (d, 2H), 6.73 (dd, 1H), 6.98 (t, 1H), 7.71 (s, 1H), 7.73 (s, 1H), 8.52 (s, 1H), 8.81 (s, 1H), 9.49 (s, 1H). LC-MS: [M + H]$^+$ = 474.1 |
| 131 | 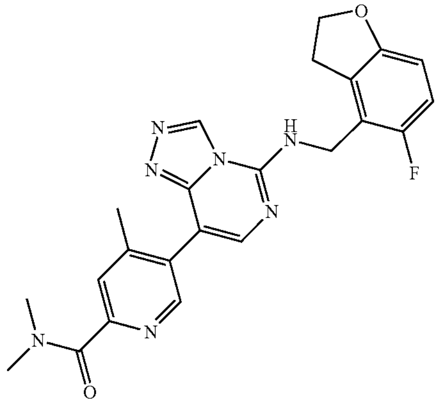 [SMILES: Cc1cc(C(=O)N(C)C)ncc1-c1cnc(NCc2c(F)ccc3c2CCO3)n2cnnc12] | δ ppm 2.30 (s, 3H), 3.03 (d, 6H), 3.37 (t, 2H), 4.57 (t, 2H), 4.73 (s, 2H), 6.74 (dd, 1H), 6.98 (t, 1H), 7.55 (s, 1H), 7.73 (s, 1H), 8.50 (s, 1H), 8.81 (s, 1H), 9.50 (s, 1H). LC-MS: [M + H]$^+$ = 448.2 |
| 132 | 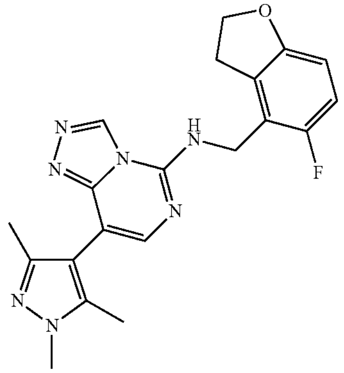 [SMILES: Cc1nn(C)c(C)c1-c1cnc(NCc2c(F)ccc3c2CCO3)n2cnnc12] | δ ppm 2.07 (s, 3H), 2.15 (s, 3H), 3.32 (t, 2H), 3.72 (s, 3H), 4.58 (t, 2H), 4.70 (d, 2H), 6.72 (dd, 1H), 6.97 (t, 1H), 7.47 (s, 1H), 8.54 (t, 1H), 9.43 (s, 1H). LC-MS: [M + H]$^+$ = 394.2 |

TABLE 2-continued
| Ex # | Structure | $^1$H NMR (400 MHz, DMSO-$d_6$) or otherwise indicated/LC-MS Data |
|---|---|---|
| 133 | 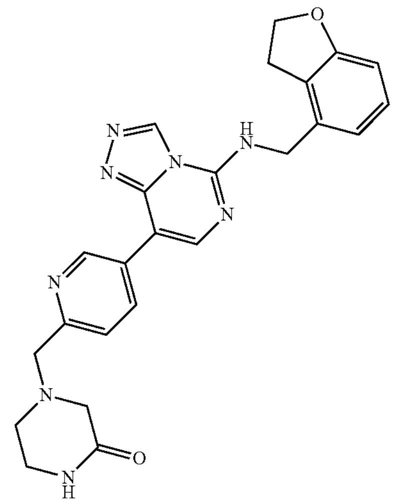 [SMILES: O=C1CN(Cc2ccc(-c3cnc(NCc4cccc5c4CCO5)n4cnnc34)cn2)CCN1] | δ ppm 2.64 (t, 2H), 3.02 (s, 2H), 3.18 (s, 2H), 3.25 (t, 2H), 3.72 (s, 2H), 4.55 (t, 2H), 4.73 (s, 2H), 6.70 (d, 1H), 6.89 (d, 1H), 7.07 (t, 1H), 7.54 (d, 1H), 7.79 (s, 1H), 8.13 (s, 1H), 8.51 (dd, 1H), 8.93 (s, 1H), 9.21 (d, 1H), 9.52 (s, 1H). LC-MS: $[M + H]^+$ = 457.2 |
| 134 | 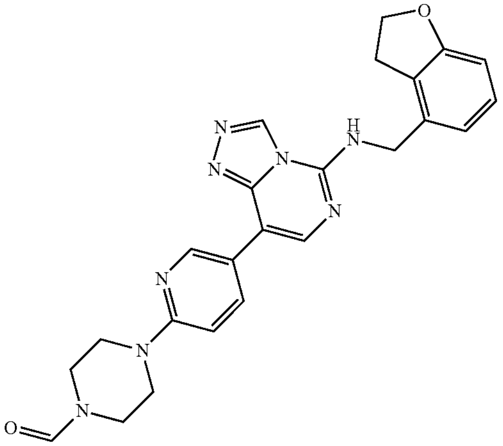 [SMILES: O=CN1CCN(c2ccc(-c3cnc(NCc4cccc5c4CCO5)n4cnnc34)cn2)CC1] | δ ppm 3.24 (t, 2H), 3.50-3.62 (m, 8H), 4.55 (t, 2H), 4.68 (s, 2H), 6.68 (d, 1H), 6.88 (d, 1H), 7.00-7.08 (d, 1H), 7.94 (s, 1H), 8.12 (s, 1H), 8.28 (d, 1H), 8.85 (s, 1H), 9.44 (s, 1H). LC-MS: $[M + H]^+$ = 457.2 |
| 135 | 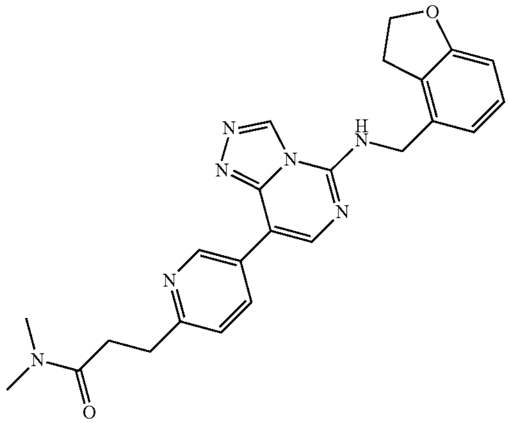 [SMILES: CN(C)C(=O)CCc1ccc(-c2cnc(NCc3cccc4c3CCO4)n3cnnc23)cn1] | δ ppm 2.76-2.82 (m, 5H), 2.98-3.02 (m, 5H), 3.22 (t, 2H), 4.55 (t, 2H), 4.72 (s, 2H), 6.69 (d, 1H), 6.87 (d, 1H), 7.08 (t, 1H), 7.39 (d, 1H), 8.08 (s, 1H), 8.37 (dd, 1H), 8.91 (s, 1H), 9.14 (d, 1H), 9.51 (s, 1H). LC-MS: $[M + H]^+$= 444.0 |

TABLE 2-continued
| Ex # | Structure | $^1$H NMR (400 MHz, DMSO-$d_6$) or otherwise indicated/LC-MS Data |
|---|---|---|
| 136 | 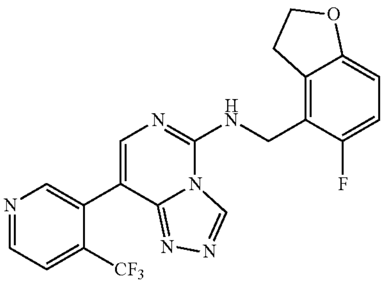 [SMILES: Fc1ccc2c(c1CNc1ncc(-c3cnccc3C(F)(F)F)c3nncn13)CCO2] | δ ppm 3.33 (t, 2H), 4.56 (t, 2H), 4.76 (s, 2H), 6.73 (dd, 1H), 6.96 (t, 1H), 8.16 (d, 1H), 8.41 (s, 1H), 8.96 (dd, 1H), 9.05 (s, 1H), 9.54 (d, 2H). LC-MS: $[M + H]^+$ = 431.1 |
| 137 | 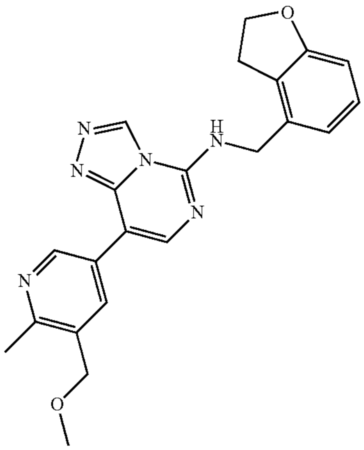 [SMILES: COCc1cc(-c2cnc(NCc3cccc4c3CCO4)n3cnnc23)cnc1C] | δ ppm 2.49 (s, 3H), 3.25 (t, 2H), 3.41 (s, 3H), 4.53 (t, 2H), 4.51 (s, 2H), 4.72 (s, 2H), 6.70 (d, 1H), 6.88 (d, 1H), 7.08 (t, 1H), 8.08 (s, 1H), 8.41 (d, 1H), 8.90 (t, 1H), 9.03 (d, 1H), 9.51 (s, 1H). LC-MS: $[M + H]^+$ = 403.2 |
| 138 | 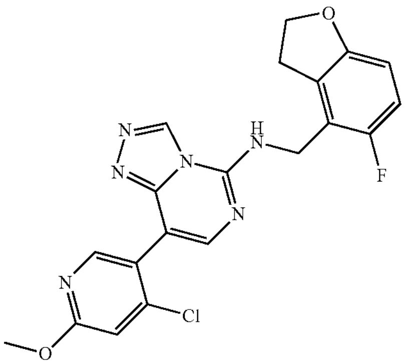 [SMILES: COc1cc(Cl)c(-c2cnc(NCc3c(F)ccc4c3CCO4)n3cnnc23)cn1] | δ ppm 3.36 (t, 2H), 3.94 (s, 3H), 4.57 (t, 2H), 4.72 (s, 2H), 6.74 (dd, 1H), 6.97 (t, 1H), 7.19 (s, 1H), 7.69 (s, 1H), 8.31 (s, 1H), 8.82 (Brs, 1H), 9.48 (s, 1H). LC-MS: $[M + H]^+$ = 427.0 |
| 139 | 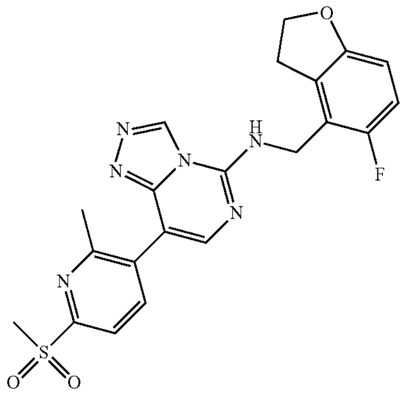 [SMILES: Cc1nc(S(C)(=O)=O)ccc1-c1cnc(NCc2c(F)ccc3c2CCO3)n2cnnc12] | δ ppm 2.54 (s, 3H), 3.24-3.34 (m, 5H), 4.56 (t, 2H), 4.74 (s, 2H), 6.72 (dd, 1H), 6.98 (t, 1H), 7.78 (s, 1H), 7.98 (d, 1H), 8.14 (d, 1H), 8.87 (s, 1H), 9.51 (s, 1H). LC-MS: $[M + H]^+$ = 454.9 |

TABLE 2-continued
| Ex # | Structure | $^1H$ NMR (400 MHz, DMSO-$d_6$) or otherwise indicated/LC-MS Data |
|---|---|---|
| 140 | 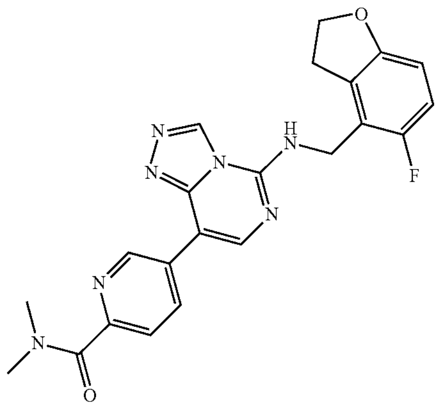 [SMILES: CN(C)C(=O)c1ccc(-c2cnc(NCc3c(F)ccc4c3CCO4)n3cnnc23)cn1] | δ ppm 2.50 (s, 2H), 2.54 (s, 2H), 3.33 (t, 2H), 4.56 (t, 2H), 4.74 (s, 2H), 6.73 (dd, 1H), 6.96 (t, 1H), 7.78 (s, 1H), 7.99 (d, 1H), 8.14 (d, 1H), 8.87 (s, 1H), 9.50 (s, 1H). LC-MS: $[M + H]^+$ = 434.1 |
| 141 | 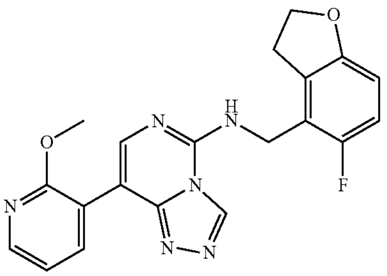 [SMILES: COc1ncccc1-c1cnc(NCc2c(F)ccc3c2CCO3)n2cnnc12] | $^1H$ NMR (400 MHz, MeOH-$d_4$) δ ppm 3.38 (t, 2H), 3.92 (s, 3H), 4.56-4.60 (m, 2H), 4.82 (s, 2H), 6.62-6.68 (m, 1H), 6.87 (dd, 1H), 7.08 (dd, 1H), 7.89 (s, 1H), 8.00 (dd, 1H), 8.18 (dd, 1H), 9.30 (s, 1H). LC-MS: $[M + H]^+$ = 393.0 |
| 142 | 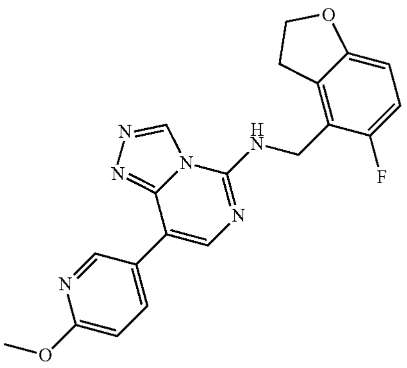 [SMILES: COc1ccc(-c2cnc(NCc3c(F)ccc4c3CCO4)n3cnnc23)cn1] | $^1H$ NMR (400 MHz, MeOH-$d_4$) δ ppm 3.34-3.40 (m, 2H), 3.95 (s, 3H), 4.58 (d, 2H), 4.81 (s, 2H), 6.64 (dd, 1H), 6.85 (t, 1H), 6.91 (d, 1H), 7.92 (s, 1H), 8.21 (dd, 1H), 8.68 (d, 1H), 9.32 (s, 1H). LC-MS: $[M + H]^+$ = 393.0 |
| 143 | 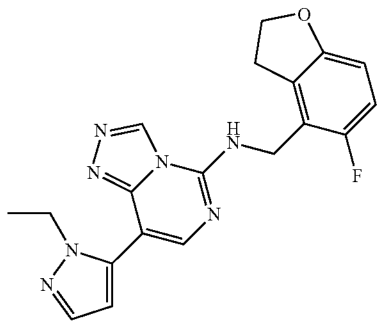 [SMILES: CCn1nccc1-c1cnc(NCc2c(F)ccc3c2CCO3)n2cnnc12] | δ ppm 1.34 (t, J = 7.18 Hz, 3H) 3.29-3.38 (m, 2H) 4.17 (q, J = 7.15 Hz, 2H) 4.60 (t, J = 8.72 Hz, 2H) 4.76 (s, 2H) 6.40-6.50 (m, 1H), 6.75 (dd, J = 8.63, 3.80 Hz, 1H) 7.00 (t, J = 9.44 Hz, 1H) 7.55-7.62 (m, 1H) 7.72 (s, 1 H) 9.44 (s, 1 H). LC-MS: $[M + H]^+$ = 379.9 |

TABLE 2-continued
| Ex # | Structure | $^1H$ NMR (400 MHz, DMSO-$d_6$) or otherwise indicated/LC-MS Data |
|---|---|---|
| 144 | 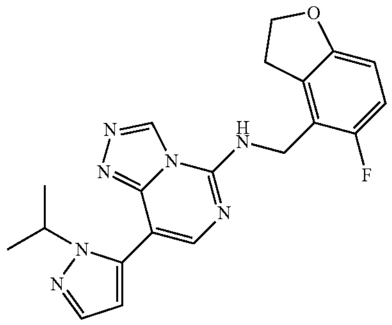 [SMILES: CC(C)n1nccc1-c1cnc(NCc2c(F)ccc3c2CCO3)n2cnnc12] | δ ppm 1.31-1.39 (m, 6H), 3.39 (m, 2H), 4.40-4.49 (m, 1H), 4.56 (t, J = 8.8 Hz, 2H), 4.72 (s, 2H), 6.36 (d, J = 1.8 Hz, 1H), 6.73 (dd, J = 8.7, 3.9 Hz, 1H), 6.93-7.01 (m, 1H), 7.57 (d, J = 1.5 Hz, 1H), 7.68 (s, 1H), 9.48 (s, 1H). LC-MS: $[M + H]^+$ = 394.0 |
| 145 | 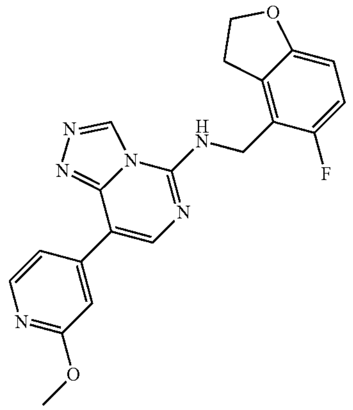 [SMILES: COc1cc(-c2cnc(NCc3c(F)ccc4c3CCO4)n3cnnc23)ccn1] | δ ppm 3.31 (t, 2H), 3.89 (s, 3H), 4.55 (t, 2H), 4.75 (s, 2H), 6.71 (q, 1H), 6.96 (t, 1 H), 7.77 (t, 2H), 8.21 (t, 1H), 8.37 (s, 1H), 8.97 (s, 1H), 9.51 (s, 1H). LC-MS: $[M + H]^+$ = 393.2 |
| 146 | 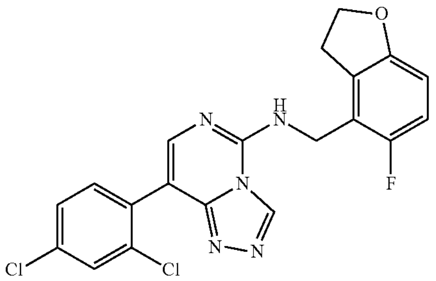 [SMILES: Fc1ccc2c(c1CNc1ncc(-c3ccc(Cl)cc3Cl)c3nncn13)CCO2] | $^1H$ NMR (400 MHz, MeOH-$d_4$) δ ppm 3.38 (t, 2H), 4.58 (td, 2H), 4.82 (s, 2H), 6.65 (dd, 1H), 6.81-6.89 (m, 1H), 7.45-7.49 (m, 2H), 7.55 (ddd, 2H), 7.61-7.66 (m, 2H), 7.91-7.95 (m, 2H), 7.97 (s, 1H), 9.33 (s, 1H). LC-MS: $[M + H]^+$: $[M + H]^+$ = 429.9 |
| 147 | 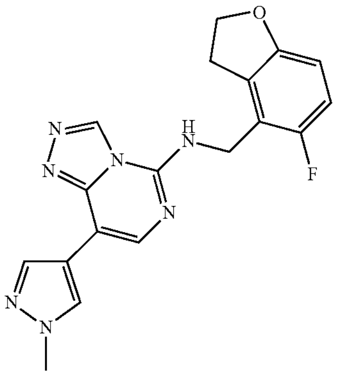 | δ ppm 3.25 (t, 2H), 3.88 (s, 3H), 4.54 (t, 2H), 4.67 (s, 2H), 6.70 (d, 1H), 6.95 (t, 1H), 8.04 (s, 1H), 8.12 (s, 1H), 8.44 (s, 1H), 8.54 (s, 1H), 9.46 (s, 1H). LC-MS: $[M + H]^+$ = 366.1 |

TABLE 2-continued
| Ex # | Structure | $^1$H NMR (400 MHz, DMSO-$d_6$) or otherwise indicated/LC-MS Data |
| --- | --- | --- |
| 148 | 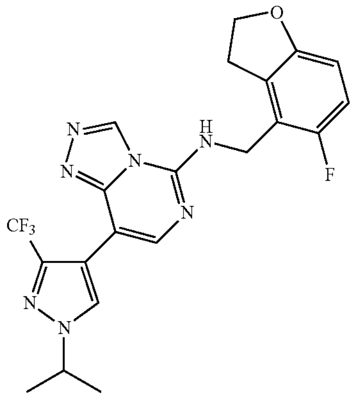 [SMILES: CC(C)n1cc(-c2cnc(NCc3c(F)ccc4c3CCO4)n3cnnc23)c(C(F)(F)F)n1] | δ ppm 1.50 (d, 6H), 3.30 (t, 2H), 4.55 (t, 2H), 4.71 (s, 3H), 6.72 (dd, 1H), 6.97 (t, 1H), 7.67 (s, 1H), 8.50 (s, 1H), 8.73 (s, 1H), 9.48 (s, 1H). LC-MS: $[M + H]^+$ = 462.0 |
| 149 | 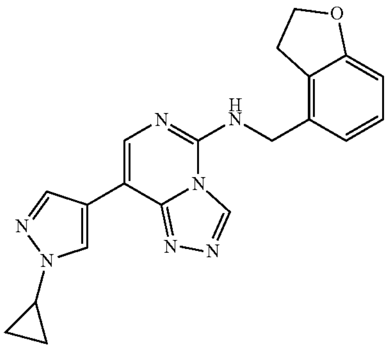 [SMILES: c1cc(CNc2ncc(-c3cnn(C4CC4)c3)c3nncn23)c2c(c1)OCC2] | δ ppm 1.00-1.09 (m, 4H), 3.23 (t, 2H), 3.81 (dd, 1H), 4.54 (t, 2H), 4.68 (d, 2H), 6.69 (d, 1H), 6.87 (d, 1H), 7.07 (t, 1H), 8.01 (s, 1H), 8.13 (s, 1H), 8.48 (s, 1H), 8.67 (s, 1H), 9.47 (s, 1H). LC-MS: $[M + H]^+$ = 374.2 |
| 150 | 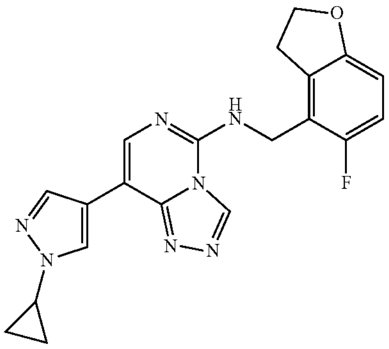 [SMILES: Fc1ccc2c(c1CNc1ncc(-c3cnn(C4CC4)c3)c3nncn13)CCO2] | δ ppm 0.97-1.09 (m, 4H), 3.30 (t, 2H), 3.79-3.83 (m, 1H), 4.54 (t, 2H), 4.70 (s, 2H), 6.71 (dd, 1H), 6.95 (t, 1H), 8.05 (s, 1H), 8.14 (s, 1H), 8.48 (s, 1H), 8.56 (d, 1H), 9.46 (s, 1H). LC-MS: $[M + H]^+$ = 392.2 |
| 151 | 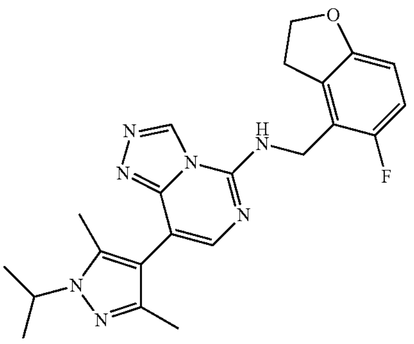 [SMILES: Cc1nn(C(C)C)c(C)c1-c1cnc(NCc2c(F)ccc3c2CCO3)n2cnnc12] | δ ppm 1.39 (d, 6H), 2.08 (s, 3H), 2.16 (s, 3H), 3.36 (t, 2H), 4.48-4.58 (m, 3H), 4.70 (d, 2H), 6.74 (dd, 1H), 6.99 (t, 1H), 7.49 (s, 1H), 8.54 (t, 1H), 9.44 (s, 1H). LC-MS: $[M + H]^+$ = 422.2 |

TABLE 2-continued
| Ex # | Structure | $^1$H NMR (400 MHz, DMSO-$d_6$) or otherwise indicated/LC-MS Data |
|---|---|---|
| 152 | 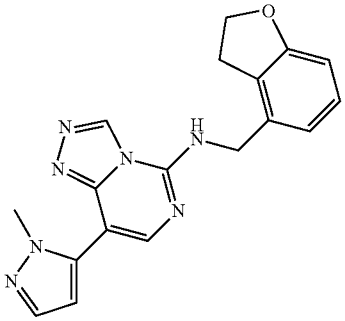 [SMILES: Cn1nccc1-c1cnc(NCc2cccc3c2CCO3)n2cnnc12] | δ ppm 3.25 (t, 2H), 3.83 (s, 3H), 4.56 (t, 2H), 4.72 (d, 2H), 6.51 (d, 1H), 6.71 (d, 1H), 6.90 (d, 1H), 7.09 (t, 1H), 7.51 (s, 1H), 7.75 (s, 1H), 8.98 (d, 1H), 9.50 (s, 1H). LC-MS: $[M + H]^+$ = 348.2 |
| 153 | 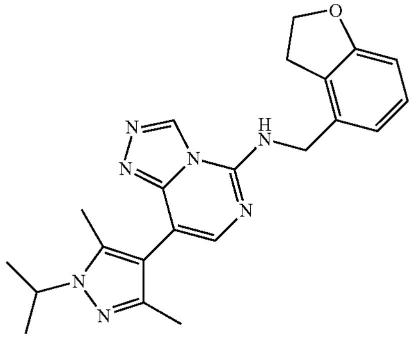 [SMILES: Cc1nn(C(C)C)c(C)c1-c1cnc(NCc2cccc3c2CCO3)n2cnnc12] | δ ppm 1.39 (d, 6H), 2.08 (s, 3H), 2.16 (s, 3H), 3.25 (t, 2H), 4.46-4.57 (m, 3H), 4.69 (s, 2H), 6.71 (d, 1H), 6.91 (d, 1H), 7.10 (t, 1H), 7.45 (s, 1H), 8.66 (s, 1H), 9.45 (s, 1H). LC-MS: $[M + H]^+$ = 404.2 |
| 154 | 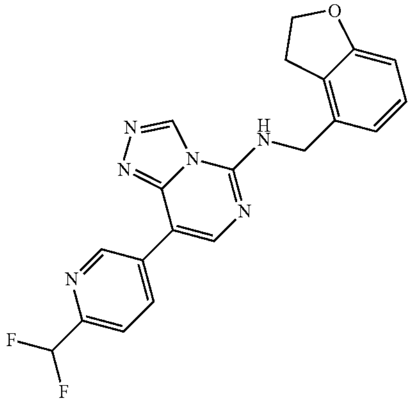 [SMILES: FC(F)c1ccc(-c2cnc(NCc3cccc4c3CCO4)n3cnnc23)cn1] | δ ppm 3.25 (t, 2H), 4.55 (t, 2H), 4.74 (d, 2H), 6.70 (d, 1H), 6.88 (t, 1H), 7.02-7.16 (m, 2H), 7.81 (d, 1H), 8.27 (s, 1H), 8.77 (dd, 1H), 9.05 (t, 1H), 9.41 (d, 1H), 9.54 (s, 1H). LC-MS: $[M + H]^+$ = 395.1 |
| 155 | 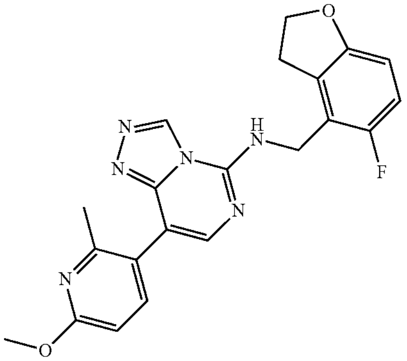 [SMILES: COc1ccc(-c2cnc(NCc3c(F)ccc4c3CCO4)n3cnnc23)c(C)n1] | $^1$H NMR (400 MHz, MeOH-$d_4$) δ ppm 2.35 (s, 3H), 3.36-3.42 (m, 2H), 3.94 (s, 4H), 4.57 (d, 2H), 4.81 (s, 2H), 6.62-6.67 (m, 1H), 6.68-6.74 (m, 1H), 6.87 (t, 1H), 7.62 (d, 2H), 9.31 (s, 1H). LC-MS: $[M + H]^+$ = 407.0 |

TABLE 2-continued
| Ex # | Structure | $^1$H NMR (400 MHz, DMSO-$d_6$) or otherwise indicated/LC-MS Data |
|---|---|---|
| 156 | 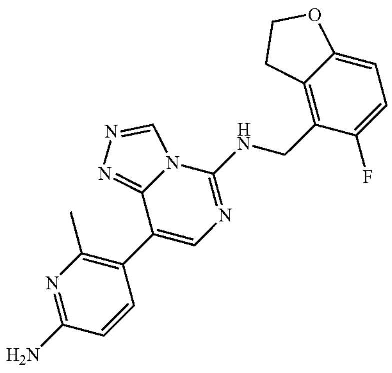 [SMILES: Cc1nc(N)ccc1-c1cnc(NCc2c(F)ccc3c2CCO3)n2cnnc12] | $^1$H NMR (400 MHz, MeOH-$d_4$) δ ppm 2.25 (s, 3H), 3.36-3.41 (m, 2H), 4.58 (t, 2H), 4.80 (s, 2H), 6.52 (d, 1H), 6.65 (dd, 1H), 6.83-6.89 (m, 1H), 7.43 (d, 1H), 7.60 (s, 1H), 9.29 (s, 1H). LC-MS: $[M + H]^+$ = 392.0 |
| 157 | 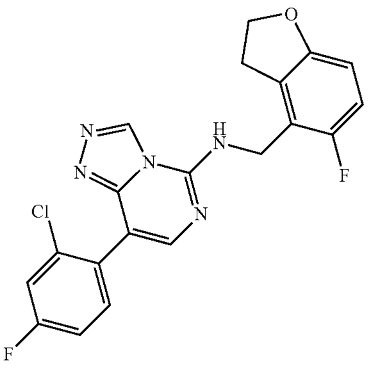 [SMILES: Fc1ccc(-c2cnc(NCc3c(F)ccc4c3CCO4)n3cnnc23)c(Cl)c1] | $^1$H NMR (400 MHz, MeOH-$d_4$) δ ppm 3.39 (t, 2H), 4.58 (t, 2H), 4.82 (s, 2H), 6.65 (dd, 1H), 6.86 (d, 1H), 7.20 (td, 2.9 Hz, 2H), 7.40 (dd, 1H), 7.56 (dd, 1H), 7.71 (s, 1H), 7.90-7.96 (m, 1H), 9.31 (s, 1H). LC-MS: $[M + H]^+$ = 414.0 |
| 158 | 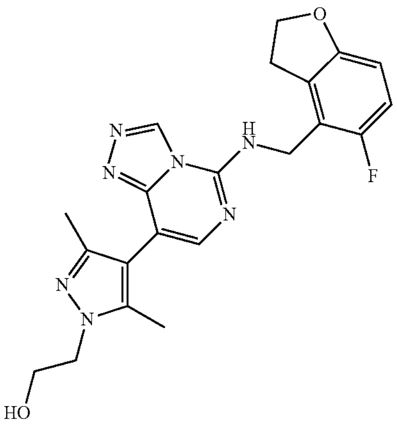 [SMILES: Cc1nn(CCO)c(C)c1-c1cnc(NCc2c(F)ccc3c2CCO3)n2cnnc12] | δ ppm 2.08 (s, 3H), 2.18 (s, 3H), 3.31 (t, 2H), 3.73 (dd, 3H), 4.06 (t, 2H), 4.56 (t, 2H), 4.70 (d, 2H), 4.93 (t, 1H), 6.74 (dd, 1H), 6.99 (t, 1H), 7.47 (s, 1H), 8.55 (s, 1H), 9.44 (s, 1H). LC-MS: $[M + H]^+$ = 424.2 |
| 159 | 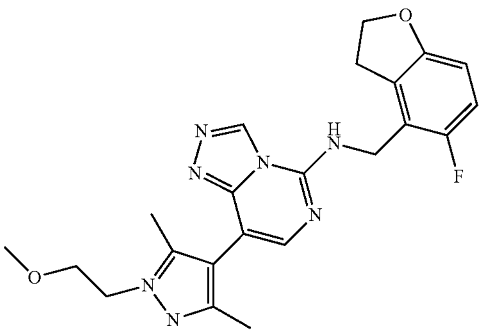 | δ ppm 2.08 (s, 3H), 2.16 (s, 3H), 3.26 (s, 3H), 3.31 (t, 2H), 3.69 (t, 2H), 4.18 (t, 2H), 4.58 (t, 2H), 4.70 (d, 1H), 6.74 (dd, 1H), 6.99 (t, 1H), 7.48 (s, 1H), 8.55 (t, 1H), 9.43 (s, 1H). LC-MS: $[M + H]^+$ = 438.2 |

TABLE 2-continued
| Ex # | Structure | $^1$H NMR (400 MHz, DMSO-$d_6$) or otherwise indicated/LC-MS Data |
|---|---|---|
| 160 | 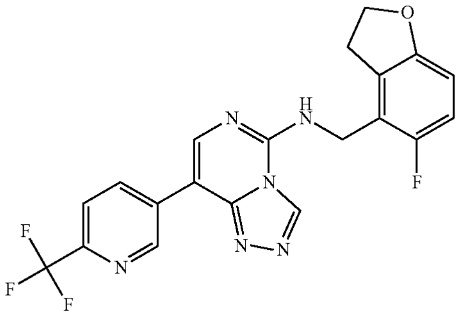 [SMILES: Fc1ccc2c(c1CNc1ncc(-c3ccc(C(F)(F)F)nc3)c3nncn13)CCO2] | δ ppm 3.33 (t, 2H), 4.57 (t, 2H), 4.77 (s, 2H), 6.72 (dd, 1H), 6.97 (t, 1H), 8.02 (d, 1H), 8.38 (s, 1H), 8.89 (d, 1H), 9.02 (s, 1H), 9.50 (s, 1H), 9.54 (s, 1H). LC-MS: $[M + H]^+$ = 431.2 |
| 161 | 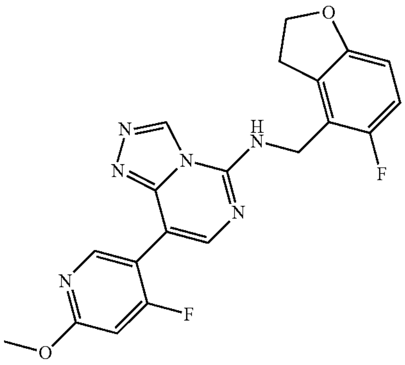 [SMILES: COc1cc(F)c(-c2cnc(NCc3c(F)ccc4c3CCO4)n3cnnc23)cn1] | δ ppm 3.30-3.33 (m, 2H), 3.94 (s, 3H), 4.57 (t, 2H), 4.73 (s, 2H), 6.73 (dd, 1H), 6.92-6.99 (m, 2H), 7.80 (s, 1H), 8.58 (d, 1H), 8.82 (s, 1H), 9.48 (s, 1H). LC-MS: $[M + H]^+$ = 411.2 |
| 162 | 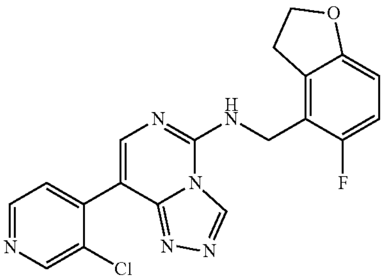 [SMILES: Fc1ccc2c(c1CNc1ncc(-c3ccncc3Cl)c3nncn13)CCO2] | δ ppm 3.28 (t, 2H), 4.56 (t, 2H), 4.74 (s, 2H), 6.73 (m, 1H), 6.97 (t, 1H), 7.71 (d, 1H), 7.88 (s, 1H), 8.61 (d, 1H), 8.78 (s, 1H), 8.97 (s, 1H), 9.50 (s, 1H). LC-MS: $[M + H]^+$ = 397.1 |
| 163 | 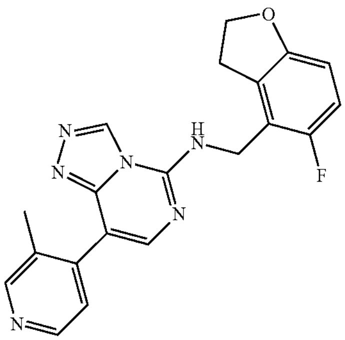 [SMILES: Cc1cnccc1-c1cnc(NCc2c(F)ccc3c2CCO3)n2cnnc12] | δ ppm 2.25 (s, 3H), 3.34 (d, 2H), 4.56 (t, 2H), 4.73 (s, 2H), 6.73 (dd, 1H), 6.96 (t, 1H), 7.42 (d, 1H), 7.71 (s, 1H), 8.47 (d, 1H), 8.53 (s, 1H), 8.81 (s, 1H), 9.49 (s, 1H). LC-MS: $[M + H]^+$ = 377.1 |

TABLE 2-continued
| Ex # | Structure | $^1H$ NMR (400 MHz, DMSO-$d_6$) or otherwise indicated/LC-MS Data |
| --- | --- | --- |
| 164 | 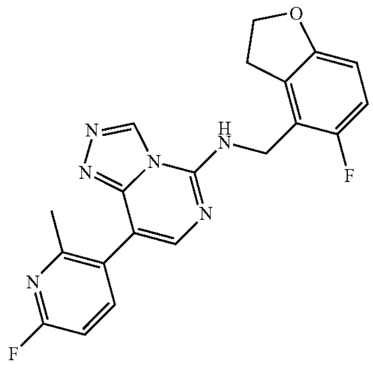 [SMILES: Cc1nc(F)ccc1-c1cnc(NCc2c(F)ccc3c2CCO3)n2cnnc12] | $^1H$ NMR (400 MHz, MeOH-$d_4$) δ ppm 2.42 (d, 3H), 3.44 (t, 2H), 4.62 (t, 2H), 4.85 (s, 3H), 6.63-6.74 (m, 1H), 6.90 (t, 1H), 704 (d, 1H), 7.73 (d, 1H), 7.94 (t, 1H), 9.36 (d, 1H). LC-MS: $[M + H]^+$ = 395.0 |
| 165 | 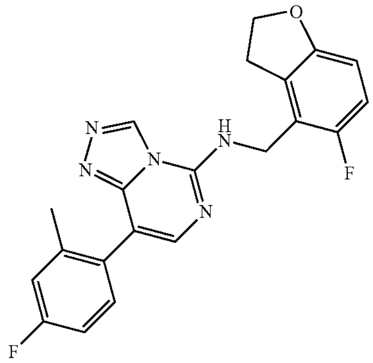 [SMILES: Cc1cc(F)ccc1-c1cnc(NCc2c(F)ccc3c2CCO3)n2cnnc12] | $^1H$ NMR (400 MHz, MeOH-$d_4$) δ ppm 2.25 (s, 3H), 3.43 (t, 2H), 4.63 (d, 2H), 4.84 (s, 2H), 6.69 (dd, 1H), 6.90 (t, 1H), 7.04 (t, 1H), 7.12 (dd, 1H), 7.36 (dd, 1H), 7.64 (s, 1H), 9.34 (s, 1H). LC-MS: $[M + H]^+$ = 394.0 |
| 166 | 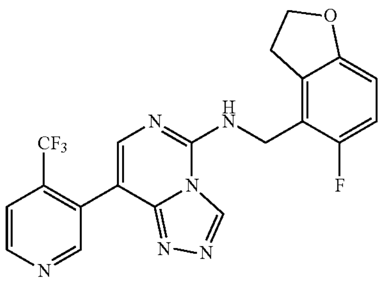 [SMILES: Fc1ccc2c(c1CNc1ncc(-c3cnccc3C(F)(F)F)c3nncn13)CCO2] | $^1H$ NMR (400 MHz, MeOH-$d_4$) δ ppm 3.42 (t, 2H), 4.62 (td, 2H), 4.87 (d, 3H), 6.66-6.72 (m, 1H), 6.91 (t, 1H), 7.70 (s, 1H), 7.79 (dd, 1H), 8.09 (d, 1H), 8.80 (d, 1H), 9.36 (d, 1H). LC-MS: $[M + H]^+$ = 431.1 |
| 167 | 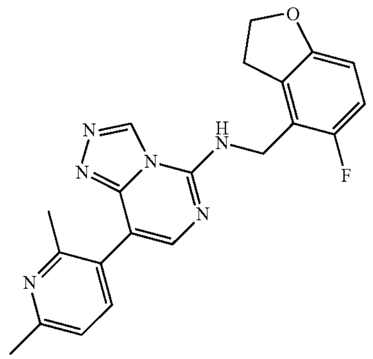 [SMILES: Cc1ccc(-c2cnc(NCc3c(F)ccc4c3CCO4)n3cnnc23)c(C)n1] | δ ppm 2.35 (s, 3H), 2.44 (s, 3H), 3.31 (t, 2H), 4.56 (t, 2H), 4.72 (s, 2H), 6.73 (dd, 1H), 6.97 (t, 1H), 7.16 (d, 1H), 7.62 (d, 2H), 8.70 (s, 1H), 9.47 (s, 1H). LC-MS: $[M + H]^+$ = 391.1 |

TABLE 2-continued
| Ex # | Structure | $^1$H NMR (400 MHz, DMSO-$d_6$) or otherwise indicated/LC-MS Data |
|---|---|---|
| 168 | 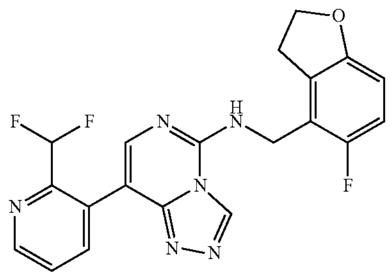 [SMILES: Fc1ccc2c(c1CNc1ncc(-c3cccnc3C(F)F)c3nncn13)CCO2] | δ ppm 3.37 (t, 2H), 4.57 (t, 2H), 4.73 (s, 2H), 6.72-7.06 (m, 3H), 7.64 (s, 1H), 7.71 (dd, 1H), 8.03 (d, 1H), 8.78 (d, 2H), 8.83 (d, 2H), 9.49 (s, 1H). LC-MS: $[M + H]^+ = 413.2$ |
| 169 | 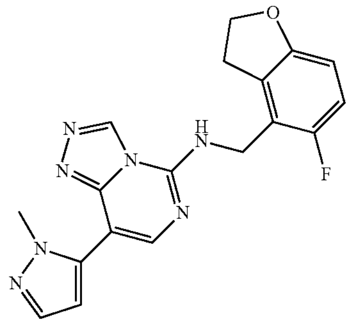 [SMILES: Cn1nccc1-c1cnc(NCc2c(F)ccc3c2CCO3)n2cnnc12] | δ ppm 3.32 (t, 2H), 3.83 (s, 3H), 4.56 (t, 2H), 4.73 (d, 2H), 6.52 (d, 1H), 6.72 (dd, 1H), 6.97 (t, 1H), 7.51 (d, 1H), 7.78 (s, 1H), 8.87 (d, 1H), 9.49 (s, 1H). LC-MS: $[M + H]^+ = 366.2$ |
| 170 | 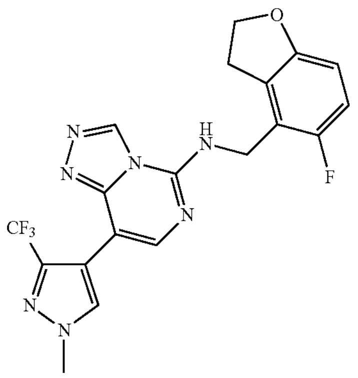 [SMILES: Cn1cc(-c2cnc(NCc3c(F)ccc4c3CCO4)n3cnnc23)c(C(F)(F)F)n1] | δ ppm 3.30 (t, 2H), 4.02 (s, 3H), 4.55 (t, 2H), 4.71 (d, 2H), 6.72 (d, 1H), 6.97 (t, 1H), 7.67 (s, 1H), 8.47 (s, 1H), 8.73 (d, 1H), 9.48 (s, 1H). LC-MS: $[M + H]^+ = 434.1$ |
| 171 | 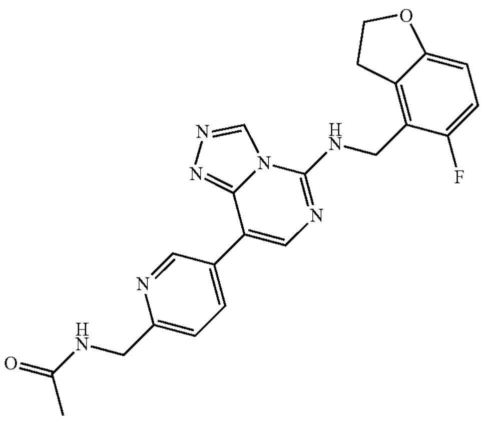 [SMILES: CC(=O)NCc1ccc(-c2cnc(NCc3c(F)ccc4c3CCO4)n3cnnc23)cn1] | δ ppm 1.93 (s, 3H), 3.32 (t, 2H), 4.42 (d, 2H), 4.55 (t, 2H), 4.74 (s, 2H), 6.72 (dd, 2H), 6.97 (t, 1H), 7.48 (s, 1H), 8.19 (s, 1H), 8.55 (d, 2H), 8.87 (s, 1H), 9.26 (s, 1H), 9.52 (s, 1H). LC-MS: $[M + H]^+ = 434.3$ |

TABLE 2-continued
| Ex # | Structure | $^1$H NMR (400 MHz, DMSO-$d_6$) or otherwise indicated/LC-MS Data |
|---|---|---|
| 172 | 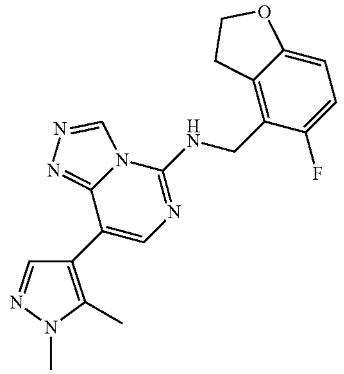 [SMILES: Cc1c(-c2cnc(NCc3c(F)ccc4c3CCO4)n3cnnc23)cnn1C] | δ ppm 2.37 (s, 3H), 3.29 (t, 2H), 3.82 (s, 3H), 4.56 (t, 2H), 4.70 (s, 2H), 6.71 (dd, 1H), 6.97 (t, 1H), 7.62 (s, 1H), 7.76 (s, 1H), 8.53 (s, 1H), 9.45 (s, 1H). LC-MS: $[M + H]^+$ = 380.2 |
| 173 | 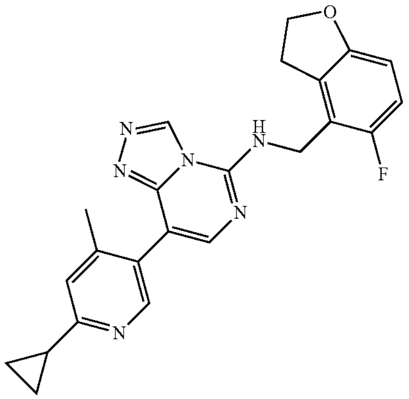 [SMILES: Cc1cc(C2CC2)ncc1-c1cnc(NCc2c(F)ccc3c2CCO3)n2cnnc12] | δ ppm 0.93-1.03 (m, 4H), 2.09-2.13 (m, 1H), 2.19 (s, 3H), 3.33 (t, 2H), 4.55 (t, 2H), 4.71 (d, 2H), 6.72 (q, 1H), 6.96 (t, 1H), 7.27 (s, 1H), 7.61 (s, 1H), 8.28 (s, 1H), 8.709 (t, 1H), 9.46 (s, 1H). LC-MS: $[M + H]^+$ = 417.3 |
| 174 | 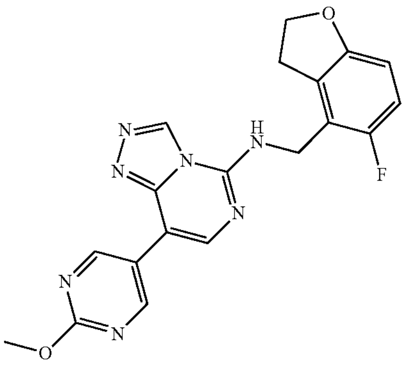 [SMILES: COc1ncc(-c2cnc(NCc3c(F)ccc4c3CCO4)n3cnnc23)cn1] | δ ppm 3.31 (t, 2H), 3.98 (s, 3H), 4.55 (t, 2H), 4.74 (s, 2H), 6.71 (q, 1H), 6.96 (t, 1H), 8.17 (s, 1H), 8.84 (s, 1H), 9.30 (s, 2H), 9.51 (s, 1H). LC-MS: $[M + H]^+$ = 394.2 |
| 175 | 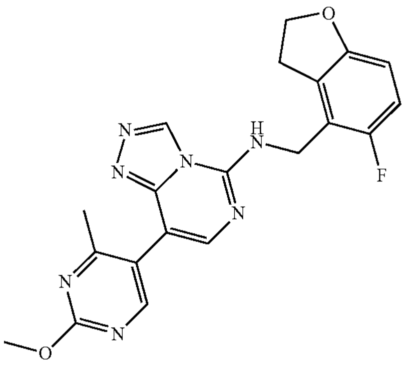 [SMILES: COc1ncc(-c2cnc(NCc3c(F)ccc4c3CCO4)n3cnnc23)c(C)n1] | δ ppm 2.36 (s, 3H), 3.27 (s, 2H), 3.96 (s, 3H), 4.56 (t, 2H), 4.71 (s, 2H), 6.72 (dd, 1H), 6.98 (t, 1H), 7.66 (s, 1H), 8.50 (s, 1H), 8.79 (s, 1H), 9.43 (s, 1H). LC-MS: $[M + H]^+$ = 408.2 |

TABLE 2-continued
| Ex # | Structure | $^1$H NMR (400 MHz, DMSO-$d_6$) or otherwise indicated/LC-MS Data |
|---|---|---|
| 176 | 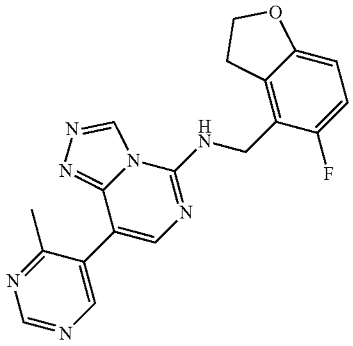 [SMILES: Cc1ncncc1-c1cnc(NCc2c(F)ccc3c2CCO3)n2cnnc12] | δ ppm 2.45 (s, 3H), 3.26 (t, 2H), 4.57 (t, 2H), 4.74 (s, 2H), 6.72 (dd, 1H), 6.97 (t, 1H), 7.77 (s, 1H), 8.74 (s, 1H), 9.09 (s, 1H), 9.50 (s, 1H). LC-MS: $[M + H]^+$ = 378.2 |
| 177 | 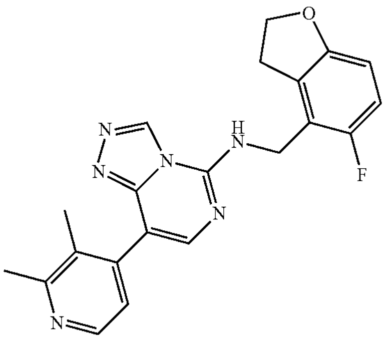 [SMILES: Cc1nccc(-c2cnc(NCc3c(F)ccc4c3CCO4)n3cnnc23)c1C] | δ ppm 2.14 (s, 3H), 2.51 (s, 3H), 3.30 (t, 2H), 4.54 (t, 2H), 4.69 (s, 2H), 6.68 (q, 1H), 6.94 (t, 1H), 7.72 (d, 1H), 7.58 (s, 1H), 8.27 (d, 1H), 8.81 (s, 1H), 9.31 (s, 1H). LC-MS: $[M + H]^+$ = 391.2 |
| 178 | 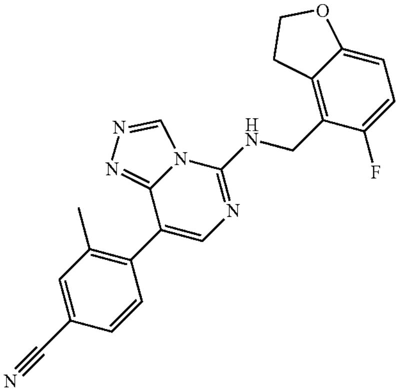 [SMILES: Cc1cc(C#N)ccc1-c1cnc(NCc2c(F)ccc3c2CCO3)n2cnnc12] | δ ppm 2.34 (s, 3H), 3.43 (d, 2H), 4.64 (s, 2H), 4.85 (d, 2H), 6.71 (d, 1H), 6.93 (d, 1H), 7.58 (d, 1H), 7.70 (d, 1H), 7.74 (s, 1H), 7.77 (s, 1H), 9.38 (s, 1H). LC-MS: $[M + H]^+$ = 401.0 |
| 179 | 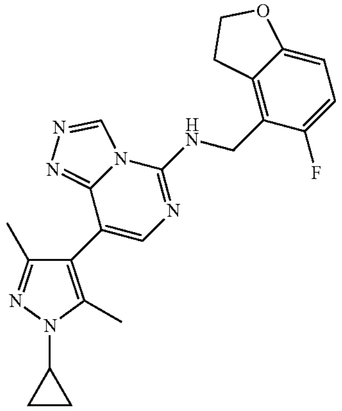 [SMILES: Cc1nn(C2CC2)c(C)c1-c1cnc(NCc2c(F)ccc3c2CCO3)n2cnnc12] | δ ppm 0.97-1.04 (m, 4H), 2.04 (s, 3H), 2.24 (s, 3H), 3.48-3.51 (m, 3H), 4.55 (t, 2H), 4.68 (d, 2H), 6.72 (t, 1H), 6.95 (t, 1H), 7.47 (s, 1H), 8.54 (t, 1H), 9.42 (s, 1H). LC-MS: $[M + H]^+$ = 420.3 |

TABLE 2-continued
| Ex # | Structure | $^1$H NMR (400 MHz, DMSO-$d_6$) or otherwise indicated/LC-MS Data |
|---|---|---|
| 180 | 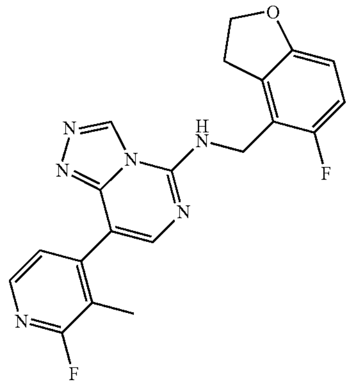 [SMILES: Cc1c(-c2cnc(NCc3c(F)ccc4c3CCO4)n3cnnc23)ccnc1F] | δ ppm 2.17 (s, 3H), 3.33 (t, 2H), 4.57 (t, 2H), 4.73 (d, 2H), 6.72 (dd, 1H), 6.95 (t, 1H), 7.42 (d, 1H), 7.77 (s, 1H), 8.12 (d, 1H), 8.89 (s, 1H), 9.50 (s, 1H). LC-MS: $[M + H]^+$ = 395.1 |
| 181 | 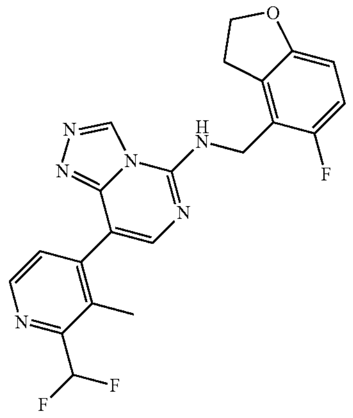 [SMILES: Cc1c(-c2cnc(NCc3c(F)ccc4c3CCO4)n3cnnc23)ccnc1C(F)F] | $^1$H NMR (400 MHz, MeOH-$d_4$) δ ppm 2.43 (t, 3H), 3.46 (s, 2H), 4.63 (d, 2H), 4.87-4.89 (m, 3H), 6.71 (dd, 1H), 6.83-7.00 (m, 2H), 7.61 (d, 1H), 7.80 (s, 1H), 8.57 (d, 1H), 9.39 (s, 1H). LC-MS: $[M + H]^+$ = 427.0 |
| 182 | 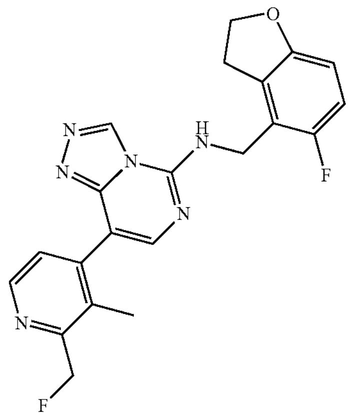 [SMILES: Cc1c(-c2cnc(NCc3c(F)ccc4c3CCO4)n3cnnc23)ccnc1CF] | $^1$H NMR (400 MHz, MeOH-$d_4$) δ ppm 2.36 (d, 3H), 3.46 (t, 2H), 4.64 (t, 2H), 4.88 (d, 2H), 5.61 (s, 1H), 5.73 (s, 1H), 6.72 (d, 1H), 6.86-6.97 (m, 1H), 7.48-7.55 (m, 1H), 7.79 (s, 1H), 8.51 (d, 1H), 9.39 (s, 1H). LC-MS: $[M + H]^+$ = 409.0 |

TABLE 2-continued
| Ex # | Structure | $^1$H NMR (400 MHz, DMSO-$d_6$) or otherwise indicated/LC-MS Data |
|---|---|---|
| 183 | 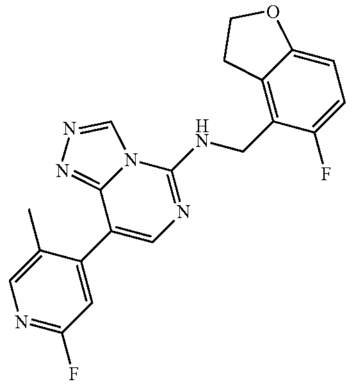 [SMILES: Cc1cnc(F)cc1-c1cnc(NCc2c(F)ccc3c2CCO3)n2cnnc12] | δ ppm 2.23 (s, 3H), 3.27 (s, 2H), 4.56 (t, 2H), 4.73 (s, 2H), 6.73 (dd, 1H), 6.97 (t, 1H), 7.26 (s, 1H), 7.78 (s, 1H), 8.19 (s, 1H), 8.90 (s, 1H), 9.50 (s, 1H). LC-MS: $[M + H]^+$ = 395.2 |
| 184 | 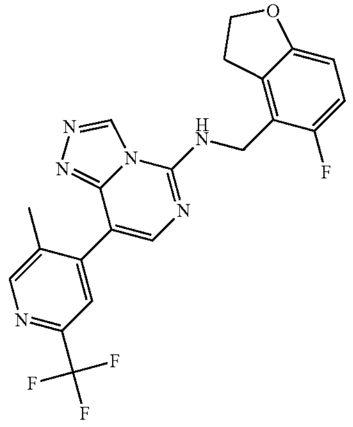 [SMILES: Cc1cnc(C(F)(F)F)cc1-c1cnc(NCc2c(F)ccc3c2CCO3)n2cnnc12] | δ ppm 2.37 (s, 3H), 3.33 (t, 2H), 4.56 (t, 2H), 4.74 (d, 2H), 6.73 (dd, 1H), 6.98 (t, 1H), 7.85 (s, 1H), 7.96 (s, 1H), 8.75 (s, 1H), 8.94 (t, 1H), 9.51 (s, 1H). LC-MS: $[M + H]^+$ = 445.1 |
| 185 | 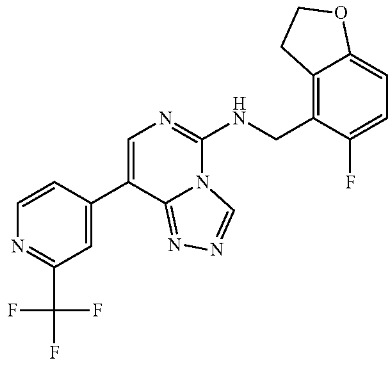 [SMILES: Fc1ccc2c(c1CNc1ncc(-c3ccnc(C(F)(F)F)c3)c3nncn13)CCO2] | δ ppm 3.35 (d, 2H), 4.56 (t, 2H), 4.77 (s, 2H), 6.72 (dd, 1H), 6.96 (t, 1H), 8.55 (d, 1H), 8.59 (s, 1H), 8.80 (d, 1H), 8.85 (s, 1H), 9.15 (s, 1H), 9.54 (s, 1H). LC-MS: $[M + H]^+$ = 431.1 |
| 186 | 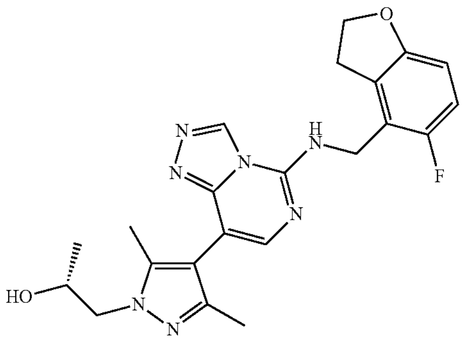 [SMILES: Cc1nn(C[C@@H](C)O)c(C)c1-c1cnc(NCc2c(F)ccc3c2CCO3)n2cnnc12] | δ ppm 1.10 (d, 3H), 2.07 (s, 3H), 2.17 (s, 3H), 3.24 (m, 2H), 3.87-3.92 (m, 2H), 3.96-4.00 (m, 1H), 4.55 (t, 2H), 4.69 (s, 2H), 4.91 (d, 1H), 6.72 (q, 1H), 6.96 (t, 1H), 7.47 (s, 1H), 8.53 (s, 1H), 9.42 (s, 1H). LC-MS: $[M + H]^+$ = 438.2 |

TABLE 2-continued
| Ex # | Structure | $^{1}H$ NMR (400 MHz, DMSO-$d_6$) or otherwise indicated/LC-MS Data |
|---|---|---|
| 187 | 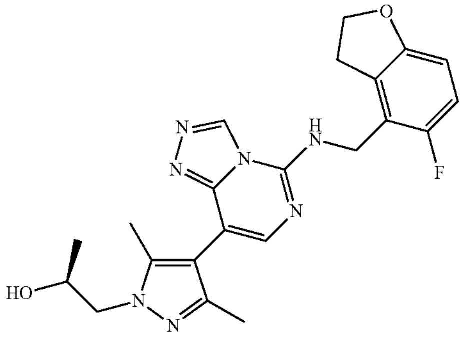 [SMILES: Cc1nn(C[C@H](C)O)c(C)c1-c1cnc(NCc2c(F)ccc3c2CCO3)n2cnnc12] | δ ppm 1.10 (d, 3H), 2.08 (s, 3H), 2.17 (s, 3H), 3.35 (m, 2H), 3.89-3.93 (m, 2H), 3.96-4.00 (m, 1H), 4.55 (t, 2H), 4.69 (d, 2H), 4.91 (d, 1H), 6.71 (q, 1H), 6.96 (t, 1H), 7.47 (s, 1H), 8.53 (t, 1H), 9.43 (s, 1H). LC-MS: $[M + H]^+$ = 438.2 |
| 188 | 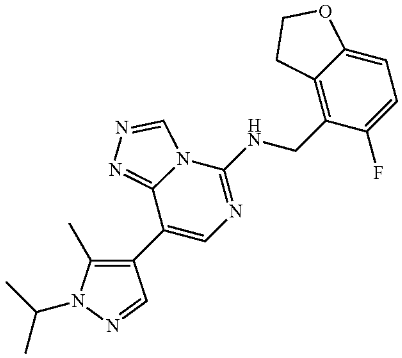 [SMILES: Cc1c(-c2cnc(NCc3c(F)ccc4c3CCO4)n3cnnc23)cnn1C(C)C] | δ ppm 1.41 (d, 6H), 2.36 (s, 3H), 3.30 (t, 2H), 4.54 (t, 2H), 4.59-4.63 (m, 1H), 4.69 (s, 2H), 6.71 (q, 1H), 6.93 (t, 1H), 7.60 (s, 1H), 7.77 (s, 1H), 8.58 (t, 1H), 9.46 (s, 1H). LC-MS: $[M + H]^+$ = 408.3 |
| 189 | 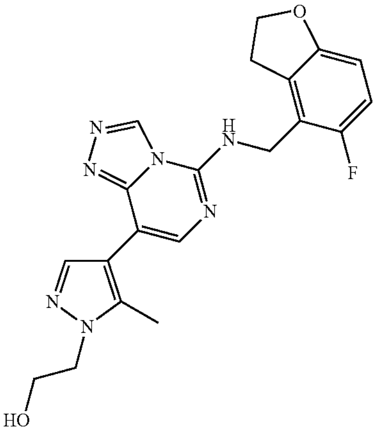 [SMILES: Cc1c(-c2cnc(NCc3c(F)ccc4c3CCO4)n3cnnc23)cnn1CCO] | δ ppm 2.38 (s, 3H), 2.53 (s, 1H), 3.31 (t, 2H), 3.75 (t, 2H), 4.16 (t, 2H), 4.57 (t, 2H), 4.70 (d, 2H), 6.71 (dd, 1H), 6.96 (t, 1H), 7.63 (s, 1H), 7.79 (s, 1H), 8.57 (s, 1H), 9.46 (s, 1H). LC-MS: $[M + H]^+$ = 410.2 |
| 190 | 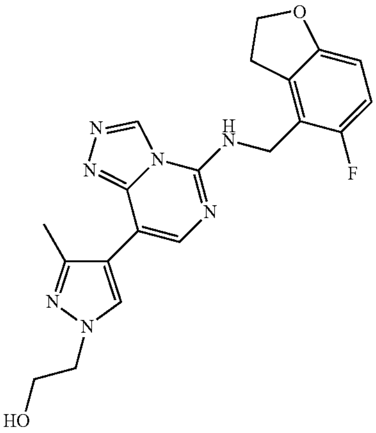 [SMILES: Cc1nn(CCO)cc1-c1cnc(NCc2c(F)ccc3c2CCO3)n2cnnc12] | δ ppm 2.36 (s, 3H), 3.30 (t, 3H), 3.75 (t, 2H), 4.12 (t, 2H), 4.55 (t, 2H), 4.70 (d, 2H), 6.72 (dd, 1H), 6.96 (t, 1H), 7.74 (s, 1H), 8.32 (s, 1H), 8.52 (s, 1H), 9.46 (s, 1H). LC-MS: $[M + H]^+$ = 410.2 |

TABLE 2-continued
| Ex # | Structure | $^1$H NMR (400 MHz, DMSO-$d_6$) or otherwise indicated/LC-MS Data |
|---|---|---|
| 191 | 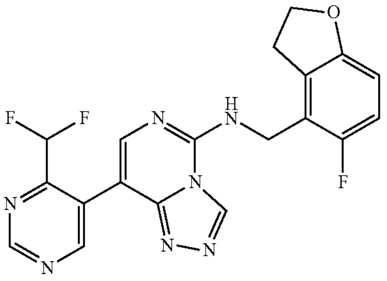 [SMILES: Fc1ccc2c(c1CNc1ncc(-c3cncnc3C(F)F)c3nncn13)CCO2] | δ ppm 3.37 (t, 2H), 4.56 (t, 2H), 4.74 (s, 2H), 6.73 (dd, 1H), 6.90-7.21 (m, 2H), 7.78 (s, 1H), 8.95 (s, 1H), 9.12 (s, 1H), 9.42 (s, 1H), 9.50 (s, 1H). LC-MS: $[M + H]^+$ = 414.1 |
| 192 | 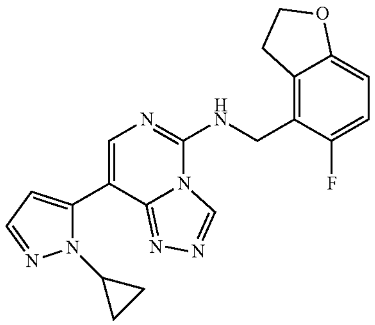 [SMILES: Fc1ccc2c(c1CNc1ncc(-c3ccnn3C3CC3)c3nncn13)CCO2] | δ ppm 0.84-0.86 (m, 2H), 0.95-0.97 (m, 2H), 3.30 (t, 2H), 3.77-3.80 (m, 1H), 4.55 (t, 2H), 4.73 (d, 2H), 6.61 (d, 1H), 6.71 (q, 1H), 6.97 (t, 1H), 7.47 (d, 1H), 7.93 (s, 1H), 8.83 (t, 1H), 9.49 (s, 1H). LC-MS: $[M + H]^+$ = 392.2 |
| 193 | 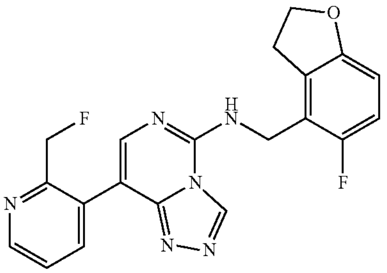 [SMILES: FCc1ncccc1-c1cnc(NCc2c(F)ccc3c2CCO3)n2cnnc12] | $^1$H-NMR (500 MHz, DMSO-$d_6$) δ ppm 3.32 (s, 2H), 4.56 (s, 2H), 4.73 (s, 2H), 5.44 (d, 2H), 6.72 (dd, 1H), 6.97 (m, 1H), 7.55-7.57 (m, 1H), 7.69 (s, 1H), 7.98 (d, 1H), 8.68 (dd, 1H), 8.79 (s, 1H), 9.48 (s, 1H). LC-MS: [M + H]+ = 395.1 |
| 194 | 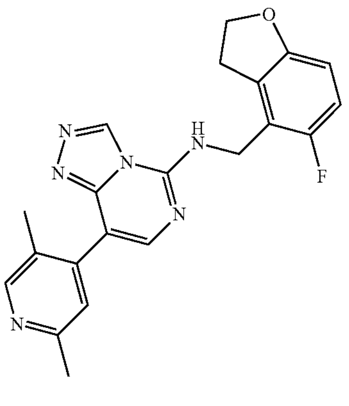 [SMILES: Cc1cc(-c2cnc(NCc3c(F)ccc4c3CCO4)n3cnnc23)c(C)cn1] | $^1$H-NMR (500 MHz, DMSO-$d_6$) δ ppm 2.18 (s, 3H), 2.46 (s, 3H), 3.35 (t, 2H), 4.56 (t, 2H), 4.72 (s, 2H), 6.72 (dd, 1H), 6.96 (t, 1H), 7.27 (s, 1H), 7.67 (s, 1H), 8.38 (s, 1H), 8.79 (s, 1H), 9.50 (s, 1H). LC-MS: $[M + H]^+$ = 391.2 |

TABLE 2-continued

| Ex # | Structure | $^1$H NMR (400 MHz, DMSO-$d_6$) or otherwise indicated/LC-MS Data |
|---|---|---|
| 195 | 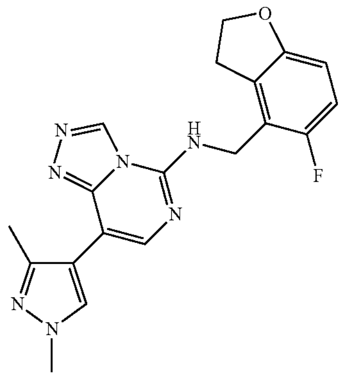 [SMILES: Cc1nn(C)cc1-c1cnc(NCc2c(F)ccc3c2CCO3)n2cnnc12] | $^1$H-NMR (500 MHz, DMSO-$d_6$) δ ppm 2.35 (s, 3H), 3.30 (t, 2H), 3.84 (s, 3H), 4.55 (t, 2H), 4.71 (s, 2H), 6.72 (dd, 1H), 6.96 (t, 1H), 7.74 (s, 1H), 8.28 (s, 1H), 8.51 (s, 1H), 9.46 (s, 1H). LC-MS: $[M + H]^+ = 380.2$ |
| 196 | 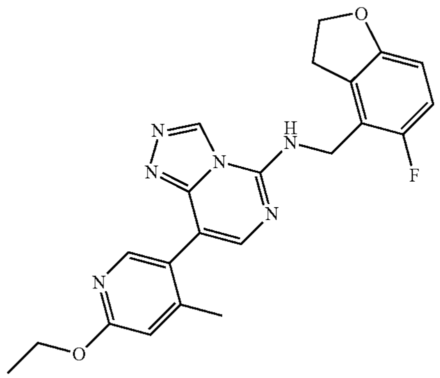 [SMILES: CCOc1cc(C)c(-c2cnc(NCc3c(F)ccc4c3CCO4)n3cnnc23)cn1] | $^1$H-NMR (400 MHz, DMSO-$d_6$) δ ppm 1.34 (t, 3H), 2.18 (s, 3H), 3.34 (t, 2H), 4.34 (dd, 2H), 4.57 (t, 2H), 4.72 (s, 2H), 6.72 (dd, 1H), 6.78 (s, 1H), 6.97 (t, 1H), 7.59 (s, 1H), 8.05 (s, 1H), 8.68 (s, 1H), 9.46 (s, 1H). LC-MS: $[M + H]^+ = 421.3$ |
| 197 | 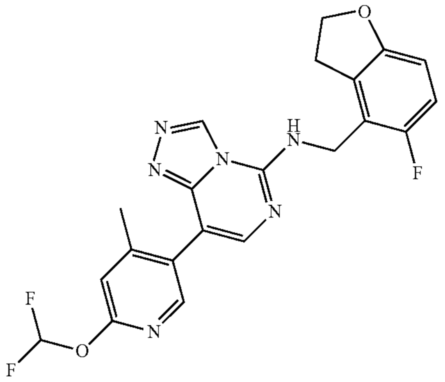 [SMILES: Cc1cc(OC(F)F)ncc1-c1cnc(NCc2c(F)ccc3c2CCO3)n2cnnc12] | $^1$HNMR (500 MHz, DMSO-$d_6$) δ ppm 2.27 (s, 3H), 3.36 (t, 2H), 4.56 (t, 2H), 4.73 (d, 2H), 6.73 (dd, 1H), 6.98 (t, 1H), 7.12 (s, 1H), 7.61-7.90 (m, 2H), 8.18 (s, 1H), 8.77 (t, 1H), 9.48 (s, 1H). LC-MS: $[M + H]^+ = 443.1$ |
| 198 | 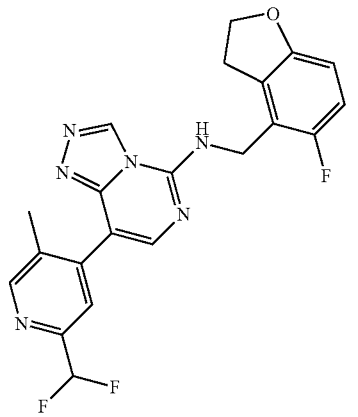 [SMILES: Cc1cnc(C(F)F)cc1-c1cnc(NCc2c(F)ccc3c2CCO3)n2cnnc12] | $^1$H-NMR (500 MHz, DMSO-$d_6$) δ ppm 2.33 (s, 3H), 3.38 (t, 2H), 4.56 (t, 2H), 4.74 (s, 2H), 6.72 (dd, 1H), 6.87-7.09 (m, 2H), 7.74 (s, 1H), 7.79 (s, 1H), 8.66 (s, 1H), 8.88 (s, 1H), 9.50 (s, 1H). LC-MS: $[M + H]^+ = 427.4$ |

TABLE 2-continued
| Ex # | Structure | $^1$H NMR (400 MHz, DMSO-$d_6$) or otherwise indicated/LC-MS Data |
|---|---|---|
| 199 | 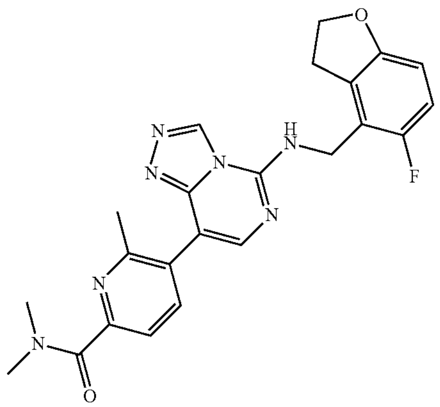 [SMILES: Cc1nc(C(=O)N(C)C)ccc1-c1cnc(NCc2c(F)ccc3c2CCO3)n2cnnc12] | $^1$H-NMR (500 MHz, DMSO-$d_6$) δ ppm 2.44 (s, 3H), 3.03 (d, 6H), 3.35 (t, 2H), 4.56 (t, 2H), 4.73 (s, 2H), 6.73 (dd, 1H), 6.97 (t, 1H), 7.46 (d, 1H), 7.71 (s, 1H), 7.87 (d, 1H), 8.76 (s, 1H), 9.49 (s, 1H). LC-MS: $[M + H]^+ = 448.2$ |
| 200 | 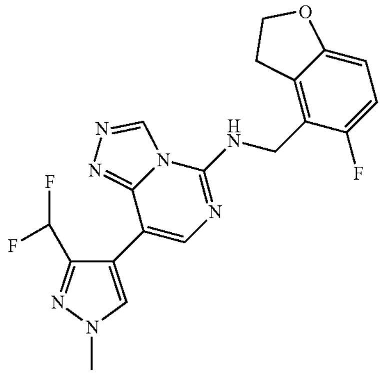 [SMILES: Cn1cc(-c2cnc(NCc3c(F)ccc4c3CCO4)n3cnnc23)c(C(F)F)n1] | δ ppm 3.34 (t, 2H), 3.87 (s, 3H), 4.55 (t, 2H), 4.72 (s, 2H), 6.71 (q, 1H), 6.77 (s, 1H), 6.90 (s, 0.25H), 6.95 (t, 1H), 7.01 (s, 0.5H), 7.12 (s, 0.25H), 7.83 (s, 1H), 9.51 (s, 1H). LC-MS: $[M + H]^+ = 416.1$ |
| 201 | 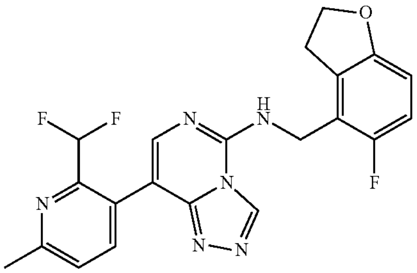 [SMILES: Cc1ccc(-c2cnc(NCc3c(F)ccc4c3CCO4)n3cnnc23)c(C(F)F)n1] | $^1$H-NMR (500 MHz, DMSO-$d_6$) δ ppm 2.61 (s, 3H), 3.34 (t, 2H), 4.56 (t, 2H), 4.73 (s, 2H), 6.71-6.99 (m, 3H), 7.55 (d, 1H), 7.59 (s, 1H), 7.89 (d, 1H), 8.80 (s, 1H), 9.48 (s, 1H). LC-MS: $[M + H]^+ = 427.2$ |
| 202 | 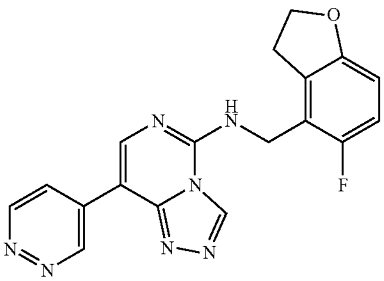 [SMILES: Fc1ccc2c(c1CNc1ncc(-c3ccnnc3)c3nncn13)CCO2] | $^1$H NMR (400 MHz, $CD_3OD$) δ ppm 3.27 (t, 2H), 3.43 (d, 2H), 4.51 (t, 2H), 4.71 (s, 2H), 6.63 (s, 1H), 6.89 (t, 1H), 8.35-8.52 (m, 2H), 9.01 (s, 1H), 9.97 (s, 1H) LC-MS: $[M + H]^+ = 363.9$ |

TABLE 2-continued
| Ex # | Structure | $^1$H NMR (400 MHz, DMSO-$d_6$) or otherwise indicated/LC-MS Data |
|---|---|---|
| 203 | 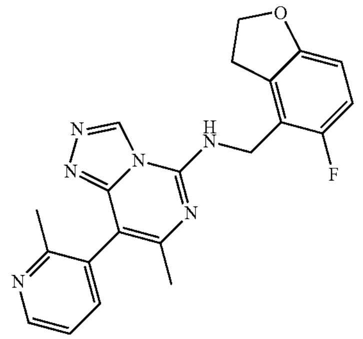 [SMILES: Cc1ncccc1-c1c(C)nc(NCc2c(F)ccc3c2CCO3)n2cnnc12] | $^1$H NMR (400 MHz, $CD_3OD$) δ ppm 2.08 (s, 3H), 2.24 (s, 3H), 4.58 (t, 2H), 4.63-4.73 (m, 2H), 6.72 (dd, 1H), 6.91-7.02 (m, 1H), 7.32 (dd, 1H), 7.62 (dd, 1H), 8.51 (dd, 1H), 8.66 (s, 1H), 9.38 (s, 1H) LC-MS: $[M + H]^+$ = 390.9 |
| 204 | 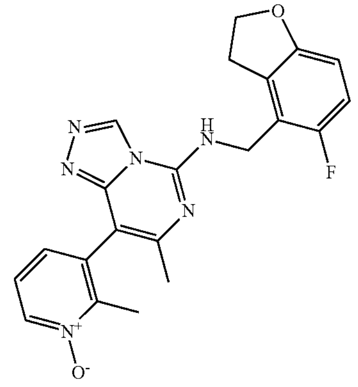 | $^1$H-NMR (500 MHz, DMSO-$d_6$) δ ppm 2.25 (s, 3H), 3.30 (s, 2H), 4.56 (t, 2H), 4.73 (s, 2H), 6.72 (dd, 1H), 6.97 (t, 1H), 7.36-7.38 (m, 2H), 7.72 (s, 1H), 8.36 (dd, 1H), 8.82 (s, 1H), 9.48 (s, 1H). LC-MS: $[M + H]^+$ = 393.1 |
| 205 | 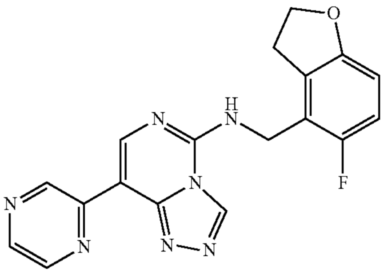 [SMILES: Fc1ccc2c(c1CNc1ncc(-c3cnccn3)c3nncn13)CCO2] | $^1$H NMR (500 MHz, DMSO-$d_6$) δ ppm 3.28 (t, 2H), 4.55 (t, 2H), 4.78 (s, 2H), 6.72 (dd, 1H), 6.97 (t, 1H), 8.59 (d, 1H), 8.66 (s, 1H), 8.71 (t, 1H), 9.07 (s, 1H), 9.56 (s, 1H), 9.93 (d, 1H); LC-MS: $[M + H]^+$ = 364.1 |
| 206 | 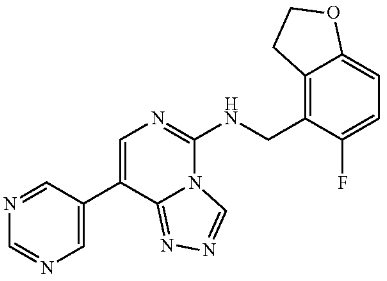 [SMILES: Fc1ccc2c(c1CNc1ncc(-c3cncnc3)c3nncn13)CCO2] | δ ppm 3.29 (br. s., 2H), 4.54 (t, J = 8.72 Hz, 2H), 4.74 (s, 2H), 6.70 (dd, J = 3.86, 8.63 Hz, 1H), 6.95 (t, J = 9.44 Hz, 1H), 8.29 (s, 1H), 9.11 (s, 1H), 9.43 (s, 1H), 9.53 (s, 2H). LC-MS: $[M + H]^+$ = 363.9 |

TABLE 2-continued
| Ex # | Structure | $^1$H NMR (400 MHz, DMSO-$d_6$) or otherwise indicated/LC-MS Data |
| --- | --- | --- |
| 208 | 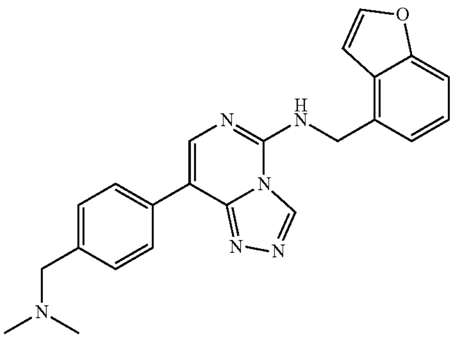 [SMILES: CN(C)Cc1ccc(-c2cnc(NCc3cccc4occc34)n3cnnc23)cc1] | $^1$H NMR (400 MHz, Methanol-$d_4$) δ ppm 2.28 (s, 6H), 3.54 (s, 2H), 5.09 (s, 2H), 7.05 (d, 1H), 7.31 (dt, 2H), 7.45 (t, 3H), 7.78 (d, 1H), 7.91 (d, 2H), 7.95 (s, 1H), 9.30 (s, 1H). LC-MS: $[M + H]^+$ = 398.9 |
| 209 | 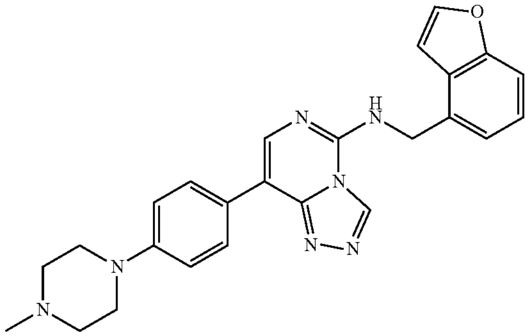 [SMILES: CN1CCN(c2ccc(-c3cnc(NCc4cccc5occc45)n4cnnc34)cc2)CC1] | δ ppm 2.29 (s, 3H), 2.46 (t, 4H), 3.19 (t, 4H), 5.00 (d, 2H), 7.01 (d, 2H), 7.16 (dd, 1H), 7.30 (m, 2H), 7.52 (d, 1H), 7.91 (m, 4H), 8.82 (m, 1H), 9.47 (s, 1H). LC-MS: $[M + H]^+$ = 440.2 |
| 210 | 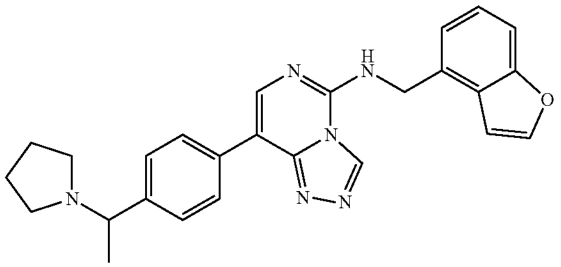 [SMILES: CC(c1ccc(-c2cnc(NCc3cccc4occc34)n3cnnc23)cc1)N1CCCC1] | δ ppm 1.34 (d, 3H), .1.69 (s, 4H), 2.34 (q, 2H), 3.25 (q, 3H), 5.04 (d, 2H), 7.18 (m, 1H), 7.34 (m, 5H), 8.02 (m, 4H), 8.96 (t, 1H), 9.50 (s, 1H). LC-MS: $[M + H]^+$ = 439.3 |
| 211 | 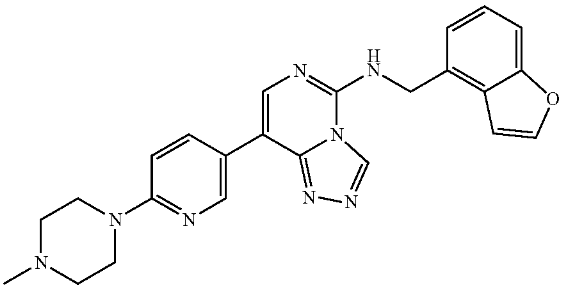 [SMILES: CN1CCN(c2ccc(-c3cnc(NCc4cccc5occc45)n4cnnc34)cn2)CC1] | δ ppm 2.23 (s, 3H), .2.41 (d, 4H), 3.54 (t, 4H), 5.02 (d, 2H), 6.95 (d, 1H), 7.30 (m, 3H), 7.53 (d, 1H), 7.95 (s, 2H), 8.24 (q, 1H), 8.83 (m, 2H), 9.49 (s, 1H). LC-MS: $[M + H]^+$ = 441.2 |
| 212 | 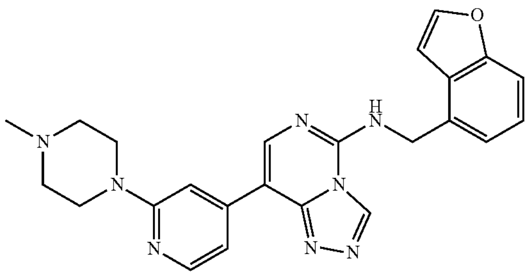 [SMILES: CN1CCN(c2cc(-c3cnc(NCc4cccc5occc45)n4cnnc34)ccn2)CC1] | δ ppm 2.23 (s, 3H), 2.43 (s, 4H), 3.53 (s, 4H), 5.04 (d, 2H), 7.17 (m, 1H), 7.27 (m, 2H), 7.39 (dd, 1H), 7.53 (d, 1H), 7.74 (s, 1H), 8.01 (d, 1H), 8.14 (d, 1H), 8.29 (s, 1H), 9.15 (t, 1H), 9.50 (s, 1H). LC-MS: $[M + H]^+$ = 441.2 |

TABLE 2-continued
| Ex # | Structure | $^1$H NMR (400 MHz, DMSO-$d_6$) or otherwise indicated/LC-MS Data |
|---|---|---|
| 213 | 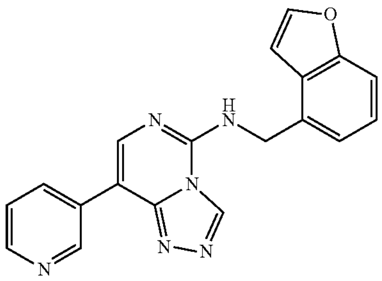 [SMILES: c1cncc(-c2cnc(NCc3cccc4occc34)n3cnnc23)c1] | δ ppm 5.04 (s, 2H), 7.17 (m, 1H), 7.27 (m, 2H), 7.48 (m, 2H), 8.02 (d, 1H), 8.15 (s, 1H), 8.49 (m, 2H), 9.08 (s, 1H), 9.28 (dd, 1H), 9.52 (s, 1H). LC-MS: $[M + H]^+$ = 343.2 |
| 214 | 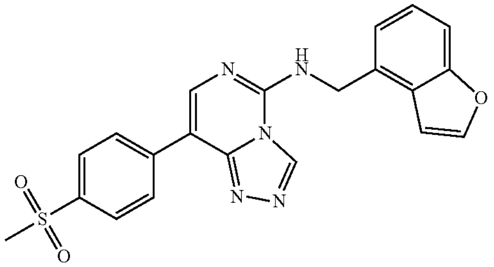 [SMILES: CS(=O)(=O)c1ccc(-c2cnc(NCc3cccc4occc34)n3cnnc23)cc1] | δ ppm 3.26 (s, 3H), 5.06 (s, 2H), 7.19 (t, 1H), 7.32 (m, 2H), 7.54 (d, 1H), 8.01 (m, 3H), 8.25 (s, 1H), 8.45 (d, 2H), 9.54 (s, 1H). LC-MS: $[M + H]^+$ = 420.1 |
| 215 | 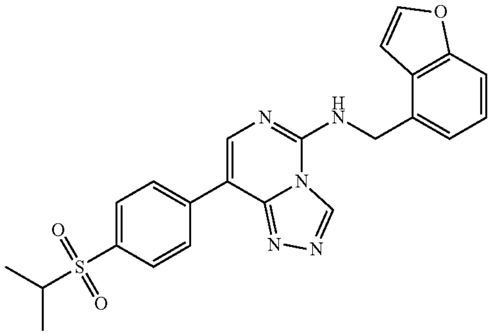 [SMILES: CC(C)S(=O)(=O)c1ccc(-c2cnc(NCc3cccc4occc34)n3cnnc23)cc1] | δ ppm 1.18 (d, 6H), 3.45 (m, 1H), 5.06 (s, 2H), 7.18 (d, 1H), 7.31 (m, 2H), 7.54 (d, 1H), 7.91 (d, 2H), 8.02 (d, 1H), 8.26 (s, 1H), 8.45 (d, 2H), 9.17 (s, 1H), 9.53 (s, 1H). LC-MS: $[M + H]^+$ = 448.2 |
| 216 | 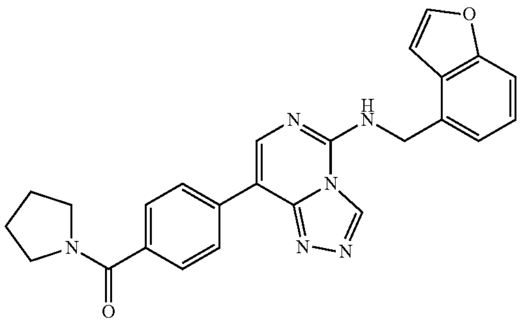 [SMILES: O=C(c1ccc(-c2cnc(NCc3cccc4occc34)n3cnnc23)cc1)N1CCCC1] | δ ppm 1.82 (m, 4H), 3.46 (m, 4H), 5.03 (s, 2H), 7.17 (dd, 1H), 7.29 (m, 2H), 7.52 (d, 1H), 7.59 (d, 2H), 8.01 (d, 1H), 8.11 (s, 1H), 8.18 (d, 2H), 9.03 (s, 1H), 9.48 (s, 1H). LC-MS: $[M + H]^+$ = 439.2 |
| 217 | 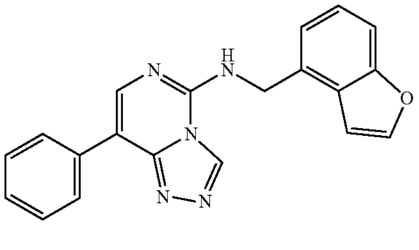 [SMILES: c1ccc(-c2cnc(NCc3cccc4occc34)n3cnnc23)cc1] | δ ppm 5.04 (s, 2H), 7.18 (m, 1H), 7.34 (m, 3H), 7.47 (m, 2H), 7.54 (m, 1H), 8.10 (m, 4H), 9.51 (s, 1H). LC-MS: $[M + H]^+$ = 342.1 |

TABLE 2-continued
| Ex # | Structure | $^1H$ NMR (400 MHz, DMSO-$d_6$) or otherwise indicated/LC-MS Data |
|---|---|---|
| 218 | 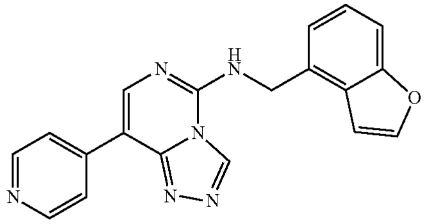 [SMILES: c1cc(CNc2ncc(-c3ccncc3)c3nncn23)c2ccoc2c1] | δ ppm 5.06 (s, 2H), 7.28 (t, 1H), 7.33 (m, 2H), 7.56 (d, 1H), 8.03 (d, 1H), 8.23 (t, 2H), 8.37 (s, 1H), 8.63 (t, 3H), 9.53 (s, 1H). LC-MS: $[M + H]^+$ = 343.1 |
| 219 | 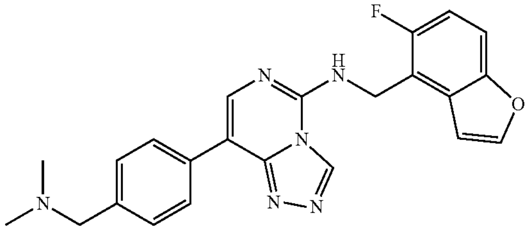 [SMILES: CN(C)Cc1ccc(-c2cnc(NCc3c(F)ccc4occc34)n3cnnc23)cc1] | $^1H$ NMR (400 MHz, Methanol-$d_4$) δ ppm 2.32 (s, 6H), 3.58 (s, 2H), 5.13 (s, 2H), 7.06-7.18 (m, 2H), 7.40-7.54 (m, 3H), 7.84 (d, 1H), 7.94 (d, 2H), 8.01 (s, 1H), 9.32 (s, 1H). LC-MS: $[M + H]^+$ = 417.2 |
| 220 | 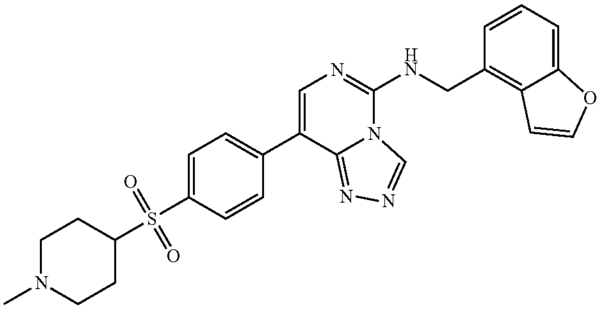 [SMILES: CN1CCC(S(=O)(=O)c2ccc(-c3cnc(NCc4cccc5occc45)n4cnnc34)cc2)CC1] | δ ppm 1.54 (q, 2H), 1.83 (t, 4H), 2.11 (s, 3H), 2.80 (d, 2H), 3.22 (t, 1H), 5.06 (s, 2H), 7.19 (s, 1H), 7.31 (m, 2H), 7.54 (d, 1H), 7.90 (d, 2H), 8.03 (d, 1H), 8.26 (s, 1H), 8.45 (d, 2H), 9.15 (s, 1H), 9.55 (s, 1H). LC-MS: $[M + H]^+$ = 503.2 |
| 221 | 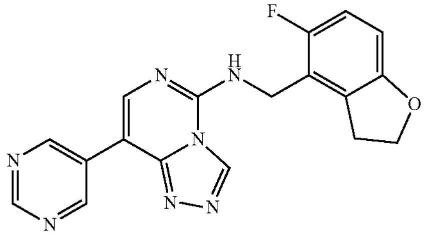 [SMILES: Fc1ccc2c(c1CNc1ncc(-c3cncnc3)c3nncn13)CCO2] | δ ppm 9.53 (s, 2H), 9.43 (s, 1H), 9.11 (s, 1H), 8.29 (s, 1H), 6.95 (t, 1H), 6.70 (dd, 1H), 4.74 (s, 2H), 4.54 (t, 2H), 3.29 (t, 2H). LC-MS: $[M + H]^+$ = 363.9 |
| 222 | 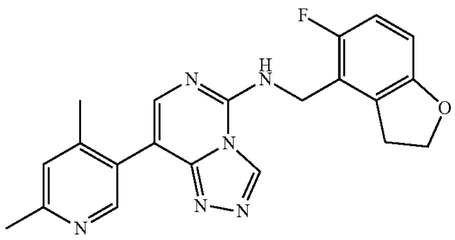 [SMILES: Cc1cc(C)c(-c2cnc(NCc3c(F)ccc4c3CCO4)n3cnnc23)cn1] | $^1H$ NMR (500 MHz, DMSO-$d_6$) δ ppm 2.19 (s, 3H), 2.48 (s, 3H), 3.34 (d, 2H), 4.56 (t, 2H), 4.72 (d, 2H), 6.72 (dd, 1H), 6.96 (t, 1H), 7.23 (s, 1H), 7.62 (s, 1H), 8.33 (s, 1H), 8.70 (t, 1H), 9.46 (s, 1H). LC-MS: $[M + H]^+$ = 391.1. |

TABLE 2-continued

| Ex # | Structure | $^1$H NMR (400 MHz, DMSO-$d_6$) or otherwise indicated/LC-MS Data |
|---|---|---|
| 223 | 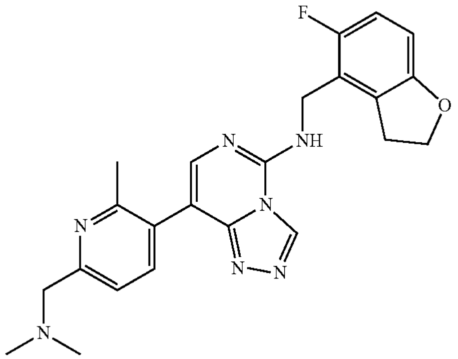 [SMILES: Cc1nc(CN(C)C)ccc1-c1cnc(NCc2c(F)ccc3c2CCO3)n2cnnc12] | $^1$H NMR (600 MHz, DMOS-$d_6$) δ ppm 2.23 (s, 6H) 2.38 (s, 3H) 2.50 (s, 7H) 3.33-3.37 (m, 2H) 3.50-3.57 (m, 2H) 4.51-4.61 (m, 2H) 4.67-4.78 (m, 2H) 6.69-6.76 (m, 1H) 6.92-7.00 (m, 1H) 7.29-7.37 (m, 1H) 7.61-7.68 (m, 1H) 7.69-7.75 (m, 1H) 8.65-8.74 (m, 1H) 9.42-9.51 (m, 1H). LC-MS: $[M + H]^+$ = 434.2 |
| 224 | 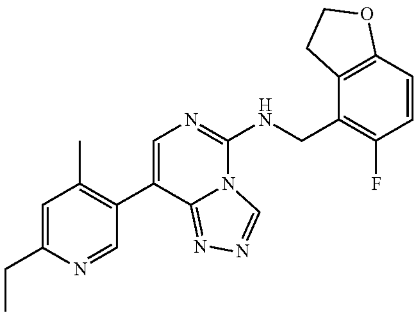 [SMILES: CCc1cc(C)c(-c2cnc(NCc3c(F)ccc4c3CCO4)n3cnnc23)cn1] | δ ppm 1.27 (t, 3H), 2.21 (s, 3H), 2.76 (q, 2H), 3.34 (d, 2H), 4.56 (t, 2H), 4.72 (s, 2H), 6.72 (dd, 1H), 6.94-7.00 (m, 1H), 7.24 (s, 1H), 7.63 (s, 1H), 8.36 (s, 1H), 8.70 (s, 1H), 9.47 (s, 1H). LC-MS: $[M + H]^+$ = 405.2. |
| 225 | 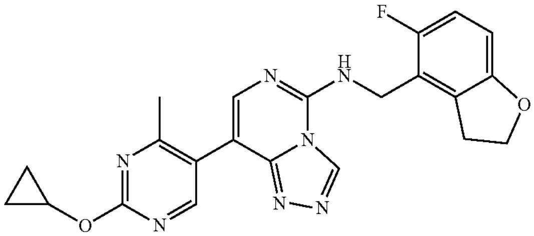 [SMILES: Cc1nc(OC2CC2)ncc1-c1cnc(NCc2c(F)ccc3c2CCO3)n2cnnc12] | $^1$H NMR (500 MHz, DMSO-$d_6$) δ ppm 0.72-0.85 (m, 4H), 2.36 (s, 3H), 3.34 (t, 2H), 4.35 (tt, 1H), 4.56 (t, 2H), 4.72 (s, 2H), 6.72 (dd, 1H), 6.96 (dd, 1H), 7.69 (s, 1H), 8.51 (s, 1H), 8.77 (s, 1H), 9.47 (s, 1H). LC-MS: $[M + H]^+$ = 434.1 |
| 226 | 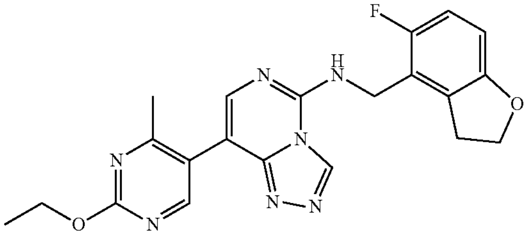 [SMILES: CCOc1ncc(-c2cnc(NCc3c(F)ccc4c3CCO4)n3cnnc23)c(C)n1] | $^1$H NMR (500 MHz, DMSO-$d_6$) δ ppm 1.36 (t, 3H), 2.35 (s, 3H), 3.34 (t, 2H), 4.40 (q, 2H), 4.56 (t, 2H), 4.72 (s, 2H), 6.72 (dd, 1H), 6.92-7.00 (m, 1H), 7.68 (s, 1H), 8.48 (s, 1H), 8.76 (s, 1H), 9.47 (s, 1H). LC-MS: $[M + H]^+$ = 422.2 |
| 227 | 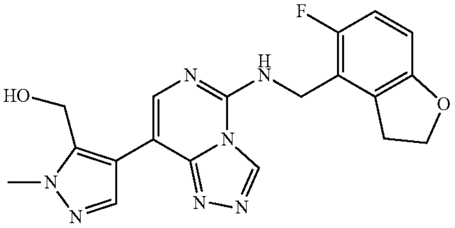 [SMILES: Cn1ncc(-c2cnc(NCc3c(F)ccc4c3CCO4)n3cnnc23)c1CO] | $^1$H NMR (500 MHz, DMSO-$d_6$) δ ppm 3.29-3.33 (m, 2H), 3.91 (s, 3H), 4.55 (dd, 4H), 4.71 (d, 2H), 5.59 (t, 1H), 6.71 (dd, 1H), 6.95 (t, 1H), 7.76 (s, 1H), 7.81 (s, 1H), 8.58 (t, 1H), 9.45 (s, 1H). LC-MS: $[M + H]^+$ = 396.1 |

TABLE 2-continued

| Ex # | Structure | $^1$H NMR (400 MHz, DMSO-$d_6$) or otherwise indicated/LC-MS Data |
|---|---|---|
| 228 | 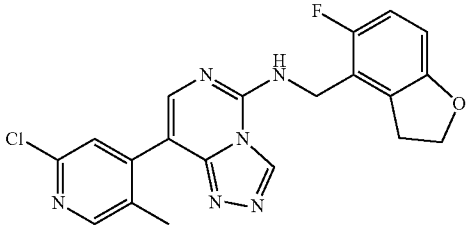 [SMILES: Cc1cnc(Cl)cc1-c1cnc(NCc2c(F)ccc3c2CCO3)n2cnnc12] | δ ppm 2.24 (s, 3H), 4.56 (t, 2H), 4.73 (s, 2H), 6.73 (dd, 1H), 6.92-7.01 (m, 1H), 7.58 (s, 1H), 7.79 (s, 1H), 8.38 (s, 1H), 9.50 (s, 1H). LC-MS: $[M + H]^+$ = 410.8 |
| 229 | 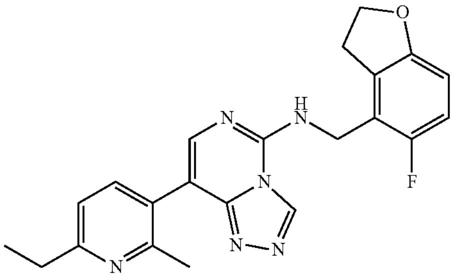 [SMILES: CCc1ccc(-c2cnc(NCc3c(F)ccc4c3CCO4)n3cnnc23)c(C)n1] | $^1$H NMR (500 MHz, DMSO-$d_6$) δ ppm 1.26 (t, 3H). 2.37 (s, 3H), 2.77 (q, 2H), 3.34 (s, 2H), 4.56 (t, 2H), 4.72 (s, 2H), 6.72 (dd, 1H), 6.97 (t, 1H), 7.18 (d, 1H), 7.68-7.58 (m, 2H), 8.70 (s, 1H), 9.47 (s, 1H). LC-MS: $[M + H]^+$ = 405.3 |
| 230 | 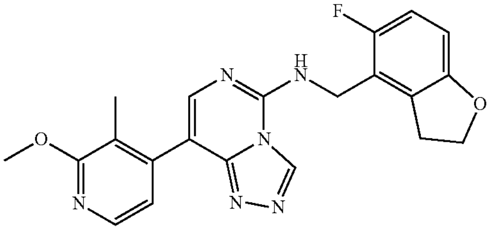 [SMILES: COc1nccc(-c2cnc(NCc3c(F)ccc4c3CCO4)n3cnnc23)c1C] | $^1$H NMR (500 MHz, DMSO-$d_6$) δ ppm 2.04 (s, 3H), 3.31 (s, 2H), 3.93 (s, 3H), 4.55 (t, 2H), 4.72 (s, 2H), 6.72 (dd, 1H), 6.99-6.92 (m, 1H), 7.02 (d, 1H), 7.65 (s, 1H), 8.05 (d, 1H), 8.78 (s, 1H), 9.45 (s, 1H). LC-MS: $[M + H]^+$ = 407.1 |
| 231 | 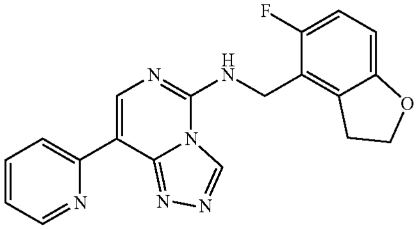 [SMILES: Fc1ccc2c(c1CNc1ncc(-c3ccccn3)c3nncn13)CCO2] | $^1$H NMR (500 MHz, DMSO-$d_6$) δ ppm 3.31 (s, 2H), 4.55 (t, 2H), 4.76 (s, 2H), 6.72 (dd, 1H), 7.00-6.93 (m, 1H), 7.35-7.31 (m, 1H), 7.92 (td, 1H), 8.65 (d, 1H), 8.68 (s, 1H), 8.81 (d, 1H), 8.90 (s, 1H), 9.53 (s, 1H). LC-MS: $[M + H]^+$ = 363.1 |
| 232 | 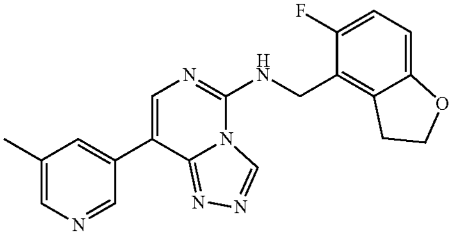 [SMILES: Cc1cncc(-c2cnc(NCc3c(F)ccc4c3CCO4)n3cnnc23)c1] | δ ppm 2.38 (s, 3H), 3.32 (d, 2H), 4.56 (t, 2H), 4.74 (s, 2H), 6.71 (dd, 1H), 6.96 (dd, 1H), 8.15 (s, 1H), 8.32-8.40 (m, 2H), 8.80 (s, 1H), 9.09 (d, 1H), 9.46 (s, 1H). LC-MS: $[M + H]^+$ = 376.9 |
| 233 | 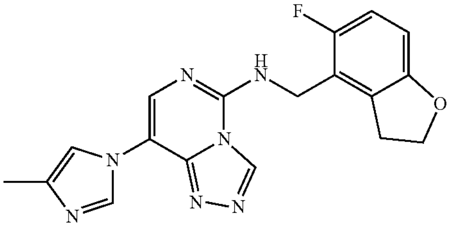 [SMILES: Cc1cn(-c2cnc(NCc3c(F)ccc4c3CCO4)n3cnnc23)cn1] | $^1$H NMR (500 MHz, DMSO-$d_6$) δ ppm 2.19 (s, 3H), 3.31 (t, 2H), 4.55 (t, 2H), 4.70 (s, 2H), 6.71 (dd, 1H), 6.93-6.98 (m, 1H), 7.53 (s, 1H), 7.99 (s, 1H), 8.25 (d, 1H), 8.78 (s, 1H), 9.52 (s, 1H). LC-MS: $[M + H]^+$ = 366.1 |

TABLE 2-continued

| Ex # | Structure | $^1$H NMR (400 MHz, DMSO-$d_6$) or otherwise indicated/LC-MS Data |
|---|---|---|
| 234 | 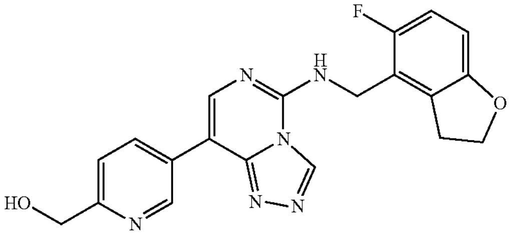 [SMILES: OCc1ccc(-c2cnc(NCc3c(F)ccc4c3CCO4)n3cnnc23)cn1] | δ ppm 3.25-3.34 (m, 2H), 4.55 (t, 2H), 4.62 (d, 2H), 4.74 (s, 2H), 5.48 (t, 1H), 6.72 (dd, 1H), 6.96 (dd, 1H), 7.56 (d, 1H), 8.15 (s, 1H), 8.51 (dd, 1H), 8.81 (s, 1H), 9.19 (dd, 1H), 9.51 (s, 1H). LC-MS: $[M + H]^+$ = 392.9 |
| 235 | 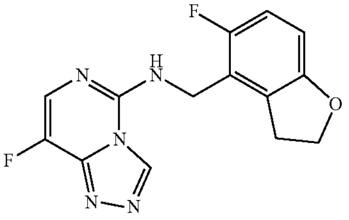 [SMILES: Fc1ccc2c(c1CNc1ncc(F)c3nncn13)CCO2] | $^1$H NMR (400 MHz, Methanol-$d_4$) δ ppm 3.38 (d, 2H), 4.59 (t, 2H), 4.75 (d, 2H), 6.66 (dd, 1H), 6.80-6.93 (m, 1H), 7.71 (d, 1H), 9.33 (d, 1H). LC-MS: $[M + H]^+$ = 303.9 |
| 236 | 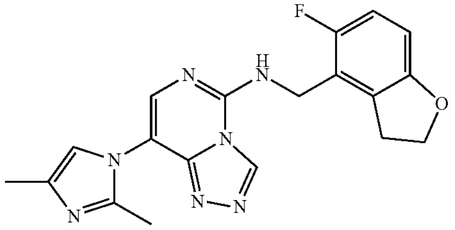 [SMILES: Cc1cn(-c2cnc(NCc3c(F)ccc4c3CCO4)n3cnnc23)c(C)n1] | $^1$H NMR (500 MHz, DMSO-$d_6$) δ ppm 2.10 (s, 3H), 2.16 (s, 3H), 3.31 (s, 2H), 4.56 (t, 2H), 4.70 (s, 2H), 6.72 (dd, 1H), 6.92 (s, 1H), 6.94-6.99 (m, 1H), 7.78 (s, 1H), 8.88 (s, 1H), 9.50 (s, 1H). LC-MS: $[M + H]^+$ = 379.9 |
| 237 | 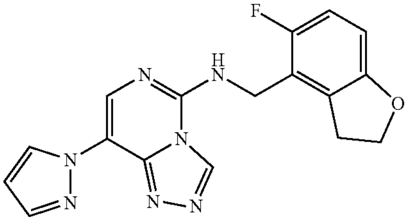 [SMILES: Fc1ccc2c(c1CNc1ncc(-n3cccn3)c3nncn13)CCO2] | $^1$H NMR (500 MHz, DMSO-$d_6$) δ ppm 3.30 (d, 2H), 4.55 (t, 2H), 4.71 (s, 2H), 6.56-6.60 (m, 1H), 6.71 (dd, 1H), 6.92-6.99 (m, 1H), 7.78 (d, 1H), 8.18 (s, 1H), 8.79 (d, 1H), 9.54 (s, 1H). LC-MS: $[M + H]^+$ = 352.1 |
| 238 | 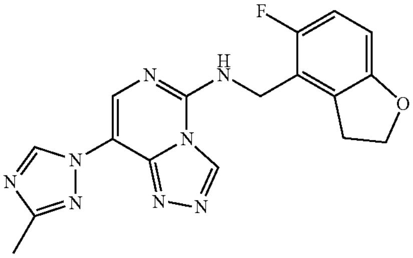 [SMILES: Cc1ncn(-c2cnc(NCc3c(F)ccc4c3CCO4)n3cnnc23)n1] | $^1$H NMR (500 MHz, DMSO-$d_6$) δ ppm 2.39 (s, 3H), 3.31 (d, 2H), 4.55 (t, 2H), 4.72 (s, 2H), 6.72 (dd, 1H), 6.97 (t, 1H), 8.14 (s, 1H), 8.91 (s, 1H), 9.22 (s, 1H), 9.56 (s, 1H). LC-MS: $[M + H]^+$ = 367.1 |
| 239 | 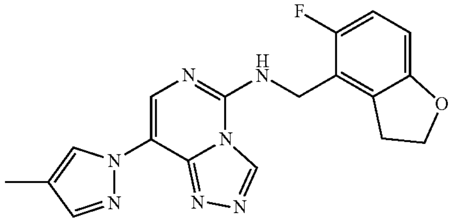 [SMILES: Cc1cnn(-c2cnc(NCc3c(F)ccc4c3CCO4)n3cnnc23)c1] | $^1$H NMR (500 MHz, DMSO-$d_6$) δ ppm 2.14 (s, 3H), 3.30 (d, 2H), 4.54 (t, 2H), 4.70 (s, 2H), 6.71 (dd, 1H), 6.93-6.99 (m, 1H), 7.59 (s, 1H), 8.13 (s, 1H), 8.59 (s, 1H), 8.70 (s, 1H), 9.54 (s, 1H). LC-MS: $[M + H]^+$ = 366.1 |

TABLE 2-continued

| Ex # | Structure | $^1$H NMR (400 MHz, DMSO-$d_6$) or otherwise indicated/LC-MS Data |
|---|---|---|
| 240 | 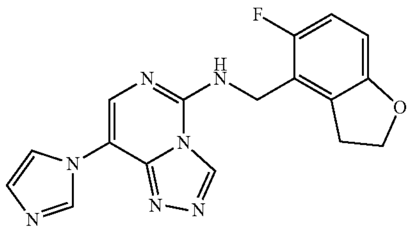 [SMILES: Fc1ccc2c(c1CNc1ncc(-n3ccnc3)c3nncn13)CCO2] | $^1$H NMR (500 MHz, DMSO-$d_6$) δ ppm 3.31 (d, 2H), 4.54 (d, 2H), 4.71 (s, 2H), 6.72 (s, 1H), 6.96 (s, 1H), 7.14 (s, 1H), 7.83 (s, 1H), 8.05 (s, 1H), 8.36 (s, 1H), 8.83 (s, 1H), 9.53 (s, 1H). LC-MS: $[M + H]^+$= 352.1 |
| 241 | 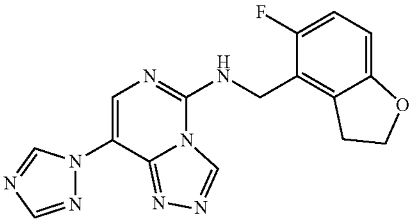 [SMILES: Fc1ccc2c(c1CNc1ncc(-n3cncn3)c3nncn13)CCO2] | $^1$H NMR (500 MHz, DMSO-$d_6$) δ ppm 3.32 (t, 2H), 4.55 (t, 2H), 4.73 (d, 2H), 6.72 (dd, 1H), 6.97 (t, 1H), 8.19 (s, 1H), 8.31 (s, 1H), 8.97 (s, 1H), 9.34 (s, 1H), 9.57 (s, 1H). LC-MS: $[M + H]^+$ = 353.1 |
| 242 | 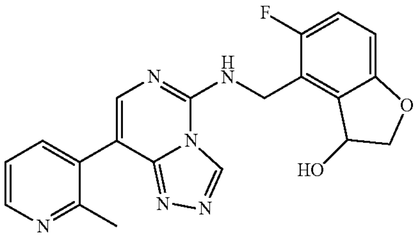 [SMILES: Cc1ncccc1-c1cnc(NCc2c(F)ccc3c2C(O)CO3)n2cnnc12] | $^1$H NMR (400 MHz, Methanol-$d_4$) δ ppm 2.48 (s, 3H), 4.49-4.40 (m, 1H), 4.61-4.52 (m, 2H), 5.07 (d, 2H), 5.72 (d, 1H), 6.81 (dd, 1H), 7.12-6.98 (m, 1H), 7.44-7.36 (m, 1H, 7.66 (s, 1H), 7.83 (d, 1H), 8.51 (d, 1H), 9.34 (s, 1H). LC-MS: $[M + H]^+$ = 392.9 |
| 243 | 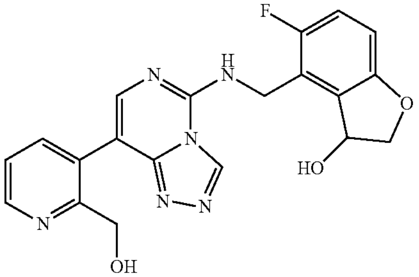 [SMILES: OCc1ncccc1-c1cnc(NCc2c(F)ccc3c2C(O)CO3)n2cnnc12] | $^1$H NMR (400 MHz, Methanol-$d_4$) δ ppm 4.46 (dd, 1H), 4.59 (dd, 1H), 4.65 (s, 2H), 4.86 (br s., 1H) 5.07 (d, 2H) 5.72 (d, 1H) 6.81 (dd, 1H) 7.06 (t, 1H) 7.49 (dd, 1H) 7.75 (s, 1H) 7.89-7.96 (m, 1H) 8.64 (d, 1H) 9.34 (s, 1H). LC-MS: $[M + H]^+$ = 408.8 |
| 244 | 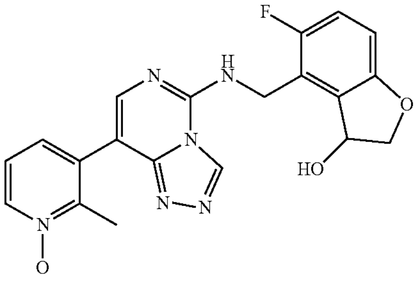 | $^1$H NMR (400 MHz, Methanol-$d_4$) δ ppm 2.41-2.50 (m, 3H) 4.46 (dd, 1H) 4.59 (dd, 1H) 4.87 (br s., 1H) 5.08 (d, 1H) 5.68-5.76 (m, 1H) 6.81 (dd, 1H) 7.06 (t, 1H) 7.50 (t, 1H) 7.64 (d, 1H) 7.75 (s, 1H) 8.46 (d, 1H) 9.34 (s, 1H). LC-MS: $[M + H]^+$ = 408.8 |
| 245 | 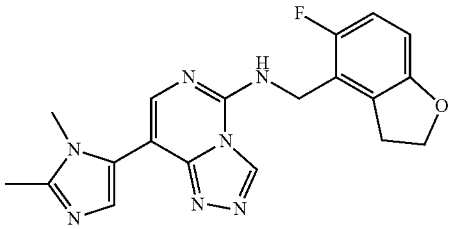 [SMILES: Cc1ncc(-c2cnc(NCc3c(F)ccc4c3CCO4)n3cnnc23)n1C] | $^1$H NMR (500 MHz, DMSO-$d_6$) δ ppm 2.25 (s, 3H), 3.31 (t, 2H), 3.43 (s, 3H), 4.45 (t, 2H), 4.70 (s, 2H), 6.53 (dd, 1H), 6.78-6.66 (m, 1H), 6.83 (s, 1H), 7.52 (s, 1H), 9.11 (s, 1H). LC-MS: $[M + H]^+$ = 379.9 |

VI. Pharmacology and Utility

As a key component of PRC2 complex, EED has no intrinsic enzymatic activity. However, it is critical for proper PRC2 function. EED directly binds to H3K27me3 and this binding event localizes the PRC2 complex to the chromatin substrate and allosterically activates the methyltransferase activity. Targeting the allosteric site within the regulatory EED subunit of PRC2, may offer a novel and unique angle to be advantageous to, or complementary to, directly targeting the SAM competition mechanism of EZH2 or PRC2. Therefore, targeting EED represents a highly attractive strategy for the development of a novel therapy for the treatment of many forms of cancers. In particular, the need exists for small molecules that inhibit the activity of PRC2 through targeting EED. It has now been found that triazolopyrimidine derivatives as presently disclosed are useful to target EED for the treatment of EED or PRC2-mediated diseases or disorders, especially cancers.

The utility of the compounds of the present invention may be demonstrated using any one of the following test procedures. Compounds of the present disclosure were assessed for their ability to inhibit PRC2 activity in a pentameric complex of EZH2, SUZ12, EED, Rbap48 and AEBP in biochemical assays. The ability of compounds of the present disclosure to inhibit cellular activity of PRC2 was assessed by analysing histone H3 lysine 27 methylation in human cell lines. The ability of compounds of the present disclosure to inhibit cancers was derived from their ability to modulate activity in human cancer cell lines bearing specific dependence to PRC2 activity to maintain cancerous growth.

EED-H3K27Me3 Peptide Competition Binding Assay by AlphaScreen (α-Screen)

To assess the compounds potency in the EED-H3K27Me3 competition binding assay, compounds were serially diluted 3-fold in DMSO to obtain a total of twelve concentrations. Then compounds at each concentration (75 nL of each) were transferred by Mosquito into a 384-well Perkin Elmer ProxiPlate 384 plus plates. 8 uL of solutions containing 30 nM EED (1-441)-His protein and 15 nM biotin-H3K27Me3 (19-33) peptide in the buffer (25 mM HEPES, pH 8, 0.02% Tween-20, 0.5% BSA) were added to the wells and then incubated with compound for 20 min. AlphaScreen detection beads mix was prepared immediately before use by mixing nickel chelate acceptor beads and streptavidin donor beads in a 1:1 ratio (Perkin Elmer, Product No. 6760619C/M/R) into the buffer described above. Then 4 μL of detection beads mix was added to the plate and incubate in the dark at the rt for 1 h. The final concentration of donor and acceptor beads was 10 μg/mL for each. Plates were read on EnVision (PerkinElmer) using the AlphaScreen setting adapted for optimal signal detection with a 615 nm filter, after sample excitation at 680 nm. The emission signal at 615 nm was used to quantify compounds inhibition. AlphaScreen signals were normalized based on the reading coming from the positive (maximum signal control) and negative controls (minimum signal control) to give percentage of activities left. The data were then fit to a dose response equation using the program Helios (Novartis) to get the IC50 values. Helios is a Novartis in-house assay data analysis software using the methods described by Normolle, D. P., *Statistics in Medicine,* 12:2025-2042 (1993); Formenko, I. et al, *Computer Methods and Programs in Biomedicine,* 82, 31-37 (2006); Sebaugh, J. L., *Pharmaceutical Statistics,* 10:128-134 (2011); Kelly, C. et al., *Biometrics,* 46(4):1071-1085 (1990); and Kahm, M. et al., *Journal of Statistical Software,* 33(7): (2010) (grofit: Fitting Biological Growth Curves with R, pages 1-21, available at http://www.jstatsoft.org/).

Each compound was counterscreened to determine if it interfered with the AlphaScreen beads. Compounds were diluted as described in the preceding section, and the assay was performed by adding 12 μL of 10 nM biotin-miniPEG-His6 peptide in the above buffer and incubating for 20 min at rt prior to addition of the beads to 10 μg/mL each. The plates were then incubated for 1 h at rt in dark before being read on EnVison.

EED LC-MS Assay

Representative compounds of the present disclosure were serially and separately diluted 3-fold in DMSO to obtain a total of eight or twelve concentrations. Then the test compounds at each concentration (120 nL of each) were transferred by Mosquito into a 384-well Perkin Elmer ProxiPlate 384 plus plates. Solutions (6 μL) of 24 nM the wild type PRC2 (wtPRC2) complex and 2 μM SAM in reaction buffer (20 mM Tris, pH 8.0, 0.1% BSA, 0.01% Triton, 0.5 mM DTT) were added to the wells that were then incubated with the test compound for 20 min. A 6 μL solution of 3 μM of the peptide substrate H3K27Me0 (histone H3[21-44]-biotin) in reaction buffer was added to initiate each reaction. The final components in the reaction solution include 12 nM wtPRC2 complex, 1 μM SAM, and 1.5 μM H3K27me0 peptide with varying concentration of the compounds. A positive control consisted of the enzyme, 1 μM SAM and 1.5 μM substrate in the absence of the test compound, and a negative control consisted of 1 μM SAM and 1.5 μM substrate only. Each reaction was incubated at rt for 120 min, then stopped by addition of 3 μL per of quench solution (2.5% TFA with 320 nM d4-SAH). The reaction mixture was centrifuged (Eppendorf centrifuge 5810, Rotor A-4-62) for 2 min at 2000 rpm and read on an API 4000 triple quadrupole mass spec with Turbulon Spray (Applied Biosystem) coupled with Prominence UFLC (Shimadzu). The levels of SAH production were then normalized based on the values coming from the positive and negative controls to give percent enzyme activities. The data were then fit to a dose response equation using the program Helios to get the $IC_{50}$ values of the test compound.

ELISA (H3K27 Methylation) Assay

Representative compounds of the present disclosure were serially and separately diluted 3-fold in DMSO to obtain a total of eight or twelve concentrations. Then the compounds were added to G401 cell cultured in 384-well plate at 1:500 dilution to obtain the highest concentration of 20 μM. The cells were further cultured for 48 h before ELISA procedure.

Histone extraction: Cells, in 384-well plate, were washed with PBS (10×PBS buffer (80 g NaCl (Sigma, S3014), 2 g KCl (Sigma, 60128), 14.4 g $Na_2HPO_4$ (Sigma, S5136), 2.4 g $KH_2PO_4$ (Sigma, P9791) to 1 L water, pH to 7.4) and lysed with the addition of lysis buffer (0.4N HCl; 45 μL per well). The plate was gently agitated at 4° C. for 30 min. The cell lysate was neutralized with neutralization buffer (0.5 M sodium phosphate dibasic, pH 12.5, 1 mM DTT; 36 μL per well). The plate was agitated to ensure the lysates were well mixed prior to the ELISA protocol.

ELISA protocol: Cell lysates were transferred to the wells of a 384-well plate and the final volume was adjusted to 50 μL per well with PBS. The plate was sealed, centrifuged at 2,000 rpm for 2 min and incubated at 4'C for about 16 h. The plate was washed with TBST buffer (1×TBS (10×TBS: 24.2 g Tris (Sigma, T6066), 80 g NaCl (Sigma, S3014) to 1 L of water and adjust pH to 7.6 with HCl) with 0.1% Tween-20). Blocking buffer (TBST, 5% BSA; 50 μL per well) was added and the plate was incubated for 1 h at rt. The blocking buffer was removed and primary antibody was added (30 μL per well). The following dilutions were performed with blocking buffer: for anti-H3K27me3 antibody (Cell Signaling Technology, #9733), dilution was 1:1000; for anti-H3K27me2 antibody (Cell Signaling Technology, #9288), dilution was 1:100; for anti-H3 antibody (Abcam, Cat #24834), dilution was 1:1000. The primary antibody was incubated in the plate at rt for 1 h. The wells were washed with TBST and incubated with secondary antibody for 1 h at rt. For secondary antibodies, the following dilutions were carried out with blocking buffer: anti-rabbit antibody (Jackson ImmunoResearch, #111-035-003), dilution was 1:2000; and anti-mouse antibody (Cell signaling technology, #7076), dilution was 1:1000. After 1 h of incubation at rt, the wells were washed with TBST. ECL substrate (Pierce, #34080) was added at 30 μL per well and the plates were centrifuged at 2,000 rpm for 2 min. The signal was read using a PerkinElmer Envision Reader. The H3K27 methylation readouts were normalized using H3 signal and then percentage inhibition was calculated against the samples treated with DMSO. The data were then fit to a dose response curve using the program Helios to get the $IC_{50}$ values of the test compound.

Western Blot Analysis

Representative compounds of the present disclosure were analyzed for their ability to selectively inhibit PRC2. Western blot was performed using standard molecular biology techniques. Cell was lysed in SDS lysis buffer (Millipore, Cat #20-163) and protein concentration was measured by BCA protein assay (Pierce, Cat #PI-23221). Antibodies for western blots: anti-EZH2 (#3147), anti-H3 (#9715), anti-H3K4me1 (#9723), anti-H3K4me2 (#9725), anti-H3K4me3 (#9727), anti-H3K9me2 (#9753), anti-H3K36me2 (#9758), anti-H3K27me2 (#9755), and anti-H3K27me3 (#9756) were purchased from Cell Signaling Technology (Danvers, Mass., USA). Anti-H3K9me1 (#07-395), anti-H3K27me1 (#07-448), and anti-H3K36me1 (#07-548) were purchased from Millipore (Billerica, Mass., USA). Anti-H3K36me3 (ab9050-100) was purchased from Abcam (Cambridge, UK). Anti-H3K9me3 (#39161) was purchased from Active Motif (Carlsbad, Calif., USA).

Compounds of the present disclosure specifically inhibit the methylation of the PRC2 substrate H3K27. This can be demonstrated by their ability to inhibit H3K27me2 and H3K27me3 in a number of human cancer cell lines, examples include rhabdoid cells (G401) and lymphoma cells (WSU-DLCL2, KARPAS422, SU-DHL4). Selectivity is profiled against a number of other methylation marks, for example: H3K4me2; H3K9me2; H3K36me3; and H3K79me3.

Analysis of Cell Proliferation

B cell lymphoma cell KARPAS422 was cultured using standard cell culture conditions in RPMI-1640 (Invitrogen, cat #11875) supplemented with 15% FBS (Invitrogen, cat #10099-141) in humidified incubator at 37° C., 5% $CO_2$. To assess the effect of PRC2 inhibition on cell proliferation, exponentially growing cells were seeded at a density of $1\times10^5$ cells/mL in 12-well plate (Corning, cat #CLS3513). After cell seeding, a compound of the present disclosure was added to the cell media (in concentrations ranging from 0 to 100 μM, 3× dilution series). Viable cell numbers were determined every 3-4 days for up to 14 days using Vi-CELL (Beckman Coulter). On days of cell counting, fresh growth media and compound were replenished and cells split back to a density of $1\times10^5$ cells/mL. Total cell number is expressed as split-adjusted viable cells per mL. The dose response curves and $IC_{50}$ values were generated using Prism.

Analysis of Pharmacokinetic Properties

Pharmacokinetic properties of the compounds as presently disclosed can be determined by using the below described protocol.

A representative compound of the present disclosure was dissolved in 10% PEG300, 10% Solutol HS 15 and 80% pH 4.65 Acetate buffer to yield a final concentration of 0.2 mg/mL for intravenous (IV) and oral administration (PO).

For rat PK studies, a total of three male Sprague Dawley rats each were used for rat IV and PO PK study, respectively. The formulation solution was administered via a single bolus IV at 1 mg/kg and a single oral gavage (PO) at 2 mg/kg, respectively. Blood samples (approximately 150 μL) were collected via jugular cannula at appropriate time points.

For mouse PK study, a total of twelve male ICR mice were used for IV and PO study, respectively. The formulation solution was administered via a single bolus IV at 1 mg/kg and a single oral gavage (PO) at 2 mg/kg, respectively. Blood samples (approximately 150 μL) were collected via retro-orbital puncture (~150 μL/mouse) after anesthetized by isoflurane or via cardiac puncture (terminal collection) at appropriate time points (n=3).

Samples were collected in tubes containing K3-EDTA and stored on ice until centrifuged. The blood samples were centrifuged at approximately 8000 rpm for 6 min at 2-8° C. and the resulting plasma was separated and stored frozen at approximately −80° C. After adding the internal standard, the plasma samples were quantified by LC-MS/MS using the calibration curve. PK parameters including area under concentration curve (AUC), mean residence time (MRT), plasma clearance (Cl), steady state volume of distribution (Vdss), elimination half-life ($t_{1/2}$), maximum concentration (Cmax), time of maximum concentration (Tmax) and oral bioavailability (F %) were calculated using the following equations:

$$AUC = \int_0^\infty C\,dt$$

$$MRT = \frac{\int_0^\infty tC\,dt}{\int_0^\infty C\,dt} = \frac{AUMC}{AUC}$$

t is time and C is plasma concentration at the time (t); $Dose_{iv}$ is the dose for intravenous administration; and $Dose_{oral}$ is the dose for oral administration.

$$Cl = Dose_{iv}/AUC$$

$$t_{1/2} = 0.693\times MRT$$

$$Vdss = Cl*MRT$$

$$F\,\% = (Dose_{iv}\times AUC_{oral})/Dose_{oral}\times AUC_{iv})\times100\%$$

Protocol for High-Throughput Equilibrium Solubility Assay

Compounds of the present disclosure were first solubilized at 10 mM in pure DMSO. 20 μL each of the DMSO stock solution was then transferred into 6 wells on 96-well plate. The DMSO solvent was dried with GeneVac solvent evaporator at 30° C., 1 mbar vacuum for 1 h. After the addition of 200 μL of buffer solutions (pH 6.8, or FaSSIF), the plate was sealed and shaken at 160 rpm for 24 h at rt. The plate was centrifuged at 3750 rpm for 20 min, 5 μL of supernatant is mixed with 495 μL of MeOH/$H_2O$ (1:1). 0.01 μM, 0.1 μM, 1 μM, 10 μM stock solutions were prepared by series of dilution for the calibration curves. The supernatant was quantified by HPLC or LC/MS using the calibration curve. High-Throughput equilibrium solubility was determined based on the concentration of the supernatant.

Efficacy Studies in Mouse Xenograph Model

All experiments conducted were performed in female athymic Nude-nu mice in an AAALAC certificated facility. The animals were kept under SPF conditions in individual ventilation cages at constant temperature and humidity (i.e., 20-26° C.; 40-70%) with 5 or less animals in each cage. Animals had free access to irradiation sterilized dry granule food and sterile drinking water. All procedures and protocols were approved by the Institutional Animal Care and Use and interal committee.

The cells Karpas 422 human B cell lymphoma were cultured in RPMI-1640 medium (Gibco; 11875-093) supplemented with 15% FBS (Gibco; 10099-141) and 1% Pen Strep (Gibco; 15140-122) at 37° C. in an atmosphere of 5% CO2 in air. Cells were maintained in suspension cultures at concentrations between $0.5\text{-}2\times10^6$ cells/ml. Cells were split at 1:3 every 2-4 days. To establish xenograft tumor models the cells were collected, suspended in PBS, mixed with Matrigel (BD Bioscience) at a volume ratio of 1:1 at a concentration of $1\times10^8$ cells/mL and then injected subcutaneously into the right flank of balb/c nude mice (Vital River) at a concentration of $5\times10^6$ cells per animal.

The compound was formulated as a suspension in 0.5% methyl cellulose (MC) and 0.5% Tween 80 in 50 mM pH6.8 buffer (prepared in house according to the USP) and administered orally by gavage at specific doses.

Treatment was initiated when the average tumor volume reached 100-300 $mm^3$. Tumor growth and body weights were monitored at regular intervals. The two largest diameters, width (W) and length (L), of the xenograft tumors were measured manually with calipers and the tumor volume was estimated using the formula: $0.5\times L\times W^2$.

When applicable, results are presented as mean±SEM. Graphing and statistical analysis was performed using GraphPad Prism 5.00 (GraphPad Software). Tumor and body weight change data were analyzed statistically. If the variances in the data were normally distributed (Bartlett's test for equal variances), the data were analyzed using one-way ANOVA with post hoc Dunnet's test for comparison of treatment versus control group. The post hoc Tukey test was used for intragroup comparison. Otherwise, the Kruskal-Wallis ranked test post hoc Dunn's was used.

As a measure of efficacy the % T/C value is calculated at the end of the experiment according to:

$$(\Delta\text{tumor volume}^{treated}/\Delta\text{tumor volume}^{control})*100$$

Tumor regression was calculated according to:

$$-(\Delta\text{tumor volume}^{treated}/\text{tumor volume}^{treated\ at\ start})*100$$

Where Δtumor volumes represent the mean tumor volume on the evaluation day minus the mean tumor volume at the start of the experiment.

The exemplified Examples disclosed below were tested in the EED Alphascreen binding, LC-MS and/or ELISA assays described above and found having EED inhibitory activity. A range of $IC_{50}$ values of ≤5 μM (5000 nM) was observed.

Table 3 below lists $IC_{50}$ values in the EED (a) Alphascreen binding Qualified, (b) LC-MS Qualified and/or (c) ELISA Qualified assays measured for the following examples. "N/A" stands for "not assessed".

TABLE 3

| Ex # | IUPAC name | (a) $IC_{50}$ (μM) | (b) $IC_{50}$ (μM) | (c) $IC_{50}$ (μM) |
|---|---|---|---|---|
| 1 | 8-(1,3-dimethyl-1H-pyrazol-5-yl)-N-((5-fluoro-2,3-dihydrobenzofuran-4-yl)methyl)-[1,2,4]triazolo[4,3-c]pyrimidin-5-amine | 0.0041 | 0.0082 | 0.0009 |
| 2 | N-((5-fluoro-2,3-dihydrobenzofuran-4-yl)methyl)-8-(2-methylpyridin-3-yl)-[1,2,4]triazolo[4,3-c]pyrimidin-5-amine | 0.0059 | 0.0089 | 0.0026 |
| 3 | 8-(2,4-dimethylpyrimidin-5-yl)-N-((5-fluoro-2,3-dihydrobenzofuran-4-yl)methyl)-[1,2,4]triazolo[4,3-c]pyrimidin-5-amine | 0.0038 | 0.0064 | 0.0034 |
| 4 | N-((5-fluoro-2,3-dihydrobenzofuran-4-yl)methyl)-8-(1-isopropyl-3-methyl-1H-pyrazol-4-yl)-[1,2,4]triazolo[4,3-c]pyrimidin-5-amine | 0.0032 | 0.0039 | 0.0021 |
| 5 | N-((5-fluoro-2,3-dihydrobenzofuran-4-yl)methyl)-8-(6-methoxy-4-methylpyridin-3-yl)-[1,2,4]triazolo[4,3-c]pyrimidin-5-amine | 0.0048 | 0.0097 | 0.0029 |
| 6 | 8-(6-cyclopropyl-2-methylpyridin-3-yl)-N-((5-fluoro-2,3-dihydrobenzofuran-4-yl)methyl)-[1,2,4]triazolo[4,3-c]pyrimidin-5-amine | 0.0052 | 0.0077 | 0.0038 |
| 7 | (3-(5-(((5-fluoro-2,3-dihydrobenzofuran-4-yl)methyl)amino)-[1,2,4]triazolo[4,3-c]pyrimidin-8-yl)pyridin-2-yl)methanol | 0.0048 | 0.0093 | 0.0052 |
| 8 | 8-(2-cyclopropyl-4-methylpyrimidin-5-yl)-N-((5-fluoro-2,3-dihydrobenzofuran-4-yl)methyl)-[1,2,4]triazolo[4,3-c]pyrimidin-5-amine | 0.0049 | 0.0072 | 0.0029 |
| 9 | N-((5-fluoro-2,3-dihydrobenzofuran-4-yl)methyl)-8-(2-isopropoxy-4-methylpyrimidin-5-yl)-[1,2,4]triazolo[4,3-c]pyrimidin-5-amine | 0.0041 | 0.0079 | 0.0035 |
| 10 | 3-(5-(((5-fluoro-2,3-dihydrobenzofuran-4-yl)methyl)amino)-[1,2,4]triazolo[4,3-c]pyrimidin-8-yl)pyridine 1-oxide | 0.0073 | 0.0138 | 0.001 |
| 11 | N-((2,3-dihydrobenzofuran-4-yl)methyl)-8-(4-((dimethylamino)methyl)phenyl)-[1,2,4]triazolo[4,3-c]pyrimidin-5-amine | 0.0069 | 0.02 | 0.0144 |
| 12 | N-((2,3-dihydrobenzofuran-4-yl)methyl)-8-(4-(methylsulfonyl)phenyl)-[1,2,4]triazolo[4,3-c]pyrimidin-5-amine | 0.0079 | 0.0159 | 0.0176 |
| 13 | N-((2,3-dihydrobenzofuran-4-yl)methyl)-8-phenyl-[1,2,4]triazolo[4,3-c]pyrimidin-5-amine | 0.0536 | 0.0477 | 0.1393 |
| 14 | N-((2,3-dihydrobenzofuran-4-yl)methyl)-8-(4-(1-(pyrrolidin-1-yl)ethyl)phenyl)-[1,2,4]triazolo[4,3-c]pyrimidin-5-amine | 0.0078 | 0.0128 | 0.0274 |
| 15 | 4-(5-(((2,3-dihydrobenzofuran-4-yl)methyl)amino)-[1,2,4]triazolo[4,3-c]pyrimidin-8-yl)-N,N-dimethylbenzenesulfonamide | 0.0128 | 0.0206 | 0.0198 |
| 16 | N-((2,3-dihydrobenzofuran-4-yl)methyl)-8-(pyridin-3-yl)-[1,2,4]triazolo[4,3-c]pyrimidin-5-amine | 0.0108 | 0.024 | 0.0604 |
| 17 | N-((2,3-dihydrobenzofuran-4-yl)methyl)-8-(pyridin-4-yl)-[1,2,4]triazolo[4,3-c]pyrimidin-5-amine | 0.0115 | 0.017 | 0.0315 |
| 18 | N-((2,3-dihydrobenzofuran-4-yl)methyl)-8-(2-(4-methylpiperazin-1-yl)pyridin-4-yl)-[1,2,4]triazolo[4,3-c]pyrimidin-5-amine | 0.0185 | 0.0279 | N/A |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 19 | N-(4-(5-(((2,3-dihydrobenzofuran-4-yl)methyl)amino)-[1,2,4]triazolo[4,3-c]pyrimidin-8-yl) phenyl)methanesulfonamide | 0.0189 | 0.0192 | 0.0401 |
| 20 | N-((2,3-dihydrobenzofuran-4-yl)methyl)-8-(6-(4-methylpiperazin-1-yl)pyridin-3-yl)-[1,2,4]triazolo[4,3-c]pyrimidin-5-amine | 0.0144 | 0.0171 | 0.0783 |
| 21 | N-((2,3-dihydrobenzofuran-4-yl)methyl)-8-(6-methoxypyridin-3-yl)-[1,2,4]triazolo[4,3-c]pyrimidin-5-amine | 0.0252 | 0.026 | 0.1503 |
| 22 | 8-(4-((dimethylamino)methyl)phenyl)-N-((2-methyl-2,3-dihydrobenzofuran-4-yl)methyl)-[1,2,4]triazolo[4,3-c]pyrimidin-5-amine | 1.9822 | 1.8195 | N/A |
| 23 | 8-(4-((dimethylamino)methyl)phenyl)-N-((5-fluoro-2,3-dihydrobenzofuran-4-yl)methyl)-[1,2,4]triazolo[4,3-c]pyrimidin-5-amine | 0.0311 | 0.0257 | 0.0424 |
| 24 | N-((2,3-dihydrobenzofuran-4-yl)methyl)-8-(1,3,5-trimethyl-1H-pyrazol-4-yl)-[1,2,4]triazolo [4,3-c]pyrimidin-5-amine | 0.0304 | 0.037 | 0.162 |
| 25 | N-((2,3-dihydrobenzofuran-4-yl)methyl)-8-(1-methyl-1H-pyrazol-4-yl)-[1,2,4]triazolo [4,3-c]pyrimidin-5-amine | 0.0307 | 0.0449 | 0.4061 |
| 26 | N-((2,3-dihydrobenzofuran-4-yl)methyl)-8-(2-fluoro-4-(methylsulfonyl)phenyl)-[1,2,4]triazolo [4,3-c]pyrimidin-5-amine | 0.0099 | 0.0171 | 0.0448 |
| 27 | N-((2,3-dihydrobenzofuran-4-yl)methyl)-8-(3-(methylsulfonyl)phenyl)-[1,2,4]triazolo [4,3-c]pyrimidin-5-amine | 0.0199 | 0.0472 | 0.3655 |
| 28 | N-((2,3-dihydrobenzofuran-4-yl)methyl)-8-(6-(methylsulfonyl)pyridin-3-yl)-[1,2,4]triazolo [4,3-c]pyrimidin-5-amine | 0.0111 | 0.0276 | 0.4153 |
| 29 | N-((2,3-dihydrobenzofuran-4-yl)methyl)-8-(4-(piperidin-4-ylsulfonyl)phenyl)-[1,2,4]triazolo [4,3-c]pyrimidin-5-amine | 0.0081 | 0.0145 | 0.214 |
| 30 | N-((2,3-dihydrobenzofuran-4-yl)methyl)-8-(1,3-dimethyl-1H-pyrazol-4-yl)-[1,2,4]triazolo [4,3-c]pyrimidin-5-amine | 0.0053 | 0.0248 | 0.069 |
| 31 | N-((2,3-dihydrobenzofuran-4-yl)methyl)-8-(2-fluorophenyl)-[1,2,4]triazolo[4,3-c]pyrimidin-5-amine | 0.0302 | 0.0215 | 0.0298 |
| 32 | 8-(2-chlorophenyl)-N-((2,3-dihydrobenzofuran-4-yl)methyl)-[1,2,4]triazolo[4,3-c]pyrimidin-5-amine | 0.0434 | 0.0229 | 0.1154 |
| 33 | N-(4-(5-(((2,3-dihydrobenzofuran-4-yl)methyl)amino)-[1,2,4]triazolo[4,3-c]pyrimidin-8-yl)-2-fluorophenyl)methanesulfonamide | 0.0285 | 0.0175 | 0.2974 |
| 34 | 2-(4-(5-(((2,3-dihydrobenzofuran-4-yl)methyl)amino)-[1,2,4]trizaolo[4,3-c]pyrimidin-8-yl)-1H-pyrazol-1-yl)ethanol | 0.0375 | 0.0494 | 1.9507 |
| 35 | N-((2,3-dihydrobenzofuran-4-yl)methyl)-8-(4-(2-(dimethylamino)ethyl)phenyl)-[1,2,4]triazolo [4,3-c]pyrimidin-5-amine | 0.0083 | 0.0153 | 0.0334 |
| 36 | N-((2,3-dihydrobenzofuran-4-yl)methyl)-8-(5-methyl-6-(4-methylpiperazin-1-yl)pyridin-3-yl)-[1,2,4]triazolo[4,3-c]pyrimidin-5-amine | 0.0185 | 0.0224 | 0.0683 |
| 37 | N-((5-fluoro-2,3-dihydrobenzofuran-4-yl)methyl)-8-(4-(methylsulfonyl)phenyl)-[1,2,4]triazolo[4,3-c] pyrimidin-5-amine | 0.0123 | 0.0207 | 0.0134 |
| 38 | 2-(4-(5-(((2,3-dihydrobenzofuran-4-yl)methyl)amino)-[1,2,4]triazolo[4,3-c]pyrimidin-8-yl) phenoxy)ethanol | 0.0242 | 0.0349 | 0.2017 |
| 39 | N-(2-fluoro-4-(5-(((5-fluoro-2,3-dihydrobenzofuran-4-yl)methyl)amino)-[1,2,4]triazolo[4,3-c] pyrimidin-8-yl)phenyl)methanesulfonamide | 0.0178 | 0.0175 | 0.0227 |
| 40 | 4-(5-(((2,3-dihydrobenzofuran-4-yl)methyl)amino)-[1,2,4]triazolo[4,3-c]pyrimidin-8-yl)-N-(2-hydroxyethypenzenesulfonamide | 0.0562 | 0.0566 | 1.3368 |
| 41 | (4-(5-(((2,3-dihydrobenzofuran-4-yl)methyl)amino)-[1,2,4]triazolo[4,3-c]pyrimidin-8-yl) phenyl)(piperazin-1-yl)methanone | 0.0132 | 0.0097 | 0.3748 |
| 42 | 4-(5-(((2,3-dihydrobenzofuran-4-yl)methyl)amino)-[1,2,4]triazolo[4,3-c]pyrimidin-8-yl)-N,N-dimethylbenzamide | 0.0525 | 0.0861 | 0.2203 |
| 43 | 3-(5-(((2,3-dihydrobenzofuran-4-yl)methyl)amino)-[1,2,4]triazolo[4,3-c]pyrimidin-8-yl)-N,N-dimethylbenzamide | 0.0309 | 0.0331 | 0.2471 |
| 44 | N-((5-fluoro-2,3-dihydrobenzofuran-4-yl)methyl)-8-(pyridin-3-yl)-[1,2,4] triazolo[4,3-c]pyrimidin-5-amine | 0.0128 | 0.0192 | 0.0097 |
| 45 | N-((5-fluoro-2,3-dihydrobenzofuran-4-yl)methyl)-8-(pyridin-4-yl)-[1,2,4] triazolo[4,3-c]pyrimidin-5-amine | 0.02 | 0.0328 | 0.0086 |
| 46 | N-((5-fluoro-2,3-dihydrobenzofuran-4-yl)methyl)-8-(4-(1-(pyrrolidin-1-yl)ethyl)phenyl)-[1,2,4]triazolo[4,3-c]pyrimidin-5-amine | 0.0435 | 0.064 | 0.0048 |
| 47 | N-((5-fluoro-2,3-dihydrobenzofuran-4-yl)methyl)-8-(4-fluoropyridin-3-yl)-[1,2,4]-triazolo[4,3-c]pyrimidin-5-amine | 0.0052 | 0.0049 | 0.0103 |
| 48 | 8-(6-aminopyridin-3-yl)-N-((2,3-dihydrobenzofuran-4-yl)methyl)-[1,2,4]triazolo [4,3-c]pyrimidin-5-amine | 0.0129 | 0.0302 | 0.2606 |
| 49 | 4-(5-(((2,3-dihydrobenzofuran-4-yl)methyl)amino)-[1,2,4]triazolo[4,3-c]pyrimidin-8-yl)-N,N,2-trimethylbenzamide | 0.0125 | 0.0128 | 0.3662 |
| 50 | 8-(4-chloropyridin-3-yl)-N-((2,3-dihydrobenzofuran-4-yl)methyl)-[1,2,4] triazolo[4,3-c]pyrimidin-5-amine | 0.0191 | 0.0412 | 0.1198 |
| 51 | N-((2,3-dihydrobenzofuran-4-yl)methyl)-8-(pyrimidin-5-yl)-[1,2,4]triazolo[4,3-c]pyrimidin-5-amine | 0.136 | 0.3458 | N/A |
| 52 | N4(2,3-dihydrobenzofuran-4-yl)methyl)-8-(6-methylpyridin-3-yl)-[1,2,4]triazolo[4,3-c]pyrimidin-5-amine | 0.0709 | 0.047 | 0.1061 |
| 53 | N-((2,3-dihydrobenzofuran-4-yl)methyl)-8-(6-(2-(dimethylamino)ethyl)pyridin-3-yl)-[1,2,4]triazolo[4,3-c]pyrimidin-5-amine | 0.0124 | 0.0287 | 0.141 |
| 54 | N-((2,3-dihydrobenzofuran-4-yl)methyl)-8-(2-methoxypyrimidin-5-yl)-[1,2,4]triazolo[4,3-c] pyrimidin-5-amine | 0.0291 | 0.0546 | 0.1439 |
| 55 | 4-(5-(((5-fluoro-2,3-dihydrobenzofuran-4-yl)methyl)amino)-[1,2,4]triazolo[4,3-c]pyrimidin-8-yl)-N,N-dimethylbenzamide | 0.0211 | 0.0318 | 0.0131 |
| 56 | N-((5-fluoro-2,3-dihydrobenzofuran-4-yl)methyl)-8-(6-(methylsulfonyl)pyridin-3-yl)-[1,2,4] triazolo[4,3-c]pyrimidin-5-amine | 0.0196 | 0.0309 | 0.0493 |
| 57 | N-((5-fluoro-2,3-dihydrobenzofuran-4-yl)methyl)-8-(6-methylpyridin-3-yl)-[1,2,4]triazolo[4,3-c] pyrimidin-5-amine | 0.0084 | 0.0186 | 0.0334 |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 58 | 8-(6-amino-4-fluoropyridin-3-yl)-N-((2,3-dihydrobenzofuran-4-yl)methyl)-[1,2,4]triazolo[4,3-c] pyrimidin-5-amine | 0.0063 | 0.013 | 0.1241 |
| 59 | N-((2,3-dihydrobenzofuran-4-yl)methyl)-8-(3,5-dimethylisoxazol-4-yl)-[1,2,4]triazolo[4,3-c] pyrimidin-5-amine | 0.0318 | 0.0387 | 0.086 |
| 60 | N-((2,3-dihydrobenzofuran-4-yl)methyl)-8-(2-methylpyrimidin-5-yl)-[1,2,4] triazolo[4,3-c]pyrimidin-5-amine | 0.0195 | 0.047 | 0.2994 |
| 61 | N-((2,3-dihydrobenzofuran-4-yl)methyl)-8-(6-(dimethylamino)pyridin-3-yl)-[1,2,4]triazolo [4,3-c]pyrimidin-5-amine | 0.0129 | 0.0197 | 0.1754 |
| 62 | 5-(5-(((2,3-dihydrobenzofuran-4-yl)methyl)amino)-[1,2,4]triazolo[4,3-c]pyrimidin-8-yl)picolinonitrile | 0.016 | 0.0294 | 0.3394 |
| 63 | N-((2,3-dihydrobenzofuran-4-yl)methyl)-8-(6-ethoxypyridin-3-yl)-[1,2,4]triazolo[4,3-c]pyrimidin-5-amine | 0.0756 | 0.0686 | 0.1984 |
| 64 | N-((2,3-dihydrobenzofuran-4-yl)methyl)-8-(1,5-dimethyl-1H-pyrazol-4-yl)-[1,2,4]triazolo[4,3-c] pyrimidin-5-amine | 0.0124 | 0.0413 | 0.0978 |
| 65 | 8-(6-cyclopropylpyridin-3-yl)-N-((2,3-dihydrobenzofuran-4-yl)methyl)-[1,2,4]triazolo[4,3-c] pyrimidin-5-amine | 0.0183 | 0.02 | 0.1096 |
| 66 | N-((2,3-dihydrobenzofuran-4-yl)methyl)-8-(1-(2-methoxyethyl)-3,5-dimethyl-1H-pyrazol-4-yl)-[1,2,4]triazolo[4,3-c]pyrimidin-5-amine | 0.0156 | 0.0447 | 0.0803 |
| 67 | 2-(4-(5-(((2,3-dihydrobenzofuran-4-yl)methyl)amino)-[1,2,4]triazolo[4,3-c]pyrimidin-8-yl)-3,5-dimethyl-1H-pyrazol-1-yl)ethanol | 0.0309 | 0.0902 | 0.5206 |
| 68 | (5-(5-(((2,3-dihydrobenzofuran-4-yl)methyl)amino)-[1,2,4]triazolo[4,3-c]pyrimidin-8-yl)pyridin-2-yl) (morpholino)methanone | 0.0197 | 0.0367 | 0.378 |
| 69 | N-((2,3-dihydrobenzofuran-4-yl)methyl)-8-(6-morpholinopyridin-3-yl)-[1,2,4]triazolo[4,3-c] pyrimidin-5-amine | 0.182 | 0.3769 | N/A |
| 70 | N-((2,3-dihydrobenzofuran-4-yl)methyl)-8-(5-methyl-6-(methylsulfonyl)pyridin-3-yl)-[1,2,4]triazolo[4,3-c]pyrimidin-5-amine | 0.0115 | 0.0211 | 0.0839 |
| 71 | 8-(3,5-dimethylisoxazol-4-yl)-N-((5-fluoro-2,3-dihydrobenzofuran-4-yl)methyl)-[1,2,4]triazolo [4,3-c]pyrimidin-5-amine | 0.009 | 0.0189 | 0.0426 |
| 72 | (4-(5-(((5-fluoro-2,3-dihydrobenzofuran-4-yl)methyl)amino)-[1,2,4]triazolo[4,3-c]pyrimidin-8-yl) phenyl)(4-methylpiperazin-1-yl)methanone | 0.0093 | 0.0175 | 0.0097 |
| 73 | N-((2,3-dihydrobenzofuran-4-yl)methyl)-8-(5-methyl-6-morpholinopyridin-3-yl)-[1,2,4]triazolo [4,3-c]pyrimidin-5-amine | 0.0125 | 0.0174 | 0.3317 |
| 74 | N-((2,3-dihydrobenzofuran-4-yl)methyl)-8-(6-(2,6-dimethylmorpholino)pyridin-3-yl)-[1,2,4]triazolo [4,3-c]pyrimidin-5-amine | 0.0896 | 0.1391 | N/A |
| 75 | N-((2,3-dihydrobenzofuran-4-yl)methyl)-8-(4-(2-(methylsulfonyl)ethoxy)phenyl)-[1,2,4]triazolo [4,3-c]pyrimidin-5-amine | 0.034 | 0.0375 | 0.2981 |
| 76 | 8-(4-aminopyridin-3-yl)-N-((2,3-dihydrobenzofuran-4-yl)methyl)-[1,2,4]triazolo [4,3-c]pyrimidin-5-amine | 0.0275 | 0.0569 | 0.3196 |
| 77 | N-((2,3-dihydrobenzofuran-4-yl)methyl)-8-(5-(piperazin-1-yl)pyridin-3-yl)-[1,2,4]triazolo [4,3-c]pyrimidin-5-amine | 0.0216 | 0.0523 | 0.581 |
| 78 | 8-(6-(difluoromethoxy)pyridin-3-yl)-N-((2,3-dihydrobenzofuran-4-yl)methyl)-[1,2,4]triazolo [4,3-c]pyrimidin-5-amine | 0.1034 | 0.1598 | N/A |
| 79 | 5-(5-(((2,3-dihydrobenzofuran-4-yl)methyl)amino)-[1,2,4]triazolo[4,3-c]pyrimidin-8-yl)-N-methylpicolinamide | 0.0575 | 0.1029 | N/A |
| 80 | (5-(5-(((2,3-dihydrobenzofuran-4-yl)methyl)amino)-[1,2,4]triazolo[4,3-c]pyrimidin-8-yl)pyridin-2-yl) (pyrrolidin-1-yl)methanone | 0.0037 | 0.0088 | 0.1315 |
| 81 | N-((2,3-dihydrobenzofuran-4-yl)methyl)-8-(6-thiomorpholinopyridin-3-yl)-[1,2,4]triazolo [4,3-c]pyrimidin-5-amine | 0.0146 | 0.0191 | 0.1554 |
| 82 | N-((2,3-dihydrobenzofuran-4-yl)methyl)-8-(1-isopropyl-3-methyl-1H-pyrazol-4-yl)-[1,2,4]triazolo[4,3-c]pyrimidin-5-amine | 0.0167 | 0.0309 | 0.1072 |
| 83 | N-((2,3-dihydrobenzofuran-4-yl)methyl)-8-(6-(methoxymethyl)-5-methylpyridin-3-yl)-[1,2,4]triazolo[4,3-c]pyrimidin-5-amine | 0.0105 | 0.0228 | 0.1402 |
| 84 | 1-(5-(5-(((2,3-dihydrobenzofuran-4-yl)methyl)amino)-[1,2,4]triazolo[4,3-c]pyrimidin-8-yl) pyridin-2-yl)ethanol | 0.0063 | 0.0129 | 0.1478 |
| 85 | N-((2,3-dihydrobenzofuran-4-yl)methyl)-8-(4-fluoropyridin-3-yl)-[1,2,4]triazolo[4,3-c]pyrimidin-5-amine | 0.0083 | 0.026 | 0.0333 |
| 86 | N-((2,3-dihydrobenzofuran-4-yl)methyl)-8-(6-(2-methoxyethyl)pyridin-3-yl)-[1,2,4]triazolo [4,3-c]pyrimidin-5-amine | 0.0111 | 0.0267 | 0.0758 |
| 87 | 1-(5-(5-(((2,3-dihydrobenzofuran-4-yl)methyl)amino)-[1,2,4]triazolo[4,3-c]pyrimidin-8-yl) pyridin-3-yl)pyrrolidin-2-one | 0.0418 | 0.0839 | 0.7071 |
| 88 | N-((2,3-dihydrobenzofuran-4-yl)methyl)-8-(2-(dimethylamino)pyrimidin-5-yl)-[1,2,4]triazolo [4,3-c]pyrimidin-5-amine | 0.0257 | 0.0347 | 0.2375 |
| 89 | N-((2,3-dihydrobenzofuran-4-yl)methyl)-8-(3-(2-(dimethylamino)ethyl)phenyl)-[1,2,4]triazolo [4,3-c]pyrimidin-5-amine | 0.0045 | 0.0103 | 0.1009 |
| 90 | N-((2,3-dihydrobenzofuran-4-yl)methyl)-8-(5-(4,4-dimethyl-4,5-dihydrooxazol-2-yl)pyridin-3-yl)-[1,2,4]triazolo[4,3-c]pyrimidin-5-amine | 0.0131 | 0.0303 | 0.6753 |
| 91 | N-((5-fluoro-2,3-dihydrobenzofuran-4-yl)methyl)-8-(6-thiomorpholinopyridin-3-yl)-[1,2,4]triazolo [4,3-c]pyrimidin-5-amine | 0.0099 | 0.0153 | 0.0225 |
| 92 | N-((5-fluoro-2,3-dihydrobenzofuran-4-yl)methyl)-8-(6-morpholinopyridin-3-yl)-[1,2,4]triazolo [4,3-c]pyrimidin-5-amine | 0.0192 | 0.0515 | 0.0409 |
| 93 | 5-(5-(((5-fluoro-2,3-dihydrobenzofuran-4-yl)methyl)amino)-[1,2,4]triazolo[4,3-c]pyrimidin-8-yl) picolinonitrile | 0.0079 | 0.0125 | 0.0241 |
| 94 | N-((5-fluoro-2,3-dihydrobenzofuran-4-yl)methyl)-8-(2-fluorophenyl)-[1,2,4]triazolo[4,3-c]pyrimidin-5-amine | 0.0113 | 0.0186 | 0.0257 |
| 95 | 5-(5-(((2,3-dihydrobenzofuran-4-yl)methyl)amino)-[1,2,4]triazolo[4,3-c]pyrimidin-8-yl)-N,N-dimethylpicolinamide | 0.0052 | 0.0128 | 0.1581 |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 96 | N-((2,3-dihydrobenzofuran-4-yl)methyl)-8-(6-(2-methylpyrrolidin-1-yl)pyridin-3-yl)-[1,2,4]triazolo[4,3-c]pyrimidin-5-amine | 0.026 | 0.0132 | 0.3286 |
| 97 | methyl 4-(5-(5-(((2,3-dihydrobenzofuran-4-yl)methyl)amino)-[1,2,4]triazolo[4,3-c]pyrimidin-8-yl) pyridin-2-yl)piperazine-1-carboxylate | 0.0061 | 0.0086 | 0.1828 |
| 98 | N-((2,3-dihydrobenzofuran-4-yl)methyl)-8-(5-(3-(methylsulfonyl)propoxy)pyridin-3-yl)-[1,2,4]triazolo[4,3-c]pyrimidin-5-amine | 0.0217 | 0.0356 | 1.4173 |
| 99 | 2-(5-(5-(((2,3-dihydrobenzofuran-4-yl)methyl)amino)-[1,2,4]triazolo[4,3-c]pyrimidin-8-yl) pyridin-2-yl)propan-2-ol | 0.0042 | 0.0067 | 0.1075 |
| 100 | 8-(6-(2-(3,3-difluoropyrrolidin-1-yl)ethyl)pyridin-3-yl)-N-((2,3-dihydrobenzofuran-4-yl)methyl)-[1,2,4]triazolo[4,3-c]pyrimidin-5-amine | 0.014 | 0.0315 | 0.181 |
| 101 | N-((2,3-dihydrobenzofuran-4-yl)methyl)-8-(6-(4,4-dimethyl-4,5-dihydrooxazol-2-yl)pyridin-3-yl)-[1,2,4]triazolo[4,3-c]pyrimidin-5-amine | 0.0117 | 0.0136 | 0.7614 |
| 102 | 5-(5-(((2,3-dihydrobenzofuran-4-yl)methyl)amino)-[1,2,4]triazolo[4,3-c]pyrimidin-8-yl)-N-(2-(dimethylamino)ethyl)-N-methylpicolinamide | 0.0339 | 0.0688 | 0.285 |
| 103 | N-((2,3-dihydrobenzofuran-4-yl)methyl)-8-(5-methyl-6-(pyrrolidin-1-yl)pyridin-3-yl)-[1,2,4]triazolo[4,3-c]pyrimidin-5-amine | 0.7284 | 0.4306 | N/A |
| 104 | 4-(5-(5-(((2,3-dihydrobenzofuran-4-yl)methyl)amino)-[1,2,4]triazolo[4,3-c]pyrimidin-8-yl) pyridin-2-yl)piperazin-2-one | 0.0096 | 0.012 | 2.3341 |
| 105 | 4-(5-(5-(((2,3-dihydrobenzofuran-4-yl)methyl)amino)-[1,2,4]triazolo[4,3-c]pyrimidin-8-yl)-3-methylpyridin-2-yl)piperazin-2-one | 0.0269 | 0.0326 | 2.4238 |
| 106 | N-((2,3-dihydrobenzofuran-4-yl)methyl)-8-(5-(2-(methylsulfonyl)ethoxy)pyridin-3-yl)-[1,2,4]triazolo[4,3-c]pyrimidin-5-amine | 0.025 | 0.0341 | 2.6999 |
| 107 | 4-(2-(5-(5-(((2,3-dihydrobenzofuran-4-yl)methyl)amino)-[1,2,4]triazolo[4,3-c]pyrimidin-8-yl) pyridin-2-yl)ethyl)piperazine-1-carbaldehyde | 0.0124 | 0.025 | 0.1612 |
| 108 | 1-(4-(2-(5-(5-(((2,3-dihydrobenzofuran-4-yl)methyl)amino)-[1,2,4]triazolo[4,3-c]pyrimidin-8-yl) pyridin-2-yl)ethyl)piperazin-1-yl)ethanone | 0.0067 | 0.011 | 0.1734 |
| 109 | 4-(2-(5-(5-(((2,3-dihydrobenzofuran-4-yl)methyl)amino)-[1,2,4]triazolo[4,3-c]pyrimidin-8-yl)pyridin-2-yl)ethyl)piperazin-2-one | 0.0088 | 0.0137 | 1.2085 |
| 110 | 2-(4-(5-(5-(((2,3-dihydrobenzofuran-4-yl)methyl)amino)-[1,2,4]triazolo[4,3-c]pyrimidin-8-yl)pyridin-2-yl)piperazin-1-yl)ethanol | 0.0093 | 0.0152 | 0.1239 |
| 111 | N-((2,3-dihydrobenzofuran-4-yl)methyl)-8-(4-fluoro-6-(methylamino)pyridin-3-yl)-[1,2,4]triazolo [4,3-c]pyrimidin-5-amine | 0.019 | 0.0174 | 0.1395 |
| 112 | N-((2,3-dihydrobenzofuran-4-yl)methyl)-8-(6-(dimethylamino)-4-fluoropyridin-3-yl)-[1,2,4]triazolo[4,3-c]pyrimidin-5-amine | 0.0177 | 0.0176 | 0.3889 |
| 113 | 4-(5-(5-(((2,3-dihydrobenzofuran-4-yl)methyl)amino)-[1,2,4]triazolo[4,3-c]pyrimidin-8-yl) pyridin-2-yl)-1,4-diazepane-1-carbaldehyde | 0.0127 | 0.0157 | 0.7202 |
| 114 | 5-(5-(((2,3-dihydrobenzofuran-4-yl)methyl)amino)-[1,2,4]triazolo[4,3-c]pyrimidin-8-yl)-N-ethylpicolinamide | 0.0154 | 0.0186 | 1.9792 |
| 115 | N-((5-fluoro-2,3-dihydrobenzofuran-4-yl)methyl)-8-(2-fluoropyridin-3-yl)-[1,2,4]triazolo[4,3-c]pyrimidin-5-amine | 0.0047 | 0.0069 | 0.0243 |
| 116 | N-((5-fluoro-2,3-dihydrobenzofuran-4-yl)methyl)-8-(2-methylpyridin-4-yl)-[1,2,4]triazolo[4,3-c] pyrimidin-5-amine | 0.0047 | 0.0076 | 0.0072 |
| 117 | 3-(5-(5-(((2,3-dihydrobenzofuran-4-yl)methyl)amino)-[1,2,4]triazolo[4,3-c]pyrimidin-8-yl) pyridin-2-yl)oxazolidin-2-one | 0.0235 | 0.0294 | 0.4803 |
| 118 | N-((5-fluoro-2,3-dihydrobenzofuran-4-yl)methyl)-8-(4-methylpyridin-3-yl)-[1,2,4]triazolo[4,3-c] pyrimidin-5-amine | 0.0101 | 0.0182 | 0.0177 |
| 119 | 8-(6-cyclopropylpyridin-3-yl)-N-((5-fluoro-2,3-dihydrobenzofuran-4-yl)methyl)-[1,2,4]triazolo [4,3-c]pyrimidin-5-amine | 0.004 | 0.0066 | 0.0108 |
| 120 | N-((5-fluoro-2,3-dihydrobenzofuran-4-yl)methyl)-8-(2-morpholinopyridin-4-yl)-[1,2,4]triazolo [4,3-c]pyrimidin-5-amine | 0.0156 | 0.0256 | 0.0721 |
| 121 | 2-(5-(((5-fluoro-2,3-dihydrobenzofuran-4-yl)methyl)amino)-[1,2,4]triazolo[4,3-c]pyrimidin-8-yl)-benzonitrile | 0.0134 | 0.0221 | 0.0142 |
| 122 | 2-(5-(((5-fluoro-2,3-dihydrobenzofuran-4-yl)methyl)amino)-[1,2,4]triazolo[4,3-c]pyrimidin-8-yl) benzamide | 0.0192 | 0.0437 | 0.1354 |
| 123 | N-((2,3-dihydrobenzofuran-4-yl)methyl)-8-(2-methylpyridin-3-yl)-[1,2,4]triazolo[4,3-c] pyrimidin-5-amine | 0.0123 | 0.0234 | 0.0197 |
| 124 | 8-(4-chloropyridin-3-yl)-N4(5-fluoro-2,3-dihydrobenzofuran-4-yl)methyl)-[1,2,4]triazolo [4,3-c]pyrimidin-5-amine | 0.01 | 0.0154 | 0.006 |
| 125 | 1-(5-(5-(((2,3-dihydrobenzofuran-4-yl)methyl)amino)-[1,2,4]triazolo[4,3-c]pyrimidin-8-yl) pyridin-2-yl)piperazin-2-one | 0.0085 | 0.0234 | N/A |
| 126 | 1-(5-(5-(((2,3-dihydrobenzofuran-4-yl)methyl)amino)-[1,2,4]triazolo[4,3-c]pyrimidin-8-yl) pyridin-2-yl)azetidin-3-ol | 0.0129 | 0.0172 | 0.6559 |
| 127 | N-((5-fluoro-2,3-dihydrobenzofuran-4-yl)methyl)-8-(4-methyl-6-(methylsulfonyl)pyridin-3-yl)-[1,2,4]triazolo[4,3-c]pyrimidin-5-amine | 0.0026 | 0.0088 | 0.028 |
| 128 | N-((5-fluoro-2,3-dihydrobenzofuran-4-yl)methyl)-8-(2-methyl-4-(methylsulfonyl)phenyl)-[1,2,4]triazolo[4,3-c]pyrimidin-5-amine | 0.0086 | 0.0165 | 0.0037 |
| 129 | (5-(5-(((5-fluoro-2,3-dihydrobenzofuran-4-yl)methyl)amino)-[1,2,4]triazolo[4,3-c]pyrimidin-8-yl) pyridin-2-yl)(pyrrolidin-l-yl)methanone | 0.0039 | 0.0084 | 0.0019 |
| 130 | (5-(5-(((5-fluoro-2,3-dihydrobenzofuran-4-yl)methyl)amino)-[1,2,4]triazolo[4,3-c]pyrimidin-8-yl)-4-methylpyridin-2-yl)(pyrrolidin-l-yl)methanone | 0.005 | 0.0137 | 0.0013 |
| 131 | 5-(5-(((5-fluoro-2,3-dihydrobenzofuran-4-yl)methyl)amino)-[1,2,4]triazolo[4,3-c]pyrimidin-8-yl)-N,N,4-trimethylpicolinamide | 0.004 | 0.0106 | 0.0033 |
| 132 | N-((5-fluoro-2,3-dihydrobenzofuran-4-yl)methyl)-8-(1,3,5-trimethyl-1H-pyrazol-4-yl)-[1,2,4]triazolo[4,3-c]pyrimidin-5-amine | 0.0062 | 0.0102 | 0.0077 |
| 133 | 4-((5-(5-(((2,3-dihydrobenzofuran-4-yl)methyl)amino)-[1,2,4]triazolo[4,3-c]pyrimidin-8-yl)pyridin-2-yl)methyl)piperazin-2-one | 0.0087 | 0.0223 | 0.1422 |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 134 | 4-(5-(5-(((2,3-dihydrobenzofuran-4-yl)methyl)amino)-[1,2,4]triazolo[4,3-c]pyrimidin-8-yl) pyridin-2-yl)piperazine-1-carbaldehyde | 0.0173 | 0.0305 | 0.1648 |
| 135 | 3-(5-(5-(((2,3-dihydrobenzofuran-4-yl)methyl)amino)-[1,2,4]triazolo[4,3-c]pyrimidin-8-yl) pyridin-2-yl)-N,N-dimethylpropanamide | 0.0057 | 0.0112 | 0.3214 |
| 136 | N-((5-fluoro-2,3-dihydrobenzofuran-4-yl)methyl)-8-(4-(trifluoromethyl)pyridin-3-yl)-[1,2,4]triazolo[4,3-c]pyrimidin-5-amine | 0.0159 | 0.0418 | 0.0804 |
| 137 | N-((2,3-dihydrobenzofuran-4-yl)methyl)-8-(5-(methoxymethyl)-6-methylpyridin-3-yl)-[1,2,4]triazolo[4,3-c]pyrimidin-5-amine | 0.022 | 0.0296 | 0.2263 |
| 138 | 8-(4-chloro-6-methoxypyridin-3-yl)-N-((5-fluoro-2,3-dihydrobenzofuran-4-yl)methyl)-[1,2,4]triazolo[4,3-c]pyrimidin-5-amine | 0.0019 | 0.0084 | 0.0072 |
| 139 | N-((5-fluoro-2,3-dihydrobenzofuran-4-yl)methyl)-8-(2-methyl-6-(methylsulfonyl)pyridin-3-yl)-[1,2,4]triazolo[4,3-c]pyrimidin-5-amine | 0.0017 | 0.006 | 0.0016 |
| 140 | 5-(5-(((5-fluoro-2,3-dihydrobenzofuran-4-yl)methyl)amino)-[1,2,4]triazolo[4,3-c]pyrimidin-8-yl)-N,N-dimethylpicolinamide | 0.0127 | 0.0551 | 0.0263 |
| 141 | N-((5-fluoro-2,3-dihydrobenzofuran-4-yl)methyl)-8-(2-methoxypyridin-3-yl)-[1,2,4]triazolo [4,3-c]pyrimidin-5-amine | 0.0171 | 0.042 | 0.0351 |
| 142 | N-((5-fluoro-2,3-dihydrobenzofuran-4-yl)methyl)-8-(6-methoxypyridin-3-yl)-[1,2,4]triazolo [4,3-c]pyrimidin-5-amine | 0.0024 | 0.0051 | 0.0043 |
| 143 | 8-(1-ethyl-1H-pyrazol-5-yl)-N-((5-fluoro-2,3-dihydrobenzofuran-4-yl)methyl)-[1,2,4]triazolo [4,3-c]pyrimidin-5-amine | 0.0181 | 0.0315 | 0.0106 |
| 144 | N-((5-fluoro-2,3-dihydrobenzofuran-4-yl)methyl)-8-(1-isopropyl-1H-pyrazol-5-yl)-[1,2,4]triazolo [4,3-c]pyrimidin-5-amine | 0.0063 | 0.0178 | 0.0683 |
| 145 | N-((5-fluoro-2,3-dihydrobenzofuran-4-yl)methyl)-8-(2-methoxypyridin-4-yl)-[1,2,4]triazolo [4,3-c]pyrimidin-5-amine | 0.0024 | 0.0118 | 0.0052 |
| 146 | 8-(2,4-dichlorophenyl)-N-((5-fluoro-2,3-dihydrobenzofuran-4-yl)methyl)-[1,2,4]triazolo [4,3-c]pyrimidin-5-amine | 0.023 | 0.0382 | 0.0744 |
| 147 | N-((5-fluoro-2,3-dihydrobenzofuran-4-yl)methyl)-8-(1-methyl-1H-pyrazol-4-yl)-[1,2,4]triazolo [4,3-c]pyrimidin-5-amine | 0.0036 | 0.0159 | 0.0113 |
| 148 | N-((5-fluoro-2,3-dihydrobenzofuran-4-yl)methyl)-8-(1-isopropyl-3-(trifluoromethyl)-1H-pyrazol-4-yl)-[1,2,4]triazolo[4,3-c]pyrimidin-5-amine | 0.0052 | 0.018 | 0.0252 |
| 149 | 8-(1-cyclopropyl-1H-pyrazol-4-yl)-N-((2,3-dihydrobenzofuran-4-yl)methyl)-[1,2,4]triazolo [4,3-c]pyrimidin-5-amine | 0.0169 | 0.0337 | 0.2202 |
| 150 | 8-(1-cyclopropyl-1H-pyrazol-4-yl)-N-((5-fluoro-2,3-dihydrobenzofuran-4-yl)methyl)-[1,2,4]triazolo[4,3-c]pyrimidin-5-amine | 0.0045 | 0.007 | 0.0148 |
| 151 | N-((5-fluoro-2,3-dihydrobenzofuran-4-yl)methyl)-8-(1-isopropyl-3,5-dimethyl-1H-pyrazol-4-yl)-[1,2,4]triazolo[4,3-c]pyrimidin-5-amine | 0.0131 | 0.0216 | 0.0086 |
| 152 | N-((2,3-dihydrobenzofuran-4-yl)methyl)-8-(1-methyl-1H-pyrazol-5-yl)-[1,2,4]triazolo [4,3-c]pyrimidin-5-amine | 0.0055 | 0.0069 | 0.008 |
| 153 | N-((2,3-dihydrobenzofuran-4-yl)methyl)-8-(1-isopropyl-3,5-dimethyl-1H-pyrazol-4-yl)-[1,2,4]triazolo[4,3-c]pyrimidin-5-amine | 0.0078 | 0.0148 | 0.0073 |
| 154 | 8-(6-(difluoromethyl)pyridin-3-yl)-N-((2,3-dihydrobenzofuran-4-yl)methyl)-[1,2,4]triazolo [4,3-c]pyrimidin-5-amine | 0.0201 | 0.0369 | 0.0968 |
| 155 | N-((5-fluoro-2,3-dihydrobenzofuran-4-yl)methyl)-8-(6-methoxy-2-methylpyridin-3-yl)-[1,2,4] triazolo[4,3-c]pyrimidin-5-amine | 0.017 | 0.0453 | 0.078 |
| 156 | 8-(6-amino-2-methylpyridin-3-yl)-N-((5-fluoro-2,3-dihydrobenzofuran-4-yl)methyl)-[1,2,4] triazolo[4,3-c]pyrimidin-5-amine | 0.004 | 0.0173 | 0.0261 |
| 157 | 8-(2-chloro-4-fluorophenyl)-N-((5-fluoro-2,3-dihydrobenzofuran-4-yl)methyl)-[1,2,4]triazolo [4,3-c]pyrimidin-5-amine | 0.0223 | 0.0463 | 0.4454 |
| 158 | 2-(4-(5-(((5-fluoro-2,3-dihydrobenzofuran-4-yl)methyl)amino)-[1,2,4]triazolo[4,3-c]pyrimidin-8-yl)-3,5-dimethyl-1H-pyrazol-1-yl)ethanol | 0.0051 | 0.0096 | 0.0067 |
| 159 | N-((5-fluoro-2,3-dihydrobenzofuran-4-yl)methyl)-8-(1-(2-methoxyethyl)-3,5-dimethyl-1H-pyrazol-4-yl)-[1,2,4]triazolo[4,3-c]pyrimidin-5-amine | 0.005 | 0.0103 | N/A |
| 160 | N-((5-fluoro-2,3-dihydrobenzofuran-4-yl)methyl)-8-(6-(trifluoromethyl)pyridin-3-yl)-[1,2,4]triazolo [4,3-c]pyrimidin-5-amine | 0.0059 | 0.0113 | N/A |
| 161 | N-((5-fluoro-2,3-dihydrobenzofuran-4-yl)methyl)-8-(4-fluoro-6-methoxypyridin-3-yl)-[1,2,4]triazolo [4,3-c]pyrimidin-5-amine | 0.0036 | 0.0098 | N/A |
| 162 | 8-(3-chloropyridin-4-yl)-N-((5-fluoro-2,3-dihydrobenzofuran-4-yl)methyl)-[1,2,4]triazolo [4,3-c]pyrimidin-5-amine | 0.0057 | 0.0211 | 0.0273 |
| 163 | N-((5-fluoro-2,3-dihydrobenzofuran-4-yl)methyl)-8-(3-methylpyridin-4-yl)-[1,2,4]triazolo [4,3-c]pyrimidin-5-amine | 0.0041 | 0.0109 | N/A |
| 164 | N-((5-fluoro-2,3-dihydrobenzofuran-4-yl)methyl)-8-(6-fluoro-2-methylpyridin-3-yl)-[1,2,4]triazolo [4,3-c]pyrimidin-5-amine | 0.0042 | 0.0139 | N/A |
| 165 | N-((5-fluoro-2,3-dihydrobenzofuran-4-yl)methyl)-8-(4-fluoro-2-methylphenyl)-[1,2,4]triazolo [4,3-c]pyrimidin-5-amine | 0.0045 | 0.0074 | N/A |
| 166 | N-((5-fluoro-2,3-dihydrobenzofuran-4-yl)methyl)-8-(2-(trifluoromethyl)pyridin-3-yl)-[1,2,4]triazolo [4,3-c]pyrimidin-5-amine | 0.0111 | 0.031 | 0.0266 |
| 167 | 8-(2,6-dimethylpyridin-3-yl)-N-((5-fluoro-2,3-dihydrobenzofuran-4-yl)methyl)-[1,2,4]triazolo [4,3-c]pyrimidin-5-amine | 0.0033 | 0.0052 | 0.0393 |
| 168 | 8-(2-(difluoromethyl)pyridin-3-yl)-N-((5-fluoro-2,3-dihydrobenzofuran-4-yl)methyl)-[1,2,4]triazolo [4,3-c]pyrimidin-5-amine | 0.0046 | 0.0112 | 0.002 |
| 169 | N-((5-fluoro-2,3-dihydrobenzofuran-4-yl)methyl)-8-(1-methyl-1H-pyrazol-5-yl)-[1,2,4]triazolo [4,3-c]pyrimidin-5-amine | 0.0045 | 0.0066 | 0.0029 |
| 170 | N-((5-fluoro-2,3-dihydrobenzofuran-4-yl)methyl)-8-(1-methyl-3-(trifluoromethyl)-1H-pyrazol-4-yl)-[1,2,4]triazolo[4,3-c]pyrimidin-5-amine | 0.0107 | 0.0121 | 0.0232 |
| 171 | N-((5-(5-(((5-fluoro-2,3-dihydrobenzofuran-4-yl)methyl)amino)-[1,2,4]triazolo[4,3-c]pyrimidin-8-yl) pyridin-2-yl)methyl)acetamide | 0.006 | 0.0073 | 0.0265 |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 172 | 8-(1,5-dimethyl-1H-pyrazol-4-yl)-N-((5-fluoro-2,3-dihydrobenzofuran-4-yl)methyl)-[1,2,4]triazolo [4,3-c]pyrimidin-5-amine | 0.0066 | 0.0071 | 0.0044 |
| 173 | 8-(6-cyclopropyl-4-methylpyridin-3-yl)-N-((5-fluoro-2,3-dihydrobenzofuran-4-yl)methyl)-[1,2,4]triazolo[4,3-c]pyrimidin-5-amine | 0.0075 | 0.0077 | 0.0152 |
| 174 | N-((5-fluoro-2,3-dihydrobenzofuran-4-yl)methyl)-8-(2-methoxypyrimidin-5-yl)-[1,2,4]triazolo [4,3-c]pyrimidin-5-amine | 0.0047 | 0.0062 | 0.0042 |
| 175 | N-((5-fluoro-2,3-dihydrobenzofuran-4-yl)methyl)-8-(2-methoxy-4-methylpyrimidin-5-yl)-[1,2,4]triazolo[4,3-c]pyrimidin-5-amine | 0.0063 | 0.0092 | 0.0034 |
| 176 | N-((5-fluoro-2,3-dihydrobenzofuran-4-yl)methyl)-8-(4-methylpyrimidin-5-yl)-[1,2,4]triazolo [4,3-c]pyrimidin-5-amine | 0.0059 | 0.0083 | 0.0046 |
| 177 | 8-(2,3-dimethylpyridin-4-yl)-N-((5-fluoro-2,3-dihydrobenzofuran-4-yl)methyl)-[1,2,4]triazolo [4,3-c]pyrimidin-5-amine | 0.0038 | 0.0044 | 0.0044 |
| 178 | 4-(5-(((5-fluoro-2,3-dihydrobenzofuran-4-yl)methyl)amino)-[1,2,4]triazolo[4,3-c]pyrimidin-8-yl)-3-methylbenzonitrile | 0.0054 | 0.007 | 0.0114 |
| 179 | 8-(1-cyclopropyl-3,5-dimethyl-1H-pyrazol-4-yl)-N-((5-fluoro-2,3-dihydrobenzofuran-4-yl)methyl)-[1,2,4]triazolo[4,3-c]pyrimidin-5-amine | 0.0124 | 0.0161 | 0.0091 |
| 180 | N-((5-fluoro-2,3-dihydrobenzofuran-4-yl)methyl)-8-(2-fluoro-3-methylpyridin-4-yl)-[1,2,4]triazolo [4,3-c]pyrimidin-5-amine | 0.0073 | 0.0079 | 0.0124 |
| 181 | 8-(2-(difluoromethyl)-3-methylpyridin-4-yl)-N-((5-fluoro-2,3-dihydrobenzofuran-4-yl)methyl)-[1,2,4]triazolo[4,3-c]pyrimidin-5-amine | 0.0026 | 0.006 | 0.0208 |
| 182 | N-((5-fluoro-2,3-dihydrobenzofuran-4-yl)methyl)-8-(2-(fluoromethyl)-3-methylpyridin-4-yl)-[1,2,4]triazolo[4,3-c]pyrimidin-5-amine | 0.0031 | 0.0056 | 0.0025 |
| 183 | N-((5-fluoro-2,3-dihydrobenzofuran-4-yl)methyl)-8-(2-fluoro-5-methylpyridin-4-yl)-[1,2,4]triazolo [4,3-c]pyrimidin-5-amine | 0.0048 | 0.0081 | 0.0106 |
| 184 | N-((5-fluoro-2,3-dihydrobenzofuran-4-yl)methyl)-8-(5-methyl-2-(trifluoromethyl)pyridin-4-yl)-[1,2,4]triazolo[4,3-c]pyrimidin-5-amine | 0.0054 | 0.0132 | 0.0777 |
| 185 | N-((5-fluoro-2,3-dihydrobenzofuran-4-yl)methyl)-8-(2-(trifluoromethyl)pyridin-4-yl)-[1,2,4]triazolo [4,3-c]pyrimidin-5-amine | 0.0044 | 0.0067 | 0.0468 |
| 186 | (2R)-1-(4-(5-(((5-fluoro-2,3-dihydrobenzofuran-4-yl)methyl)amino)-[1,2,4]triazolo[4,3-c] pyrimidin-8-yl)-3,5-dimethyl-1H-pyrazol-1-yl)propan-2-ol | 0.0035 | 0.006 | 0.0068 |
| 187 | (2S)-1-(4-(5-(((5-fluoro-2,3-dihydrobenzofuran-4-yl)methyl)amino)-[1,2,4]triazolo[4,3-c] pyrimidin-8-yl)-3,5-dimethyl-1H-pyrazol-1-yl)propan-2-ol | 0.0082 | 0.0125 | 0.012 |
| 188 | N-((5-fluoro-2,3-dihydrobenzofuran-4-yl)methyl)-8-(1-isopropyl-5-methyl-1H-pyrazol-4-yl)-[1,2,4]triazolo[4,3-c]pyrimidin-5-amine | 0.0023 | 0.0038 | 0.0036 |
| 189 | 2-(4-(5-(((5-fluoro-2,3-dihydrobenzofuran-4-yl)methyl)amino)-[1,2,4]triazolo[4,3-c]pyrimidin-8-yl)-5-methyl-1H-pyrazol-1-yl)ethanol | 0.0042 | 0.0087 | 0.0052 |
| 190 | 2-(4-(5-(((5-fluoro-2,3-dihydrobenzofuran-4-yl)methyl)amino)-[1,2,4]triazolo[4,3-c]pyrimidin-8-yl)-3-methyl-1H-pyrazol-1-yl)ethanol | 0.0045 | 0.0171 | 0.0025 |
| 191 | 8-(4-(difluoromethyl)pyrimidin-5-yl)-N-((5-fluoro-2,3-dihydrobenzofuran-4-yl)methyl)-[1,2,4]triazolo[4,3-c]pyrimidin-5-amine | 0.0038 | 0.0131 | 0.0344 |
| 192 | 8-(1-cyclopropyl-1H-pyrazol-5-yl)-N-((5-fluoro-2,3-dihydrobenzofuran-4-yl)methyl)-[1,2,4] triazolo[4,3-c]pyrimidin-5-amine | 0.0035 | 0.0126 | 0.0104 |
| 193 | N-((5-fluoro-2,3-dihydrobenzofuran-4-yl)methyl)-8-(2-(fluoromethyl)pyridin-3-yl)-[1,2,4] triazolo[4,3-c]pyrimidin-5-amine | 0.004 | 0.013 | 0.0054 |
| 194 | 8-(2,5-dimethylpyridin-4-yl)-N-((5-fluoro-2,3-dihydrobenzofuran-4-yl)methyl)-[1,2,4]triazolo [4,3-c]pyrimidin-5-amine | 0.0024 | 0.007 | 0.0241 |
| 195 | 8-(1,3-dimethyl-1H-pyrazol-4-yl)-N-((5-fluoro-2,3-dihydrobenzofuran-4-yl)methyl)-[1,2,4]triazolo [4,3-c]pyrimidin-5-amine | 0.0059 | 0.0116 | 0.0024 |
| 196 | 8-(6-ethoxy-4-methylpyridin-3-yl)-N-((5-fluoro-2,3-dihydrobenzofuran-4-yl)methyl)-[1,2,4]triazolo [4,3-c]pyrimidin-5-amine | 0.0036 | 0.0082 | 0.0263 |
| 197 | 8-(6-(difluoromethoxy)-4-methylpyridin-3-yl)-N-((5-fluoro-2,3-dihydrobenzofuran-4-yl)methyl)-[1,2,4]triazolo[4,3-c]pyrimidin-5-amine | 0.0022 | 0.0057 | 0.0149 |
| 198 | 8-(2-(difluoromethyl)-5-methylpyridin-4-yl)-N-((5-fluoro-2,3-dihydrobenzofuran-4-yl)methyl)-[1,2,4]triazolo[4,3-c]pyrimidin-5-amine | 0.0044 | 0.0173 | 0.0078 |
| 199 | 5-(5-(((5-fluoro-2,3-dihydrobenzofuran-4-yl)methyl)amino)-[1,2,4]triazolo[4,3-c]pyrimidin-8-yl)-N,N,6-trimethylpicolinamide | 0.0042 | 0.0072 | 0.005 |
| 200 | 8-(3-(difluoromethyl)-1-methyl-1H-pyrazol-4-yl)-N-((5-fluoro-2,3-dihydrobenzofuran-4-yl)methyl)-[1,2,4]triazolo[4,3-c]pyrimidin-5-amine | 0.0075 | 0.0095 | 0.003 |
| 201 | 8-(2-(difluoromethyl)-6-methylpyridin-3-yl)-N-((5-fluoro-2,3-dihydrobenzofuran-4-yl)methyl)-[1,2,4]triazolo[4,3-c]pyrimidin-5-amine | 0.0059 | 0.0073 | 0.0036 |
| 202 | N-((5-fluoro-2,3-dihydrobenzofuran-4-yl)methyl)-8-(pyridazin-4-yl)-[1,2,4]triazolo[4,3-c] pyrimidin-5-amine | 0.0096 | 0.0187 | 0.0206 |
| 203 | N-((5-fluoro-2,3-dihydrobenzofuran-4-yl)methyl)-7-methyl-8-(2-methylpyridin-3-yl)-[1,2,4] triazolo[4,3-c]pyrimidin-5-amine | 0.0424 | 0.3385 | N/A |
| 204 | 3-(5-(((5-fluoro-2,3-dihydrobenzofuran-4-yl)methyl)amino)-[1,2,4]triazolo[4,3-c]pyrimidin-8-yl)-2-methylpyridine 1-oxide | 0.0106 | 0.0193 | 0.0103 |
| 205 | N-((5-fluoro-2,3-dihydrobenzofuran-4-yl)methyl)-8-(pyrazin-2-yl)-[1,2,4]triazolo[4,3-c]pyrimidin-5-amine | 0.0073 | 0.0082 | 0.0167 |
| 206 | N-((5-fluoro-2,3-dihydrobenzofuran-4-yl)methyl)-8-(pyrimidin-5-yl)-[1,2,4]triazolo[4,3-c]pyrimidin-5-amine | 0.0091 | 0.0095 | 0.0159 |
| 207 | N-((5-fluorobenzofuran-4-yl)methyl)-8-(2-methylpyridin-3-yl)-[1,2,4]triazolo[4,3-c]pyrimidin-5-amine | 0.0795 | 0.1817 | 0.0036 |
| 208 | N-(benzofuran-4-ylmethyl)-8-(4-((dimethylamino)methyl)phenyl)-[1,2,4]triazolo [4,3-c]pyrimidin-5-amine | 0.0062 | 0.0127 | 0.0190 |
| 209 | N-(benzofuran-4-ylmethyl)-8-(4-(4-methylpiperazin-1-yl)phenyl)-[1,2,4]triazolo [4,3-c]pyrimidin-5-amine | 0.0369 | 0.0290 | 0.1179 |

TABLE 3-continued

| Ex # | IUPAC name | (a) $IC_{50}$ (μM) | (b) $IC_{50}$ (μM) | (c) $IC_{50}$ (μM) |
|---|---|---|---|---|
| 210 | N-(benzofuran-4-ylmethyl)-8-(4-(1-(pyrrolidin-1-yl)ethyl)phenyl)-[1,2,4]triazolo [4,3-c]pyrimidin-5-amine | 0.0185 | 0.0214 | N/A |
| 211 | N-(benzofuran-4-ylmethyl)-8-(6-(4-methylpiperazin-1-yl)pyridin-3-yl)-[1,2,4]triazolo [4,3-c]pyrimidin-5-amine | 0.0322 | 0.0288 | N/A |
| 212 | N-(benzofuran-4-ylmethyl)-8-(2-(4-methylpiperazin-1-yl)pyridin-4-yl)-[1,2,4]triazolo [4,3-c]pyrimidin-5-amine | 0.0312 | 0.0338 | N/A |
| 213 | N-(benzofuran-4-ylmethyl)-8-(pyridin-3-yl)-[1,2,4]triazolo[4,3-c]pyrimidin-5-amine | 0.0366 | 0.0256 | N/A |
| 214 | N-(benzofuran-4-ylmethyl)-8-(4-(methylsulfonyl)phenyl)-[1,2,4]triazolo[4,3-c] pyrimidin-5-amine | 0.0374 | 0.0225 | N/A |
| 215 | N-(benzofuran-4-ylmethyl)-8-(4-(isopropylsulfonyl)phenyl)-[1,2,4]triazolo[4,3-c] pyrimidin-5-amine | 0.0203 | 0.0212 | N/A |
| 216 | (4-(5-((benzofuran-4-ylmethyl)amino)-[1,2,4]triazolo[4,3-c]pyrimidin-8-yl) phenyl)(pyrrolidin-1-yl)methanone | 0.1315 | 0.1834 | N/A |
| 217 | N-(benzofuran-4-ylmethyl)-8-phenyl-[1,2,4]triazolo[4,3-c]pyrimidin-5-amine | 0.3632 | 0.1113 | N/A |
| 218 | N-(benzofuran-4-ylmethyl)-8-(pyridin-4-yl)-[1,2,4]triazolo[4,3-c]pyrimidin-5-amine | 0.0386 | 0.0263 | N/A |
| 219 | 8-(4-((dimethylamino)methyl)phenyl)-N-((5-fluorobenzofuran-4-yl)methyl)-[1,2,4]triazolo [4,3-c]pyrimidin-5-amine | 0.0065 | 0.0068 | 0.0079 |
| 220 | N-(benzofuran-4-ylmethyl)-8-(4-((1-methylpiperidin-4-yl)sulfonyl)phenyl)-[1,2,4]triazolo [4,3-c]pyrimidin-5-amine | 0.0141 | 0.0216 | 0.4667 |
| 221 | N-((5-fluoro-2,3-dihydrobenzofuran-4-yl)methyl)-8-(pyrimidin-5-yl)-[1,2,4]triazolo[4,3-c] pyrimidin-5-amine | 0.0091 | 0.0095 | 0.0159 |
| 222 | 8-(4,6-dimethylpyridin-3-yl)-N-((5-fluoro-2,3-dihydrobenzofuran-4-yl)methyl)-[1,2,4]triazolo [4,3-c]pyrimidin-5-amine | 0.0117 | 0.0140 | 0.0576 |
| 223 | 8-(6-((dimethylamino)methyl)-2-methylpyridin-3-yl)-N4(5-fluoro-2,3-dihydrobenzofuran-4-yl)methyl)-[1,2,4]triazolo[4,3-c]pyrimidin-5-amine | 0.0084 | 0.0184 | 0.0014 |
| 224 | 8-(6-ethyl-4-methylpyridin-3-yl)-N-((5-fluoro-2,3-dihydrobenzofuran-4-yl)methyl)-[1,2,4] triazolo[4,3-c]pyrimidin-5-amine | 0.0015 | 0.0019 | 0.0022 |
| 225 | 8-(2-cyclopropoxy-4-methylpyrimidin-5-yl)-N-((5-fluoro-2,3-dihydrobenzofuran-4-yl)methyl)-[1,2,4]triazolo[4,3-c]pyrimidin-5-amine | 0.0075 | 0.0106 | 0.0045 |
| 226 | 8-(2-ethoxy-4-methylpyrimidin-5-yl)-N-((5-fluoro-2,3-dihydrobenzofuran-4-yl)methyl)-[1,2,4]triazolo[4,3-c]pyrimidin-5-amine | 0.0039 | 0.0050 | 0.0061 |
| 227 | (4-(5-(((5-fluoro-2,3-dihydrobenzofuran-4-yl)methyl)amino)-[1,2,4]triazolo[4,3-c]pyrimidin-8-yl)-1-methyl-1H-pyrazol-5-yl)methanol | 0.0061 | 0.0075 | 0.0091 |
| 228 | 8-(2-chloro-5-methylpyridin-4-yl)-N-((5-fluoro-2,3-dihydrobenzofuran-4-yl)methyl)-[1,2,4] triazolo[4,3-c]pyrimidin-5-amine | 0.0082 | 0.0090 | 0.0292 |
| 229 | 8-(6-ethyl-2-methylpyridin-3-yl)-N-((5-fluoro-2,3-dihydrobenzofuran-4-yl)methyl)-[1,2,4] triazolo[4,3-c]pyrimidin-5-amine | 0.0059 | 0.0067 | 0.0027 |
| 230 | N-((5-fluoro-2,3-dihydrobenzofuran-4-yl)methyl)-8-(2-methoxy-3-methylpyridin-4-yl)-[1,2,4] triazolo[4,3-c]pyrimidin-5-amine | 0.0129 | 0.0245 | 0.0252 |
| 231 | N-((5-fluoro-2,3-dihydrobenzofuran-4-yl)methyl)-8-(pyridin-2-yl)-[1,2,4]triazolo [4,3-c]pyrimidin-5-amine | 0.0061 | 0.0060 | 0.0358 |
| 232 | N-((5-fluoro-2,3-dihydrobenzofuran-4-yl)methyl)-8-(5-methylpyridin-3-yl)-[1,2,4]triazolo[4,3-c]pyrimidin-5-amine | 0.0062 | 0.0131 | 0.0133 |
| 233 | N-((5-fluoro-2,3-dihydrobenzofuran-4-yl)methyl)-8-(4-methyl-1H-imidazol-1-yl)-[1,2,4]triazolo [4,3-c]pyrimidin-5-amine | 0.0039 | 0.0115 | 0.0020 |
| 234 | (5-(5-(((5-fluoro-2,3-dihydrobenzofuran-4-yl)methyl)amino)-[1,2,4]triazolo[4,3-c]pyrimidin-8-yl) pyridin-2-yl)methanol | 0.0054 | 0.0112 | 0.0045 |
| 235 | 8-fluoro-N-((5-fluoro-2,3-dihydrobenzofuran-4-yl)methyl)-[1,2,4]triazolo[4,3-c]pyrimidin-5-amine | 0.0399 | 0.0653 | 0.1918 |
| 236 | 8-(2,4-dimethyl-1H-imidazol-1-yl)-N-((5-fluoro-2,3-dihydrobenzofuran-4-yl)methyl)-[1,2,4]triazolo[4,3-c]pyrimidin-5-amine | 0.0102 | 0.0232 | 0.0076 |
| 237 | N-((5-fluoro-2,3-dihydrobenzofuran-4-yl)methyl)-8-(1H-pyrazol-1-yl)-[1,2,4]triazolo [4,3-c]pyrimidin-5-amine | 0.0031 | 0.0100 | 0.0101 |
| 238 | N-((5-fluoro-2,3-dihydrobenzofuran-4-yl)methyl)-8-(3-methyl-1H-1,2,4-triazol-1-yl)-[1,2,4]triazolo[4,3-c]pyrimidin-5-amine | 0.0047 | 0.0144 | 0.0179 |
| 239 | N-((5-fluoro-2,3-dihydrobenzofuran-4-yl)methyl)-8-(4-methyl-1H-pyrazol-1-yl)-[1,2,4]triazolo [4,3-c]pyrimidin-5-amine | 0.0068 | 0.0159 | 0.0382 |
| 240 | N-((5-fluoro-2,3-dihydrobenzofuran-4-yl)methyl)-8-(1H-imidazol-1-yl)-[1,2,4] triazolo[4,3-c]pyrimidin-5-amine | 0.0049 | 0.0143 | 0.0014 |
| 241 | N-((5-fluoro-2,3-dihydrobenzofuran-4-yl)methyl)-8-(1H-1,2,4-triazol-1-yl)-[1,2,4]triazolo [4,3-c]pyrimidin-5-amine | 0.0113 | 0.0300 | 0.0284 |
| 242 | 5-fluoro-4-(((8-(2-methylpyridin-3-yl)-[1,2,4]triazolo[4,3-c]pyrimidin-5-yl) amino)methyl)-2,3-dihydrobenzofuran-3-ol | 0.0138 | 0.0500 | 0.0634 |
| 243 | 5-fluoro-4-(((8-(2-(hydroxymethyl)pyridin-3-yl)-[1,2,4]triazolo[4,3-c] pyrimidin-5-yl)amino)methyl)-2,3-dihydrobenzofuran-3-ol | 0.0154 | 0.0590 | 0.0409 |
| 244 | 3-(5-(((5-fluoro-3-hydroxy-2,3-dihydrobenzofuran-4-yl)methyl)amino)-[1,2,4]triazolo [4,3-c]pyrimidin-8-yl)-2-methylpyridine 1-oxide | 0.0117 | 0.0389 | 0.2415 |
| 245 | 8-(1,2-dimethyl-1H-imidazol-5-yl)-N-((5-fluoro-2,3-dihydrobenzofuran-4-yl) methyl)-[1,2,4]triazolo[4,3-c]pyrimidin-5-amine | 0.0672 | 0.2232 | N/A |

Table 4 below lists antiproliferative activities ($IC_{50}$ values) in B cell lymphoma cell KARPAS422 after 14 days of treatment for the following examples

TABLE 4

| Ex # | $IC_{50}$ (μM) |
|---|---|
| 1 | 0.0004 |
| 2 | 0.0030 |
| 3 | 0.0007 |
| 4 | 0.0003 |
| 5 | 0.0008 |
| 6 | 0.0002 |
| 7 | 0.0030 |
| 8 | 0.0006 |
| 9 | 0.0006 |
| 10 | 0.0174 |
| 207 | 0.0010 |

Accordingly, the compounds of the present disclosure have been found to inhibit EED and therefore useful in the treatment of diseases or disorders associated with EED and PRC2, which include, but are not limited to, diffused large B cell lymphoma (DLBCL), follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neurobalstoma, glioma, glioblastoma and astrocytoma, cervical cancer, colon cancer, melanoma, endometrial cancer, esophageal cancer, head and neck cancer, lung cancer, nasopharhyngeal carcinoma, ovarian cancer, pancreatic cancer, renal cell carcinoma, rectal cancer, thyroid cancers, parathyroid tumors, uterine tumors, and soft tissue sarcomas selected from rhabdomyosarcoma (RMS), Kaposi sarcoma, synovial sarcoma, osteosarcoma and Ewing's sarcoma.

V. Pharmaceutical Compositions and Combinations

The compounds of the present invention are typically used as a pharmaceutical composition (e.g., a compound of the present invention and at least one pharmaceutically acceptable carrier). A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012). For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above.

The compounds of this disclosure can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The compound of the present invention is typically formulated into pharmaceutical dosage forms to provide an easily controllable dosage of the drug and to give the patient an elegant and easily handleable product. The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. Compounds of this disclosure may be administered in a single daily dose, or the total daily dosage may be administered in divided doses of two, three, or four times daily.

In certain instances, it may be advantageous to administer the compound of the present invention in combination with at least one additional pharmaceutical (or therapeutic) agent, such as other anti-cancer agents, immunomodulators, anti-allergic agents, anti-nausea agents (or anti-emetics), pain relievers, cytoprotective agents, and combinations thereof.

The term "combination therapy" refers to the administration of two or more therapeutic agents to treat a therapeutic disease, disorder or condition described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. The compound of the present disclosure and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present disclosure include:

Cyclin-Dependent Kinase (CDK) inhibitors: (Chen, S. et al., *Nat Cell Biol.*, 12(11):1108-14 (2010); Zeng, X. et al., *Cell Cycle,* 10(4):579-83 (2011)) Aloisine A; Alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); Crizotinib (PF-02341066, CAS 877399-52-5); 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-Methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); Indisulam (E7070); Roscovitine (CYC202); 6-Acetyl-8-cyclopentyl-5-methyl-2-(5-piperazin-1-yl-pyridin-2-ylamino)-8H-pyrido[2,3-d]pyrimidin-7-one, hydrochloride (PD0332991); Dinaciclib (SCH727965); N-[5-[[(5-tert-Butyloxazol-2-yl)methyl]thio]thiazol-2-yl]piperidine-4-carboxamide (BMS 387032, CAS 345627-80-7); 4-[[9-Chloro-7-(2,6-difluorophenyl)-5H-pyrimido[5,4-d][2]benzazepin-2-yl]amino]-benzoic acid (MLN8054, CAS 869363-13-3); 5-[3-(4,6-Difluoro-1H-benzimidazol-2-yl)-1H-indazol-5-yl]-N-ethyl-4-methyl-3-pyridinemethanamine (AG-024322, CAS 837364-57-5); 4-(2,6-Dichlorobenzoylamino)-1H-pyrazole-3-carboxylic acid N-(piperidin-4-yl)amide (AT7519, CAS 844442-38-2); 4-[2-Methyl-1-(1-methylethyl)-1H-imidazol-5-yl]-N-[4-(methylsulfonyl)phenyl]-2-pyrimidinamine (AZD5438, CAS 602306-29-6); Palbociclib (PD-0332991); and (2R,3R)-3-[[2-[[3-[[S(R)]-S-cyclopropylsulfonimidoyl]-phenyl]amino]-5-(trifluoromethyl)-4-pyrimidinyl]oxy]-2-butanol (BAY 10000394).

Checkpoint Kinase (CHK) inhibitors: (Wu, Z. et al., *Cell Death Differ.,* 18(11):1771-9 (2011)) 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N-[(S)-piperidin-3-yl] amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRR-LYRSPAMPENL), and CBP501 ((d-Bpa)sws(d-Phe-F5)(d-Cha)rrrqrr); and (αR)-α-amino-N-[5,6-dihydro-2-(1-methyl-1H-pyrazol-4-yl)-6-oxo-1H-pyrrolo[4,3,2-ef][2,3]benzodiazepin-8-yl]-Cyclohexaneacetamide (PF-0477736).

Protein Kinase B (PKB) orAKT inhibitors: (Rojanasakul, Y., *Cell Cycle,* 12(2):202-3 (2013); Chen B. et al., *Cell Cycle,* 12(1):112-21 (2013)) 8-[4-(1-Aminocyclobutyl)phenyl]-9-phenyl-1,2,4-triazolo[3,4-f][1,6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Tricirbine (6-Amino-4-methyl-8-(p-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

C-RAFInhibitors: (Chang, C. et al., *Cancer Cell,* 19(1):86-100 (2011)) Sorafenib (Nexavar®); 3-(Dimethylamino)-N-[3-[(4-hydroxybenzoyl)amino]-4-methylphenyl]-benzamide (ZM336372, CAS 208260-29-1); and 3-(1-cyano-1-methylethyl)-N-[3-[(3,4-dihydro-3-methyl-4-oxo-6-quinazolinyl)amino]-4-methylphenyl]-benzamide (AZ628, CAS 1007871-84-2).

Phosphoinositide 3-kinase (PI3K) inhibitors: (Gonzalez, M. et al., *Cancer Res.,* 71(6): 2360-2370 (2011)) 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-36-6); 2-Amino-8-ethyl-4-methyl-6-(1H-pyrazol-5-yl)pyrido[2,3-d]pyrimidin-7(8H)-one (SAR 245409 or XL 765); 1,3-Dihydro-8-(6-methoxy-3-pyridinyl)-3-methyl-1-[4-(1-piperazinyl)-3-(trifluoromethyl)phenyl]-2H-imidazo[4,5-c]quinolin-2-one, (2Z)-2-butenedioate (1:1) (BGT 226); 5-Fluoro-3-phenyl-2-[(1S)-1-(9H-purin-6-ylamino)ethyl]-4(3H)-quinazolinone (CAL101); 2-Amino-N-[3-[N-[3-[(2-chloro-5-methoxyphenyl)amino]quinoxalin-2-yl]sulfamoyl]phenyl]-2-methylpropanamide (SAR 245408 or XL 147); and (S)-Pyrrolidine-1, 2-dicarboxylic acid 2-amide 1-({4-methyl-5-[2-(2,2,2-trifluoro-1,1-dimethyl-ethyl)-pyridin-4-yl]-thiazol-2-yl}-amide) (BYL719).

BCL-2 inhibitors: (Béguelin, W. et al., *Cancer Cell,* 23(5):677-92(2013)) 4-[4-[[2-(4-Chlorophenyl)-5,5-dimethyl-1-cyclohexen-1-yl]methyl]-1-piperazinyl]-N-[[4-[[(1 R)-3-(4-morpholinyl)-1-[(phenylthio)methyl]propyl] amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1 R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Mitogen-activated protein kinase (MEK) inhibitors: (Chang, C. J. et al., *Cancer Cell,* 19(1):86-100 (2011)) XL-518 (also known as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); Benimetinib (6-(4-bromo-2-fluorophenylamino)-7-fluoro-3-methyl-3H-benzoimidazole-5-carboxylic acid (2-hydroxyethyoxy)-amide, also known as MEK162, CAS 1073666-70-2, described in PCT Publication No. WO2003077914); 2-[(2-Chloro-4-iodophenyl) amino]-N-(cyclopropylmethoxy)-3,4-difluoro-benzamide (also known as Cl-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3, 4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S, 4R,5Z,8S,9S,11E)-14-(Ethylamino)-8,9,16-trihydroxy-3,4-dimethyl-3,4,9, 19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2, 3-d]pyrimidine-4,7(3H,8H)-dione (TAK-733, CAS 1035555-63-5); Pimasertib (AS-703026, CAS 1204531-26-9); Trametinib dimethyl sulfoxide (GSK-1120212, CAS 1204531-25-80); 2-(2-Fluoro-4-iodophenylamino)-N-(2-hydroxyethoxy)-1,5-dimethyl-6-oxo-1,6-dihydropyridine-3-carboxamide (AZD 8330); and 3,4-Difluoro-2-[(2-fluoro-4-iodophenyl)amino]-N-(2-hydroxyethoxy)-5-[(3-oxo-[1,2] oxazinan-2-yl)methyl]benzamide (CH 4987655 or Ro 4987655).

Aromatase inhibitors: (Pathiraja, T. et al., *Sci. Transl. Med.,* 6(229):229 ra41 (2014)) Exemestane (Aromasin®); Letrozole (Femara®); and Anastrozole (Arimidex®).

Topoisomerase II inhibitors: (Bai, J. et al., *Cell Prolif.,* 47(3):211-8 (2014)) Etoposide (VP-16 and Etoposide phosphate, Toposar®, VePesid® and Etopophos®); Teniposide (VM-26, Vumon®); and Tafluposide.

SRC inhibitors: (Hebbard, L., *Oncogene,* 30(3):301-12 (2011)) Dasatinib (Sprycel®); Saracatinib (AZD0530, CAS 379231-04-6); Bosutinib (SKI-606, CAS 380843-75-4); 5-[4-[2-(4-Morpholinyl)ethoxy]phenyl]-N-(phenylmethyl)-2-pyridineacetamide (KX2-391, CAS 897016-82-9); and 4-(2-Chloro-5-methoxyanilino)-6-methoxy-7-(1-methylpiperidin-4-ylmethoxy)quinazoline (AZM475271, CAS 476159-98-5).

Histone deacetylase (HDAC) inhibitors: (Yamaguchi, J. et al., *Cancer Sci.,* 101(2):355-62 (2010)) Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(aS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-q-oxo-L-α-aminooxiraneoctanoyl-D-prolyl] (HC-toxin); Cyclo[(aS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide); and Depudecin (4,5:8,9-dianhydro-1,2,6,7,11-pentadeoxy-D-threo-D-ido-Undeca-1,6-dienitol).

Anti-tumor antibiotics: (Bai, J. et al., *Cell Prolif.,* 47(3): 211-8 (2014)) Doxorubicin (Adriamycin® and Rubex®); Bleomycin (Ienoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence™); Idarubicin (Idamycin®, Idamycin PFS®); Mitomycin C (Mutamycin®); Geldanamycin; Herbimycin; Ravidomycin; and Desacetylravidomycin.

Demethylating agents: (Musch, T. et al., *PLoS One,* (5):el0726 (2010)) 5-Azacitidine (Vidaza®); and Decitabine (Dacogen®).

Anti-estrogens: (Bhan, A. et al., *J Mol Biol.*, S0022-2836 (14)00373-8 (2014)) Tamoxifen (Novaldex®); Toremifene (Fareston®); and Fulvestrant (Faslodex®).

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Immunomodulators of particular interest for combinations with the compounds of the present disclosure include one or more of: an activator of a costimulatory molecule or an inhibitor of an immune checkpoint molecule (e.g., one or more inhibitors of PD-1, PD-L1, LAG-3, TIM-3 or CTLA4) or any combination thereof.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term “inhibition” or “inhibitor” includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium “The Merck Index” or from databases, e.g. Patents International (e.g. IMS World Publications).

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy for treatment of a malignancy, the compound of the present disclosure and other anti-cancer agent(s) may be administered simultaneously, concurrently or sequentially with no specific time limits, wherein such administration provides therapeutically effective levels of the two compounds in the body of the subject.

In a preferred embodiment, the compound of the present disclosure and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In another aspect of the present invention, kits that include one or more compound of the present disclosure and a combination partner as disclosed herein are provided. Representative kits include (a) a compound of the present disclosure or a pharmaceutically acceptable salt thereof, (b) at least one combination partner, e.g., as indicated above, whereby such kit may comprise a package insert or other labeling including directions for administration.

In the combination therapies of the invention, the compound of the present disclosure and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The compounds of the present disclosure are also useful as standard or reference compounds, for example as a quality standard or control, in tests or assays involving EED and/or PRC2. Such compounds may be provided in a commercial kit, for example, for use in pharmaceutical research involving myeloperoxidase activity. For example, a compound of the present disclosure could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present disclosure could be used to test their effectiveness. The compounds of the present disclosure may also be used in diagnostic assays involving EED and/or PRC2.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

What is claimed is:

1. A method for treating a disease or disorder mediated by Embryonic Ectoderm Development (EED) or Polycomb Repressive Complex 2 (PRC2), wherein the method comprises administering to a patient in need thereof a therapeutically effective amount of a compound of Formula (IA), or a pharmaceutically acceptable salt thereof:

(IA)

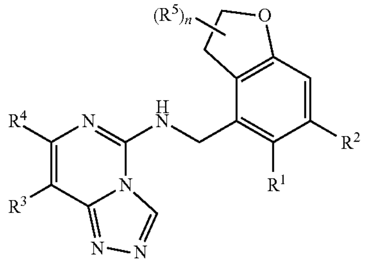

wherein:

$R^1$ and $R^2$ are independently H or halogen;

$R^3$ is independently selected from: halogen, phenyl, and a 5- to 6-membered heteroaryl comprising carbon atoms and 1-4 heteroatoms selected from N, $NR^a$, O and $S(O)_p$; wherein said phenyl and heteroaryl are substituted with 0-3 $R^{3A}$;

each $R^{3A}$ is independently selected from: halogen, CN, $—(O)_m—(C_1\text{-}C_6$ alkyl substituted with 0-1 $R^{3B})$, $C_1\text{-}C_6$ haloalkyl, $C_1\text{-}C_6$ haloalkoxy, $R^{3C}$, $—OR^{3c}$, $—C(=O)R^{3D}$, $NR^{3E}R^{3F}$, $—C(=O)NR^{3E}R^{3F}$, $—NHC(=O)R^{3D}$, $—S(=O)_2R^{3D}$, $—S(=O)_2NR^{3E}R^{3F}$, $—NHS(=O)_2(C_1\text{-}C_4$ alkyl), and $—CR^{3C}R^{3E}R^{3G}$;

$R^{3B}$ is independently selected from: OH, $NR^eR^f$, $C_1\text{-}C_4$ alkoxy, $—C(=O)NR^eR^f$, $—S(=O)_2(C_1\text{-}C_4$ alkyl), $—NHC(=O)(C_1\text{-}C_4$ alkyl), and a 5- to 6-membered heterocycloalkyl comprising carbon atoms and 1-2 heteroatoms selected from N, $NR^a$, O, and $S(O)_p$; wherein said heterocycloalkyl is substituted with 0-2 $R^c$;

each $R^{3C}$ is independently selected from: $C_3\text{-}C_6$ cycloalkyl, phenyl, and a 4- to 7-membered heterocycle comprising carbon atoms and 1-4 heteroatoms selected from N, $NR^a$, O, and $S(O)_p$; wherein each moiety is substituted with 0-2 $R^c$;

each $R^{3D}$ is independently selected from: $C_1\text{-}C_4$ alkyl and $R^{3C}$;

$R^{3E}$ and $R^{3G}$ are, at each occurrence, independently selected from: H and $C_1\text{-}C_4$ alkyl;

each $R^{3F}$ is independently selected from: H and $C_1\text{-}C_4$ alkyl substituted with 0-1 $R^d$;

$R^4$ is independently selected from: H, halogen and $C_1\text{-}C_4$ alkyl;

$R^5$ is independently selected from OH and $C_1\text{-}C_4$ alkyl;

each $R^a$ is independently selected from: H, $\rightarrow$O, $C_1\text{-}C_4$ alkyl substituted with 0-1 $R^b$, $—C(=O)H$, $—C(=O)(C_1\text{-}C_4$ alkyl), $—CO_2(C_1\text{-}C_4$ alkyl), $C_3\text{-}C_6$ cycloalkyl, and benzyl;

$R^b$ is independently selected from: halogen, OH and $C_1\text{-}C_4$ alkoxy;

each $R^c$ is independently selected from: =O, halogen, OH, $C_1\text{-}C_4$ alkyl, $C_1\text{-}C_4$haloalkyl, $C_1\text{-}C_4$ alkoxy, and $C_1\text{-}C_4$ haloalkoxy;

$R^d$ is independently selected from: OH and $NR^eR^f$;

$R^e$ and $R^f$ are, at each occurrence, independently selected from: H and $C_1\text{-}C_4$ alkyl;

each p is independently selected from 0, 1 and 2; and m and n are, at each occurrence, independently selected from 0 and 1, and wherein the disease or disorder is diffused large B cell lymphoma, follicular lymphoma, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, neuroblastoma, schwannoma, glioma, glioblastoma, astrocytoma, cervical cancer, colon cancer, melanoma, endometrial cancer, esophageal cancer, head and neck cancer, lung cancer, nasopharyngeal carcinoma, ovarian cancer, pancreatic cancer, renal cell carcinoma, rectal cancer, thyroid cancers, parathyroid tumors, uterine tumors, and soft tissue sarcoma.

2. The method of claim 1, wherein:

each $R^{3A}$ is independently selected from: halogen, CN, $—(O)_m—(C_1\text{-}C_4$ alkyl substituted with 0-1 $R^{3B})$, $C_1\text{-}C_4$ haloalkyl, $C_1\text{-}C_4$ haloalkoxy, $R^{3C}$, $—C(=O)R^{3D}$, $NR^{3E}R^{3F}$, $—C(=O)NR^{3E}R^{3F}$, $—S(=O)_2R^{3D}$, $—S(=O)_2NHR^{3F}$, $—NHS(=O)_2(C_1\text{-}C_4$ alkyl), $—O—C_3\text{-}C_6$ cycloalkyl, and

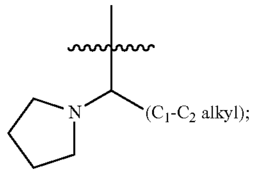

$R^a$ is independently selected from: H, →O, $C_1$-$C_4$ alkyl substituted with 0-1 $R^b$, —C(=O)H, —C(=O)($C_1$-$C_4$ alkyl), —$CO_2$($C_1$-$C_4$ alkyl), and $C_3$-$C_6$ cycloalkyl;

$R^4$ is H;

m is independently selected from 0 and 1; and n is 0.

3. The method of claim 1, wherein:

$R^1$ is independently H or F;

$R^2$ is H; and $R^3$ is independently selected from: phenyl, and a 6-membered heteroaryl comprising carbon atoms and 1-2 heteroatoms selected from N and $NR^a$; wherein said phenyl and heteroaryl are substituted with 0-3 $R^{3A}$.

4. The method of claim 3, wherein:

$R^3$ is independently selected from: phenyl, pyridyl, pyrimidyl, pyridazinyl and pyrazinyl; wherein each moiety is substituted with 0-3 $R^{3A}$.

5. The method of claim 4, wherein:

$R^3$ is independently selected from:

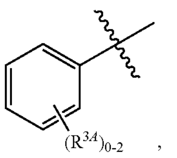
,
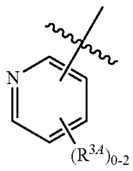
, and
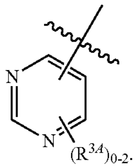
.

6. The method of claim 4, wherein:

$R^3$ is independently selected from:

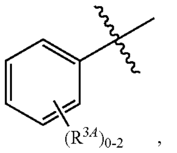
,
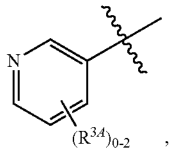
,
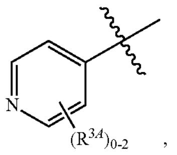
, and
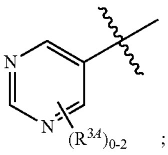
;

each $R^{3A}$ is independently selected from: halogen, CN, —$(O)_m$—($C_1$-$C_4$ alkyl substituted with 0-1 $R^{3B}$), $C_1$-$C_4$ haloalkyl, $C_1$-$C_4$ haloalkoxy, —C(=O)$NH_2$, —C(=O)NH($C_1$-$C_4$ alkyl), —C(=O)N($C_1$-$C_4$ alkyl)$_2$, —C(=O)N($C_1$-$C_4$ alkyl)$(CH_2)_2$N($C_1$-$C_4$ alkyl)$_2$, —$CH_2$NHC(=O)($C_1$-$C_4$ alkyl), —S(=O)$_2R^{3D}$, —S(=O)$_2$NH($C_1$-$C_4$ alkyl substituted with 0-1 OH), —NHS(=O)$_2$($C_1$-$C_4$ alkyl), $NH_2$, —NH($C_1$-$C_4$ alkyl), —N($C_1$-$C_4$ alkyl)$_2$, $C_3$-$C_6$ cycloalkyl,

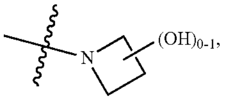
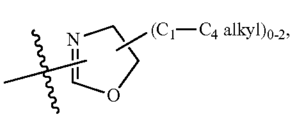
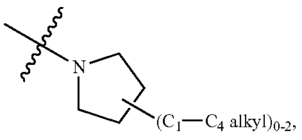
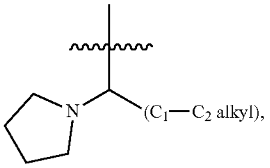
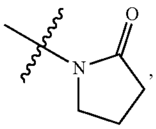
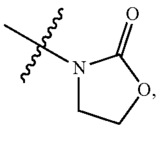
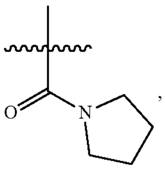
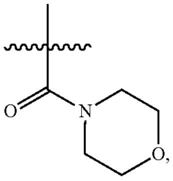
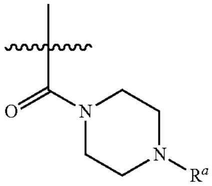
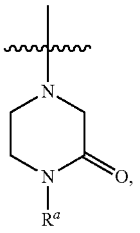
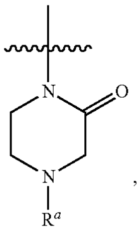
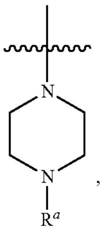
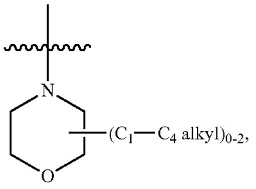
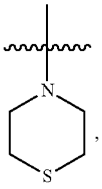
, and
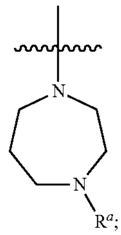

$R^{3B}$ is independently selected from: OH, $NH_2$, NH($C_1$-$C_4$ alkyl), N($C_1$-$C_4$ alkyl)$_2$, $C_1$-$C_4$ alkoxy, —C(=O)N($C_1$-$C_4$ alkyl)$_2$, —S(=O)$_2$($C_1$-$C_4$ alkyl),

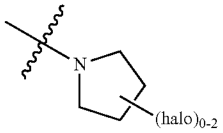, 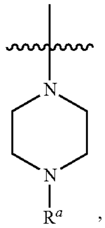, and

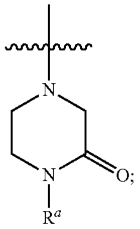

$R^{3D}$ is independently selected from: $C_1$-$C_4$ alkyl and 1H-piperidin-4-yl; and each $R^a$ is independently selected from: H, $C_1$-$C_4$ alkyl, —C(═O)H, —C(═O)($C_1$-$C_4$ alkyl), and —$CO_2$($C_1$-$C_4$ alkyl).

7. The method of claim 6, wherein:

$R^3$ is independently selected from:

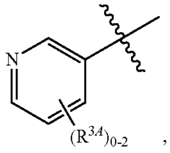, and 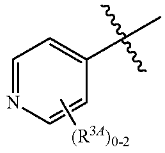;

each $R^{3A}$ is independently selected from: halogen, CN, —$(O)_m$—($C_1$-$C_4$ alkyl substituted with 0-1 $R^{3B}$), $C_1$-$C_4$ haloalkyl, $C_1$-$C_4$ haloalkoxy, —C(═O)$NH_2$, —C(═O)NH($C_1$-$C_4$ alkyl), —C(═O)N($C_1$-$C_4$ alkyl)$_2$, —C(═O)N($C_1$-$C_4$ alkyl)$(CH_2)_2$N($C_1$-$C_4$ alkyl)$_2$, —$CH_2$NHC(═O)($C_1$-$C_4$ alkyl), —S(═O)$_2$($C_1$-$C_4$ alkyl), $NH_2$, NH($C_1$-$C_4$ alkyl), N($C_1$-$C_4$ alkyl)$_2$, $C_3$-$C_6$ cycloalkyl,

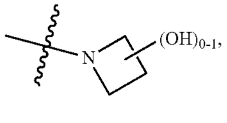, 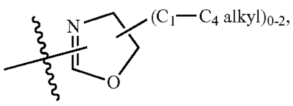,

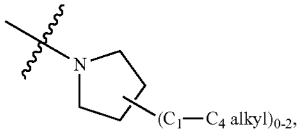,

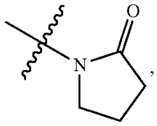,

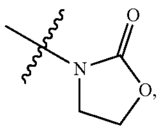, 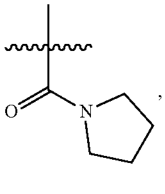,

-continued

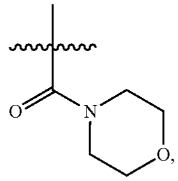, 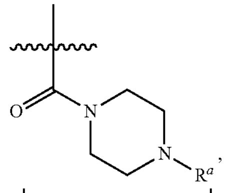,

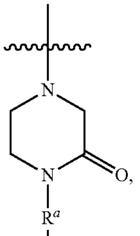, 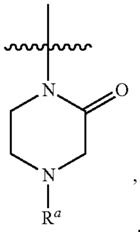, 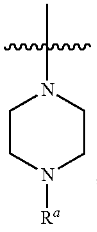,

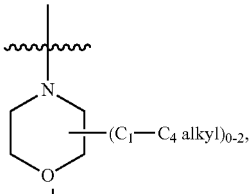, 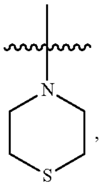, and

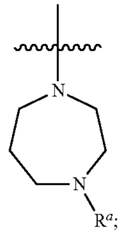;

$R^{3B}$ is independently sleeted from: OH, N($C_1$-$C_4$ alkyl), $C_1$-$C_4$ alkoxy, —C(═O)N($C_1$-$C_4$ alkyl)$_2$, —S(═O)$_2$($C_1$-$C_4$ alkyl),

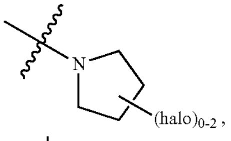, 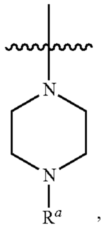, and

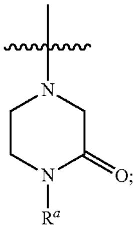;

and each $R^a$ is independently selected from: H, $C_1$-$C_4$ alkyl, —C(═O)H, —C(═O)($C_1$-$C_4$ alkyl), and —$CO_2$($C_1$-$C_4$ alkyl).

8. The method of claim 7, wherein:

each $R^{3A}$ is independently selected from: F, Cl, $CH_3$, —$CH_2$OH, $CH_2$F, $CHF_2$, $CF_3$, CN, —$OCH_3$, —$OCH_2CH_3$, —$OCH(CH_3)_2$, —$OCHF_2$, —C(═O)N$(CH_3)_2$, —$CH_2$NHC(═O)$CH_3$, —S(═O)$_2CH_3$, $NH_2$, cyclopropyl,

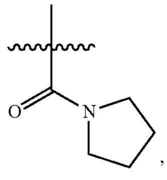
,
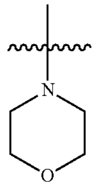
, and
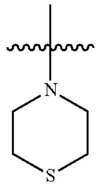
.

9. The method of claim 1, wherein said compound, or a pharmaceutically acceptable salt thereof, is of Formula (IA-1):

(IA-1)

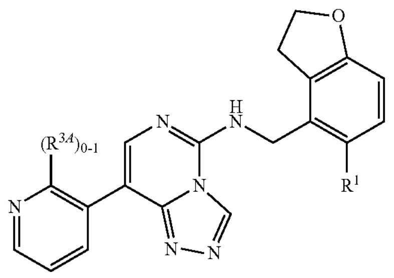

or a pharmaceutically acceptable salt thereof, wherein:

$R^1$ is independently H or F; and $R^{3A}$ is independently selected from: F, $CH_3$, $—CH_2OH$, $CH_2F$, $CHF_2$, $CF_3$, and $—OCH_3$.

10. The method of claim 1, wherein:

$R^1$ is independently H or F;

$R^2$ is H;

$R^3$ is independently a 5-membered heteroaryl comprising carbon atoms and 1-4 heteroatoms selected from N, $NR^a$, O, and $S(O)_p$; wherein said heteroaryl is substituted with 0-3 $R^{3A}$; and $R^a$ is independently selected from: H, $C_1$-$C_4$ alkyl substituted with 0-1 $R^b$, $—C(=O)H$, $—C(=O)(C_1$-$C_4$ alkyl), $—CO_2(C_1$-$C_4$ alkyl), $C_3$-$C_6$ cycloalkyl, and benzyl.

11. The method of claim 1, wherein:

$R^3$ is independently selected from:

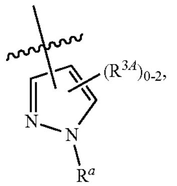
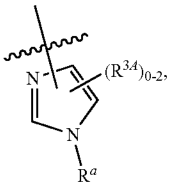
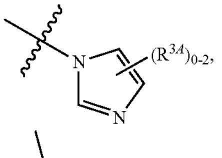
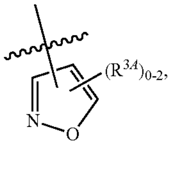
and
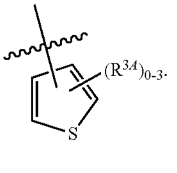

12. The method of claim 1, wherein:

$R^1$ is F.

13. The method of claim 1, wherein said compound is selected from 8-(1,3-dimethyl-1H-pyrazol-5-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-methylpyridin-3-yl)-[1,2,4]triazolo[4,3-c]pyrimidin-5-amine;

8-(2,4-dimethylpyrimidin-5-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1-isopropyl-3-methyl-1H-pyrazol-4-yl)-[1,2,4]triazolo[4,3-c]pyrimidin-5-amine;

N-((5-fluoro-2,3-dihydrobenzofuran-4-yl)methyl)-8-(6-methoxy-4-methylpyridin-3-yl)-[1,2,4]triazolo[4,3-c]pyrimidin-5-amine;

8-(6-cyclopropyl-2-methylpyridin-3-yl)-N-((5-fluoro-2,3-dihydrobenzofuran-4-yl)methyl)-[1,2,4]triazolo[4,3-c]pyrimidin-5-amine;

(3-(5-(((5-fluoro-2,3-dihydrobenzofuran-4-yl)methyl)amino)-[1,2,4]triazolo[4,3-c]pyrimidin-8-yl)pyridin-2-yl)methanol;

8-(2-cyclopropyl-4-methylpyrimidin-5-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-isopropoxy-4-methylpyrimidin-5-yl)-[1,2,4]triazolo[4,3-c]pyrimidin-5-amine;

3-(5-(((5-fluoro-2,3-dihydrobenzofuran-4-yl)methyl)amino)-[1,2,4]triazolo[4,3-c]pyrimidin-8-yl)pyridine 1-oxide;

N-((2,3-dihydrobenzofuran-4-yl)methyl)-8-(4-((dimethylamino)methyl)phenyl)-[1,2,4]triazolo[4,3-c]pyrimidin-5-amine;

N-((2,3-dihydrobenzofuran-4-yl)methyl)-8-(4-(methylsulfonyl)phenyl)-[1,2,4]triazolo[4,3-c]pyrimidin-5-amine;

N-((2,3-dihydrobenzofuran-4-yl)methyl)-8-phenyl-[1,2,4]triazolo[4,3-c]pyrimidin-5-amine;

N-((2,3-dihydrobenzofuran-4-yl)methyl)-8-(4-(1-(pyrrolidin-1-yl)ethyl)phenyl)-[1,2,4]triazolo[4,3-c]pyrimidin-5-amine;

4-(5-(((2,3-dihydrobenzofuran-4-yl)methyl)amino)-[1,2,4]triazolo[4,3-c]pyrimidin-8-yl)-N,N-dimethylbenzenesulfonamide;

N-((2,3-dihydrobenzofuran-4-yl)methyl)-8-(pyridin-3-yl)-[1,2,4]triazolo[4,3-c]pyrimidin-5-amine;

N-((2,3-dihydrobenzofuran-4-yl)methyl)-8-(pyridin-4-yl)-[1,2,4]triazolo[4,3-c]pyrimidin-5-amine;

N-((2,3-dihydrobenzofuran-4-yl)methyl)-8-(2-(4-methylpiperazin-1-yl)pyridin-4-yl)-[1,2,4]triazolo[4,3-c]pyrimidin-5-amine;

N-(4-(5-(((2,3-dihydrobenzofuran-4-yl)methyl)amino)-[1,2,4]triazolo[4,3-c]pyrimidin-8-yl)phenyl)methanesulfonamide;

N-((2,3-dihydrobenzofuran-4-yl)methyl)-8-(6-(4-methylpiperazin-1-yl)pyridin-3-yl)-[1,2,4]triazolo[4,3-c]pyrimidin-5-amine;

N-((2,3-dihydrobenzofuran-4-yl)methyl)-8-(6-methoxypyridin-3-yl)-[1,2,4]triazolo[4,3-c]pyrimidin-5-amine;

8-(4-((dimethylamino)methyl)phenyl)-N-((2-methyl-2,3-dihydrobenzofuran-4-yl)methyl)-[1,2,4]triazolo[4,3-c]pyrimidin-5-amine;

8-(4-((dimethylamino)methyl)phenyl)-N-((5-fluoro-2,3-dihydrobenzofuran-4-yl)methyl)-[1,2,4]triazolo[4,3-c]pyrimidin-5-amine;

N-((2,3-dihydrobenzofuran-4-yl)methyl)-8-(1,3,5-trimethyl-1H-pyrazol-4-yl)-[1,2,4]triazolo[4,3-c]pyrimidin-5-amine;

N-((2,3-dihydrobenzofuran-4-yl)methyl)-8-(1-methyl-1H-pyrazol-4-yl)-[1,2,4]triazolo[4,3-c]pyrimidin-5-amine;

N-((2,3-dihydrobenzofuran-4-yl)methyl)-8-(2-fluoro-4-(methylsulfonyl)phenyl)-[1,2,4]triazolo[4,3-c]pyrimidin-5-amine;

N-((2,3-dihydrobenzofuran-4-yl)methyl)-8-(3-(methylsulfonyl)phenyl)-[1,2,4]triazolo[4,3-c]pyrimidin-5-amine;

N-((2,3-dihydrobenzofuran-4-yl)methyl)-8-(6-(methylsulfonyl)pyridin-3-yl)-[1,2,4]triazolo[4,3-c]pyrimidin-5-amine;

N-((2,3-dihydrobenzofuran-4-yl)methyl)-8-(4-(piperidin-4-ylsulfonyl)phenyl)-[1,2,4]triazolo[4,3-c]pyrimidin-5-amine;

N-((2,3-dihydrobenzofuran-4-yl)methyl)-8-(1,3-dimethyl-1H-pyrazol-4-yl)-[1,2,4]triazolo[4,3-c]pyrimidin-5-amine;

N-((2,3-dihydrobenzofuran-4-yl)methyl)-8-(2-fluorophenyl)-[1,2,4]triazolo[4,3-c]pyrimidin-5-amine;

8-(2-chlorophenyl)-N-((2,3-dihydrobenzofuran-4-yl)methyl)-[1,2,4]triazolo[4,3-c]pyrimidin-5-amine;

N-(4-(5-(((2,3-dihydrobenzofuran-4-yl)methyl)amino)-[1,2,4]triazolo[4,3-c]pyrimidin-8-yl)-2-fluorophenyl)methanesulfonamide;

2-(4-(5-(((2,3-dihydrobenzofuran-4-yl)methyl)amino)-[1,2,4]triazolo[4,3-c]pyrimidin-8-yl)-1H-pyrazol-1-yl)ethanol;

N-((2,3-dihydrobenzofuran-4-yl)methyl)-8-(4-(2-(dimethylamino)ethyl)phenyl)-[1,2,4]triazolo[4,3-c]pyrimidin-5-amine;

N-((2,3-dihydrobenzofuran-4-yl)methyl)-8-(5-methyl-6-(4-methylpiperazin-1-yl)pyridin-3-yl)-[1,2,4]triazolo[4,3-c]pyrimidin-5-amine;

N-((5-fluoro-2,3-dihydrobenzofuran-4-yl)methyl)-8-(4-(methylsulfonyl)phenyl)-[1,2,4]triazolo[4,3-c]pyrimidin-5-amine;

2-(4-(5-(((2,3-dihydrobenzofuran-4-yl)methyl)amino)-[1,2,4]triazolo[4,3-c]pyrimidin-8-yl)phenoxy)ethanol;

N-(2-fluoro-4-(5-(((5-fluoro-2,3-dihydrobenzofuran-4-yl)methyl)amino)-[1,2,4]triazolo[4,3-c]pyrimidin-8-yl)phenyl)methanesulfonamide;

4-(5-(((2,3-dihydrobenzofuran-4-yl)methyl)amino)-[1,2,4]triazolo[4,3-c]pyrimidin-8-yl)-N-(2-hydroxyethyl)benzenesulfonamide;

(4-(5-(((2,3-dihydrobenzofuran-4-yl)methyl)amino)-[1,2,4]triazolo[4,3-c]pyrimidin-8-yl)phenyl)(piperazin-1-yl)methanone;

4-(5-(((2,3-dihydrobenzofuran-4-yl)methyl)amino)-[1,2,4]triazolo[4,3-c]pyrimidin-8-yl)-N,N-dimethylbenzamide;

3-(5-(((2,3-dihydrobenzofuran-4-yl)methyl)amino)-[1,2,4]triazolo[4,3-c]pyrimidin-8-yl)-N,N-dimethylbenzamide;

N-((5-fluoro-2,3-dihydrobenzofuran-4-yl)methyl)-8-(pyridin-3-yl)-[1,2,4]triazolo[4,3-c]pyrimidin-5-amine;

N-((5-fluoro-2,3-dihydrobenzofuran-4-yl)methyl)-8-(pyridin-4-yl)-[1,2,4]triazolo[4,3-c]pyrimidin-5-amine;

N-((5-fluoro-2,3-dihydrobenzofuran-4-yl)methyl)-8-(4-(1-(pyrrolidin-1-yl)ethyl)phenyl)-[1,2,4]triazolo[4,3-c]pyrimidin-5-amine;

N-((5-fluoro-2,3-dihydrobenzofuran-4-yl)methyl)-8-(4-fluoropyridin-3-yl)-[1,2,4]triazolo[4,3-c]pyrimidin-5-amine;

8-(6-aminopyridin-3-yl)-N-((2,3-dihydrobenzofuran-4-yl)methyl)-[1,2,4]triazolo[4,3-c]pyrimidin-5-amine;

4-(5-(((2,3-dihydrobenzofuran-4-yl)methyl)amino)-[1,2,4]triazolo[4,3-c]pyrimidin-8-yl)-N,N,2-trimethylbenzamide;

8-(4-chloropyridin-3-yl)-N-((2,3-dihydrobenzofuran-4-yl)methyl)-[1,2,4]triazolo[4,3-c]pyrimidin-5-amine;

N-((2,3-dihydrobenzofuran-4-yl)methyl)-8-(pyrimidin-5-yl)-[1,2,4]triazolo[4,3-c]pyrimidin-5-amine;

N-((2,3-dihydrobenzofuran-4-yl)methyl)-8-(6-methylpyridin-3-yl)-[1,2,4]triazolo[4,3-c]pyrimidin-5-amine;

N-((2,3-dihydrobenzofuran-4-yl)methyl)-8-(6-(2-(dimethylamino)ethyl)pyridin-3-yl)-[1,2,4]triazolo[4,3-c]pyrimidin-5-amine;

N-((2,3-dihydrobenzofuran-4-yl)methyl)-8-(2-methoxypyrimidin-5-yl)-[1,2,4]triazolo[4,3-c]pyrimidin-5-amine;

4-(5-(((5-fluoro-2,3-dihydrobenzofuran-4-yl)methyl)amino)-[1,2,4]triazolo[4,3-c]pyrimidin-8-yl)-N,N-dimethylbenzamide;

N-((5-fluoro-2,3-dihydrobenzofuran-4-yl)methyl)-8-(6-(methylsulfonyl)pyridin-3-yl)-[1,2,4]triazolo[4,3-c]pyrimidin-5-amine;

N-((5-fluoro-2,3-dihydrobenzofuran-4-yl)methyl)-8-(6-methylpyridin-3-yl)-[1,2,4]triazolo[4,3-c]pyrimidin-5-amine;

8-(6-amino-4-fluoropyridin-3-yl)-N-((2,3-dihydrobenzofuran-4-yl)methyl)-[1,2,4]triazolo[4,3-c]pyrimidin-5-amine;

N-((2,3-dihydrobenzofuran-4-yl)methyl)-8-(3,5-dimethylisoxazol-4-yl)-[1,2,4]triazolo[4,3-c]pyrimidin-5-amine;

N-((2,3-dihydrobenzofuran-4-yl)methyl)-8-(2-methylpyrimidin-5-yl)-[1,2,4]triazolo[4,3-c]pyrimidin-5-amine;

N-((2,3-dihydrobenzofuran-4-yl)methyl)-8-(6-(dimethylamino)pyridin-3-yl)-[1,2,4]triazolo[4,3-c]pyrimidin-5-amine;

5-(5-(((2,3-dihydrobenzofuran-4-yl)methyl)amino)-[1,2,4]triazolo[4,3-c]pyrimidin-8-yl)picolinonitrile;

N-((2,3-dihydrobenzofuran-4-yl)methyl)-8-(6-ethoxypyridin-3-yl)-[1,2,4]triazolo[4,3-c]pyrimidin-5-amine;

N-((2,3-dihydrobenzofuran-4-yl)methyl)-8-(1,5-dimethyl-1H-pyrazol-4-yl)-[1,2,4]triazolo[4,3-c]pyrimidin-5-amine;

8-(6-cyclopropylpyridin-3-yl)-N-((2,3-dihydrobenzofuran-4-yl)methyl)-[1,2,4]triazolo[4,3-c]pyrimidin-5-amine;

N-((2,3-dihydrobenzofuran-4-yl)methyl)-8-(1-(2-methoxyethyl)-3,5-dimethyl-1H-pyrazol-4-yl)-[1,2,4]triazolo[4,3-c]pyrimidin-5-amine;

2-(4-(5-(((2,3-dihydrobenzofuran-4-yl)methyl)amino)-[1,2,4]triazolo[4,3-c]pyrimidin-8-yl)-3,5-dimethyl-1H-pyrazol-1-yl)ethanol;

(5-(5-(((2,3-dihydrobenzofuran-4-yl)methyl)amino)-[1,2,4]triazolo[4,3-c]pyrimidin-8-yl)pyridin-2-yl)(morpholino)methanone;

N-((2,3-dihydrobenzofuran-4-yl)methyl)-8-(6-morpholinopyridin-3-yl)-[1,2,4]triazolo[4,3-c]pyrimidin-5-amine;

N-((2,3-dihydrobenzofuran-4-yl)methyl)-8-(5-methyl-6-(methylsulfonyl)pyridin-3-yl)-[1,2,4]triazolo[4,3-c]pyrimidin-5-amine;

8-(3,5-dimethylisoxazol-4-yl)-N-((5-fluoro-2,3-dihydrobenzofuran-4-yl)methyl)-[1,2,4]triazolo[4,3-c]pyrimidin-5-amine;

(4-(5-(((5-fluoro-2,3-dihydrobenzofuran-4-yl)methyl)amino)-[1,2,4]triazolo[4,3-c]pyrimidin-8-yl)phenyl)(4-methylpiperazin-1-yl)methanone;

N-((2,3-dihydrobenzofuran-4-yl)methyl)-8-(5-methyl-6-morpholinopyridin-3-yl)-[1,2,4]triazolo[4,3-c]pyrimidin-5-amine;

N-((2,3-dihydrobenzofuran-4-yl)methyl)-8-(6-(2,6-dimethylmorpholino)pyridin-3-yl)-[1,2,4]triazolo[4,3-c]pyrimidin-5-amine;

N-((2,3-dihydrobenzofuran-4-yl)methyl)-8-(4-(2-(methylsulfonyl)ethoxy)phenyl)-[1,2,4]triazolo[4,3-c]pyrimidin-5-amine;

8-(4-aminopyridin-3-yl)-N-((2,3-dihydrobenzofuran-4-yl)methyl)-[1,2,4]triazolo[4,3-c]pyrimidin-5-amine;

N-((2,3-dihydrobenzofuran-4-yl)methyl)-8-(5-(piperazin-1-yl)pyridin-3-yl)-[1,2,4]triazolo[4,3-c]pyrimidin-5-amine;

8-(6-(difluoromethoxy)pyridin-3-yl)-N-((2,3-dihydrobenzofuran-4-yl)methyl)-[1,2,4]triazolo[4,3-c]pyrimidin-5-amine;

5-(5-(((2,3-dihydrobenzofuran-4-yl)methyl)amino)-[1,2,4]triazolo[4,3-c]pyrimidin-8-yl)-N-methylpicolinamide;

(5-(5-(((2,3-dihydrobenzofuran-4-yl)methyl)amino)-[1,2,4]triazolo[4,3-c]pyrimidin-8-yl)pyridin-2-yl)(pyrrolidin-1-yl)methanone;

N-((2,3-dihydrobenzofuran-4-yl)methyl)-8-(6-thiomorpholinopyridin-3-yl)-[1,2,4]triazolo[4,3-c]pyrimidin-5-amine;

N-((2,3-dihydrobenzofuran-4-yl)methyl)-8-(1-isopropyl-3-methyl-1H-pyrazol-4-yl)-[1,2,4]triazolo[4,3-c]pyrimidin-5-amine;

N-((2,3-dihydrobenzofuran-4-yl)methyl)-8-(6-(methoxymethyl)-5-methylpyridin-3-yl)-[1,2,4]triazolo[4,3-c]pyrimidin-5-amine;

1-(5-(5-(((2,3-dihydrobenzofuran-4-yl)methyl)amino)-[1,2,4]triazolo[4,3-c]pyrimidin-8-yl)pyridin-2-yl)ethanol;

N-((2,3-dihydrobenzofuran-4-yl)methyl)-8-(4-fluoropyridin-3-yl)-[1,2,4]triazolo[4,3-c]pyrimidin-5-amine;

N-((2,3-dihydrobenzofuran-4-yl)methyl)-8-(6-(2-methoxyethyl)pyridin-3-yl)-[1,2,4]triazolo[4,3-c]pyrimidin-5-amine;

1-(5-(5-(((2,3-dihydrobenzofuran-4-yl)methyl)amino)-[1,2,4]triazolo[4,3-c]pyrimidin-8-yl)pyridin-3-yl)pyrrolidin-2-one;

N-((2,3-dihydrobenzofuran-4-yl)methyl)-8-(2-(dimethylamino)pyrimidin-5-yl)-[1,2,4]triazolo[4,3-c]pyrimidin-5-amine;

N-((2,3-dihydrobenzofuran-4-yl)methyl)-8-(3-(2-(dimethylamino)ethyl)phenyl)-[1,2,4]triazolo[4,3-c]pyrimidin-5-amine;

N-((2,3-dihydrobenzofuran-4-yl)methyl)-8-(5-(4,4-dimethyl-4,5-dihydrooxazol-2-yl)pyridin-3-yl)-[1,2,4]triazolo[4,3-c]pyrimidin-5-amine;

N-((5-fluoro-2,3-dihydrobenzofuran-4-yl)methyl)-8-(6-thiomorpholinopyridin-3-yl)-[1,2,4]triazolo[4,3-c]pyrimidin-5-amine;

N-((5-fluoro-2,3-dihydrobenzofuran-4-yl)methyl)-8-(6-morpholinopyridin-3-yl)-[1,2,4]triazolo[4,3-c]pyrimidin-5-amine;

5-(5-(((5-fluoro-2,3-dihydrobenzofuran-4-yl)methyl)amino)-[1,2,4]triazolo[4,3-c]pyrimidin-8-yl)picolinonitrile;

N-((5-fluoro-2,3-dihydrobenzofuran-4-yl)methyl)-8-(2-fluorophenyl)-[1,2,4]triazolo[4,3-c]pyrimidin-5-amine;

5-(5-(((2,3-dihydrobenzofuran-4-yl)methyl)amino)-[1,2,4]triazolo[4,3-c]pyrimidin-8-yl)-N,N-dimethylpicolinamide;

N-((2,3-dihydrobenzofuran-4-yl)methyl)-8-(6-(2-methylpyrrolidin-1-yl)pyridin-3-yl)-[1,2,4]triazolo[4,3-c]pyrimidin-5-amine;

methyl 4-(5-(5-(((2,3-dihydrobenzofuran-4-yl)methyl)amino)-[1,2,4]triazolo[4,3-c]pyrimidin-8-yl)pyridin-2-yl)piperazine-1-carboxylate;

N-((2,3-dihydrobenzofuran-4-yl)methyl)-8-(5-(3-(methylsulfonyl)propoxy)pyridin-3-yl)-[1,2,4]triazolo[4,3-c]pyrimidin-5-amine;

2-(5-(5-(((2,3-dihydrobenzofuran-4-yl)methyl)amino)-[1,2,4]triazolo[4,3-c]pyrimidin-8-yl)pyridin-2-yl)propan-2-ol;

8-(6-(2-(3,3-difluoropyrrolidin-1-yl)ethyl)pyridin-3-yl)-N-((2,3-dihydrobenzofuran-4-yl)methyl)-[1,2,4]triazolo[4,3-c]pyrimidin-5-amine;

N-((2,3-dihydrobenzofuran-4-yl)methyl)-8-(6-(4,4-dimethyl-4,5-dihydrooxazol-2-yl)pyridin-3-yl)-[1,2,4]triazolo[4,3-c]pyrimidin-5-amine;

5-(5-(((2,3-dihydrobenzofuran-4-yl)methyl)amino)-[1,2,4]triazolo[4,3-c]pyrimidin-8-yl)-N-(2-(dimethylamino)ethyl)-N-methylpicolinamide;

N-((2,3-dihydrobenzofuran-4-yl)methyl)-8-(5-methyl-6-(pyrrolidin-1-yl)pyridin-3-yl)-[1,2,4]triazolo[4,3-c]pyrimidin-5-amine;

4-(5-(5-(((2,3-dihydrobenzofuran-4-yl)methyl)amino)-[1,2,4]triazolo[4,3-c]pyrimidin-8-yl)pyridin-2-yl)piperazin-2-one;

4-(5-(5-(((2,3-dihydrobenzofuran-4-yl)methyl)amino)-[1,2,4]triazolo[4,3-c]pyrimidin-8-yl)-3-methylpyridin-2-yl)piperazin-2-one;

N-((2,3-dihydrobenzofuran-4-yl)methyl)-8-(5-(2-(methylsulfonyl)ethoxy)pyridin-3-yl)-[1,2,4]triazolo[4,3-c]pyrimidin-5-amine;

4-(2-(5-(5-(((2,3-dihydrobenzofuran-4-yl)methyl)amino)-[1,2,4]triazolo[4,3-c]pyrimidin-8-yl)pyridin-2-yl)ethyl)piperazine-1-carbaldehyde;

1-(4-(2-(5-(5-(((2,3-dihydrobenzofuran-4-yl)methyl)amino)-[1,2,4]triazolo[4,3-c]pyrimidin-8-yl)pyridin-2-yl)ethyl)piperazin-1-yl)ethanone;

4-(2-(5-(5-(((2,3-dihydrobenzofuran-4-yl)methyl)amino)-[1,2,4]triazolo[4,3-c]pyrimidin-8-yl)pyridin-2-yl)ethyl)piperazin-2-one;

2-(4-(5-(5-(((2,3-dihydrobenzofuran-4-yl)methyl)amino)-[1,2,4]triazolo[4,3-c]pyrimidin-8-yl)pyridin-2-yl)piperazin-1-yl)ethanol;

N-((2,3-dihydrobenzofuran-4-yl)methyl)-8-(4-fluoro-6-(methylamino)pyridin-3-yl)-[1,2,4]triazolo[4,3-c]pyrimidin-5-amine;

N-((2,3-dihydrobenzofuran-4-yl)methyl)-8-(6-(dimethylamino)-4-fluoropyridin-3-yl)-[1,2,4]triazolo[4,3-c]pyrimidin-5-amine;

4-(5-(5-(((2,3-dihydrobenzofuran-4-yl)methyl)amino)-[1,2,4]triazolo[4,3-c]pyrimidin-8-yl)pyridin-2-yl)-1,4-diazepane-1-carbaldehyde;

5-(5-(((2,3-dihydrobenzofuran-4-yl)methyl)amino)-[1,2,4]triazolo[4,3-c]pyrimidin-8-yl)-N-ethylpicolinamide;

N-((5-fluoro-2,3-dihydrobenzofuran-4-yl)methyl)-8-(2-fluoropyridin-3-yl)-[1,2,4]triazolo[4,3-c]pyrimidin-5-amine;

N-((5-fluoro-2,3-dihydrobenzofuran-4-yl)methyl)-8-(2-methylpyridin-4-yl)-[1,2,4]triazolo[4,3-c]pyrimidin-5-amine;

3-(5-(5-(((2,3-dihydrobenzofuran-4-yl)methyl)amino)-[1,2,4]triazolo[4,3-c]pyrimidin-8-yl)pyridin-2-yl)oxazolidin-2-one;

N-((5-fluoro-2,3-dihydrobenzofuran-4-yl)methyl)-8-(4-methylpyridin-3-yl)-[1,2,4]triazolo[4,3-c]pyrimidin-5-amine;

8-(6-cyclopropylpyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-morpholinopyridin-4-yl)-[1,2,4]triazolo[4,3-c]pyrimidin-5-amine;

2-(5-(((5-fluoro-2,3-dihydrobenzofuran-4-yl)methyl)amino)-[1,2,4]triazolo[4,3-c]pyrimidin-8-yl)benzonitrile;

2-(5-(((5-fluoro-2,3-dihydrobenzofuran-4-yl)methyl)amino)-[1,2,4]triazolo[4,3-c]pyrimidin-8-yl)benzamide;

N-((2,3-dihydrobenzofuran-4-yl)methyl)-8-(2-methylpyridin-3-yl)-[1,2,4]triazolo[4,3-c]pyrimidin-5-amine;

8-(4-chloropyridin-3-yl)-N-((5-fluoro-2,3-dihydrobenzofuran-4-yl)methyl)-[1,2,4]triazolo[4,3-c]pyrimidin-5-amine;

1-(5-(5-(((2,3-dihydrobenzofuran-4-yl)methyl)amino)-[1,2,4]triazolo[4,3-c]pyrimidin-8-yl)pyridin-2-yl)piperazin-2-one;

1-(5-(5-(((2,3-dihydrobenzofuran-4-yl)methyl)amino)-[1,2,4]triazolo[4,3-c]pyrimidin-8-yl)pyridin-2-yl)azetidin-3-ol;

N-((5-fluoro-2,3-dihydrobenzofuran-4-yl)methyl)-8-(4-methyl-6-(methylsulfonyl)pyridin-3-yl)-[1,2,4]triazolo[4,3-c]pyrimidin-5-amine;

N-((5-fluoro-2,3-dihydrobenzofuran-4-yl)methyl)-8-(2-methyl-4-(methylsulfonyl)phenyl)-[1,2,4]triazolo[4,3-c]pyrimidin-5-amine;

(5-(5-(((5-fluoro-2,3-dihydrobenzofuran-4-yl)methyl)amino)-[1,2,4]triazolo[4,3-c]pyrimidin-8-yl)pyridin-2-yl)(pyrrolidin-1-yl)methanone;

(5-(5-(((5-fluoro-2,3-dihydrobenzofuran-4-yl)methyl)amino)-[1,2,4]triazolo[4,3-c]pyrimidin-8-yl)-4-methylpyridin-2-yl)(pyrrolidin-1-yl)methanone;

5-(5-(((5-fluoro-2,3-dihydrobenzofuran-4-yl)methyl)amino)-[1,2,4]triazolo[4,3-c]pyrimidin-8-yl)-N,N,4-trimethylpicolinamide;

N-((5-fluoro-2,3-dihydrobenzofuran-4-yl)methyl)-8-(1,3,5-trimethyl-1H-pyrazol-4-yl)-[1,2,4]triazolo[4,3-c]pyrimidin-5-amine;

4-((5-(5-(((2,3-dihydrobenzofuran-4-yl)methyl)amino)-[1,2,4]triazolo[4,3-c]pyrimidin-8-yl)pyridin-2-yl)methyl)piperazin-2-one;

4-(5-(5-(((2,3-dihydrobenzofuran-4-yl)methyl)amino)-[1,2,4]triazolo[4,3-c]pyrimidin-8-yl)pyridin-2-yl)piperazine-1-carbaldehyde;

3-(5-(5-(((2,3-dihydrobenzofuran-4-yl)methyl)amino)-[1,2,4]triazolo[4,3-c]pyrimidin-8-yl)pyridin-2-yl)-N,N-dimethylpropanamide;

N-((5-fluoro-2,3-dihydrobenzofuran-4-yl)methyl)-8-(4-(trifluoromethyl)pyridin-3-yl)-[1,2,4]triazolo[4,3-c]pyrimidin-5-amine;

N-((2,3-dihydrobenzofuran-4-yl)methyl)-8-(5-(methoxymethyl)-6-methylpyridin-3-yl)-[1,2,4]triazolo[4,3-c]pyrimidin-5-amine;

8-(4-chloro-6-methoxypyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-methyl-6-(methylsulfonyl)pyridin-3-yl)-[1,2,4]triazolo[4,3-c]pyrimidin-5-amine;

5-(5-(((5-fluoro-2,3-dihydrobenzofuran-4-yl)methyl)amino)-[1,2,4]triazolo[4,3-c]pyrimidin-8-yl)-N,N-dimethylpicolinamide;

N-((5-fluoro-2,3-dihydrobenzofuran-4-yl)methyl)-8-(2-methoxypyridin-3-yl)-[1,2,4]triazolo[4,3-c]pyrimidin-5-amine;

N-((5-fluoro-2,3-dihydrobenzofuran-4-yl)methyl)-8-(6-methoxypyridin-3-yl)-[1,2,4]triazolo[4,3-c]pyrimidin-5-amine;

8-(1-ethyl-1H-pyrazol-5-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1-isopropyl-1H-pyrazol-5-yl)-[1,2,4]triazolo[4,3-c]pyrimidin-5-amine;

N-((5-fluoro-2,3-dihydrobenzofuran-4-yl)methyl)-8-(2-methoxypyridin-4-yl)-[1,2,4]triazolo[4,3-c]pyrimidin-5-amine;

8-(2,4-dichlorophenyl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1-methyl-1H-pyrazol-4-yl)-[1,2,4]triazolo[4,3-c]pyrimidin-5-amine;

N-((5-fluoro-2,3-dihydrobenzofuran-4-yl)methyl)-8-(1-isopropyl-3-(trifluoromethyl)-1H-pyrazol-4-yl)-[1,2,4]triazolo[4,3-c]pyrimidin-5-amine;

8-(1-cyclopropyl-1H-pyrazol-4-yl)-N-((2,3-dihydrobenzofuran-4-yl)methyl)-[1,2,4]triazolo[4,3-c]pyrimidin-5-amine;

8-(1-cyclopropyl-1H-pyrazol-4-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1-isopropyl-3,5-dimethyl-1H-pyrazol-4-yl)-[1,2,4]triazolo[4,3-c]pyrimidin-5-amine;

N-((2,3-dihydrobenzofuran-4-yl)methyl)-8-(1-methyl-1H-pyrazol-5-yl)-[1,2,4]triazolo[4,3-c]pyrimidin-5-amine;

N-((2,3-dihydrobenzofuran-4-yl)methyl)-8-(1-isopropyl-3,5-dimethyl-1H-pyrazol-4-yl)-[1,2,4]triazolo[4,3-c]pyrimidin-5-amine;

8-(6-(difluoromethyl)pyridin-3-yl)-N-((2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(6-methoxy-2-methylpyridin-3-yl)-[1,2,4]triazolo[4,3-c]pyrimidin-5-amine;

8-(6-amino-2-methylpyridin-3-yl)-N-((5-fluoro-2,3-dihydrobenzofuran-4-yl)methyl)-[1,2,4]triazolo[4,3-c]pyrimidin-5-amine;

8-(2-chloro-4-fluorophenyl)-N-((5-fluoro-2,3-dihydrobenzofuran-4-yl)methyl)-[1,2,4]triazolo[4,3-c]pyrimidin-5-amine;

2-(4-(5-(((5-fluoro-2,3-dihydrobenzofuran-4-yl)methyl)amino)-[1,2,4]triazolo[4,3-c]pyrimidin-8-yl)-3,5-dimethyl-1H-pyrazol-1-yl)ethanol;

N-((5-fluoro-2,3-dihydrobenzofuran-4-yl)methyl)-8-(1-(2-methoxyethyl)-3,5-dimethyl-1H-pyrazol-4-yl)-[1,2,4]triazolo[4,3-c]pyrimidin-5-amine;

N-((5-fluoro-2,3-dihydrobenzofuran-4-yl)methyl)-8-(6-(trifluoromethyl)pyridin-3-yl)-[1,2,4]triazolo[4,3-c]pyrimidin-5-amine;

N-((5-fluoro-2,3-dihydrobenzofuran-4-yl)methyl)-8-(4-fluoro-6-methoxypyridin-3-yl)-[1,2,4]triazolo[4,3-c]pyrimidin-5-amine;

8-(3-chloropyridin-4-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(3-methylpyridin-4-yl)-[1,2,4]triazolo[4,3-c]pyrimidin-5-amine;

N-((5-fluoro-2,3-dihydrobenzofuran-4-yl)methyl)-8-(6-fluoro-2-methylpyridin-3-yl)-[1,2,4]triazolo[4,3-c]pyrimidin-5-amine;

N-((5-fluoro-2,3-dihydrobenzofuran-4-yl)methyl)-8-(4-fluoro-2-methylphenyl)-[1,2,4]triazolo[4,3-c]pyrimidin-5-amine;

N-((5-fluoro-2,3-dihydrobenzofuran-4-yl)methyl)-8-(2-(trifluoromethyl)pyridin-3-yl)-[1,2,4]triazolo[4,3-c]pyrimidin-5-amine;

8-(2,6-dimethylpyridin-3-yl)-N-((5-fluoro-2,3-dihydrobenzofuran-4-yl)methyl)-[1,2,4]triazolo[4,3-c]pyrimidin-5-amine;

8-(2-(difluoromethyl)pyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1-methyl-1H-pyrazol-5-yl)-[1,2,4]triazolo[4,3-c]pyrimidin-5-amine;

N-((5-fluoro-2,3-dihydrobenzofuran-4-yl)methyl)-8-(1-methyl-3-(trifluoromethyl)-1H-pyrazol-4-yl)-[1,2,4]triazolo[4,3-c]pyrimidin-5-amine;

N-((5-(5-(((5-fluoro-2,3-dihydrobenzofuran-4-yl)methyl)amino)-[1,2,4]triazolo[4,3-c]pyrimidin-8-yl)pyridin-2-yl)methyl)acetamide;

8-(1,5-dimethyl-1H-pyrazol-4-yl)-N-((5-fluoro-2,3-dihydrobenzofuran-4-yl)methyl)-[1,2,4]triazolo[4,3-c]pyrimidin-5-amine;

8-(6-cyclopropyl-4-methylpyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-methoxypyrimidin-5-yl)-[1,2,4]triazolo[4,3-c]pyrimidin-5-amine;

N-((5-fluoro-2,3-dihydrobenzofuran-4-yl)methyl)-8-(2-methoxy-4-methylpyrimidin-5-yl)-[1,2,4]triazolo[4,3-c]pyrimidin-5-amine;

N-((5-fluoro-2,3-dihydrobenzofuran-4-yl)methyl)-8-(4-methylpyrimidin-5-yl)-[1,2,4]triazolo[4,3-c]pyrimidin-5-amine;

8-(2,3-dimethylpyridin-4-yl)-N-((5-fluoro-2,3-dihydrobenzofuran-4-yl)methyl)-[1,2,4]triazolo[4,3-c]pyrimidin-5-amine;

4-(5-(((5-fluoro-2,3-dihydrobenzofuran-4-yl)methyl)amino)-[1,2,4]triazolo[4,3-c]pyrimidin-8-yl)-3-methylbenzonitrile;

8-(1-cyclopropyl-3,5-dimethyl-1H-pyrazol-4-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-fluoro-3-methylpyridin-4-yl)-[1,2,4]triazolo[4,3-c]pyrimidin-5-amine;

8-(2-(difluoromethyl)-3-methylpyridin-4-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-(fluoromethyl)-3-methylpyridin-4-yl)-[1,2,4]triazolo[4,3-c]pyrimidin-5-amine;

N-((5-fluoro-2,3-dihydrobenzofuran-4-yl)methyl)-8-(2-fluoro-5-methylpyridin-4-yl)-[1,2,4]triazolo[4,3-c]pyrimidin-5-amine;

N-((5-fluoro-2,3-dihydrobenzofuran-4-yl)methyl)-8-(5-methyl-2-(trifluoromethyl)pyridin-4-yl)-[1,2,4]triazolo[4,3-c]pyrimidin-5-amine;

N-((5-fluoro-2,3-dihydrobenzofuran-4-yl)methyl)-8-(2-(trifluoromethyl)pyridin-4-yl)-[1,2,4]triazolo[4,3-c]pyrimidin-5-amine;

(2R)-1-(4-(5-(((5-fluoro-2,3-dihydrobenzofuran-4-yl)methyl)amino)-[1,2,4]triazolo[4,3-c]pyrimidin-8-yl)-3,5-dimethyl-1H-pyrazol-1-yl)propan-2-ol;

(2S)-1-(4-(5-(((5-fluoro-2,3-dihydrobenzofuran-4-yl)methyl)amino)-[1,2,4]triazolo[4,3-c]pyrimidin-8-yl)-3,5-dimethyl-1H-pyrazol-1-yl)propan-2-ol;

N-((5-fluoro-2,3-dihydrobenzofuran-4-yl)methyl)-8-(1-isopropyl-5-methyl-1H-pyrazol-4-yl)-[1,2,4]triazolo[4,3-c]pyrimidin-5-amine;

2-(4-(5-(((5-fluoro-2,3-dihydrobenzofuran-4-yl)methyl)amino)-[1,2,4]triazolo[4,3-c]pyrimidin-8-yl)-5-methyl-1H-pyrazol-1-yl)ethanol;

2-(4-(5-(((5-fluoro-2,3-dihydrobenzofuran-4-yl)methyl)amino)-[1,2,4]triazolo[4,3-c]pyrimidin-8-yl)-3-methyl-1H-pyrazol-1-yl)ethanol;

8-(4-(difluoromethyl)pyrimidin-5-yl)-N-((5-fluoro-2,3-dihydrobenzofuran-4-yl)methyl)-[1,2,4]triazolo[4,3-c]pyrimidin-5-amine;

8-(1-cyclopropyl-1H-pyrazol-5-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-(fluoromethyl)pyridin-3-yl)-[1,2,4]triazolo[4,3-c]pyrimidin-5-amine;

8-(2,5-dimethylpyridin-4-yl)-N-((5-fluoro-2,3-dihydrobenzofuran-4-yl)methyl)-[1,2,4]triazolo[4,3-c]pyrimidin-5-amine;

8-(1,3-dimethyl-1H-pyrazol-4-yl)-N-((5-fluoro-2,3-dihydrobenzofuran-4-yl)methyl)-[1,2,4]triazolo[4,3-c]pyrimidin-5-amine;

8-(6-ethoxy-4-methylpyridin-3-yl)-N-((5-fluoro-2,3-dihydrobenzofuran-4-yl)methyl)-[1,2,4]triazolo[4,3-c]pyrimidin-5-amine;

8-(6-(difluoromethoxy)-4-methylpyridin-3-yl)-N-((5-fluoro-2,3-dihydrobenzofuran-4-yl)methyl)-[1,2,4]triazolo[4,3-c]pyrimidin-5-amine;

8-(2-(difluoromethyl)-5-methylpyridin-4-yl)-N-((5-fluoro-2,3-dihydrobenzofuran-4-yl)methyl)-[1,2,4]triazolo[4,3-c]pyrimidin-5-amine;

5-(5-(((5-fluoro-2,3-dihydrobenzofuran-4-yl)methyl)amino)-[1,2,4]triazolo[4,3-c]pyrimidin-8-yl)-N,N,6-trimethylpicolinamide;

8-(3-(difluoromethyl)-1-methyl-1H-pyrazol-4-yl)-N-((5-fluoro-2,3-dihydrobenzofuran-4-yl)methyl)-[1,2,4]triazolo[4,3-c]pyrimidin-5-amine;

8-(2-(difluoromethyl)-6-methylpyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(pyridazin-4-yl)-[1,2,4]triazolo[4,3-c]pyrimidin-5-amine;

N-((5-fluoro-2,3-dihydrobenzofuran-4-yl)methyl)-7-methyl-8-(2-methylpyridin-3-yl)-[1,2,4]triazolo[4,3-c]pyrimidin-5-amine;

3-(5-(((5-fluoro-2,3-dihydrobenzofuran-4-yl)methyl)amino)-[1,2,4]triazolo[4,3-c]pyrimidin-8-yl)-2-methylpyridine 1-oxide;

N-((5-fluoro-2,3-dihydrobenzofuran-4-yl)methyl)-8-(pyrazin-2-yl)-[1,2,4]triazolo[4,3-c]pyrimidin-5-amine;

N-((5-fluoro-2,3-dihydrobenzofuran-4-yl)methyl)-8-(pyrimidin-5-yl)-[1,2,4]triazolo[4,3-c]pyrimidin-5-amine;

N-((5-fluoro-2,3-dihydrobenzofuran-4-yl)methyl)-8-(pyrimidin-5-yl)-[1,2,4]triazolo[4,3-c]pyrimidin-5-amine;

8-(4,6-dimethylpyridin-3-yl)-N-((5-fluoro-2,3-dihydrobenzofuran-4-yl)methyl)-[1,2,4]triazolo[4,3-c]pyrimidin-5-amine;

8-(6-((dimethylamino)methyl)-2-methylpyridin-3-yl)-N-((5-fluoro-2,3-dihydrobenzofuran-4-yl)methyl)-[1,2,4]triazolo[4,3-c]pyrimidin-5-amine;

8-(6-ethyl-4-methylpyridin-3-yl)-N-((5-fluoro-2,3-dihydrobenzofuran-4-yl)methyl)-[1,2,4]triazolo[4,3-c]pyrimidin-5-amine;

8-(2-cyclopropoxy-4-methylpyrimidin-5-yl)-N-((5-fluoro-2,3-dihydrobenzofuran-4-yl)methyl)-[1,2,4]triazolo[4,3-c]pyrimidin-5-amine;

8-(2-ethoxy-4-methylpyrimidin-5-yl)-N-((5-fluoro-2,3-dihydrobenzofuran-4-yl)methyl)-[1,2,4]triazolo[4,3-c]pyrimidin-5-amine;

(4-(5-(((5-fluoro-2,3-dihydrobenzofuran-4-yl)methyl)amino)-[1,2,4]triazolo[4,3-c]pyrimidin-8-yl)-1-methyl-1H-pyrazol-5-yl)methanol;

8-(2-chloro-5-methylpyridin-4-yl)-N-((5-fluoro-2,3-dihydrobenzofuran-4-yl)methyl)-[1,2,4]triazolo[4,3-c]pyrimidin-5-amine;

8-(6-ethyl-2-methylpyridin-3-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(2-methoxy-3-methylpyridin-4-yl)-[1,2,4]triazolo[4,3-c]pyrimidin-5-amine;

N-((5-fluoro-2,3-dihydrobenzofuran-4-yl)methyl)-8-(pyridin-2-yl)-[1,2,4]triazolo[4,3-c]pyrimidin-5-amine;

N-((5-fluoro-2,3-dihydrobenzofuran-4-yl)methyl)-8-(5-methylpyridin-3-yl)-[1,2,4]triazolo[4,3-c]pyrimidin-5-amine;

N-((5-fluoro-2,3-dihydrobenzofuran-4-yl)methyl)-8-(4-methyl-1H-imidazol-1-yl)-[1,2,4]triazolo[4,3-c]pyrimidin-5-amine;

(5-(5-(((5-fluoro-2,3-dihydrobenzofuran-4-yl)methyl)amino)-[1,2,4]triazolo[4,3-c]pyrimidin-8-yl)pyridin-2-yl)methanol;

8-fluoro-N-((5-fluoro-2,3-dihydrobenzofuran-4-yl)methyl)-[1,2,4]triazolo[4,3-c]pyrimidin-5-amine;

8-(2,4-dimethyl-1H-imidazol-1-yl)-N-((5-fluoro-2,3-dihydrobenzofuran-4-yl)methyl)-[1,2,4]triazolo[4,3-c]pyrimidin-5-amine;

N-((5-fluoro-2,3-dihydrobenzofuran-4-yl)methyl)-8-(1H-pyrazol-1-yl)-[1,2,4]triazolo[4,3-c]pyrimidin-5-amine;

N-((5-fluoro-2,3-dihydrobenzofuran-4-yl)methyl)-8-(3-methyl-1H-1,2,4-triazol-1-yl)-[1,2,4]triazolo[4,3-c]pyrimidin-5-amine;

N-((5-fluoro-2,3-dihydrobenzofuran-4-yl)methyl)-8-(4-methyl-1H-pyrazol-1-yl)-[1,2,4]triazolo[4,3-c]pyrimidin-5-amine;

N-((5-fluoro-2,3-dihydrobenzofuran-4-yl)methyl)-8-(1H-imidazol-1-yl)-[1,2,4]triazolo[4,3-c]pyrimidin-5-amine;

N-((5-fluoro-2,3-dihydrobenzofuran-4-yl)methyl)-8-(1H-1,2,4-triazol-1-yl)-[1,2,4]triazolo[4,3-c]pyrimidin-5-amine;

5-fluoro-4-(((8-(2-methylpyridin-3-yl)-[1,2,4]triazolo[4,3-c]pyrimidin-5-yl)amino)methyl)-2,3-dihydrobenzofuran-3-ol;

5-fluoro-4-(((8-(2-(hydroxymethyl)pyridin-3-yl)-[1,2,4]triazolo[4,3-c]pyrimidin-5-yl)amino)methyl)-2,3-dihydrobenzofuran-3-ol;

3-(5-(((5-fluoro-3-hydroxy-2,3-dihydrobenzofuran-4-yl)methyl)amino)-[1,2,4]triazolo[4,3-c]pyrimidin-8-yl)-2-methylpyridine 1-oxide and 8-(1,2-dimethyl-1H-imidazol-5-yl)-N-((5-fluoro-2,3-dihydrobenzofuran-4-yl)methyl)-[1,2,4]triazolo[4,3-c]pyrimidin-5-amine.

14. The method of claim 1, wherein said compound is selected from:

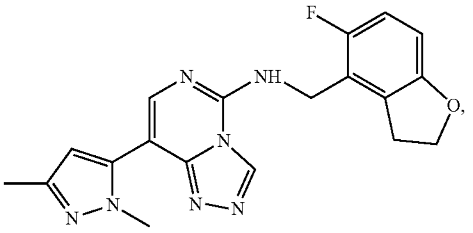

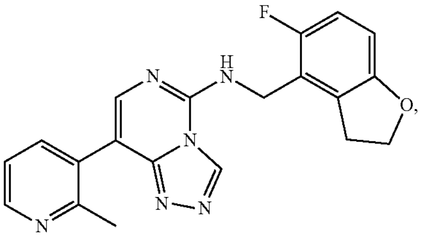

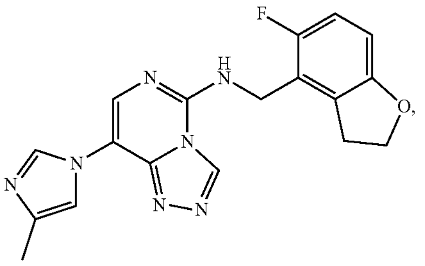

-continued

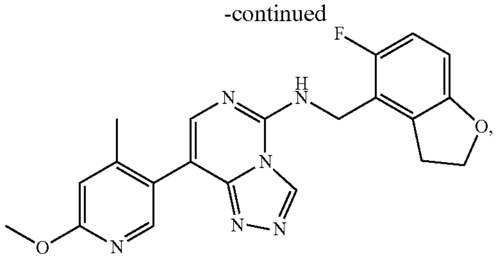

and

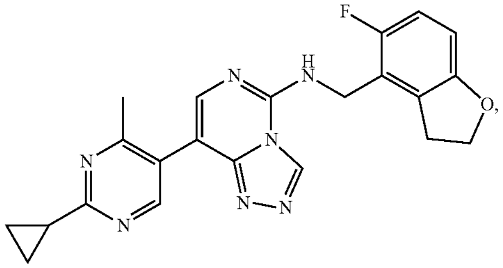

or a pharmaceutically acceptable salt thereof.

15. The method of claim 1, wherein said disease or disorder is gastric cancer.

16. The method of claim 1, wherein the compound is N-((5-fluoro-2,3-dihydrobenzofuran-4-yl)methyl)-8-(2-methylpyridin-3-yl)-[1,2,4]triazolo[4,3-c]pyrimidin-5-amine, or a pharmaceutically acceptable salt thereof, and the disease or disorder is gastric cancer.

17. The method of claim 1, wherein the compound is

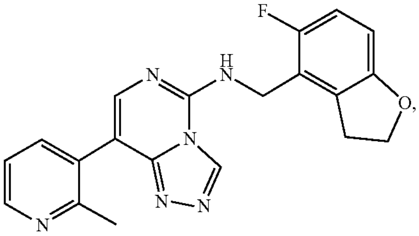 [SMILES: Cc1ncccc1-c1cnc(NCc2c(F)ccc3c2CCO3)n2cnnc12]

or a pharmaceutically acceptable salt thereof, and the disease or disorder is gastric cancer.

18. A method for treating a disease or disorder mediated by Embryonic Ectoderm Development (EED) or Polycomb Repressive Complex 2 (PRC2), wherein the method comprises administering to a patient in need thereof a therapeutically effective amount of N-((5-fluoro-2,3-dihydrobenzofuran-4-yl)methyl)-8-(2-methylpyridin-3-yl)-[1,2,4]triazolo[4,3-c]pyrimidin-5-amine, or a pharmaceutically acceptable salt thereof, and wherein the disease or disorder is gastric cancer.

19. A method for treating gastric cancer, wherein the method comprises administering to a patient in need thereof a therapeutically effective amount of N-((5-fluoro-2,3-dihydrobenzofuran-4-yl)methyl)-8-(2-methylpyridin-3-yl)-[1,2,4]triazolo[4,3-c]pyrimidin-5-amine, or a pharmaceutically acceptable salt thereof.

* * * * *